United States Patent
Crombez et al.

(10) Patent No.: US 9,623,090 B2
(45) Date of Patent: Apr. 18, 2017

(54) COMPOSITIONS AND METHODS FOR TREATING TYPE III GAUCHER DISEASE

(71) Applicant: SHIRE HUMAN GENETIC THERAPIES, INC., Lexington, MA (US)

(72) Inventors: Eric Crombez, Boston, MA (US); Kiran Bhirangi, Demarest, NJ (US); Gabriel Martin Cohn, East Longmeadow, MA (US)

(73) Assignee: SHIRE HUMAN GENETIC THERAPIES, INC., Lexington, MA (US)

( * ) Notice: Subject to any disclaimer, the term of this patent is extended or adjusted under 35 U.S.C. 154(b) by 0 days.

(21) Appl. No.: 14/381,680

(22) PCT Filed: Mar. 1, 2013

(86) PCT No.: PCT/US2013/028608
§ 371 (c)(1),
(2) Date: Aug. 28, 2014

(87) PCT Pub. No.: WO2013/130963
PCT Pub. Date: Sep. 6, 2013

(65) Prior Publication Data
US 2015/0071907 A1  Mar. 12, 2015

Related U.S. Application Data

(60) Provisional application No. 61/606,089, filed on Mar. 2, 2012.

(51) Int. Cl.
*A61K 38/47* (2006.01)
*G01N 33/68* (2006.01)
*G01N 33/538* (2006.01)
*A61K 9/00* (2006.01)

(52) U.S. Cl.
CPC ...... *A61K 38/47* (2013.01); *C12Y 302/01045* (2013.01); *G01N 33/538* (2013.01); *G01N 33/6854* (2013.01); *A61K 9/0019* (2013.01); *G01N 2333/924* (2013.01); *G01N 2800/044* (2013.01); *G01N 2800/52* (2013.01)

(58) Field of Classification Search
CPC ..................................................... A61K 38/47
See application file for complete search history.

(56) References Cited

U.S. PATENT DOCUMENTS

| | | | |
|---|---|---|---|
| 4,925,796 A | 5/1990 | Bergh et al. |
| 5,236,838 A | 8/1993 | Rasmussen et al. |
| 5,272,066 A | 12/1993 | Bergh et al. |
| 5,549,892 A | 8/1996 | Friedman et al. |
| 5,620,884 A | 4/1997 | Shorr et al. |
| 5,641,670 A | 6/1997 | Treco et al. |
| 5,670,132 A | 9/1997 | Griffiths et al. |
| 5,911,983 A | 6/1999 | Barranger et al. |
| 5,929,304 A | 7/1999 | Radin et al. |
| 5,939,279 A | 8/1999 | Smith et al. |
| 5,955,324 A | 9/1999 | Fan et al. |
| 6,074,864 A | 6/2000 | Ginns et al. |
| 6,270,989 B1 | 8/2001 | Treco et al. |
| 6,340,746 B1 | 1/2002 | Roberts et al. |
| 6,534,300 B1 | 3/2003 | Canfield |
| 6,537,785 B1 | 3/2003 | Canfield |
| 6,642,038 B1 | 11/2003 | Canfield |
| 6,670,165 B2 | 12/2003 | Canfield |
| 6,770,468 B1 | 8/2004 | Canfield |
| 6,818,233 B2 | 11/2004 | Perkes |
| 7,138,262 B1 | 11/2006 | Daniel |
| 7,348,000 B2 | 3/2008 | Dwek et al. |
| 7,833,766 B2 | 11/2010 | Zhu et al. |
| 8,673,298 B2 | 3/2014 | Zhu et al. |
| 2002/0025550 A1 | 2/2002 | Canfield |
| 2003/0148460 A1 | 8/2003 | Canfield |
| 2004/0063639 A1 | 4/2004 | Gentz et al. |
| 2004/0202666 A1 | 10/2004 | Griffiths |
| 2004/0204379 A1 | 10/2004 | Cheng et al. |
| 2006/0008415 A1 | 1/2006 | Kaisheva et al. |
| 2006/0194256 A1 | 8/2006 | Miao et al. |
| 2007/0031945 A1 | 2/2007 | Daniel |
| 2007/0197439 A1 | 8/2007 | Zhu et al. |
| 2007/0280925 A1 | 12/2007 | Meeker et al. |
| 2008/0003626 A1 | 1/2008 | White et al. |
| 2011/0027254 A1* | 2/2011 | Daniel et al. ............ 424/94.61 |

FOREIGN PATENT DOCUMENTS

| | | |
|---|---|---|
| CN | 1335505 A | 2/2002 |
| ES | 2391657 | 11/2012 |
| ES | 2391657 T3 | 11/2012 |
| JP | 07-313183 | 12/1995 |
| JP | 07-313183 A | 12/1995 |
| JP | H10500570 A | 1/1998 |
| JP | 10-273500 | 10/1998 |
| JP | 10-273500 A | 10/1998 |
| JP | 10-306099 | 11/1998 |
| JP | 10-306099 A | 11/1998 |
| JP | H 11-318441 A | 11/1999 |
| JP | 2003505430 A | 2/2003 |
| JP | 3-503721 B2 | 3/2004 |
| JP | 5364362 B2 | 12/2013 |
| JP | 5683407 B2 | 3/2015 |

(Continued)

OTHER PUBLICATIONS

Palamarczyk et al., "1,4-Dideoxy-1,4-imino . . . ," Archives of Biochemistry and Biophysics, 243(1):35-45 (1985).
Passot et al. "Physical characterization of formulations for the development of two stable freeze-dried proteins during both dried and liquid storage" European Journal of Pharmaceutics and Biopharmaceutics, 60(3):335-348, (2005).
Pastores et al. "Thereapreutic Goals in the Treatment of Gaucher Disease" Seminars in Hematology 41 (suppl5):4-14 (2004).

(Continued)

*Primary Examiner* — Bin Shen
(74) *Attorney, Agent, or Firm* — Troutman Sanders LLP

(57) ABSTRACT

Methods and compositions for treating Gaucher disease are described.

16 Claims, 28 Drawing Sheets

(56) References Cited

FOREIGN PATENT DOCUMENTS

| WO | 9007573 A1 | 7/1990 |
| --- | --- | --- |
| WO | 9213067 A1 | 8/1992 |
| WO | 9412628 A1 | 6/1994 |
| WO | 9413311 A1 | 6/1994 |
| WO | 9414837 A1 | 7/1994 |
| WO | 9732591 A1 | 9/1997 |
| WO | 98/02161 A1 | 1/1998 |
| WO | 98/11206 A2 | 3/1998 |
| WO | 9822136 A2 | 5/1998 |
| WO | 9940206 A1 | 8/1999 |
| WO | 9951724 A1 | 10/1999 |
| WO | 9957325 A2 | 11/1999 |
| WO | 9961592 A1 | 12/1999 |
| WO | 9964587 A1 | 12/1999 |
| WO | 0034490 A1 | 6/2000 |
| WO | 00/76480 A2 | 12/2000 |
| WO | 01/07078 A1 | 2/2001 |
| WO | 01/19955 A2 | 3/2001 |
| WO | 0149830 A2 | 7/2001 |
| WO | 2004069190 A2 | 8/2004 |
| WO | 2011017177 A1 | 2/2011 |
| WO | 2011107992 A2 | 9/2011 |
| WO | 2012012461 A2 | 1/2012 |

OTHER PUBLICATIONS

Peterson et al., "Comparison of in vitro cellular uptake at velaglucerase alfa to that of imiclucerase" Department of Research and Development, Shire Genetic Therapies, P34 (presented at the 9th annual EWGGD, Cologne, Germany) (2010).

Reinke et al., "Efficacy and Tolerability of Velaglucerase Alfa in Treatment of 7 patients with Type I Gaucher Disease—First Observations"Children's Hospital, Gutenberg-University of Mainz, P38 (presented at the 9th annual EWGGD, Cologne, Germany) (2010).

Richards et al. "Antibody Response in Patients with Gaucher Disease After Repeated Infusion with Macrophage-Targeted Glucocerebrosidese" Blood, vol. 82, No. 5, pp. 1402-1409, (1993).

Rosenberg et al., "Immunosurveillance of alglucerase enzyme therapy for Gaucher patients: Induction of humoral tolerance in seroconverted patients after repeat administration"; Blood, vol. 93, pp. 2081-2088 (1999).

Rudd et al., "Diversification of the . . . ," Molecular Immunology, 28(12):1369-1378, (1991).

Sato et al., "Binding, Internalization, and . . . ," J. Clin. Invest., 91:1909-1917, (1993).

Schutzbach et al. "Calcium Ion Activation of Rabbit Liver .alpha.1, 2-Mannosidase" J. Biol. Chem. 265(5)2546-2549 (1990).

Shah et al. Biochemistry,vol. 42, pp. 13612-13816 (2003).

Shire Human Genetic Therapies. Study of GA-GCB Enzyme Replacement Therapy in Type 1 Gaucher Disease Patients Previously Treated with Imiglucerase Clinicaltrials.gove (2008).

Starzyk et al. "The long-term international safety experience of imiglucerase therapy for Gaucher disease" Molecular Genetics and Metabolism 90:157-163, (2007).

Takahashi et al. "Enzyme therapy in Gaucher disease type 2: an autopsy case," Tohoku J. Exp. Med., 186:143-149, (1998).

Takasaki et al., "Structure of the . . . ," The Journal of Biological Chemistry, 259(16):10112-10117, (1984).

Tremblay et al., "Characterization of a . . . ," The Journal of Biological Chemistry, 275(41):31655-31660, (2000).

Tropea et al., "Mannostatin A, a New . . . ," Biochemistry, 29(43):10062-10069, (1990).

Tsitsimpikou et al. "Studies of the effect of organic solvents on the stability of beta-glucosidase from Fusanum oxysporum", Biotechnology Letters 16(1):57-62 (1994).

Tulsiani et al., "Swainsonine Inhibits . . . ," The Journal of Biological Chemistry, 257(14):7936-7939, (1982).

Van Weely, et al. "Function of oligosaccharide modification in glucocerebrosidase, a membrane?associated lysosomal hydrolase"., EUR. J. Biochem. 191, 669-677 (1990).

Wadhwa et al., "Strategies for detection, measurement and characterization of unwanted antibodies induced by therapeutic biologicals" Journal of Immun. vol. 278, No. 1-2, pp. 1-17 (2003).

Waldmann, "Immunotherapy past, present and future" Nature Medicine 9:269-277, (2003).

Wang et al., "Neutralizing antibodies to therapeutic enzymes: considerations fro testing, prevention and treatment" Nature Biotechnology, vol. 26, No. 8 pp. 901-906 (2008).

Wang, "Lyophilization and development of solid protein pharmaceuticals" International Journal of Pharmaceutics, 203(1-2):1-60, (2000).

Weng et al., "Demonstration That a . . . ," The Journal of Biological Chemistry, 268(34):25656-25663, (1993).

Wenhui Xiao et al., "Effectiveness of enzyme replacement therapy to patients with Gaucher Disease," China Chold Blood, 2004, vol. 9, No. 5. pp. 197-200.

Winchester et al., "The strucutural basis . . . ," Biochem. J., 290:743-749, (1993).

Written Opinion dated Aug. 12, 2008 which issued during prosecution of International Application No. PCT/US2007/061657.

Wustman et al. "Pharmacological chaperone therapy for Gaucher disease: Mechansim of action, a survey of responsive mutations and phase I clinical trial results." Molecular Genetics and Metabolism vol. 93 pp. S14-S46 (2008).

Zimran et al. "A pharmacokinetic analysis of a novel enzyme replacement therapy with Gene-Activated human glucocerebrosdiase (GA-GCB) in patients with type I Gaucher diease." Blood Cells, Molecules, and Diseases vol. 39 pp. 115-118 (2007).

Zimran et al. "Home treatment with intravenous enzyme replacement therapy for Gaucher disease: an international collaborative study of 33 patients" Blood 82(4):1107-1109, (1993).

Zimran et al., The Lancet 345:451-452, (1995).

Aerts et al., "Efficient Routing of Glucocerebrosidase . . . ," Biochemical and Biophysical Research Communications, 141(2):452-458, (1986).

Ahrens, "Role of Target Cell . . . ," The Journal of Biological Chemistry, 268(1):385-391, (1993).

Andersson et al. "Stabilizing effect of chemical additives against oxidation of lactate dehydrogenase" Biotechno. Appl. Biochem. 32: 145-153, (2000).

Barton et al., "Therapeutic Response to Intravenous Infusions . . . ", Proc.Natl.Acad.Sci.USA, vol. 87,1913-1916, Mar. 1990.

Berg-Fussman et al., "Human Acid . . . ," The Journal of Biological Chemistry, 268(20):14861-14866, (1993).

Bernier et al. "Stabilization of beta-glucosidase by polyhydric alcohols", Journal of Biotechnology 7(4):293-298, (1988).

Beutler et al. Genomics, vol. 12, No. 4, pp. 795-800 (1992).

Beutler et al., "Failure of Alglucerase Infused into Gaucher Disease Patients to Localize in Marrow Macrophages", Molecular Medicine, vol. 1, No. 3, pp. 320-324 (1995).

Bijsterbosch et al., "Quantitative analysis of . . . ," Eur. J. Biochem., 237:344-349, (1996).

Bischoff et al. "The effect of 1-deoxymannojirimycin on rat liver .alpha.-mannosidases" Biochem. Biophys. Res. Commun. 125(1):324-331 (1984).

Brumshtein et al., Glycobiology 20(1):24-32, (2009).

Burton et al., "Hydrophobic charge induction chromatography; salt independent protein absorption and facile elution whit aqueous buffers" Journal of Chromatography, vol. 814, pp. 71-81 (1998).

Chotai et al., "The Uptake of Swainsonine . . . ," Journal of Cellular Biochemistry, 21:107-117, (1983).

Cleland et al. "A Specific Molar Ratio of Stabilizer to Protein in Required for Storage Stability of a Lyophilized Monoclonal Antibody", Journal of Pharmaceutical Sciences, 90(3):310-321, (2001).

Clinial Trial NCT00478647 Summary, <<http://clinicaltrials.gov/archive/NCT00478647/2008_08_03>>, Last accessed Oct. 16, 2013.

Cumming, "Glycosylation of recombinant . . . ," Glycobiology, 1(2):115-130, (1991).

(56) References Cited

OTHER PUBLICATIONS

Daniel et al., "Effects of the . . . ," Glycoconjugate, 6:229-240, (1989).
Daniel et al., "Mammalian .alpha.-mannosidases . . . ," glycobiology, 4(5):551-566, (1994).
Database EMBL [online] "H.sapriens mRNA for macrophage mannose receptor" retrieved from EPI accession No. EM_STD:X55635 database accession No. X55635. Apr. 15, 1992.
Dulsat et al., "Gaucher's disease", Drugs of the Future, Prous Science, ES, vol. 34, No. 2, pp. 147-149, (2009).
Elbein et al., "Kifunensine Inhibits . . . ," Archives of Biochemistry and Biophysics, 288(1):177-184, (1991).
Elbein et al., "Kifunensine, a Potent . . . ," The Journal of Biolgcal Chemistry, 265(26):15599-15605, (1990).
Elbein, A., The FASEB Journal 5:3055-3063, (1991).
Erickson et al., "Biosynthesis of the . . . ," The Journal of Biological Chemisry, 260(26)14319-14324, (1985).
European Search Report dated Oct. 29, 2014, which issued during prosecution of European Application No. 14170682.0.
Extended European Search Report dated Jul. 25, 2011, which issued during prosecution of European Application No. 10193725.8.
Extended European Search Report dated Apr. 29, 2011 which issued during prosecution of EP Application Serial No. 10182992.7.
Extended European Search Report dated Mar. 27, 2013 which issued during prosecution of EP Application Serial No. 10806936.
Extended European Search Report dated Jan. 31, 2014 which issued during prosecution of EP Applicatin Serial No. 11810304.3 dated.
Fleet et al., "Design Synthesis and . . . ," J. Chem. Soc., Chem. Commun., 1240-1241, (1984).
Friedman et al., "A Comparison of . . . ,"Blood, 93:2807-2816, (1999).
Furbish et al., "Uptake and Distribution of Placental Glucocerebrosidase . . . ", Biochimica et Biophysica Acta, vol. 673; 425-434 (1981).
Furbish et al.: Enzyme replacement therapy in Gaucher's disease, Large-scale purification of glucocerebrosidase suitable for human administration (hydrophobic; chromatography/cholate extraction/jt-glucosidae/concanavalin A) Medical Sciences, Jan. 1, 1977 (Jan. 1, 1977), pp. 3560-3653.
Genzyme Corporation. "Cerezyme (imiglucerase) Injection, Powder, Lyophilized, for Solution." DailyMed Archived Drug Labels (online); Feb. 1, 2006, p. 1-6. Retrieved on Nov. 11, 2010.
Giraldo et al., "Safety with Velaglucerasein Two Girls Previously Treated with Imiglucerase" Spanish Gaucher Disease Foundation, P20 (presentes at the 9th annual EWGGD, Cologne, Germany) (2010).
Gonzalez et al., J. Biol. Chem. 274(30):21375-21386 (1999).
Grabowski et al., "Enzyme Thearpy in Type 1 Gaucher Disease: Comparative Efficacy of Mannose-terminated Glucocerebrosidase from Natural and Recombinant Sources", Annals of Internal Medicine, vol. 122, No. 1, pp. 33-39 (1995).
Guerrier et al., "New method for the selective capture of antibodies under physiological conditions" Bioseparation, vol. 9, pp. 211-221 (2000).
International Preliminary Report on Patentability and Written Opinion from corresponding International Application Serial No. PCT/US2010/043586 dated Nov. 22, 2010.
International Preliminary Report on Patentability dated Aug. 12, 2008 which issued during International Application No. PCT/US2007/061657.
International Search Report dated Jan. 3, 2002, which issued during prosecution of International Application No. PCT/US01/25882.
Kishnani et al. "A randomized trial comparing the efficacy and safety of imiglucerase (Cerezyme) infusions every 4 weeks versus every 2 weeks in the maintenance therapy of adult patients with Gaucher disease type 1." Mol Genet Metab, 96(4):164-170, (2009).
Lee et al. "The Stabilization of Proteins by Sucrose", The Journal of Biologlcal Chemistry, 256(14):7193-7201, (1981).
Marcus et al., "Glucosidase and Mannosidase . . . ," The Journal of Biological Chemistry, 275(3):1987-1992, (2000).

Martin et al., "Glycosylation and Processing of High Levels of . . . ", DNA, vol. 7, No. 2; 99-106 (1988).
Miroliaei et al. "Sugars protect native and apo yeast alcohol dehydrogenase against irreversible thermoinactivation" Enzyme and Microbial Technology, 29(8-9); 54-559, (2001).
Mistry et al., "Therapeutic delivery of proteins to macrophages: implications for treatment of Gaucher's disease", The Lancet, vol. 348, No. 9041, pp. 1555-1559 (1996).
Moremen et al., "Glycosidases of the . . . ," Glycobiology, 4(2):113-125, (1994).
Murray et al: "Purification of beta-glucocerebrosidaes by preparative-scale high-performance liquid chromatography: The use of ethylene glycol-containing buffers for chromatography of hydrophobic glycoprotein enzymes", Analytical Biochemistry 147(2):301-310, (1985).
Nguyen et al., "Oxidation Degradation of Protein Pharmaceuticals" ACS Symp. Ser., No. 567, pp. 59-71, (1994).
Aviezer et al., "A Plant-Derived Recombinant Human Glucocerebrosidase Enzyme-A Preclinical and Phase I Investigation", PLoS One, vol. 4, Mar. 2009.
Kraoua et al., "A French experience of type 3 Gaucher disease: Phenotypic diversity and nuerological outcome of 10 patients", Brian and Development, Amsterdam NL, vol. 33, No. 2, (131-139) Feb. 2010.
Zang Yan et al., "14 Case report of enzyme replacement therapy to patients with Gaucher Disease" Chinese Journal of Pediatrics, vol. 39, Issue 8, (2001).
Elbein et al., "Kifunensine, a potent inhibitor of the glycoprotein processing mannosidase I" The Journal of Biological Chemistery, vol. 265, No. 26, Issue of Sep. 15, pp. 15599-15605, 1990.
Van Patten et al., "Effect of mannose chain length on targeting of glucocerebrosidase for enzyme replacement therapy of Gaucher disease" Glycobiology, vol. 17, No. 5, pp. 467-478, 2007.
Tekoah et al., "Glycosylation and functionality of recombinant β-glycocerebrosidase from various production systems" Biosci. Rep., pp. 771-783.
Brady, et al., "Management of Neutralizing Antibody to Ceredadse in a Patient with Type 3 Gaucher Disease", Pediatrics 100(6): 1-4, 1997.
European Extended Search Report, dated Oct. 20, 2015 issued in corresponding European Patent Application No. 13755466.3.
Japanese Office Action, dated Oct. 27, 2015 issued in corresponding Japanese Patent Application No. 2014-209206.
Japanese Office Action, dated Feb. 9, 2016 issued in corresponding Japanese Patent Application No. 2015-045704.
Zhao, et al., "Enzyme therapy of Gaucher disease: clinical and biochemical changes during production of and tolerization for neutralizing antibodies", Blood Cells, Molecules, and Diseases 30: 90-96, 2003.
Shire Limited Supplement Prospectus Investor, "Supplement to the Prospectus in respect of Introduction of up to 700,000,000 Ordinary Shares of 5 pence each to the Official List", Apr. 29, 2009.
Fink, et al., "Correction of glucocerebrosidase deficiency after retroviral-mediated gene transfer into hematopoietic progenitor cells from patients with Gaucher disease", PNAS 87: 2334-2338, 1990.
Havenga, et al., "Development of safe and efficient retroviral vectors for Gaucher disease," Gene Therapy 4: 1393-1400, 1997.
Japanese Office Action, dated Sep. 20, 2016, issued in corresponding Japanese Patent Appln. 2014-209206.
"Genzyme General Clarifies Position in Gaucher's Disease Market", URL: http://biz.yahoo.com/prnews/980623/ma_genzyme_2.html, Jun. 24, 1998.
Huxtable, et al., AJP 107(1): 124-126, 1982.
Lee, et al., "Position of the sulfhydryl group and the disulfide bonds of human glucocerebrosidase," J. Protein Chemistry 14(3): 127-137, 1995.
Stinchi, et al., "Targeted disruption of the lysosomal alpha-mannosidase gene results in mice resembling a mild form of human alpha-mannosidosis," Human Molecular Genetics 8(8): 1365-1372, 1999.

(56) References Cited

OTHER PUBLICATIONS

Sun, et al., "Saposin C is required for normal resistance of acid beta-gluocisidase to proteolytic degradation," J. Biol. Chem. 278(34): 31918-31923, 2003.
Bembi, et al., "Enzyme Replacement Treatment in Type 1 and Type 3 Gaucher's Disease", The Lancet 344: 1679-1682 (1994).
Gomati, et al., "Total Glycolipid and Glucosylceramide Content in Serum and Urine of Patients with Gaucher's Disease Type 3 Before and After Enzyme Replacement Therapy", Clinica Chimica Acta 271(2): 151-161 (1998).
Japanese Office Action, dated Nov. 22, 2016, issued in corresponding Japanese Patent Appln. No. 2014-560086.
Sellos-Moura, et al., "Development of a Panel of Highly Sensitive, Equivalent Assays for Detection of Antibody Responses to Velaglucerase Alfa or Imiglucerase Enzyme Replacement Therapy in Patients with Gaucher Disease", Journal of Immunological Methods 373(1-2): 45-53 (2011).
Weinreb N. J., "Imiglucerase and its use for the treatment of Gaucher's disease" Expert Opinion on Pharmacotherapy 200808 GB, vol. 9, No. 11, Aug. 2008, pp. 1987-2000, ISSN: 1465-6566.
EPO Office Action issued Feb. 9, 2017 in connection with EP Application No. 13755466.3.

\* cited by examiner

COMPOSITIONS AND METHODS FOR TREATING TYPE III GAUCHER DISEASE

CROSS REFERENCE TO RELATED APPLICATIONS

This application claims priority under 35 U.S.C. §371 to International Application No. PCT/US2013/028608, filed Mar. 1, 2013, which claims priority to U.S. Application Ser. No. 61/606,089, filed on Mar. 2, 2012. The disclosures of the prior applications are considered part of (and are incorporated by reference in) the disclosure of this application.

BACKGROUND

Gaucher disease is an autosomal recessive lysosomal storage disorder characterized by a deficiency in the lysosomal enzyme, glucocerebrosidase (GCB). GCB hydrolyzes the glycolipid glucocerebroside that is formed after degradation of glycosphingolipids in the membranes of white blood cells and red blood cells. The deficiency in this enzyme causes glucocerebroside to accumulate in large quantities in the lysosomes of phagocytic cells located in the liver, spleen and bone marrow of Gaucher patients. Accumulation of these molecules causes a range of clinical manifestations including splenomegaly, hepatomegaly, skeletal disorder, thrombocytopenia and anemia. (Beutler et al. Gaucher disease; In: The Metabolic and Molecular Bases of Inherited Disease (McGraw-Hill, Inc, New York, 1995) pp. 2625-2639)

Treatments for patients suffering from this disease include administration of analgesics for relief of bone pain, blood and platelet transfusions and, in some cases, splenectomy. Joint replacement is sometimes necessary for patients who experience bone erosion.

Enzyme replacement therapy with GCB has been used as a treatment for Gaucher disease. Current treatment of patients with Gaucher disease includes administration of a carbohydrate remodeled GCB derived from human placenta or Chinese hamster ovary (CHO) cells transfected with a GCB expression construct and known as alglucerase or imiglucerase, respectively.

SUMMARY

The disclosure is based, in part, on the discovery that velaglucerase elicits less of an immune response (e.g., less production of antibody, e.g., less production of neutralizing antibody) than imiglucerase upon administration to a subject (e.g., a subject with Type III Gaucher disease). The invention relates, inter alia, to compositions and methods for selecting a treatment for a subject with Type III Gaucher disease, selecting subjects for treatment with velaglucerase (e.g., alone or in combination with another therapy), methods for reducing injection site reaction in subjects undergoing treatment for Type III Gaucher disease, and methods of treating Type III Gaucher disease. The invention also relates, inter alia, to methods of determining antibody production, e.g., neutralizing antibody production, in a subject being treated for Type III Gaucher disease. The present disclosure is at least in part on the presmise that a glucocerebrosidase enzyme replacement therapy (e.g., velaglucerase, imiglucerase, or uplyso), will be able to cross the blood-brain barrier and thus can be used to treat, or prevent, or prevent progression of a neurological parameter or a neurological symptom, e.g., a neurological parameter or a neurological symptom associated with Type III Gaucher disease.

In some aspects, the disclosure features a method of treating a subject with Type III Gaucher disease, the method comprising administering a glucocerebrosidase enzyme replacement therapy (e.g., velaglucerase, imiglucerase, or uplyso) by intravenous infusion to the subject over a period of less than 2 hours, e.g., 90 minutes, 80 minutes, 70 minutes, 60 minutes, 50 minutes or 45 minutes, to thereby treat the subject.

In some embodiments, the glucocerebrosidase enzyme replacement therapy (e.g., velaglucerase, imiglucerase, uplyso) is administered more than once and each additional dose of the glucocerebrosidase enzyme replacement therapy (e.g., velaglucerase, imiglucerase, or uplyso) is administered by intravenous administration over a period of less than 2 hours, e.g., 90 minutes, 80 minutes, 70 minutes, 60 minutes, 50 minutes or 45 minutes), to the subject.

In some embodiments, the glucocerebrosidase enzyme replacement therapy (e.g., velaglucerase, imiglucerase, uplyso) is administered at a dose of 15 to 60 U/kg (e.g., 30 U/kg to 60 U/kg, e.g., 15 U/kg, 30 U/kg, 45 U/kg, or 60 U/kg), at a dose equal to or below 22.5 U/kg, at a dose between 22.5 and 37.5 U/kg, at a dose between 37.5 and 52.5 U/kg, or at a dose equal to or above 52.5 U/kg. In some embodiments, glucocerebrosidase enzyme replacement therapy (e.g., velaglucerase, imiglucerase, uplyso) is administered at a dose of 2.5 U/kg to 60 U/kg. In some embodiments, the glucocerebrosidase enzyme replacement therapy (e.g., velaglucerase, imiglucerase, uplyso) is administered every other week. In other embodiments, the glucocerebrosidase enzyme replacement therapy (e.g., velaglucerase, imiglucerase, uplyso) is administered every week. In some embodiments, the velaglucerase is administered three times a week by intravenous infusion, e.g., at a dose of 2.5 U/kg.

In some embodiments, the infusion of one or more dose (e.g., a dose described herein) occurs over 60 minutes.

In some embodiments, the glucocerebrosidase enzyme replacement therapy is velaglucerase and the method includes:

reconstituting lyophilized velaglucerase with a pharmaceutically acceptable carrier such as Sterile Water for Injection (e.g., reconstituting a 200 unit vial with 2.2 mL of Sterile Water for Injection or a 400 unit vial with 4.3 mL Sterile Water for Injection), thereby forming a solution, e.g., wherein the vial is not shaken after addition of the Sterile Water for Injection; optionally, inspecting the solution in the vials (and, e.g., optionally determining if the solution is discolored or if particulate matter is present, and optionally deciding not to use the solution if the solution is discolored or if particulate matter is present);

withdrawing a volume of solution to provide a preselected dose (e.g., a dose described herein such as 15 U/kg, 30 U/kg, 45 U/kg, or 60 U/kg);

diluting the volume, e.g., in 100 mL of 0.9% sodium chloride solution suitable for intravenous administration, thereby forming a diluted solution; optionally rocking the diluted solution gently, but do not shaking the diluted solution; and administering the diluted solution to the subject by intravenous infusion, e.g., wherein the diluted solution is administered over one hour or at a rate of 1 U/kg/minute.

In some embodiments, the glucocerebrosidase enzyme replacement therapy is administered at an infusion rate of 2 U/kg/minute, 1.5 U/kg/minute, 1 U/kg/minute, or 0.5 U/kg/minute.

In some embodiments, the administering comprises home therapy (e.g., in the subject's home, workplace, or other non-clinical (e.g., non-hospital) setting). In some embodiments, the administering (e.g., via infusion) is by a health care professional (e.g., nurse or physician's assistant). For example, if the subject has not experienced an adverse event (AE) (e.g., a drug-related serious AE or an infusion-related AE, e.g., an event described herein), e.g., after one, two, or three administrations (e.g., via infusion) of the glucocerebrosidase enzyme replacement therapy, the subject is eligible to receive home therapy for subsequent administrations.

In another aspect, the disclosure provides a method for identifying a subject as suitable for (e.g., being a candidate for) treatment with glucocerebrosidase enzyme replacement therapy (e.g., velaglucerase). The method includes evaluating (e.g., measuring, e.g., by a method described herein such as ELISA or radioimmunoprecipitation assay (RIP)), for the presence of antibodies (e.g., neutralizing antibodies) (e.g., IgE, IgM, IgG and/or IgA antibodies) to a glucocerebrosidase enzyme replacement therapy (e.g., to the therapy currently being administered to the subject) (e.g., imiglucerase or uplyso) in a sample from the subject, e.g., and comparing the measured value of antibody to the therapy to a standard (e.g., a negative control). For example, if the subject has measured antibody values that are greater than the value measured for the negative control (e.g., a negative control in an ELISA), the subject is identified as having antibodies to the glucocerebrosidase enzyme replacement therapy. The subject is optionally identified as suitable for treatment with an alternative Type III Gaucher disease treatment (e.g., treatment with velaglucerase), e.g., if the measured value is greater than the value for the standard, e.g., by more than 5%, 10%, 15%, 20%, 25%, 30%, 35%, 40%, 45%, 50%, 55%, 60%, 65%, 70%, 75%, 80%, 85%, or 90%.

In some embodiments, the sample is a blood or serum sample. In some embodiments, the sample has been modified. For example, the measured antibody values were obtained by contacting the sample with an analytical reagent, e.g., a labeled reagent (e.g., labeled glucocerebrosidase), and/or a substrate or cell, e.g., a substrate or cell that binds to an antibody to the glucocerebrosidase enzyme replacement therapy. In some embodiments, the measured antibody values were obtained from a sample that has been enriched for antibodies, e.g., a concentrated portion of a blood or serum sample. In some embodiments, the evaluation was obtained by a method described herein.

In some embodiments, the method includes measuring the measured antibody value, e.g., by a method described herein.

In another aspect, the disclosure provides a method for selecting a subject with Type III Gaucher disease for treatment with a glucocerebrosidase enzyme replacement therapy. Optionally, the method includes selecting a subject for such treatment on the basis that the subject has tested positive for the production of antibodies (e.g., neutralizing antibodies) to the treatment the subject is currently taking for Type III Gaucher disease. The method includes evaluating (e.g., measuring, e.g., by a method described herein such as ELISA or radioimmunoprecipitation assay (RIP)) or obtaining an evaluation of the presence of antibodies to a glucocerebrosidase enzyme replacement therapy (e.g., to the therapy currently being administered to the subject) (e.g., imiglucerase or uplyso) in a sample from the subject, e.g., and comparing the measured value of antibody to the therapy to a standard (e.g., a negative control). For example, if the subject has measured antibody values that are greater than the value measured for the negative control (e.g., negative control in an ELISA), the subject is identified as having antibodies to the glucocerebrosidase enzyme replacement therapy. The methods optionally include, selecting an alternative Type III Gaucher disease treatment for the subject (e.g., treatment with velaglucerase), e.g., if the measured value is greater than the value for the standard (e.g., negative control), e.g., by more than 5%, 10%, 15%, 20%, 25%, 30%, 35%, 40%, 45%, 50%, 55%, 60%, 65%, 70%, 75%, 80%, 85%, or 90%.

In some embodiments, the sample is a blood or serum sample. In some embodiments, the sample has been modified. For example, the measured antibody values were obtained by contacting the sample with an analytical reagent, e.g., a labeled reagent (e.g., labeled glucocerebrosidase), and/or a substrate or cell, e.g., a substrate or cell that binds to an antibody to the glucocerebrosidase enzyme replacement therapy. In some embodiments, the measured antibody values were obtained from a sample that has been enriched for antibodies, e.g., a concentrated portion of a blood or serum sample. In some embodiments, the evaluation was obtained by a method described herein.

In some embodiments, the method includes measuring the antibody value, e.g., by a method described herein.

In some embodiments, the subject tested positive for the production of IgE antibodies to the treatment the subject is currently taking for Type III Gaucher disease (e.g., imiglucerase or uplyso).

In some embodiments, the subject tested positive for the production of IgM antibodies to the treatment the subject is currently taking for Type III Gaucher disease (e.g., imiglucerase or uplyso).

In some embodiments, the subject tested positive for the production of IgG and/or IgA antibodies to the treatment the subject is currently taking for Type III Gaucher disease (e.g., imiglucerase or uplyso).

In another aspect, the disclosure provides a method for treating a subject with Type III Gaucher disease. The method includes selecting a subject on the basis that the subject has tested positive for the production of antibodies (e.g., neutralizing antibodies) to the treatment the subject is currently taking for Type III Gaucher disease, e.g., by a method described herein, or on the basis that the subject is at risk for developing antibodies (e.g., neutralizing antibodies) to a treatment for Type III Gaucher disease (e.g., imiglucerase or uplyso) and administering velaglucerase to the subject.

In some embodiments, the subject tested positive for the production of IgE antibodies to the treatment the subject is currently taking for Type III Gaucher disease (e.g., imiglucerase or uplyso).

In some embodiments, the subject tested positive for the production of IgM antibodies to the treatment the subject is currently taking for Type III Gaucher disease (e.g., imiglucerase or uplyso).

In some embodiments, the subject tested positive for the production of IgG and/or IgA antibodies to the treatment the subject is currently taking for Type III Gaucher disease (e.g., imiglucerase or uplyso).

In some embodiments, velaglucerase is administered at a dose of 15 to 60 U/kg (e.g. 30 U/kg to 60 U/kg, e.g., 15 U/kg, 30 U/kg, 45 U/kg, or 60 U/kg), at a dose equal to or below 22.5 U/kg, at a dose between 22.5 and 37.5 U/kg, at a dose between 37.5 and 52.5 U/kg, or at a dose equal to or above 52.5 U/kg. In some embodiments, velaglucerase is administered at a dose of 2.5 U/kg to 60 U/kg. In some embodiments, the velaglucerase is administered every other week by intravenous infusion. In other embodiments, the velaglucerase is administered every week by intravenous infusion.

In some embodiments, the velaglucerase is administered three times a week by intravenous infusion, e.g., at a dose of 2.5 U/kg.

In some embodiments, the infusion of the dose (e.g., a dose described herein) occurs over less than 2 hours, e.g., 90 minutes, 80 minutes, 70 minutes, 60 minutes, 50 minutes or 45 minutes. In preferred embodiments, the infusion of the dose occurs over 60 minutes.

In some embodiments, the method includes:

reconstituting lyophilized velaglucerase with a pharmaceutically acceptable carrier such as a pharmaceutically acceptable carrier such as Sterile Water for Injection (e.g., reconstituting a 200 unit vial with 2.2 mL of Sterile Water for Injection or a 400 unit vial with 4.3 mL Sterile Water for Injection), thereby forming a solution, e.g., wherein the vial is not shaken after addition of the Sterile Water for Injection; optionally, inspecting the solution in the vials (and, e.g., optionally determining if the solution is discolored or if particulate matter is present, and optionally deciding not to use the solution if the solution is discolored or if particulate matter is present);

withdrawing a volume of solution to provide a preselected dose (e.g., a dose described herein, e.g., 15 U/kg, 30 U/kg, 45 U/kg, or 60 U/kg);

diluting the volume, e.g., in 100 mL of 0.9% sodium chloride solution suitable for intravenous administration, thereby forming a diluted solution; optionally rocking the diluted solution gently, but do not shaking the diluted solution; and administering the diluted solution to the subject by intravenous infusion.

In some embodiments, velaglucerase is administered at a rate of 2 U/kg/minute, 1.5 U/kg/minute, 1 U/kg/minute, or 0.5 U/kg/minute.

In some embodiments, the administering comprises home therapy (e.g., in the subject's home, workplace, or other non-clinical (e.g., non-hospital) setting). In some embodiments, the administering (e.g., via infusion) is by a health care professional (e.g., nurse or physician's assistant). For example, if the subject has not experienced an adverse event (AE) (e.g., a drug-related serious AE or an infusion-related AE, e.g., an event described herein), e.g., after one, two, or three administrations (e.g., via infusion) of velaglucerase, the subject is eligible to receive home therapy for subsequent administrations.

In another aspect, the disclosure provides a method for identifying a subject as suitable for (e.g., being a candidate for) treatment with glucocerebrosidase enzyme replacement therapy (e.g., velaglucerase). The method includes evaluating (e.g., measuring) the subject for the presence of infusion site reaction (i.e., infusion-related adverse event) (e.g., during or within 12 hours of infusion of glucocerebrosidase enzyme replacement therapy) (e.g., to the therapy currently being administered to the subject, e.g., imiglucerase or uplyso), e.g., and comparing the measured level of the site reaction to a standard (e.g., a negative control). For example, if the subject has a measured value of site reaction to the treatment the subject is currently taking for Type III Gaucher disease that is greater than the value measured for the negative control (e.g., the site reaction observed after placebo infusion in the subject), the subject is identified as suitable for treatment with an alternative Type III Gaucher disease treatment (e.g., treatment with velaglucerase), e.g., if the measured value of site reaction to the treatment the subject is currently taking for Type III Gaucher disease is greater than the value for the standard, e.g., by more than 5%, 10%, 15%, 20%, 25%, 30%, 35%, 40%, 45%, 50%, 55%, 60%, 65%, 70%, 75%, 80%, 85%, or 90%.

In some embodiments, the method includes determining the infusion site value, e.g., by a method described herein.

In another aspect, the disclosure provides a method for selecting a subject with Type III Gaucher disease for treatment with glucocerebrosidase enzyme replacement therapy. Optionally, the method includes selecting a subject for such treatment on the basis that the subject is in need of reduced infusion site reaction (e.g., reduced as compared to the reaction associated with or caused by the treatment the subject is currently taking for Type III Gaucher disease, e.g., imiglucerase or uplyso). The method includes evaluating (e.g., measuring) or obtaining an evaluation of the subject for the presence of infusion site reaction (i.e., infusion-related adverse event) (e.g., during or within 12 hours of infusion of glucocerebrosidase enzyme replacement therapy) (e.g., to the therapy currently being administered to the subject, e.g., imiglucerase or uplyso), e.g., and comparing the measured level of the site reaction to a standard (e.g., a negative control). For example, if the subject has a measured value of site reaction to the treatment the subject is currently taking for Type III Gaucher disease that is greater than (e.g., greater by more than 5%, 10%, 15%, 20%, 25%, 30%, 35%, 40%, 45%, 50%, 55%, 60%, 65%, 70%, 75%, 80%, 85%, or 90%) the value measured for the negative control (e.g., the site reaction observed after placebo infusion in the subject), the subject is selected for an alternative Type III Gaucher disease treatment (e.g., treatment with velaglucerase), e.g., if the measured value of site reaction to the treatment the subject is currently taking for Type III Gaucher disease is greater than the value for the standard (e.g., negative control), e.g., by more than 5%, 10%, 15%, 20%, 25%, 30%, 35%, 40%, 45%, 50%, 55%, 60%, 65%, 70%, 75%, 80%, 85%, or 90%.

In some embodiments, the method includes measuring the antibody value, e.g., by a method described herein.

In another aspect, the disclosure provides a method for treating a subject with Type III Gaucher disease. The method includes selecting a subject for such treatment on the basis that the subject is in need of reduced infusion site reaction (e.g., reduced as compared to the reaction associated with or caused by the treatment the subject is currently taking for Type III Gaucher disease, e.g., imiglucerase or uplyso), e.g., by a method described herein, and administering velaglucerase to the subject.

In some embodiments, velaglucerase is administered at a dose of 15 to 60 U/kg (e.g. 30 U/kg to 60 U/kg, e.g., 15 U/kg, 30 U/kg, 45 U/kg, or 60 U/kg), at a dose equal to or below 22.5 U/kg, at a dose between 22.5 and 37.5 U/kg, at a dose between 37.5 and 52.5 U/kg, or at a dose equal to or above 52.5 U/kg. In some embodiments, velaglucerase is administered at a dose of 2.5 U/kg to 60 U/kg. In some embodiments, the velaglucerase is administered every other week by intravenous infusion. In other embodiments, the velaglucerase is administered every week by intravenous infusion. In some embodiments, the velaglucerase is administered three times a week by intravenous infusion, e.g., at a dose of 2.5 U/kg.

In some embodiments, the infusion of the dose (e.g., a dose described herein) occurs over less than 2 hours, e.g., 90 minutes, 80 minutes, 70 minutes, 60 minutes, 50 minutes or 45 minutes.

In some embodiments, the method includes:

reconstituting lyophilized velaglucerase with a pharmaceutically acceptable carrier, e.g., Sterile Water for Injection (e.g., reconstituting a 200 unit vial with 2.2 mL of Sterile Water for Injection or a 400 unit vial with 4.3 mL Sterile Water for Injection), thereby forming a solution, e.g., wherein the vial is not shaken after addition of the Sterile Water for Injection; optionally, inspecting the solution in the vials (and, e.g., optionally determining if the solution is discolored or if particulate matter is present, and optionally deciding not to use the solution if the solution is discolored or if particulate matter is present);

withdrawing a volume of solution to provide a preselected dose (e.g., a dose described herein such as 15 U/kg, 30 U/kg, 45 U/kg, or 60 U/kg);

diluting the volume, e.g., in 100 mL of 0.9% sodium chloride solution suitable for intravenous administration, thereby forming a diluted solution; optionally rocking the diluted solution gently, but do not shaking the diluted solution; and administering the diluted solution to the subject by intravenous infusion.

In some embodiments, the velaglucerase is administered at a rate of 2.0 U/kg/minute, 1.5 U/kg/minute, 1.0 U/kg/minute, or 0.5 U/kg/minute.

In some embodiments, the administering comprises home therapy (e.g., in the subject's home, workplace, or other non-clinical (e.g., non-hospital) setting). In some embodiments, the administering (e.g., via infusion) is by a health care professional (e.g., nurse or physician's assistant). For example, if the subject has not experienced an adverse event (AE) (e.g., a drug-related serious AE or an infusion-related AE, e.g., an event described herein), e.g., after one, two, or three administrations (e.g., via infusion) of velaglucerase, the subject is eligible to receive home therapy for subsequent administrations.

In some aspects, the disclosure features a method of selecting a subject with Type III Gaucher disease for treatment with velaglucerase, the method comprising identifying a subject with Type III Gaucher disease that has received a glucocerebrosidase enzyme replacement therapy (e.g., imiglucerase or uplyso) and has a platelet count less than a standard; and selecting the subject for treatment with velaglucerase on the basis that the subject has a platelet count less than the standard.

In some embodiments, the method includes evaluating (e.g., measuring platelet count or obtaining an evaluation of platelet count of a sample from the subject, and comparing the measured value of the platelet count to the standard (e.g., negative control).

In some embodiments, the sample is a blood or serum sample. In some embodiments, the sample has been modified. In some embodiments, the measured antibody values were obtained from a sample that has been enriched for platelets, e.g., a concentrated portion of a blood sample. In some embodiments, the evaluation was obtained by a method described herein.

In some embodiments, the method includes measuring the platelet count, e.g., by a method described herein.

In some embodiments, the methods further includes administering velaglucerase to the subject, e.g., at a dose and/or dosing schedule described herein.

In some embodiments, the velaglucerase is administered by intravenous infusion over a course of less than 2 hours, e.g., 90 minutes, 80 minutes, 70 minutes, 60 minutes, 50 minutes or 45 minutes. In some embodiments, the infusion occurs at a rate of 2 U/kg/minute, 1.5 U/kg/minute, 1 U/kg per minute or 0.5 U/kg/minute.

In some embodiments, the standard is a platelet count below or equal to $80 \times 10^3$ platelets/mm$^3$. In some embodiments, the standard is based on the percentage increase in mean platelet count after 6, 9, or 12 months of treatment with the glucocerebrosidase enzyme replacement therapy. For example, a subject in which the mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) is identified for treatment with velaglucerase. As another example, a subject in which the mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) is identified for treatment with velaglucerase.

In some aspects, the disclosure features a method of treating a subject with Type III Gaucher disease, the method comprising selecting a subject with Type III Gaucher disease that has received a glucocerebrosidase enzyme replacement therapy (e.g., imiglucerase or uplyso) and has a platelet count less than a standard, e.g., a subject identified by a method described herein; and administering velaglucerase to the subject.

In some embodiments, velaglucerase is administered at a dose of 15 to 60 U/kg (e.g. 30 U/kg to 60 U/kg, e.g., 15 U/kg, 30 U/kg, 45 U/kg, or 60 U/kg), at a dose equal to or below 22.5 U/kg, at a dose between 22.5 and 37.5 U/kg, at a dose between 37.5 and 52.5 U/kg, or at a dose equal to or above 52.5 U/kg. In some embodiments, velaglucerase is administered at a dose of 2.5 U/kg to 60 U/kg. In some embodiments, the velaglucerase is administered every other week by intravenous infusion. In other embodiments, the velaglucerase is administered every week by intravenous infusion. In some embodiments, the velaglucerase is administered three times a week by intravenous infusion, e.g., at a dose of 2.5 U/kg.

In some embodiments, the infusion of the dose (e.g., a dose described herein) occurs over less than 2 hours, e.g., 90 minutes, 80 minutes, 70 minutes, 60 minutes, 50 minutes or 45 minutes.

In some embodiments, the method includes:

reconstituting lyophilized velaglucerase with a pharmaceutically acceptable carrier such as Sterile Water for Injection (e.g., reconstituting a 200 unit vial with 2.2 mL of Sterile Water for Injection or a 400 unit vial with 4.3 mL Sterile Water for Injection), thereby forming a solution, e.g., wherein the vial is not shaken after addition of the Sterile Water for Injection; optionally, inspecting the solution in the vials (and, e.g., optionally determining if the solution is discolored or if particulate matter is present, and optionally deciding not to use the solution if the solution is discolored or if particulate matter is present);

withdrawing a volume of solution to provide a preselected dose (e.g., a dose described herein such as 15 U/kg, 30 U/kg, 45 U/kg, or 60 U/kg);

diluting the volume, e.g., in 100 mL of 0.9% sodium chloride solution suitable for intravenous administration, thereby forming a diluted solution; optionally rocking the diluted solution gently, but do not shaking the diluted solution; and administering the diluted solution to the subject by intravenous infusion.

In some embodiments, the velaglucerase is administered at a rate of 2 U/kg/minute, 1.5 U/kg/minute, 1 U/kg/minute or 0.5 U/kg/minute.

In some embodiments, the administering comprises home therapy (e.g., in the subject's home, workplace, or other non-clinical (e.g., non-hospital) setting). In some embodiments, the administering (e.g., via infusion) is by a health care professional (e.g., nurse or physician's assistant). For example, if the subject has not experienced an adverse event (AE) (e.g., a drug-related serious AE or an infusion-related AE, e.g., an event described herein), e.g., after one, two, or three administrations (e.g., via infusion) of velaglucerase, the subject is eligible to receive home therapy for subsequent administrations.

In another aspect, the disclosure provides a method for evaluating a subject, e.g., a subject to whom a glucocerebrosidase enzyme replacement therapy (e.g., imiglucerase, velaglucerase or uplyso) is currently being administered. The method includes evaluating (e.g., measuring) or obtaining an evaluation of one or more (e.g., 1, 2, 3, 4, 5, 6, 7, or 8) of the following parameters of the subject:

hemoglobin concentration, platelet count, liver volume (e.g., as a percentage of total body weight), spleen volume (e.g., as a percentage of total body weight), infusion site reaction, a skeletal parameter, a neurological parameter, or presence of antibodies (e.g., neutralizing antibodies) (e.g., IgE, IgM, IgG and/or IgA antibodies) to a glucocerebrosidase enzyme replacement therapy (e.g., the mean value of one or more (e.g., 1, 2, 3, 4, 5, 6, 7, or 8) of these parameters).

The skeletal parameter can be, e.g., bone mineral density (BMD) (e.g., as measured by a change (e.g., improvement) in Z score). BMD can be evaluated e.g., by dual energy X-ray absorptiometry (DEXA). Other skeletal parameters that can be evaluated include, e.g., T-score (e.g., to determine WHO classification of normal bone, osteopenia, and osteoporosis), growth of a subject (e.g., a pediatric subject); skeletal age of a subject (e.g., a pediatric subject); and bone marrow burden (BMB) (e.g., in an adult subject).

The neurological parameter can be e.g., an eye movement parameter (e.g., abnormal eye movements, abnormal vertical saccades, abnormal horizontal saccades, slow horizontal saccades, and supranuclear opthalmoplegia). Methods of assessing eye movement parameters can include but are not limited to, e.g., general ophthalmologic assessment, and saccadic eye movement assessment (e.g., sclera search coil technique, video technique, and infrared technique). The neurological parameter can be a hearing parameter (e.g., hearing loss. Methods of assessing hearing parameters can include but are not limited to, general auditory assessment. The neurological parameter can be, e.g., abnormal brainstem auditory evoked potentials, cranial nerve palsies, seizures, progressive myoclonic seizures, tremors, EEG abnormalities, dementia, cognitive impairment, ataxia, loss of muscle coordination, and poor mobility. Methods of assessing neurological parameters can include but are not limited to, e.g., EEG, brainstem auditory evoked response (BAER), measurement of auditory evoked potentials (e.g., electrode caps), measurement of sematosensory evoked potentials (e.g., median nerve stimulation and stretch evoked methods), mental state assessment (e.g., the neuropsychological mental status exam), cranial nerve exam, motor skill assessment (e.g., Bruininks-Oseretsky test of motor proficiency, the school function assessment test, the Beery-Buktenica developmental test of visual-motor integration, the clinical observation of motor and postural skills (COMPS)), seizure assessment (e.g., neuroimaging (e.g., CT, MRI, diffusion weighted imaging), EEG, patient history, physical examination), manual dexterity and hand eye coordination testing, (e.g., Purdue Pegboard test), standardized IQ testing (e.g., Wechsler IQ scale), verbal performance full scale IQ test, Rey auditory verbal learning test, measures of attention (e.g., D2 test of attention), continuous performance test, trail making test, Benton visual retention test, measures of memory (e.g., Wechsler Memory Scale-Revised, presentation of stimuli to later be recalled, California Verbal Learning Test, Rey Auditory Verbal Learning Test, selective reminding test, Benton Test of Visual Retention-Revised, Memory for Designs Test, Rey-O Complex Figure), assessment of cognitive function (e.g., Wechsler Similarities Subtest, Wisconsin card sorting test, category test, stroop test, neurological test batteries (e.g., the flexible battery, Halstead-Reitan neuropsychological battery, Luria-Nebraska neuropsychological battery), and psychometric exam. The evaluating can be performed, e.g., about every week, about every two weeks, about every three weeks, about every four weeks, about every two months, about every three months, about every four months, about every five months, about every six months, about every seven months, about every eight months, about every nine months, about every ten months, about every eleven months, or about every twelve months during the course of treatment. The evaluating can also be performed prior to commencing treatment (e.g., to establish a baseline value). The evaluating can include comparing the value of the parameter from the subject to a standard (e.g., a standard described herein, e.g., a negative control), and optionally determining if a difference exists between the value of the parameter from the subject and the value from the standard. The standard can be, e.g., a value of the parameter measured in a subject with Type III Gaucher disease being treated with a different therapy for Type III Gaucher disease (e.g., a treatment described herein), or a mean value for a cohort of such subjects (e.g., after the same length of therapy), or the baseline value for the subject (or a mean baseline value for a cohort of subjects with Type III Gaucher disease) prior to commencing therapy (e.g., prior to commencement of a glucocerebrosidase enzyme replacement therapy (e.g., imiglucerase or velaglucerase)). For example, a skeletal parameter (e.g., bone mineral density) can be evaluated for long term changes, e.g., after 1, 2, 3, 4, or more years of glucocerebrosidase enzyme replacement therapy (e.g., imiglucerase, velaglucerase or uplyso).

The evaluating can include determining if one or more of the following are present:

the difference between one or more of the hemoglobin concentration, platelet count, liver volume, spleen volume, a neurological parameter, or a skeletal parameter and that of a standard (for the given parameter) is greater than 5%, 10%, 15%, 20%, 25%, 30%, 35%, 40%, 45%, 50%, 55%, 60%, 65%, 70%, 75%, 80%, 85%, or 90%. Alternatively or in addition, the evaluating can include determining if an infusion site reaction is present (e.g., during or within 12 hours after infusion) and/or if antibodies (e.g., neutralizing antibodies) (e.g., IgE, IgM, IgG and/or IgA antibodies) to a glucocerebrosidase enzyme replacement therapy (e.g., imiglucerase or uplyso) are present.

In some embodiments, the evaluation can be of one or more of hemoglobin concentration, platelet count and determining if antibodies (e.g., neutralizing antibodies) to a glucocerebrosidase enzyme replacement therapy (e.g., imiglucerase or uplyso) are present. In some embodiments, the evaluation for one or more of these parameters is performed on a sample from the subject, e.g., a blood or serum sample.

In some embodiments, the sample has been modified. For example, the values were obtained by contacting the sample with an analytical reagent and/or a substrate or cell, e.g., a substrate or cell that binds to an antibody to the glucocerebrosidase enzyme replacement therapy. In some embodiments, the values were obtained from a sample that has been enriched for, e.g., hemoglobin, platelets and/or antibodies, e.g., a concentrated portion of a blood or serum sample. In some embodiments, the evaluation was obtained by a method described herein.

Based on the determination, a treatment decision can be made for the subject. For example, if a subject receiving a treatment for Type III Gaucher disease, such as a glucocerebrosidase enzyme replacement therapy, e.g., imiglucerase or uplyso, has a value for one or more of the parameters that differs from the value for a standard (e.g., a subject with Type III Gaucher disease who is receiving a different therapy (velaglucerase)), a decision can be made to transfer the subject currently receiving a glucocerebrosidase enzyme replacement treatment (e.g., imiglucerase treatment) to a different glucocerebrosidase enzyme replacement treatment (e.g., velaglucerase treatment). For example, if antibodies (e.g., neutralizing antibodies) (e.g., IgE, IgM, IgG and/or IgA antibodies) to imiglucerase are detected in a subject undergoing treatment with imiglucerase, the subject can be transferred to treatment with velaglucerase. As another example, if an infusion site reaction is detected during or within 12 hours of administration of imiglucerase to a subject undergoing treatment with imiglucerase, the subject can be transferred to treatment with velaglucerase. As another example, if the mean platelet count in a subject undergoing treatment with imiglucerase is lower (e.g., 5%, 10%, %, 15%, 20%, 25%, 30%, 35%, 40%, 45%, 50%, 55%, 60%, 65%, 70%, 75%, 80%, 85%, or 90% lower) than the mean platelet count value obtained for a cohort of subjects with Type III Gaucher disease treated with velaglucerase for the same duration at the same dose and same frequency of treatment administration, the subject can be transferred to velaglucerase treatment.

In another aspect, the disclosure provides a method of selecting a treatment for administration to a subject with Type III Gaucher disease, the method comprising selecting a treatment on the basis that the treatment can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase or uplyso) for Type III Gaucher disease) of infusion site reaction, change a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase or uplyso) for Type III Gaucher disease) of production of antibodies (e.g., neutralizing antibodies) (e.g., IgE, IgM, IgG and/or IgA antibodies) to the treatment. Optionally, the method can include providing the treatment to the subject, e.g., wherein providing includes administering the treatment or transferring the treatment to the subject's possession. In some embodiments, the treatment can be administered at a dose and/or dosing schedule described herein.

The method can include evaluating (e.g., measuring) or obtaining an evaluation of one or more of these parameters, e.g., by a method described herein.

In one aspect, the disclosure provides a method of selecting a treatment for administration to a subject in need of an increase in hemoglobin concentration, an increase in platelet level, a decrease in liver volume, a decrease in spleen volume, a decreased likelihood of injection site reaction, a change in a skeletal parameter (e.g., an increase in bone mineral density), a change in a neurological parameter (e.g., improvement in a neurological parameter), and/or a decreased likelihood of production of antibodies to the treatment, the method comprising selecting a treatment on the basis that the treatment can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment for Type III Gaucher disease) of infusion site reaction, change a skeletal parameter (e.g., increase bone mineral density), a change in a neurological parameter (e.g., improvement in a neurological parameter), and/or decrease likelihood (e.g., relative to a standard, e.g., a standard described herein, e.g., the likelihood for a cohort of subjects receiving a different treatment for Type III Gaucher disease) of production of antibodies (e.g., neutralizing antibodies) (e.g., IgE, IgM, IgG and/or IgA antibodies) to the treatment. Optionally, the method can include providing the treatment to the subject, e.g., wherein providing includes administering the treatment or transferring the treatment to the subject's possession. In some embodiments, the treatment can be administered at a dose and/or dosing schedule described herein.

The method can include evaluating (e.g., measuring) or obtaining an evaluation of one or more of these parameters, e.g., by a method described herein.

In another aspect, the disclosure provides a method for evaluating a subject, e.g., a subject who has been selected to receive treatment with a glucocerebrosidase enzyme replacement therapy (e.g., imiglucerase, velaglucerase or uplyso). The method includes evaluating (e.g., measuring) one or more (e.g., 1, 2, 3, 4, 5, 6, 7, or 8) of the following parameters of the subject:

hemoglobin concentration, platelet count, liver volume (e.g., as a percentage of total body weight), spleen volume (e.g., as a percentage of total body weight), infusion site reaction, a skeletal parameter, a neurological parameter, or presence of antibodies (e.g., neutralizing antibodies) (e.g., IgE, IgM, IgG and/or IgA antibodies) to a glucocerebrosidase enzyme replacement therapy (e.g., the mean value of one or more (e.g., 1, 2, 3, 4, 5, 6, 7, or 8) of these parameters).

The skeletal parameter can be, e.g., bone mineral density (BMD) (e.g., as measured by a change (e.g., improvement) in Z score). BMD can be evaluated e.g., by dual energy X-ray absorptiometry (DEXA). Other skeletal parameters that can be evaluated include, e.g., T-score (e.g., to determine WHO classification of normal bone, osteopenia, and osteoporosis), growth of a subject (e.g., a pediatric subject); skeletal age of a subject (e.g., a pediatric subject); and bone marrow burden (BMB) (e.g., in an adult subject).

The neurological parameter can be e.g., an eye movement parameter (e.g., abnormal eye movements, abnormal vertical saccades, abnormal horizontal saccades, slow horizontal saccades, and supranuclear opthalmoplegia). Methods of assessing eye movement parameters can include but are not limited to, e.g., general ophthalmologic assessment, and saccadic eye movement assessment (e.g., sclera search coil technique, video technique, and infrared technique). The neurological parameter can be a hearing parameter (e.g., hearing loss. Methods of assessing hearing parameters can include but are not limited to, general auditory assessment. The neurological parameter can be, e.g., abnormal brainstem auditory evoked potentials, cranial nerve palsies, seizures, progressive myoclonic seizures, tremors, EEG abnormalities, dementia, cognitive impairment, ataxia, loss of muscle coordination, and poor mobility. Methods of assessing neurological parameters can include but are not limited to, e.g., EEG, brainstem auditory evoked response (BAER), measurement of auditory evoked potentials (e.g., electrode caps), measurement of sematosensory evoked potentials (e.g., median nerve stimulation and stretch evoked methods), mental state assessment (e.g., the neuropsychological mental status exam), cranial nerve exam, motor skill assessment (e.g., Bruininks-Oseretsky test of motor proficiency, the school function assessment test, the Beery-Buktenica developmental test of visual-motor integration, the clinical observation of motor and postural skills (COMPS)), seizure assessment (e.g., neuroimaging (e.g., CT, MRI, diffusion weighted imaging), EEG, patient history, physical examination), manual dexterity and hand eye coordination testing, (e.g., Purdue Pegboard test), standardized IQ testing (e.g., Wechsler IQ scale), verbal performance full scale IQ test, Rey auditory verbal learning test, measures of attention (e.g., D2 test of attention), continuous performance test, trail making test, Benton visual retention test, measures of memory (e.g., Wechsler Memory Scale-Revised, presentation of stimuli to later be recalled, California Verbal Learning Test, Rey Auditory Verbal Learning Test, selective reminding test, Benton Test of Visual Retention-Revised, Memory for Designs Test, Rey-O Complex Figure), assessment of cognitive function (e.g., Wechsler Similarities Subtest, Wisconsin card sorting test, category test, stroop test, neurological test batteries (e.g., the flexible battery, Halstead-Reitan neuropsychological battery, Luria-Nebraska neuropsychological battery), and psychometric exam. The evaluating can include comparing the value of the parameter from the subject to a standard (e.g., a standard described herein, e.g., a negative control), and optionally determining if a difference exists between the value of the parameter from the subject and the value from the standard. The standard can be, e.g., a value of the parameter measured in a subject with Type III Gaucher disease being treated with a different therapy for Type III Gaucher disease (e.g., a treatment described herein), or a mean value for a cohort of such subjects (e.g., after the same length of therapy), or the baseline value for the subject (or a mean baseline value for a cohort of subjects with Type III Gaucher disease) prior to commencing therapy.

The evaluating can include determining if:

the difference between one or more of the hemoglobin concentration, platelet count, liver volume, spleen volume, a neurological parameter, or a skeletal parameter (e.g., measured as bone mineral density (BMD)) and that of a standard (for the given parameter) is greater than 5%, 10%, 15%, 20%, 25%, 30%, 35%, 40%, 45%, 50%, 55%, 60%, 65%, 70%, 75%, 80%, 85%, or 90%.

In some embodiments, the evaluation can be of one or more of hemoglobin concentration, platelet count and determining if antibodies (e.g., neutralizing antibodies) to a glucocerebrosidase enzyme replacement therapy (e.g., imiglucerase or uplyso) are present. In some embodiments, the evaluation for one or more of these parameters is performed on a sample from the subject, e.g., a blood or serum sample. In some embodiments, the sample has been modified. For example, the values were obtained by contacting the sample with an analytical reagent and/or a substrate or cell, e.g., a substrate or cell that binds to an antibody to the glucocerebrosidase enzyme replacement therapy. In some embodiments, the values were obtained from a sample that has been enriched for, e.g., hemoglobin, platelets and/or antibodies, e.g., a concentrated portion of a blood or serum sample. In some embodiments, the evaluation was obtained by a method described herein.

In another aspect, the disclosure provides a method of prescribing a glucocerebrosidase enzyme replacement therapy (e.g., imiglucerase, velaglucerase or uplyso), the method comprising:

receiving an identifier for the glucocerebrosidase enzyme replacement therapy, e.g., the chemical structure, chemical name, trade name or generic name of the glucocerebrosidase enzyme replacement therapy;

receiving information that the glucocerebrosidase enzyme replacement therapy has one or more of the following properties: can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase or uplyso) for Type III Gaucher disease) of infusion site reaction, change a skeletal parameter (e.g., increase in bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase or uplyso) for Type III Gaucher disease) of production of antibodies (e.g., neutralizing antibodies) (e.g., IgE, IgM, IgG and/or IgA antibodies) to the treatment;

selecting a subject in need of the glucocerebrosidase enzyme replacement therapy, e.g., on the basis that the subject is in need of one or more of: an increase hemoglobin concentration, an increase platelet count, a decrease liver volume, a decrease spleen volume, a decrease likelihood (e.g., relative to a standard, e.g., a standard described herein, e.g., the likelihood for a cohort of subjects receiving a different treatment (e.g., imiglucerase or uplyso) for Type III Gaucher disease) of infusion site reaction, change a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase or uplyso) for Type III Gaucher disease) of production of antibodies (e.g., neutralizing antibodies) (e.g., IgE, IgM, IgG and/or IgA antibodies) to the treatment; and causing the glucocerebrosidase enzyme replacement therapy to be prescribed, dispensed, or administered to a subject.

In some embodiments, the subject is in need of one or more of an increase in hemoglobin concentration, an increase in platelet count and decrease in the likelihood of the production of antibodies (e.g., neutralizing antibodies) to a glucocerebrosidase enzyme replacement therapy (e.g., imiglucerase or uplyso), or a change in a neurological parameter (e.g., improvement in a neurological parameter). In some embodiments, a determination that a subject is in need of one or more of these changes is based upon an evaluation of one or more of these parameters performed on a sample from the subject, e.g., a blood or serum sample. In some embodiments, the sample has been modified. For example, the values were obtained by contacting the sample with an analytical reagent and/or a substrate or cell, e.g., a substrate or cell that binds to an antibody to the glucocerebrosidase enzyme replacement therapy. In some embodiments, the values were obtained from a sample that has been enriched for, e.g., hemoglobin, platelets and/or antibodies, e.g., a concentrated portion of a blood sample. In some embodiments, the evaluation was obtained by a method described herein.

In another aspect, the disclosure provides a method of providing a recipient with information about, or with guidelines for, the use of a glucocerebrosidase enzyme replacement therapy (e.g., imiglucerase or velaglucerase), the method comprising:

communicating to the recipient an identifier for the glucocerebrosidase enzyme replacement therapy, e.g., the chemical structure, chemical name, trade name or generic name of the glucocerebrosidase enzyme replacement therapy;

communicating to the recipient information that the glucocerebrosidase enzyme replacement therapy has one or more of the following properties: can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase or uplyso) for Type III Gaucher disease) of infusion site reaction, change a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase or uplyso) for Type III Gaucher disease) of production of antibodies (e.g., neutralizing antibodies) (e.g., IgE, IgM, IgG and/or IgA antibodies) to the treatment;

receiving a request from the recipient to purchase the glucocerebrosidase enzyme replacement therapy; and selling, shipping or transferring the glucocerebrosidase enzyme replacement therapy to the recipient.

In another aspect, the disclosure provides a method of providing a recipient with information about a glucocerebrosidase enzyme replacement therapy (e.g., imiglucerase, velaglucerase or uplyso), or with guidelines for, the use of a glucocerebrosidase enzyme replacement therapy (e.g., imiglucerase or velaglucerase), the method comprising:

providing an identifier for the glucocerebrosidase enzyme replacement therapy, e.g., the chemical structure, chemical name, trade name or generic name of the glucocerebrosidase enzyme replacement therapy;

providing information that the glucocerebrosidase enzyme replacement therapy has one or more of the following properties: can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase) for Type III Gaucher disease) of infusion site reaction, change in a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase) for Type III Gaucher disease) of production of antibodies (e.g., neutralizing antibodies) (e.g., IgE, IgM, IgG and/or IgA antibodies) to the treatment;

memorializing, e.g., in a database, the identifier and the information; and transferring the memorialization (e.g., the memorialized identifier and information) to the recipient.

In another aspect, the disclosure provides a method of providing a recipient with information about a glucocerebrosidase enzyme replacement therapy (e.g., imiglucerase, velaglucerase or uplyso), or with guidelines for the use of a glucocerebrosidase enzyme replacement therapy (e.g., imiglucerase, velaglucerase or uplyso), the method comprising:

providing an identifier for the glucocerebrosidase enzyme replacement therapy, e.g., the chemical structure, chemical name, trade name or generic name of the glucocerebrosidase enzyme replacement therapy;

providing information that the glucocerebrosidase enzyme replacement therapy has one or more of the following properties: can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase or uplyso) for Type III Gaucher disease) of infusion site reaction, change a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase or uplyso) for Type III Gaucher disease) of production of antibodies (e.g., neutralizing antibodies) (e.g., IgE, IgM, IgG and/or IgA antibodies) to the treatment;

associating the identifier with the information, e.g., in a database or by physical association; and transferring the associated identifier and information to the recipient.

In another aspect, the disclosure provides a database, medium, or computer containing or programmed to contain:

an identifier for a glucocerebrosidase enzyme replacement therapy (e.g., imiglucerase, velaglucerase or uplyso), e.g., the chemical structure, chemical name, trade name or generic name of the glucocerebrosidase enzyme replacement therapy;

information that the glucocerebrosidase enzyme replacement therapy has one or more of the following properties: can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase) for Type III Gaucher disease) of infusion site reaction, change a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase) for Type III Gaucher disease) of production of antibodies (e.g., neutralizing antibodies) (e.g., IgE, IgM, IgG and/or IgA antibodies) to the treatment; and an associative function associating the identifier with the information, e.g., in a database or by physical association.

In another aspect, the disclosure provides a method of making a glucocerebrosidase enzyme replacement therapy (e.g., imiglucerase, velaglucerase or uplyso) available to a subject, the method comprising:

providing to the subject an identifier for the glucocerebrosidase enzyme replacement therapy, e.g., the chemical structure, chemical name, trade name or generic name of the glucocerebrosidase enzyme replacement therapy;

providing to the subject information that the glucocerebrosidase enzyme replacement therapy has one or more of the following properties: can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase or uplyso) for Type III Gaucher disease) of infusion site reaction, change a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase or uplyso) for Type III Gaucher disease) of production of antibodies (e.g., neutralizing antibodies) (e.g., IgE, IgM, IgG and/or IgA antibodies) to the treatment; and placing into commerce, a dose of the glucocerebrosidase enzyme replacement therapy which can be administered to, provided to, or purchased by the subject.

In another aspect, the disclosure provides a method of causing a subject to request a glucocerebrosidase enzyme replacement therapy (e.g., imiglucerase, velaglucerase or uplyso), the method comprising:

providing to the subject an identifier for the glucocerebrosidase enzyme replacement therapy, e.g., the chemical structure, chemical name, trade name or generic name of the glucocerebrosidase enzyme replacement therapy;

providing to the subject information that the glucocerebrosidase enzyme replacement therapy has one or more of the following can increase hemoglobin concentration, increase platelet count, decrease liver volume, decrease spleen volume, decrease likelihood (e.g., relative to a standard, e.g., a standard described herein, e.g., the likelihood for a cohort of subjects receiving a different treatment (e.g., imiglucerase or uplyso) for Type III Gaucher disease) of infusion site reaction, change a skeletal parameter (e.g., increase bone mineral density), change in a neurological parameter (e.g., improvement in a neurological parameter), and/or decrease likelihood (e.g., relative to a standard, e.g., a standard described herein, e.g., the likelihood for a cohort of subjects receiving a different treatment (e.g., imiglucerase or uplyso) for Type III Gaucher disease) of production of antibodies (e.g., neutralizing antibodies) (e.g., IgE, IgM, IgG and/or IgA antibodies) to the treatment; and placing into commerce, a dose of the glucocerebrosidase enzyme replacement therapy which can be administered to, provided to, or purchased by the subject.

In another aspect, the disclosure features a method of selecting a payment class for a course of treatment with a glucocerebrosidase enzyme replacement therapy (e.g., imiglucerase, velaglucerase or uplyso) for a subject with Type III Gaucher disease. The method includes providing (e.g., receiving) an evaluation of whether or not the subject experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy; and performing at least one of (1) if the subject experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy selecting a first payment class, and (2) if the subject does not experience an infusion site reaction to a glucocerebrosidase enzyme replacement therapy or does not produce antibodies (e.g., neutralizing antibodies) (e.g., IgE, IgM, IgG and/or IgA antibodies) to a glucocerebrosidase enzyme replacement therapy selecting a second payment class.

In some embodiments, assignment of the subject is to the first class and the assignment authorizes payment for a course of treatment (e.g., velaglucerase).

In some embodiments, assignment of the subject is to the second class and the assignment authorizes payment for a course of treatment (e.g., imiglucerase, velaglucerase or uplyso).

In some embodiments, the evaluation is whether or not a subject produces antibodies (e.g., neutralizing antibodies) (e.g., IgE, IgM, IgG and/or IgA antibodies) to a glucocerebrosidase enzyme replacement therapy and the evaluation was obtained by a method described herein.

In another aspect, the disclosure features a method of selecting a payment class for a course of treatment with a glucocerebrosidase enzyme replacement therapy (e.g., imiglucerase, velaglucerase or uplyso) for a subject with Type III Gaucher disease. The method includes providing (e.g., receiving) an evaluation of whether or not a neurological parameter of the subject has changed (e.g., a neurological parameter has improved) and/or whether or not the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or a neurological parameter of the subject has changed (e.g., a neurological parameter has improved) and/or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months); and performing at least one of (1) if a neurological parameter of the subject has changed (e.g., a neurological parameter has improved) and/or if the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or if a neurological parameter of the subject has changed (e.g., a neurological parameter has improved) and/or if the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months), selecting a first payment class, and (2) if a neurological parameter of the subject has changed (e.g., a neurological parameter has improved) and/or if the subject's mean platelet count increased by 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or if a neurological parameter of the subject has changed (e.g., a neurological parameter has improved) and/or if the subject's mean platelet count increased by 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months), selecting a second payment class.

In some embodiments, assignment of the subject is to the first class and the assignment authorizes payment for a course of treatment (e.g., velaglucerase).

In some embodiments, assignment of the subject is to the second class and the assignment authorizes payment for a course of treatment (e.g., imiglucerase, velaglucerase or uplyso).

In some embodiments, the evaluation was obtained by a method described herein.

In one aspect, the disclosure features a method of providing information on which to make a decision about a subject with Type III Gaucher disease, or making such a decision. The method includes providing (e.g., by receiving) an evaluation of a subject, wherein the evaluation was made by a method described herein, e.g., by optionally, administering a glucocerebrosidase enzyme replacement therapy (e.g., imiglucerase, velaglucerase or uplyso), to the subject; providing a determination post administration of whether or not the subject experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy, thereby providing a post administration determination; providing a comparison of the post administration determination with a standard (e.g., a standard described herein), thereby, providing information on which to make a decision about a subject, or making such a decision.

In some embodiments, the method includes making the decision.

In some embodiments, the method also includes communicating the information to another party (e.g., by computer, compact disc, telephone, facsimile, email, or letter).

In some embodiments, the decision includes selecting a subject for payment, making or authorizing payment for a first course of action (e.g., treatment with velaglucerase) if the subject experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy and a second course of action (e.g., treatment with imiglucerase, velaglucerase or uplyso) if the subject does not experience an infusion site reaction to a glucocerebrosidase enzyme replacement therapy or does not produce antibodies (e.g., neutralizing antibodies) (e.g., IgE, IgM, IgG and/or IgA antibodies) to a glucocerebrosidase enzyme replacement.

In some embodiments, the subject experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy and the course of action is authorization of a course of therapy (e.g., treatment with velaglucerase).

In some embodiments, the subject experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy and the course of action is assigning the subject to a first class. In some embodiments, assignment to the first class will enable payment for a treatment (e.g., velaglucerase) provided to the subject. In some embodiments, payment is by a first party to a second party. In some embodiments, the first party is other than the subject. In some embodiments, the first party is selected from a third party payer, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the treatment. In some embodiments, the first party is an insurance company and the second party is selected from the subject, a healthcare provider, a treating physician, an HMO, a hospital, a governmental entity, or an entity which sells or supplies the treatment. In some embodiments, the first party is a governmental entity and the second party is selected from the subject, a healthcare provider, a treating physician, an HMO, a hospital, an insurance company, or an entity which sells or supplies the treatment.

In some embodiments, the subject does not experience an infusion site reaction to a glucocerebrosidase enzyme replacement therapy or does not produce antibodies (e.g., neutralizing antibodies) (e.g., IgE, IgM, IgG and/or IgA antibodies) to a glucocerebrosidase enzyme replacement and the course of action is authorization of a course of therapy (e.g., imiglucerase, velaglucerase or uplyso).

In some embodiments, the subject does not experience an infusion site reaction to a glucocerebrosidase enzyme replacement therapy or does not produce antibodies (e.g., neutralizing antibodies) (e.g., IgE, IgM, IgG and/or IgA antibodies) to a glucocerebrosidase enzyme replacement and the course of action is assigning the subject to a second class. In some embodiments, assignment to the second class will enable payment for a treatment (e.g., imiglucerase, velaglucerase or uplyso) provided to the subject. In some embodiments, payment is by a first party to a second party. In some embodiments, the first party is other than the subject. In some embodiments, the first party is selected from a third party payer, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the treatment. In some embodiments, the first party is an insurance company and the second party is selected from the subject, a healthcare provider, a treating physician, an HMO, a hospital, a governmental entity, or an entity which sells or supplies the treatment. In some embodiments, the first party is a governmental entity and the second party is selected from the subject, a healthcare provider, a treating physician, an HMO, a hospital, an insurance company, or an entity which sells or supplies the treatment.

In one aspect, the disclosure features a method of providing information on which to make a decision about a subject with Type III Gaucher disease, or making such a decision. The method includes providing (e.g., by receiving) an evaluation of a subject, wherein the evaluation was made by a method described herein, e.g., by optionally, administering a glucocerebrosidase enzyme replacement therapy (e.g., imiglucerase, velaglucerase or uplyso), to the subject; providing a determination post administration of whether or not a neurological parameter of the subject has changed (e.g., a neurological parameter has improved) and/or whether or not the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether a neurological parameter of the subject has changed (e.g., a neurological parameter has improved) and/or whether or not the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months), thereby providing a post administration determination; providing a comparison of the post administration determination with a standard (e.g., a standard described herein), thereby, providing information on which to make a decision about a subject, or making such a decision.

In some embodiments, the method includes making the decision.

In some embodiments, the method also includes communicating the information to another party (e.g., by computer, compact disc, telephone, facsimile, email, or letter).

In some embodiments, the decision includes selecting a subject for payment, making or authorizing payment for a first course of action (e.g., treatment with velaglucerase) if a neurological parameter of the subject has changed (e.g., a neurological parameter has improved) and/or if the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or if a neurological parameter of the subject has changed (e.g., a neurological parameter has improved) and/or if the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) and a second course of action (e.g., treatment with imiglucerase, velaglucerase or uplyso) if a neurological parameter of the subject has changed (e.g., a neurological parameter has improved) and/or if the subject's mean platelet count increased by 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or if a neurological parameter of the subject has changed (e.g., a neurological parameter has improved) and/or if the subject's mean platelet count increased by 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months).

In some embodiments, a neurological parameter of the subject has changed (e.g., a neurological parameter has improved) and/or the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or a neurological parameter of the subject has changed (e.g., a neurological parameter has improved) and/or the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) and the course of action is authorization of a course of therapy (e.g., treatment with velaglucerase).

In some embodiments, assignment of the subject is to the first class and the assignment authorizes payment for a course of treatment (e.g., velaglucerase).

In some embodiments, assignment of the subject is to the second class and the assignment authorizes payment for a course of treatment (e.g., imiglucerase, velaglucerase or uplyso).

In some embodiments, a neurological parameter of the subject has changed (e.g., a neurological parameter has improved) and/or the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or a neurological parameter of the subject has changed (e.g., a neurological parameter has improved) and/or the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) and the course of action is assigning the subject to a first class. In some embodiments, assignment to the first class will enable payment for a treatment (e.g., velaglucerase) provided to the subject. In some embodiments, payment is by a first party to a second party. In some embodiments, the first party is other than the subject. In some embodiments, the first party is selected from a third party payer, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the treatment. In some embodiments, the first party is an insurance company and the second party is selected from the subject, a healthcare provider, a treating physician, an HMO, a hospital, a governmental entity, or an entity which sells or supplies the treatment. In some embodiments, the first party is a governmental entity and the second party is selected from the subject, a healthcare provider, a treating physician, an HMO, a hospital, an insurance company, or an entity which sells or supplies the treatment.

In some embodiments, a neurological parameter of the subject has changed (e.g., a neurological parameter has improved) and/or the subject's mean platelet count increased by 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or a neurological parameter of the subject has changed (e.g., a neurological parameter has improved) and/or the subject's mean platelet count increased by 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) and the course of action is authorization of a course of therapy (e.g., imiglucerase, velaglucerase or uplyso).

In some embodiments, a neurological parameter of the subject has changed (e.g., a neurological parameter has improved) and/or the subject's mean platelet count increased by 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or a neurological parameter of the subject has changed (e.g., a neurological parameter has improved) and/or if the subject's mean platelet count increased by 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) and the course of action is assigning the subject to a second class. In some embodiments, assignment to the second class will enable payment for a treatment (e.g., imiglucerase, velaglucerase or uplyso) provided to the subject. In some embodiments, payment is by a first party to a second party. In some embodiments, the first party is other than the subject. In some embodiments, the first party is selected from a third party payer, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the treatment. In some embodiments, the first party is an insurance company and the second party is selected from the subject, a healthcare provider, a treating physician, an HMO, a hospital, a governmental entity, or an entity which sells or supplies the treatment. In some embodiments, the first party is a governmental entity and the second party is selected from the subject, a healthcare provider, a treating physician, an HMO, a hospital, an insurance company, or an entity which sells or supplies the treatment.

In another aspect, the disclosure features a method of selecting a payment class for a course of treatment with a glucocerebrosidase enzyme replacement therapy (e.g., velaglucerase) for a subject with Type III Gaucher disease. The method includes determining that an infusion site reaction during or within 12 hours after infusion of the therapy is present in the subject or that antibodies (e.g., neutralizing antibodies) (e.g., IgE, IgM, IgG and/or IgA antibodies) to the therapy are present in the subject, e.g., by a method described herein, and approving, making, authorizing, receiving, transmitting or otherwise allowing payment of a selected course of treatment, e.g., velaglucerase.

In another aspect, the disclosure features a method of selecting a payment class for a course of treatment with a glucocerebrosidase enzyme replacement therapy (e.g., imiglucerase velaglucerase, or uplyso) for a subject with Type III Gaucher disease. The method includes determining that an infusion site reaction during or within 12 hours after infusion of the therapy is not present in the subject or that antibodies (e.g., neutralizing antibodies) (e.g., IgE, IgM, IgG and/or IgA antibodies) to the therapy are not present in the subject, e.g., by a method described herein, and approving, making, authorizing, receiving, transmitting or otherwise allowing payment of a selected course of treatment, e.g., imiglucerase, velaglucerase or uplyso.

In one aspect, the disclosure features a method of making a data record. The method includes entering the result of a method described herein into a record, e.g., a computer readable record. In some embodiments, the record is available on the world wide web. In some embodiments, the record is evaluated by a third party payer, an insurance company, employer, employer sponsored health plan, HMO, or governmental entity, or a healthcare provider, a treating physician, an HMO, a hospital, a governmental entity, or an entity which sells or supplies the treatment, or is otherwise relied on in a method described herein.

In another aspect, the disclosure features a data record (e.g., computer readable record), wherein the record includes results from a method described herein. In some embodiments, the record is available on the world wide web. In some embodiments, the record is evaluated and/or transmitted to a third party payer, an insurance company, employer, employer sponsored health plan, HMO, or governmental entity, or a healthcare provider, a treating physician, an HMO, a hospital, a governmental entity, or an entity which sells or supplies the treatment.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, an HMO, a hospital, a governmental entity, or an entity which sells or supplies the treatment. In some embodiments, the second party is a third party payer, an insurance company, employer, employer sponsored health plan, HMO, or governmental entity. In some embodiments, the first party is selected from the subject, a healthcare provider, a treating physician, an HMO, a hospital, an insurance company, or an entity which sells or supplies the treatment and the second party is a governmental entity. In some embodiments, the first party is selected from the subject, a healthcare provider, a treating physician, an HMO, a hospital, an insurance company, or an entity which sells or supplies the treatment and the second party is an insurance company.

In one aspect, the disclosure features a method of transmitting a record described herein. The method includes a first party transmitting the record to a second party, e.g., by computer, compact disc, telephone, facsimile, email, or letter. In some embodiments, the second party is selected from the subject, a healthcare provider, a treating physician, an HMO, a hospital, a governmental entity, or an entity which sells or supplies the treatment. In some embodiments, the first party is an insurance company or government entity and the second party is selected from the subject, a healthcare provider, a treating physician, an HMO, a hospital, a governmental entity, or an entity which sells or supplies the treatment. In some embodiments, the first party is a governmental entity or insurance company and the second party is selected from the subject, a healthcare provider, a treating physician, an HMO, a hospital, an insurance company, or an entity which sells or supplies the treatment.

In one method, information, e.g., about whether or not a subject with Type III Gaucher disease experiences a change in a neurological parameter, about whether or not a subject with Type III Gaucher disease experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy (e.g., wherein the information is obtained as described herein) is provided (e.g., communicated, e.g., electronically communicated) to a third party, e.g., a hospital, clinic, a government entity, reimbursing party or insurance company (e.g., a life insurance company). For example, choice of medical procedure, payment for a medical procedure, payment by a reimbursing party, or cost for a service or insurance can be function of the information. E.g., the third party receives the information, makes a determination based at least in part on the information, and optionally communicates the information or makes a choice of procedure, payment, level of payment, coverage, etc. based on the information.

In one method, information, e.g., whether or not a subject with Type III Gaucher disease experiences a change in a neurological parameter and/or whether or not the mean platelet count of a subject with Type III Gaucher disease increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) (e.g., wherein the information is obtained as described herein) is provided (e.g., communicated, e.g., electronically communicated) to a third party, e.g., a hospital, clinic, a government entity, reimbursing party or insurance company (e.g., a life insurance company). For example, choice of medical procedure, payment for a medical procedure, payment by a reimbursing party, or cost for a service or insurance can be function of the information. E.g., the third party receives the information, makes a determination based at least in part on the information, and optionally communicates the information or makes a choice of procedure, payment, level of payment, coverage, etc. based on the information.

In one embodiment, a premium for insurance (e.g., life or medical) is evaluated as a function of information about whether or not a subject with Type III Gaucher disease experiences a change in a neurological parameter and/or whether or not a subject with Type III Gaucher disease experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy. For example, premiums can be increased (e.g., by a certain percentage) if the subject experiences an infusion site reaction to a glucocerebrosidase enzyme replacement or produces antibodies (e.g., neutralizing antibodies) (e.g., IgE, IgM, IgG and/or IgA antibodies) to a glucocerebrosidase enzyme replacement therapy.

In one embodiment, a premium for insurance (e.g., life or medical) is evaluated as a function of information about whether or not a subject with Type III Gaucher disease experiences a change in a neurological parameter and/or whether or not the mean platelet count of a subject with Type III Gaucher disease increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) (e.g., wherein the information is obtained as described herein). For example, premiums can be increased (e.g., by a certain percentage) if the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months).

Information about whether or not a subject with Type III Gaucher disease experiences a change in a neurological parameter and/or whether or not a subject with Type III Gaucher disease experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on whether or not a subject with Type III Gaucher disease experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy. An insurance premium or risk assessment can also be evaluated as function of whether or not a subject with Type III Gaucher disease experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy.

Information about whether or not a subject with Type III Gaucher disease experiences a change in a neurological parameter and/or whether or not the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on whether or not a subject with Type III Gaucher disease experiences a change in a neurological parameter and/or whether or not the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months). An insurance premium or risk assessment can also be evaluated as function of whether or not a subject with Type III Gaucher disease experiences a change in a neurological parameter and/or whether or not whether or not the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether or not a subject with Type III Gaucher disease experiences a change in a neurological parameter and/or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months).

In one embodiment, information about whether or not a subject with Type III Gaucher disease experiences a change in a neurological parameter and/or whether or not a subject with Type III Gaucher disease experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy is analyzed by a function that determines whether to authorize the transfer of funds to pay for a service or treatment provided to a subject (or make another decision referred to herein). For example, the results (e.g., that the subject experiences an infusion site reaction to a glucocerebrosidase enzyme replacement therapy or produces antibodies (e.g., neutralizing antibodies) (e.g., IgE, IgM, IgG and/or IgA antibodies) to a glucocerebrosidase enzyme replacement therapy) may indicate that a subject is suitable for treatment (e.g., velaglucerase), suggesting that a treatment course (e.g., with velaglucerase) is needed, thereby triggering an outcome that indicates or causes authorization to pay for a service or treatment (e.g., velaglucerase) provided to a subject. For example, an entity, e.g., a hospital, care giver, government entity, or an insurance company or other entity which pays for, or reimburses medical expenses, can use the outcome of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment (e.g., velaglucerase) provided to a patient. For example, a first entity, e.g., an insurance company, can use the outcome of a method described herein to determine whether to continue, discontinue, enroll an individual in an insurance plan or program, e.g., a health insurance or life insurance plan or program.

In one embodiment, information about whether or not a subject with Type III Gaucher disease experiences a change in a neurological parameter and/or whether or not the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether or not a subject with Type III Gaucher disease experiences a change in a neurological parameter and/or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months) is analyzed by a function that determines whether to authorize the transfer of funds to pay for a service or treatment provided to a subject (or make another decision referred to herein). For example, the results (e.g., that the subject's mean platelet count increased by less than 80%, 75%, 70%, 65%, 60%, or 55% after 9 or 12 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 9 months) or whether the subject's mean platelet count increased by less than 40%, 35%, 30%, or 25% after 6 months of treatment as compared to their baseline mean platelet count prior to initiating the glucocerebrosidase enzyme replacement therapy (e.g., imiglucerase treatment, e.g., imiglucerase at a dose of 60 U/kg, e.g., administered every other week for 6 months)) may indicate that a subject is suitable for treatment (e.g., velaglucerase), suggesting that a treatment course (e.g., with velaglucerase) is needed, thereby triggering an outcome that indicates or causes authorization to pay for a service or treatment (e.g., velaglucerase) provided to a subject. For example, an entity, e.g., a hospital, care giver, government entity, or an insurance company or other entity which pays for, or reimburses medical expenses, can use the outcome of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment (e.g., velaglucerase) provided to a patient. For example, a first entity, e.g., an insurance company, can use the outcome of a method described herein to determine whether to continue, discontinue, enroll an individual in an insurance plan or program, e.g., a health insurance or life insurance plan or program.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, a health maintenance organization (HMO), a hospital, a governmental entity, or an entity which sells or supplies the drug. In some embodiments, the second party is a third party payer, an insurance company, employer, employer sponsored health plan, HMO, or governmental entity. In some embodiments, the first party is selected from the subject, a healthcare provider, a treating physician, an HMO, a hospital, an insurance company, or an entity which sells or supplies the drug and the second party is a governmental entity. In some embodiments, the first party is selected from the subject, a healthcare provider, a treating physician, an HMO, a hospital, an insurance company, or an entity which sells or supplies the drug and the second party is an insurance company.

In some aspects, the disclosure provides the use of a glucocerebrosidase enzyme replacement therapy (e.g., velaglucerase, imiglucerase or uplyso), alone or in combination with another agent(s) described herein (e.g., isofagomine tartrate, miglustat, or Genz112638), for use in treatment.

In some aspects, the disclosure provides the use of a glucocerebrosidase enzyme replacement therapy (e.g., velaglucerase or imiglucerase), alone or in combination with another agent(s) described herein (e.g., isofagomine tartrate, miglustat, or Genz112638), for the preparation of a medicament, e.g., for treating Type III Gaucher disease.

In another aspect, the disclosure provides a pharmaceutical composition of velaglucerase. The composition comprises: velaglucerase, a lyoprotectant (e.g., a carbohydrate (e.g., sucrose)), a buffer salt (e.g., citrate and/or citric acid, e.g., sodium citrate and citric acid), and a stabilizing agent (e.g., polysorbate, e.g., polysorbate 20).

In some embodiments, the composition can be lyophilized. In some embodiments, the moisture content of the lyophilized composition is 1% to 6%, e.g., 1.3% to 6.2%. In some embodiments, the moisture content of the lyophilized composition is 1% to 5%. In some embodiments, the moisture content of the lyophilized composition is 3% to 5%. In some embodiments, the moisture content is greater than or equal to 3%. In some embodiments, the moisture content is 3%.

In some embodiments, the lyophilized composition can be evaluated. For example, the secondary structure of the lyophilized composition can be evaluated, e.g., by FT-IR.

In other embodiments, the composition can be a reconstituted solution. For example, the composition is a reconstituted solution in a pharmaceutically acceptable carrier such as Sterile Water for Injection (e.g., a 200 unit vial with 2.2 mL Sterile Water for Injection or a 400 unit vial with 4.3 mL Sterile Water for Injection). In some embodiments, the composition can further comprise, or consist of, sodium chloride solution suitable for intravenous administration (e.g., 0.9% sodium chloride solution suitable for intravenous administration).

In some embodiments, the reconstituted solution can be evaluated, e.g., for degradation. For example, the reconstituted solution can be evaluated by SE-HPLC and/or RP-HPLC, e.g., for the presence of degradation products.

In some embodiments, the reconstituted solution can be evaluated for oxidation. For example, the reconstituted solution can be evaluated by peptide mapping.

In some aspects, the disclosure features an assay (e.g., method) for detecting an anti-glucocerebrosidase antibody in a sample (e.g., a patient sample, e.g., blood or serum). The method includes:

providing a glucocerebrosidase (e.g., velaglucerase, imiglucerase or uplyso) immobilized on a surface (e.g., a microwell) (for example, the surface can be coated with a coupling agent such as strepavidin and the glucocerebrosidase (e.g., velaglucerase, imiglucerase or uplyso) can be bound to an agent (e.g., biotin) which associates with, e.g., binds to, the coupling agent, e.g., the glucocerebrosidase (e.g., velaglucerase, imiglucerase or uplyso) is immobilized to the surface via the biotin binding to the strepavidin;

contacting the sample to the immobilized glucocerebrosidase (e.g., velaglucerase, imiglucerase or uplyso), under conditions that allow an anti-glucocerebrosidase antibody in the sample, if present, to bind to the immobilized glucocerebrocidase, thereby forming a mixture;

optionally performing a wash step to remove from the mixture any material in the sample that is not bound to the immobilized glucocerebrosidase;

adding labeled glucocerebrosidase (e.g., velaglucerase or imiglucerase), wherein the labeled glucocerebrosidase is labeled with a detectable label (e.g., ruthenium-labeled glucocerebrosidase), to the mixture under conditions that allow the labeled glucocerebrosidase to bind to the anti-glucocerebrosidase antibody (e.g., that is bound to the immobilized glucocerebrosidase), if present, (preferably, the label is not the same as the coupling agent and/or the agent that binds to the coupling agent, e.g., if biotin is used to immobilize glucocerebrosidase to the surface, the label is not biotin);

optionally performing a wash step to remove labeled glucocerebrosidase that is not bound to the anti-glucocerebrosidase antibody from the mixture; and detecting (and optionally quantifying) the label in the mixture, e.g., wherein detection of the label indicates that an anti-glucocerebrosidase antibody is present in the sample.

In some embodiments, the detected label is quantified to a value and compared to a control, e.g., a negative control, wherein if the value of detected label is greater than the negative control, the sample contains anti-glucocerebrosidase antibody. In some embodiments, the negative control is the average negative control value (e.g., background) for a plurality of negative controls. For example, the negative control can be normal human serum (NHS), and the average negative control value can be the average for a plurality of NHS lots, or the average of the negative control values obtained from a plurality of assays. For example, the negative control value can be a value of 1, 2, 3, 4, 5 or 6 ng/ml of antibody, e.g., a value of greater than that number for a sample indicates that an anti-glucocerebrosidase antibody is present in the sample. As another example, the negative control value can be 200, 250, 300 (e.g., 306), 350, or 400, e.g., a value of greater than that number for a sample indicates that an anti-glucocerebrosidase antibody is present in the sample.

In some embodiments, the assay is for detecting anti-velaglucerase antibodies. In another embodiment, the assay is for detecting anti-imiglucerase antibodies. In some embodiments, the assay is for detecting anti-uplyso antibodies.

In some aspects, the disclosure features an assay for detecting an anti-glucocerebrosidase antibody (e.g., IgG anti-glucocerebrosidase antibody) in a sample (e.g., a patient sample, e.g., blood or serum). The method includes:

contacting the sample to labeled glucocerebrosidase (e.g., velaglucerase or imiglucerase), wherein the glucocerebrosidase is labeled with a detectable label (e.g., the glucocerebrosidase is $^{125}$I labeled), under conditions that allow an anti-glucocerebrosidase antibody in the sample, if present, to bind to labeled glucocerebrosidase, thereby forming a mixture;

applying the mixture to a resin (e.g., Protein G, Protein A, Protein A/G, or Protein L resin) (e.g., a Protein G spin column) under conditions that allow the anti-glucocerebrosidase antibody, if present, to bind to the resin;

optionally performing a wash step to remove labeled glucocerebrosidase that is not bound to the anti-glucocerebrosidase antibody from the mixture; and detecting (and optionally quantifying) the label in the mixture (e.g., on the resin), e.g., wherein detection of the label indicates that anti-glucocerebrosidase antibody is present in the sample.

In some embodiments, the assay is for detecting anti-velaglucerase antibodies. In another embodiment, the assay is for detecting anti-imiglucerase antibodies. In some embodiments, the assay is for detecting anti-uplyso antibodies.

In some embodiments, the detected label is quantified to a value and compared to a control, e.g., a negative control, wherein if the value of detected label is greater than the negative control, the sample contains anti-glucocerebrosidase antibody. In some embodiments, the negative control is the average negative control value (e.g., background) for a plurality of negative controls. For example, the negative control can be normal human serum (NHS), and the average negative control value can be the average for a plurality of NHS lots, or the average of the negative control values obtained from a plurality of assays.

In some aspects, the disclosure features an assay for detecting a human anti-glucocerebrosidase antibody in a sample (e.g., a patient sample, e.g., blood or serum). The method includes:

providing glucocerebrosidase (e.g., velaglucerase, imiglucerase or uplyso) immobilized on a surface (e.g., a microwell) (for example, the surface can be coated with a coupling agent such as strepavidin and the glucocerebrosidase can be bound to an agent (e.g., biotin) that associates with, e.g., binds to, the coupling agent, e.g., the glucocerebrosidase is immobilized to the surface via the biotin binding to the strepavidin);

contacting the sample to the immobilized glucocerebrosidase, under conditions that allow a human anti-glucocerebrosidase antibody in the sample, if present, to bind to the immobilized glucocerebrosidase, thereby forming a mixture;

optionally performing a wash step to remove from the mixture any material in the sample that is not bound to the immobilized glucocerebrosidase;

adding an antibody that binds to the human anti-glucocerebrosidase antibody to the mixture, wherein the antibody that binds to the human anti-glucocerebrosidase antibody is labeled with a detectable label (e.g., ruthenium or biotin), under conditions that allow the labeled antibody that binds to the human anti-glucocerebrosidase antibody to bind to the human anti-glucocerebrosidase antibody (e.g., that is bound to the immobilized glucocerebrosidase), if present, (preferably, the label is not the same as the coupling agent and/or the agent that binds to the coupling agent, e.g., if biotin is used to immobilize glucocerebrosidase to the surface, the label is not biotin);

optionally performing a wash step to remove labeled antibody that binds to the human anti-glucocerebrosidase antibody that is not bound to the human anti-glucocerebrosidase antibody from the mixture; and detecting (and optionally quantifying) the label in the mixture, e.g., wherein detection of the label indicates that human anti-glucocerebrosidase antibody is present in the sample.

In some embodiments, the assay detects anti-velaglucerase antibodies. In some embodiments, the assay detects anti-imiglucerase antibodies. In some embodiments, the assay detects anti-uplyso antibodies.

In some embodiments, the detected label is quantified to a value and compared to a control, e.g., a negative control, wherein if the value of detected label is greater than the negative control, the sample contains anti-velaglucerase antibody. In some embodiments, the negative control is the average negative control value (e.g., background) for a plurality of negative controls. For example, the negative control can be normal human serum (NHS), and the average negative control value can be the average for a plurality of NHS lots, or the average of the negative control values obtained from a plurality of assays.

In some embodiments, the antibody that binds to the human anti-glucocerebrosidase antibody is isotype specific, wherein the isotype specific antibody that binds to the human anti-glucocerebrosidase antibody binds specifically to a human antibody of the isotype to which it is specific.

In some embodiments, the antibody that binds to the human anti-glucocerebrosidase antibody is an IgA specific antibody and binds to an IgA human anti-glucocerebrosidase antibody in the sample.

In some embodiments, the antibody that binds to the human anti-glucocerebrosidase antibody is an IgE specific antibody and binds to an IgE human anti-glucocerebrosidase antibody in the sample.

In some embodiments, the antibody that binds to the human anti-glucocerebrosidase antibody is an IgM specific antibody and binds to an IgM human anti-glucocerebrosidase antibody in the sample.

In some embodiments, the antibody that binds to the human anti-glucocerebrosidase antibody is an IgG specific antibody and binds to an IgG human anti-glucocerebrosidase antibody in the sample.

In some aspects, the disclosure features a method of determining if an anti-glucocerebrosidase antibody (e.g., in a sample) neutralizes (e.g., inhibits) glucocerebrosidase (e.g., velaglucerase or imiglucerase) activity. The method includes:

providing a cell (e.g., a human cell, e.g., a human fibroblast cell) that expresses human macrophage mannose receptor (MMR);

contacting the anti-glucocerebrosidase antibody to the cell, thereby forming a mixture;

contacting labeled glucocerebrosidase (e.g., velaglucerase, imiglucerase or uplyso) to the mixture, wherein the glucocerebrosidase is labeled with a detectable label (e.g., the glucocerebrosidase is labeled with a fluorescent label, e.g., a green fluorescent dye, such as Alexa FLUOR® 488 or fluorescein isothiocyanate (FITC)), under conditions that allow the labeled glucocerebrosidase to bind to the MMR in the absence of an anti-glucocerebrosidase antibody (e.g., wherein binding of glucocerebrosidase to MMR allows cellular uptake of the glucocerebrosidase);

removing unbound labeled glucocerebrosidase and labeled glucocerebrosidase bound to the cell surface (e.g., via trypsin digestion); and measuring the amount of labeled glucocerebrosidase in the cell.

In some embodiments, the levels of labeled glucocerebrosidase are compared to a control, e.g., the level of labeled glucocerebrosidase detected in the absence of the anti-glucocerebrosidase antibody under identical conditions.

In some embodiments, the cells do not express an Fc receptor (e.g., human Fc receptor).

In some embodiments, the method detects whether neutralizing anti-velaglucerase antibodies are present. In some embodiments, the method detects whether neutralizing anti-imiglucerase antibodies are present. In some embodiments, the method detects whether neutralizing anti-uplyso antibodies are present.

In some embodiments, the method detects whether an anti-imiglucerase antibody neutralizes imiglucerase activity. In some embodiments, the method detects whether an anti-velaglucerase antibody neutralizes velaglucerase activity. In some embodiments, the method detects whether an anti-uplyso antibody neutralizes uplyso activity.

In some embodiments, the method detects whether an anti-imiglucerase antibody neutralizes velaglucerase and/or uplyso activity. In some embodiments, the method detects whether an anti-velaglucerase antibody neutralizes imiglucerase and/or uplyso activity. In some embodiments, the method detects whether an anti-uplyso antibody neutralizes imiglucerase and/or velaglucerase activity.

In some aspects, the disclosure features a method of determining if an anti-velaglucerase antibody (e.g., in a sample) neutralizes (e.g., inhibits) imiglucerase activity. The method includes:

providing a cell (e.g., a human cell, e.g., a human fibroblast cell) that expresses human macrophage mannose receptor (MMR);

contacting the anti-velaglucerase antibody to the cell, thereby forming a mixture;

contacting labeled imiglucerase to the mixture, wherein the imiglucerase is labeled with a detectable label (e.g., the imiglucerase is labeled with a fluorescent label, e.g., a green fluorescent dye, such as Alexa FLUOR® 488 or fluorescein isothiocyanate (FITC)), under conditions that allow the labeled imiglucerase to bind to the MMR in the absence of an anti-velaglucerase antibody (e.g., wherein binding of imiglucerase to MMR allows cellular uptake of the imiglucerase);

removing unbound labeled imiglucerase and labeled imiglucerase bound to the cell surface (e.g., via trypsin digestion); and measuring the amount of labeled imiglucerase in the cell.

In some embodiments, the levels of labeled imiglucerase are compared to a control, e.g., the level of labeled imiglucerase detected in the absence of the anti-velaglucerase antibody under identical conditions.

In some embodiments, the cells do not express an Fc receptor (e.g., human Fc receptor).

In some aspects, the disclosure features a method of determining if an anti-imiglucerase antibody (e.g., in a sample) neutralizes (e.g., inhibits) velaglucerase activity. The method includes:

providing a cell (e.g., a human cell, e.g., a human fibroblast cell) that expresses human macrophage mannose receptor (MMR);

contacting the anti-imiglucerase antibody to the cell, thereby forming a mixture;

contacting labeled velaglucerase to the mixture, wherein the velaglucerase is labeled with a detectable label (e.g., the velaglucerase is labeled with a fluorescent label, e.g., a green fluorescent dye, such as Alexa FLUOR® 488 or fluorescein isothiocyanate (FITC)), under conditions that allow the labeled velaglucerase to bind to the MMR in the absence of an anti-imiglucerase antibody (e.g., wherein binding of velaglucerase to MMR allows cellular uptake of the velaglucerase);

removing unbound labeled velaglucerase and labeled velaglucerase bound to the cell surface (e.g., via trypsin digestion); and measuring the amount of labeled velaglucerase in the cell.

In some embodiments, the levels of labeled velaglucerase are compared to a control, e.g., the level of labeled velaglucerase detected in the absence of the anti-imiglucerase antibody under identical conditions.

In some embodiments, the cells do not express an Fc receptor (e.g., human Fc receptor).

In some aspects, the disclosure features a hybrid antibody, wherein the hybrid antibody comprises a non-human anti-drug antibody and a human immunoglobulin (Ig).

In some embodiments, the non-human anti-drug IgG antibody is a sheep anti-drug IgG antibody.

In some embodiments, the anti-drug antibody binds to velaglucerase.

In some embodiments, the anti-drug antibody binds to imiglucerase.

In some embodiments, the anti-drug antibody binds to uplyso.

In some embodiments, the human Ig is IgA.
In some embodiments, the human Ig is IgE.
In some embodiments, the human Ig is IgM.
In some embodiments, the human Ig is IgG.
In some embodiments, the non-human anti-drug antibody is an IgG antibody.

In some embodiments, the non-human anti-drug antibody and the human Ig are conjugated together by a chemical crosslinker, e.g., a long spacer arm cross linker, e.g., succinimidyl 6-[3'-2-pyridyldithio-propionamido]hexanoate (LC-SPDP).

In some embodiments, the hybrid antibody is used as a positive control in assays that detect and/or measure levels and/or isotypes of anti-drug antibody in a sample, e.g., in a method described herein.

In some embodiments, the hybrid antibody is used as a positive control in assays for determining if an anti-glucocerebrosidase antibody (e.g., in a sample) neutralizes (e.g., inhibits) glucocerebrosidase (e.g., velaglucerase or imiglucerase) activity, e.g., in a method described herein. For example, the hybrid antibody is used as an anti-glucocerebrosidase antibody (e.g., in a sample) in the assay.

In some aspects, the disclosure features a method of measuring cellular uptake (e.g., internalization) of glucocerebrosidase (e.g., velaglucerase or imiglucerase) into a cell. The method includes:

contacting glucocerebrosidase (e.g., velaglucerase or imiglucerase) to a cell (e.g., a cell of a human leukemic monocyte lymphoma cell line (e.g., U937) or a cell of a murine macrophage cell line (e.g., J774)) to thereby form a mixture;

incubating the mixture (e.g., for 1, 2, 3, 4, 5, 6, or 7 hours or overnight), e.g., to allow cellular uptake of the glucocerebrosidase (e.g., velaglucerase or imiglucerase) into the cell; and measuring the amount of uptake of glucocerebrosidase (e.g., velaglucerase or imiglucerase) into the cell.

In some embodiments, the amount of uptake is measured by measuring glucocerebrosidase enzymatic activity in the cell. In some embodiments, a synthetic substrate that fluoresces upon cleavage (e.g., 4-MU-glc) is used.

In some embodiments, the amount of uptake is measured by measuring intracellular glucocerebrosidase protein levels. In some embodiments, Western blot analysis is used. In some embodiments, immunohistochemistry analysis is used (e.g., immunohistochemistry on permeabilized cells).

In some embodiments, the cell is washed one or more times prior to the measuring step.

In some embodiments, the pH of the mixture is 7.5.

In some embodiments, mannose-6-phosphate (M6P) is present in the mixture.

In some embodiments, mannan is present in the mixture.

In some embodiments, calcium is present in the mixture.

In some embodiments, the amount of uptake is compared to a standard, e.g., the measured amount of uptake in the absence of contacting glucocerebrosidase (e.g., velaglucerase or imiglucerase) to the cell, or comparing the measured amount of uptake in the presence and absence of mannose-6-phosphate, or comparing the measured amount of uptake in the presence and absence of mannan, or comparing the measured amount of uptake in the presence and absence of calcium.

In some embodiments, the glucocerebrosidase is velaglucerase.

In some embodiments, the glucocerebrosidase is imiglucerase.

In some embodiments, the amount of uptake of velaglucerase is compared to the amount of uptake of imiglucerase (e.g., under the same conditions).

The term "subject" refers to any mammal, including but not limited to, any animal classified as such, including humans, non human primates, primates, baboons, chimpanzees, monkeys, rodents (e.g., mice, rats), rabbits, cats, dogs, horses, cows, sheep, goats, pigs, etc. The term "subject" can be used interchangeably with the term "patient."

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80% 90% (w/w) pure, even more preferably, 90 to 95% pure; and, most preferably, at least 95%, 96%, 97%, 98%, 99%, 99.5%, 99.8% or 100% (w/w) pure.

As used herein, the term "about" refers to up to ±10% of the value qualified by this term. For example, about 50 mM refers to 50 mM±5 mM; about 4% refers to 4%±0.4%.

The terms "therapeutically effective dose," and "therapeutically effective amount," refer to that amount of a compound that results in prevention of symptoms (e.g., prevention of 80%, 85%, 90%, 95%, 96%, 97%, 98%, or 99% of symptoms, e.g., symptoms of Type III Gaucher disease in a subject diagnosed as having Type III Gaucher disease), delay of onset of symptoms, or amelioration of symptoms of Type III Gaucher disease. A therapeutically effective amount will, for example, be sufficient to treat, prevent, reduce the severity, delay the onset, and/or reduce the risk of occurrence of one or more symptoms of a disorder associated with Type III Gaucher disease. The effective amount can be determined by methods well known in the art and as described in subsequent sections of this description.

The terms "treatment" and "therapeutic method" refer to treatment of an existing disorder and/or prophylactic/preventative measures. Those in need of treatment may include individuals already having a particular medical disorder, as well as those at risk or having, or who may ultimately acquire the disorder. The need for treatment is assessed, for example, by the presence of one or more risk factors associated with the development of a disorder, the presence or progression of a disorder, or likely receptiveness to treatment of a subject having the disorder. Treatment may include slowing or reversing the progression of a disorder.

The term "treating" refers to administering a therapy in an amount, manner, and/or mode effective to improve or prevent a condition, symptom, or parameter associated with a disorder (e.g., a disorder described herein) or to prevent onset, progression, or exacerbation of the disorder, to either a statistically significant degree or to a degree detectable to one skilled in the art. Accordingly, treating can achieve therapeutic and/or prophylactic benefits. An effective amount, manner, or mode can vary depending on the subject and may be tailored to the subject.

"Infusion site reaction" as used herein refers to one or more symptom of hypersensitivity developed by a subject during or shortly after an infusion of a glucocerebrosidase enzyme replacement therapy (e.g., within 12 hours of infusion of a glucocerebrosidase enzyme replacement treatment to the subject). Symptoms include, for example, pruritus, burning, swelling or abscess at the site of infusion, flushing, urticara/angioedema, chest discomfort, tachycardia, cyanosis, respiratory symptoms and paraesthesia.

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order.

All publications, patent applications, patents, and other references mentioned herein are incorporated by reference in their entirety. In the case of conflict, the present specification, including definitions, controls. In addition, the materials, methods, and examples are illustrative only and not intended to be limiting.

The details of one or more embodiments of the invention are set forth in the accompanying drawings and the description below.

DETAILED DESCRIPTION

Figure 1:
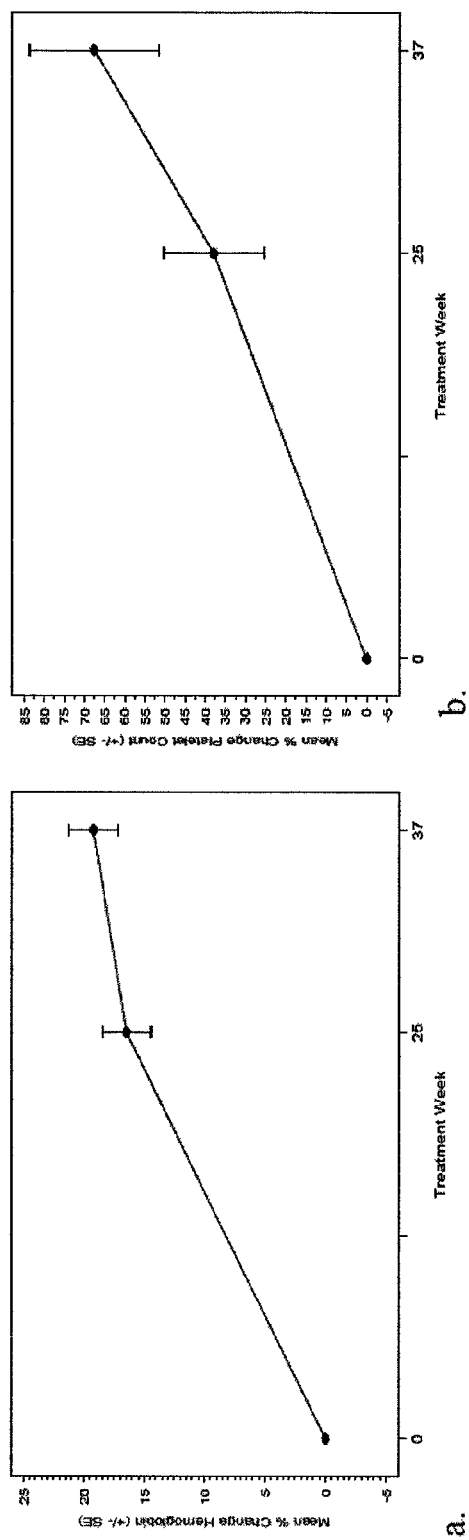
FIG. 1 (a)-(f) depicts mean % change in hematological values, organ values, and biomarkers in phase I/II trial.
Figure 1:
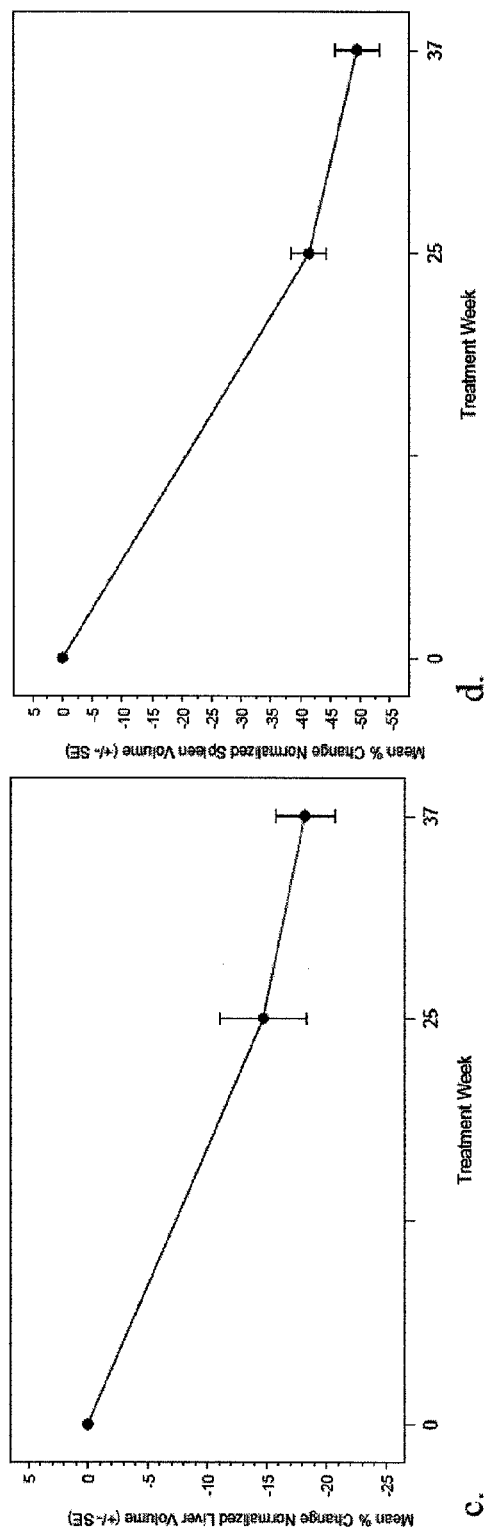
Figure 1:
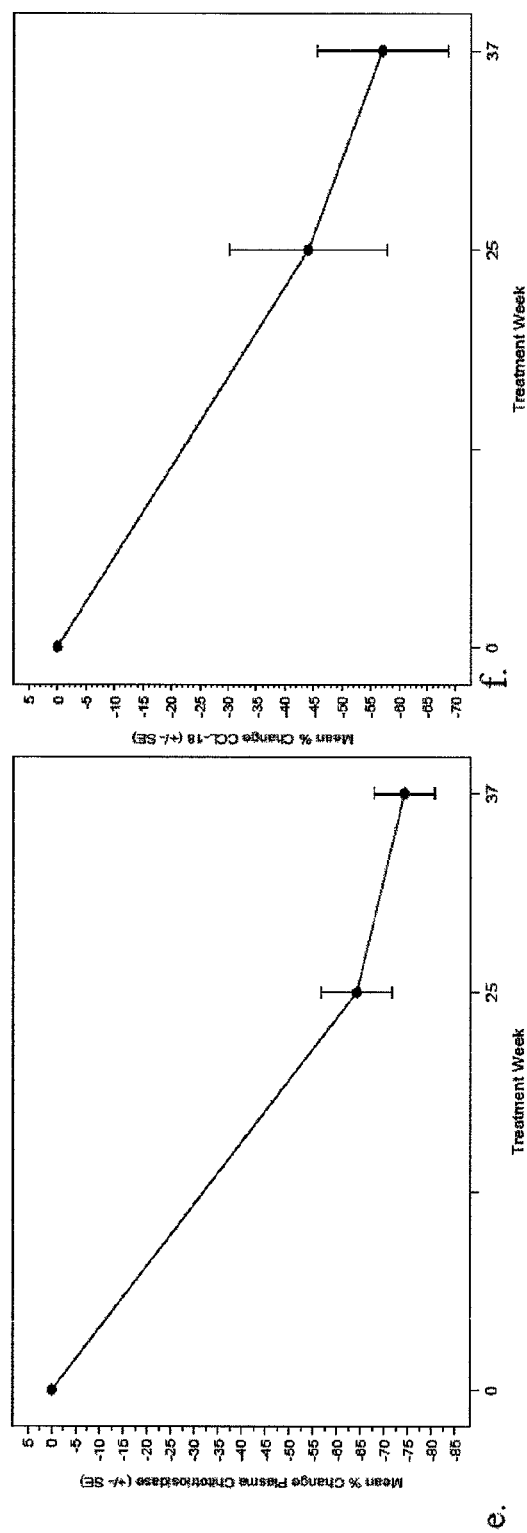

The disclosure is based, in part, on the discovery that velaglucerase elicits less of an immune response (e.g., less production of antibody, e.g., less production of neutralizing antibody) than imiglucerase upon administration to a subject (e.g., a subject with Gaucher disease). It was discovered that velaglucerase elicits less infusion site reaction upon administration to a subject (e.g., a subject with Gaucher disease) than imiglucerase and velaglucerase can result in an increase in platelet count when administered to a subject (e.g., a subject having Gaucher disease) than imiglucerase. The invention relates, inter alia, to compositions and methods for selecting a treatment for a subject with Gaucher disease, selecting subjects for treatment with velaglucerase (e.g., alone or in combination with another therapy), and methods for reducing injection site reaction in subjects undergoing treatment for Gaucher disease.

Velaglucerase

Velaglucerase is human β-glucocerebrosidase produced by gene-activation in a human cell line. Gene activation refers to targeted recombination with a promoter that activates the endogenous β-glucocerebrosidase gene in the selected human cell line. Velaglucerase is secreted as a monomeric glycoprotein of approximately 63 kDa and is composed of 497 amino acids with a sequence identical to the natural human protein. The amino acid sequence of velaglucerase is described in Zimran et al. (2007) *Blood Cells Mol Dis,* 39: 115-118.

Glycosylation of velaglucerase alfa is altered by using kifunensine, a mannosidase I inhibitor, during cell culture, which results in the secretion of a protein containing primarily high-mannose type glycans having 6-9 mannose units per glycan. A summary of the glycan structure of velaglucerase is provided below.

| Glycosylation Site | Predominant Glycan | Other Glycans |
|---|---|---|
| Asn19 | High-mannose $(Man)_9(GlcNAc)_2$ | High-mannose $(Man)_{6-8}(GlcNAc)_2$ Phosphorylated high-mannose $(Phos)_1(Man)_{8-9}(GlcNAc)_2$ GlcNAc capped phosphate $(Phos)_1(Man)_{8-9}(GlcNAc)_3$ Hybrid $(Hex)_2(Man)_3(GlcNAc)_3(Fuc)_1$ |
| Asn59 | High-mannose $(Man)_9(GlcNAc)_2$ | High-mannose $(Man)_{5-8}(GlcNAc)_2$ Phosphorylated high-mannose $(Phos)_1(Man)_{7-9}(GlcNAc)_2$ GlcNAc capped phosphate $(Phos)_1(Man)_{8-9}(GlcNAc)_3$ Hybrid $(NeuAc)_1(Gal)_1(Man)_5(GlcNAc)_3(Fuc)_1$ Complex $(NeuAc)_{0-2}(Gal)_2(Man)_3(GlcNAc)_4(Fuc)_1$ $(Gal)_3(Man)_3(GlcNAc)_5(Fuc)_1$ |
| Asn146 | High-mannose $(Man)_9(GlcNAc)_2$ | High-mannose $(Man)_{6-8}(GlcNAc)_2$ Phosphorylated high-mannose $(Phos)_1(Man)_{7-9}(GlcNAc)_2$ GlcNAc capped phosphate $(Phos)_1(Man)_9(GlcNAc)_3$ Hybrid $(NeuAc)_1(Gal)_1(Man)_5(GlcNAc)_3(Fuc)_1$ |
| Asn270 | High-mannose $(Man)_9(GlcNAc)_2$ | High-mannose $(Man)_{6-8}(GlcNAc)_2$ Phosphorylated high-mannose $(Phos)_1(Man)_{6-9}(GlcNAc)_2$ GlcNAc capped phosphate $(Phos)_1(Man)_9(GlcNAc)_3$ Hybrid $(Gal)_1Man_7GlcNAc)_3Fuc)_1$ $(NeuAc)_1(Gal)_1(Man)_5(GlcNAc)_3(Fuc)_1$ Complex $(NeuAc)_2(Gal)_2(Man)_3(GlcNAc)_4(Fuc)_1$ |
| Asn462 | Not Detected | Not Detected |

Velaglucerase has three non-contiguous domains, with the catalytic site located in domain III (residues 76-381 and 416-430), a (β/α)8 (TIM) barrel. Velaglucerase (VPRIV™) is commercially available from Shire Human Genetics Therapies, Inc. Methods of making velaglucerase are described, for example, in U.S. Pat. No. 7,138,262.

Pharmaceutical Form.

Velaglucerase (also referred to herein as velaglucerase alfa) is a sterile, white to off-white, preservative-free lyophilized powder for solution in single-use vials for intravenous (IV) infusion after reconstitution with Sterile Water for Injection.

Qualitative and Quantitative Composition.

Upon reconstitution with Sterile Water for Injection, each vial contains approximately 2.5 mg/mL (40 U/mL) of velaglucerase alfa, 50 mg/mL sucrose, 12.9 mg/mL sodium citrate dihydrate, 1.3 mg/mL citric acid monohydrate and 0.11 mg/mL polysorbate 20. Each vial contains an extractable volume of 2.0 mL for the 200 U vial and 4.0 mL for the 400 U vial. Velaglucerase is supplied in a 200 U/vial (5 mg) or 400 U/vial (10 mg) of velaglucerase alfa, one unit (U) of enzyme activity being defined as the quantity of enzyme required to convert one micromole of p-nitrophenyl β-D-glucopyranoside to p-nitrophenol per minute at 37° C.

Container and Contents.

Velaglucerase is a sterile, lyophilized powder for solution supplied in either a 5 mL (200 U/vial presentation) or 20 mL (400 U/vial presentation) type I glass vial. Each vial contains either 200 U (5 mg) or 400 U (10 mg) of velaglucerase alfa. The vials are closed with a butyl rubber stopper with a fluoro-resin coating and are sealed with an aluminum overseal with a flip-off plastic cap.

Instructions for Use.

Velaglucerase is a lyophilized powder for solution intended for intravenous infusion. Vials are single-use vials. Velaglucerase is not infused with other products in the same infusion. The total volume of infusion is delivered over a period of 60 minutes. Velaglucerase should be handled as follows:

1. Determine the number of vials to be reconstituted based on the individual patient's weight and the prescribed dose.

2. Remove the required number of vials from the refrigerator. Reconstitute 200 unit vials with 2.2 mL of Sterile Water for Injection and 400 unit vials with 4.3 mL Sterile Water for Injection. Do not shake.

3. Prior to dilution, visually inspect the solution in the vials. Do not use if the solution is discolored or if particulate matter is present.

4. Withdraw the calculated volume of drug from the appropriate number of vials.

5. Dilute the total volume required in 100 mL of 0.9% sodium chloride solution suitable for IV administration, rock gently, but do not shake.

Dose.

Velaglucerase is administered at doses between (and including) 2.5 U/kg and 60 U/kg of subject body weight, e.g., 15 U/kg to 60 U/kg (e.g., 15 U/kg, 30 U/kg, 45 U/kg, or 60 U/kg). Velaglucerase can be administered at a rate of 2 U/kg/minute, 1.5 U/kg/minute, 1 U/kg/minute or 0.5 U/kg/minute. The dose of velaglucerase is administered to the subject every other week.

Velaglucerase can be administered at a dose of 15 to 60 U/kg (e.g. 30 U/kg to 60 U/kg, e.g., 15 U/kg, 30 U/kg, 45 U/kg, or 60 U/kg), at a dose equal to or below 22.5 U/kg, at a dose between 22.5 and 37.5 U/kg, at a dose between 37.5 and 52.5 U/kg, or at a dose equal to or above 52.5 U/kg. In some embodiments, velaglucerase can be administered at a dose of 2.5 U/kg to 60 U/kg. In some embodiments, the velaglucerase can be administered every other week by intravenous infusion. In other embodiments, the velaglucerase can be administered every week by intravenous infusion. In some embodiments, the velaglucerase can be administered three times a week by intravenous infusion, e.g., at a dose of 2.5 U/kg.

In some embodiments, the infusion of the dose (e.g., a dose described herein occurs over less than 2 hours, e.g., less than 90 minutes, 80 minutes, 70 minutes, 60 minutes, 50 minutes or 45 minutes.

Recombinantly-Produced Human Glucocerebrosidase.

Other forms of recombinantly-produced human glucocerebrosidase that can be used in the compositions, assays and methods described herein. For example, imiglucerase (Cerazyme®) is recombinately produced in Chinese Hamster Ovary (CHO) cells and is commercially available. In addition, uplyso, a recombinant glucocerebrosidase (prGCD) expressed in plant cells, can be used. Plant recombinant glucocerebrosidase can be obtained by methods described, e.g., in U.S. Publication Nos: US 20090208477 and US 20080038232 and PCT Publication Nos.: WO 2004/096978 and WO 2008/132743.

Maintenance Dose

Upon improvement of a subject's condition, a maintenance dose of a treatment may be administered, if necessary. Subsequently, the dosage or frequency of administration, or both, may be reduced, as a function of the symptoms, to a level at which the improved condition is retained. Subjects may, however, require intermittent treatment on a long-term basis upon any recurrence of disease symptoms.

Subjects treated with a dose of 60 U/kg of velaglucerase every other week, and after about 15-18 months of total treatment with velaglucerase, upon showing improvements in 2 of 4 recommended therapeutic criteria (hemoglobin concentration, platelet counts, liver volume, spleen volume), were switched to a reduced dose of 30 U/kg every other week. In spite of this dose reduction, these subjects showed clinically meaningful changes in the 4 parameters (hemoglobin concentration, platelet counts, spleen volume, and liver volume) and Biomarkers (Chitotriosidase and CCL18) over the course of 48 months.

Qualitative comparison between velaglucerase and imiglucerase indicates potential additional benefit for Gaucher subjects in that, in spite of a dose reduction to almost half of that of imiglucerase, patients continued to improve clinically in the 4 parameters demonstrating a marked increase in hemoglobin concentration, continued increase in platelet count after 36 months, and a rate of decline in liver/spleen volume.

Alternative Therapy

The administration of velaglucerase (with or without the additional agent) can be used as an alternative treatment, e.g., for subjects who were previously treated with another therapy (i.e., a therapy other than velaglucerase, e.g., imiglucerase, alglucerase, uplyso, isofagomine tartrate, miglustat, or Genz112638). For example, a subject who is undergoing treatment for Gaucher disease with another therapy can be transferred to treatment with velaglucerase, e.g., if the subject is experiencing a side effect or adverse effect from the other therapy. For example, a subject who is undergoing treatment for Gaucher disease with imiglucerase can be transferred to treatment with velaglucerase, e.g., velaglucerase can be administered at the same dose and with the same frequency at which the imiglucerase was administered. For example, the subject may have experienced an infusion site reaction upon or after administration of imiglucerase and/or developed anti-imiglucerase antibodies (e.g., neutralizing antibodies to imiglucerase).

Combination Therapy

A subject who has Gaucher disease can be administered a therapy that includes velaglucerase in an amount and for a time to provide an overall therapeutic effect. The velaglucerase can be administered alone or in combination with an additional agent(s). In the case of a combination therapy, the amounts and times of administration can be those that provide, e.g., a synergistic therapeutic effect, or an additive therapeutic effect.

In some embodiments, velaglucerase can be used in combination with another therapy for Gaucher disease, e.g., a therapy other than enzyme replacement therapy, e.g., isofagomine tartrate, miglustat, or Genz112638.

Isofagomine Tartrate.

Isofagomine tartrate (AT-2101, HGT-34100, PLICERA®) ((3R,4R,5R)-3,4-Dihydroxy-5-(hydroxymethyl)piperidine L-(+)-tartrate; CAS No. 957230-65-8) selectively binds to and stabilizes glucocerebrosidase and facilitates proper trafficking of the enzyme to the lysosomes, the compartments in the cell where it is needed to break down glucocerebroside. See also U.S. Pat. No. 7,501,439.

Miglustat.

Miglustat (ZAVESCA®) ((2R,3R,4R,5S)-1-butyl-2-(hydroxymethyl)piperidine-3,4,5-triol; CAS No. 72599-27-0) is an N-alkylated imino sugar, a synthetic analogue of D-glucose and a white to off-white crystalline solid that has a bitter taste. Miglustat exhibits a large volume of distribution and has the capacity to access deep organs such as the brain, bone and lung.

Miglustat inhibits glucosylceramide synthase an essential enzyme for the synthesis of most glycosphingolipids. Miglustat is a glucosylceramide synthase inhibitor. It works by blocking an enzyme that reduces the formation of certain chemicals in the body (glucosylceramide-based glycosphingolipids). Miglustat is used to treat adults with mild to moderate type 1 Gaucher disease.

Genz112638.

Genz112638 is glucosylceramide analog given orally, and is designed to partially inhibit glucosylceramide synthase, which results in reduced production of glucosylceramide.

In some embodiments, when velaglucerase is administered in combination with an additional agent, the combination can result in a lower dose of the additional agent or velaglucerase being needed, such that side effects are reduced. The combination may result in enhanced delivery and efficacy of one or both agents.

The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of velaglucerase can also be used to reduce the dosage of another therapy, e.g., to reduce the side-effects associated with another agent that is being administered, e.g., to reduce the side-effects of a therapy other than enzyme replacement therapy. Accordingly, a combination can include administering a second agent at a dosage at least 10, 20, 30, or 50% lower than would be used in the absence of velaglucerase.

A combination therapy can include administering an agent that reduces the side effects of other therapies. For example, a corticosteroid can be administered to a subject prior to administration of the treatment for Gaucher disease to decrease infusion site reaction. As another example, iron supplement therapy can be given during the course of velaglucerase therapy.

Gaucher Disease

Gaucher disease is the most common of the lysosomal storage diseases. It is caused by a hereditary deficiency of the enzyme glucocerebrosidase (also known as acid β-glucosidase). The enzyme acts on a fatty substance glucocerebroside (also known as glucosylceramide). When the enzyme is defective, the substance accumulates, particularly in cells of the mononuclear cell lineage. Fatty material can collect in the spleen, liver, kidneys, lungs, brain and bone marrow. Symptoms may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the white of the eye (sclera). Persons affected most seriously may also be more susceptible to infection. The disease is caused by a recessive gene on chromosome 1 and affects both males and females.

Gaucher disease has three common clinical subtypes:

Type I (or non-neuropathic type) is the most common form of the disease, occurring in approximately 1 in 50,000 live births. It occurs most often among persons of Ashkenazi Jewish heritage. Symptoms may begin early in life or in adulthood and include enlarged liver and grossly enlarged spleen (together hepatosplenomegaly); the spleen can rupture and cause additional complications. Skeletal weakness and bone disease may be extensive. Spleen enlargement and bone marrow replacement cause anemia, thrombocytopenia and leucopenia. The brain is not affected, but there may be lung and, rarely, kidney impairment. Patients in this group usually bruise easily (due to low levels of platelets) and experience fatigue due to low numbers of red blood cells. Depending on disease onset and severity, type 1 patients may live well into adulthood. Many patients have a mild form of the disease or may not show any symptoms. In some embodiments, the methods and compositions described herein are used to treat type I Gaucher disease.

Type II (or acute infantile neuropathic Gaucher disease) typically begins within 6 months of birth and has an incidence rate of approximately 1 in 100,000 live births. Symptoms include an enlarged liver and spleen, extensive and progressive brain damage, eye movement disorders, spasticity, seizures, limb rigidity, and a poor ability to suck and swallow. Affected children usually die by age 2.

Type III (the chronic neuropathic form) can begin at any time in childhood or even in adulthood, and occurs in approximately 1 in 100,000 live births. It is characterized by slowly progressive but milder neurologic symptoms compared to the acute or type 2 version. Major symptoms include an enlarged spleen and/or liver, seizures, poor coordination, skeletal irregularities, eye movement disorders, blood disorders including anemia and respiratory problems. Patients often live into their early teen years and adulthood.

Bone Mineral Density

As used herein bone density (or bone mineral density) refers to the amount of matter per square centimeter of bones. Bone density can be used in clinical medicine as an indirect indicator of osteoporosis and/or fracture risk. BMD can be measured by a number of procedures, e.g., dual energy X-ray absorptiometry (DXA or DEXA), quantitative computed tomography (QCT), qualitative ultrasound (QUS), single photon absorptiometry (SPA), dual photon absorptiometry (DPA), digital X-ray radiogrammetry (DXR), and single energy X-ray absorptiometry (SEXA). Measurements can be made, e.g., over the lumbar spine, the upper part of the hip, or the forearm.

Average bone mineral density can be defined as BMC/W [$g/cm^2$], wherein BMC=bone mineral content=g/cm, and W=width at the scanned line Densitometry results can be reported in, e.g., measured density in $g\ cm^{-3}$, z-score, and t-score. Negative scores indicate lower bone density, and positive scores indicate higher.

Z-score refers to the number of standard deviations above or below the mean for the patient's age, sex and ethnicity.

T-score refers to the number of standard deviations above or below the mean for a healthy 30 year old adult of the same sex and ethnicity as the patient. The criteria of the World Health Organization are:

Normal is a T-score of −1.0 or higher.

Osteopenia is defined as less than −1.0 and greater than −2.5.

Osteoporosis is defined as −2.5 or lower, meaning a bone density that is two and a half standard deviations below the mean of a thirty year old woman.

Administration

The glucocerebrosidase enzyme replacement therapy described herein can, for example, be administered by injection, intravenously, intraarterially, subdermally, intraperitoneally, intramuscularly, or subcutaneously. Preferably the glucocerebrosidase enzyme replacement therapy is administered invtravenously, with a dosage ranging from about 10, 15, 20, 25, 30, 35, 40, 45, 50, 55, 60, 65, 70, 75 or 80 U/kg, administered every other week, or according to the requirements of the particular compound. The methods herein contemplate administration of an effective amount of compound or compound composition to achieve the desired or stated effect. Typically, the glucocerebrosidase enzyme replacement therapy can be administered as a continuous infusion, e.g., a continuous infusion over 60 minutes, 90 minutes, 120 minutes, or 150 minutes. The amount of active ingredient that may be combined with the carrier materials to produce a single dosage form will vary depending upon the host treated and the particular mode of administration. A typical preparation will contain from 5% to 95% active compound (w/w). Alternatively, such preparations contain from 20% to 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained. Subjects may, however, require intermittent treatment on a long-term basis upon any recurrence of disease symptoms.

A compound, composition or combination of this invention may be administered as a home therapy (e.g., in the subject's home, workplace, or other non-clinical (e.g., non-hospital) setting). It can be administered (e.g., via infusion) by a health care professional (e.g., nurse or physician's assistant). For example, if the subject has not experienced an adverse event (AE) (e.g., a drug-related serious AE or an infusion-related AE, e.g., an event described herein), e.g., after one, two, or three administrations (e.g., via infusion) of the compound, composition or combination, the subject is eligible to receive home therapy for subsequent administrations.

Pharmaceutical Compositions

A glucocerebrosidase enzyme replacement therapy (e.g., velaglucerase) can be incorporated into a pharmaceutical composition for administration to a subject. Such compositions typically include the glucocerebrosidase enzyme replacement therapy (e.g., velaglucerase) and a pharmaceutically acceptable carrier.

As used herein, the language "pharmaceutically acceptable carrier or adjuvant" includes solvents, dispersion media, coatings, antibacterial and antifungal agents, isotonic and absorption delaying agents, and the like, compatible with pharmaceutical administration. Supplementary active compounds can also be incorporated into the compositions.

The term "pharmaceutically acceptable carrier or adjuvant" refers to a carrier or adjuvant that may be administered to a subject, together with glucocerebrosidase, and which does not destroy the pharmacological activity thereof and is nontoxic when administered in doses sufficient to deliver a therapeutic amount of the glucocerebrosidase.

A pharmaceutical composition is formulated to be compatible with its intended route of administration. Examples of routes of administration include parenteral, e.g., intravenous, intradermal and subcutaneous. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

For intravenous administration, suitable carriers include Sterile Water for Injection, physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars such as sucrose, polyalcohols such as manitol, sorbitol, sodium chloride in the composition. Prolonged absorption of the injectable compositions can be brought about by including in the composition an agent which delays absorption, for example, aluminum monostearate and gelatin.

The pharmaceutical composition can include, for example, sterile water for injection, sucrose, sodium citrate, citric acid and polysorbate.

Sterile injectable solutions can be prepared by incorporating the glucocerebrosidase in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The pharmaceutical compositions can be included in a container, pack, or dispenser together with instructions for administration.

Kit

A glucocerebrosidase enzyme replacement therapy (e.g., velaglucerase) can be provided in a kit. The kit includes (a) the glucocerebrosidase enzyme replacement therapy, e.g., a composition that includes the glucocerebrosidase enzyme replacement therapy, and (b) informational material. The informational material can be descriptive, instructional, marketing or other material that relates to the methods described herein and/or the use of the glucocerebrosidase enzyme replacement therapy for the methods described herein. For example, the informational material describes methods for administering the glucocerebrosidase enzyme replacement therapy to treat Gaucher disease.

In one embodiment, the informational material can include instructions to administer the glucocerebrosidase enzyme replacement therapy in a suitable manner, e.g., in a suitable dose, dosage form, or mode of administration (e.g., a dose, dosage form, or mode of administration described herein). In another embodiment, the informational material can include instructions for identifying a suitable subject, e.g., a human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the modulator and/or its use in the methods described herein. Of course, the informational material can also be provided in any combination of formats.

In addition to the glucocerebrosidase enzyme replacement therapy, the composition of the kit can include other ingredients, such as a solvent or buffer, a stabilizer or a preservative, and/or a second agent for treating Gaucher disease. Alternatively, the other ingredients can be included in the kit, but in different compositions or containers than the glucocerebrosidase enzyme replacement therapy. In such embodiments, the kit can include instructions for admixing the glucocerebrosidase enzyme replacement therapy and the other ingredients (e.g., reconstituting a lyophilized therapy and/or diluting the reconstituted therapy prior to administration), or for using the glucocerebrosidase enzyme replacement therapy together with the other ingredients.

The glucocerebrosidase enzyme replacement therapy can be provided in any form, e.g., liquid, dried or lyophilized form. It is preferred that the glucocerebrosidase enzyme replacement therapy be substantially pure and/or sterile. When the glucocerebrosidase enzyme replacement therapy is provided in a liquid solution, the liquid solution preferably is an aqueous solution, with a sterile aqueous solution being preferred. When the glucocerebrosidase enzyme replacement therapy is provided as a dried form, reconstitution generally is by the addition of a suitable solvent. The solvent, e.g., sterile water or buffer, can optionally be provided in the kit.

The kit can include one or more containers for the composition containing the glucocerebrosidase enzyme replacement therapy. In some embodiments, the kit contains separate containers, dividers or compartments for the glucocerebrosidase enzyme replacement therapy (e.g., in a composition) and informational material. For example, the glucocerebrosidase enzyme replacement therapy (e.g., in a composition) can be contained in a bottle, vial, or syringe, and the informational material can be contained in a plastic sleeve or packet. In other embodiments, the separate elements of the kit are contained within a single, undivided container. For example, the glucocerebrosidase enzyme replacement therapy (e.g., in a composition) is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the glucocerebrosidase enzyme replacement therapy (e.g., in a composition). For example, the kit includes a plurality of syringes, ampules, foil packets, or blister packs, each containing a single unit dose of the glucocerebrosidase enzyme replacement therapy. The containers of the kits can be air tight and/or waterproof.

The glucocerebrosidase enzyme replacement therapy (e.g., in a composition) can be administered to a subject with Gaucher disease. The method can include evaluating a subject, e.g., as described herein and thereby identifying a subject being in need of treatment with the glucocerebrosidase enzyme replacement therapy.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

The introduction of enzyme therapy has significantly impacted the natural history of type 1 Gaucher disease. Unfortunately, the existence of a single therapeutic option represents an inherent vulnerability in the treatment of patients with type 1 Gaucher disease. Approximately 15% of imiglucerase treated patients have been reported to develop IgG antibodies and approximately half of these patients reported symptoms of hypersensitivity (Starzyk K et al., *Molec Genet Metab.* 2007; 90:157-163). Globally, the dependence upon a single product in the treatment of Gaucher disease has been underscored by the recent shortage of imiglucerase (Steinbrook R et al., *N Engl J. Med.* 2009; 361:1525-1527). Among those receiving imiglucerase infusions, an unknown number of patients require pre-medication to mitigate a potential immune-mediated response. In some instances patients require hydrocortisone, which itself is associated with medical risks including AVN. Furthermore, recently published data suggest that 59% of GD1 patients treated with imiglucerase fail to achieve at least one therapeutic goal following a minimum of 4 years of treatment regardless of dose and duration of treatment (Weinreb N et al., *Am J Hematol.* 2008; 83: 890-895).

Velaglucerase alfa is a novel enzyme replacement therapy (ERT) with unique characteristics (wild type amino acid sequence and high α-mannosyl content) that distinguishes it from imiglucerase. Some of the examples provided below describe clinical trials and extension studies to evaluate the safety and efficacy of velaglucerase alfa. These are the first clinical trial involving an ERT to implement dose reduction and home therapy.

Example 1

TKT025 and TKT025EXT Studies

Summary

This example describes a nine-month Phase I/II open-label, single center trial of velaglucerase alfa (TKT025) and ongoing extension (TKT025EXT) study conducted to evaluate safety and efficacy of velaglucerase alfa.

The primary objective of the Phase I/II trial was to assess the safety of velaglucerase alfa administered intravenously at a dose of 60 U/kg every-other-week for nine months in adult patients with symptomatic type 1 (non-neuronopathic) Gaucher disease (GD1). The secondary objective of this trial was to assess the clinical activity of velaglucerase alfa on key disease features (Barton N W et al. *N Engl J. Med.* 1991; 324:1464-1470). The extension study was similarly designed to evaluate the long-term safety and assess the effects of velaglucerase alfa on four disease measures, hemoglobin concentration, platelet count, liver volume, and spleen volume (Barton N W et al. *N Engl J Med.* 1991; 324:1464-1470).

Twelve symptomatic adult patients with type 1 Gaucher disease and intact spleens received velaglucerase alfa (60 U/kg/infusion) during the Phase I/II study. Originally thirteen patients were screened to participate in the study, but one was exluded because of the presence of anti-imiglucerase antibody. An extension study was offered to patients who completed the trial and a step-wise dose reduction (to 30 U/kg/infusion) was instituted. Eleven patients completed Phase I/II; ten entered the extension study; nine patients reached 39 months in the extension. No drug-related serious adverse events or withdrawals, and no antibodies were observed. Home therapy was successfully implemented during the extension. Statistically significant improvements (p<0.004) were noted in mean percent change from baseline to nine months and baseline to 48 months for hemoglobin (+19.2%, +21.7% respectively), platelet counts (+67.6%, +157.8% respectively), normalized liver volume (−18.2%, −42.8% respectively), and normalized spleen volume (−49.5%, −79.3% respectively). These significant clinical changes and safety profile led to Phase III trials and highlight the potential of velaglucerase alfa as alternative therapy for type 1 Gaucher disease.

Methods

The Phase I/II and extension study was conducted in a single center (Gaucher Clinic, Shaare Zedek Medical Center; Jerusalem, Israel).

Patients:

Adult, symptomatic, enzymatically confirmed patients with GD1 were screened. Eligibility criteria included age ≥18 years-old, an intact spleen, disease-related anemia (hemoglobin values at least 1 g/dL below lower limit of normal (LLN) for gender), thrombocytopenia (platelet counts below the LLN), and a negative result for hepatitis B and C antigen and human immunodeficiency virus. Patients were eligible if they were naïve to ERT or had not received imiglucerase within the 12 months prior to enrollment and were imiglucerase antibody-negative. Patients were excluded if they had received an investigational therapy for any other indication ≤30 days prior to enrollment or if they could not comply with the protocol for either medical or non-medical reasons.

Preparation and Dosing:

Velaglucerase alfa was supplied by Shire HGT as a lyophilized product and shipped at 2°-8° C. The product was reconstituted with preservative-free, sterile water for injection. The appropriate amount of velaglucerase alfa (based on body weight) was slowly mixed with normal saline to a final volume of 100 mL. The diluted velaglucerase alfa was administered intravenously across a 0.2 μm filter for a period of 60 minutes (maximum rate of 1.5 mg/kg/hour; 1 U/kg/min).

During the Phase I/II study, the first three patients received velaglucerase alfa on an every-other-week schedule at the trial site. Dose escalation was undertaken for the first three patients whereby dosing doubled from an initial dose of 15 U/kg until a final dose of 60 U/kg was achieved. The second and third patients received their initial 15 U/kg infusion only after a 7-day observation period was completed for the first and second patients respectively. Once the third patient received a single dose of 60 U/kg and was observed for a period of 7 days, nine additional patients were enrolled and received infusions of 60 U/kg every-other-week for a total of 20 doses. The patients who had undergone dose escalation were continued on an every-other-week schedule for 17 further infusions at 60 U/kg for a total of 20 infusions.

During the extension study, all patients were continued at 60 U/kg/infusion every-other-week. After approximately 6-9 months of the extension study, patients who achieved at least 2 of the 4 therapeutic goals for improvement in anemia, thrombocytopenia, hepatomegaly, and/or splenomegaly (Pastores G M et al., *Semin Hematol.* 2004; 41:4-14) were transitioned to 45 U/kg/infusion every-other-week for three months and then transitioned to 30 U/kg/infusion every-other-week. This convention of dose reduction based on achievement of therapeutic goals is in accordance with recommendations for individualization of ERT in patients on imiglucerase (Andersson H C et al., *Genet Med.* 2005; 7:105-110).

In addition, the seven patients residing in Israel were transitioned to home therapy during the extension phase.

Safety Assessments:

Safety was evaluated throughout the study by every-other-week assessments of adverse events (including infusion-related reactions), concomitant medications, and vital signs performed before, during, and after infusions. Additional safety assessments were conducted approximately every 12 weeks and included physical examinations, clinical laboratory tests (hematology, serum chemistry, urinalysis, and pregnancy test), 12-lead electrocardiograms and echocardiograms at the trial site. Determination of the presence of anti-velaglucerase alfa antibodies were conducted at 3-month intervals at Shire HGT.

Antibody Assays:

All participants were screened for circulating anti-velaglucerase alfa antibodies using a validated indirect ELISA. Microwell plates were coated with velaglucerase alfa, washed, and blocked with bovine serum albumin to limit non-specific antibody binding. They were incubated with patient serum samples diluted 100-fold in phosphate buffered saline containing 0.05% Tween 20 for 60 minutes at 37° C. The microwells were washed and then incubated with the appropriate horseradish peroxidase (HRP)-conjugated secondary antibody. They were separately probed with the following HRP-antibody, isotype-specific conjugates: 1) goat anti-human IgG Fc, 2) goat anti-human IgA α-chain, 3)

goat anti-human IgM μ-chain, or 4) goat anti-human IgE 8-chain secondary antibodies. The microwells were washed one final time and incubated with the HRP chromogenic substrate 3,3',5,5' tetramethyl benzidine. The reaction was stopped by the addition of 2N sulfuric acid, and the absorbance of each well was quantified at 450 nm ($A_{450}$) using a Molecular Devices SPECTRAmax Plus384 plate reader and SOFTMax PRO software. Antibody-positive serum samples were obtained from patients receiving imiglucerase. These patient antibodies cross-reacted with velaglucerase alfa and were used as human positive controls in the screening assay for anti-velaglucerase antibodies. These sera were therefore both anti-imiglucerase and anti-velaglucerase alfa positive. Negative, as well as positive, human serum controls were included within every assay plate.

A robust ELISA antibody positive cutpoint absorbance for anti-velaglucerase alfa antibodies was established from the mean absorbance of ERT-naïve Gaucher patient serum samples (N=108). Parametric analysis of ELISA absorbance data was used to calculate the antibody-positive lower limit (mean plus 1.645× standard deviations; where 1.645 is the $95^{th}$ percentile of the normal distribution, thus potentially accepting a 5% false-positive rate) for each antibody isotype (Mire-Sluis A R et al., *J Immunol Methods.* 2004; 289:1-16). The ELISA $A_{450}$ background for ERT-naïve Gaucher serum samples was calculated to be 0.040 for all anti-velaglucerase alfa antibody isotype assays. The ELISA antibody positive cutoff was established as a ratio ≥2.0 and an $A_{450} \geq 0.040$, where ratio is the $A_{450}$ of a patient sample taken at any time point, divided by the $A_{450}$ of the patient sample taken at baseline prior to the first ERT treatment. Any sample exceeding the ELISA positive cutoff would have been confirmed by a quantitative radioimmunoprecipitation assay and tested for neutralizing antibodies; however no sample achieved the established cutoff criteria (Mire-Sluis A R et al., *J Immunol Methods.* 2004; 289:1-16).

Clinical Activity:

The main efficacy assessments of hemoglobin concentration and platelet counts were evaluated at pre-determined tri-monthly intervals. Liver and spleen volumes were measured using quantitative abdominal MRI (on the same model apparatus) performed at baseline, six- and nine-months (at the Hadassah-Hebrew University Medical Center), and at 24, 33, and 45 months (at the MOR-MAR Imaging unit) during the extension study. Liver and spleen volumes were assessed at the end of the trial by a radiologist blinded to the patient's identity and the sequence by which the quantitative abdominal MRIs were performed. Chitotriosidase and CCL18 were measured at the Academic Medical Center; Amsterdam, the Netherlands.

Statistical Analysis:

The safety population, which was also the intent-to-treat population, was defined as all enrolled patients receiving at least one infusion (partial or full) of velaglucerase alfa, and was used for all clinical activities. No imputation was utilized.

For the primary clinical activity parameters of hemoglobin concentration, platelet count, and liver and spleen volumes, the null hypothesis is that there is no difference between the baseline value and end-of-the study value (nine months), and baseline value and end-of-48 month value. (i.e., the difference between the members of each pair of observation has median value zero.) Comparisons were performed using two-tailed hypothesis testing at the 5% level of significance. Differences between baseline and end of period values were analyzed using the Wilcoxon signed-rank test. Changes from baseline were calculated and the percentage changes from baseline are summarized using descriptive statistics.

For secondary clinical activity parameters, observed data, change from baseline, and percent change from baseline were summarized by visit including mean, standard error (SE) and median. No formal statistical testing was applied to these data sets.

Results from TKT025 Study (9M, 60 U/Kg Velaglucerase Alfa)

Velaglucerase alfa was well tolerated and no patient developed antibodies. Clinically and statistically significant improvements in hematological parameters and organ volumes were observed as early as 3 to 6 months (Table 1).

TABLE 1

TKT025 Clinical Results (N = 12)

| Clinical Activity Parameter | Median Baseline Value | Mean Change from Baseline ± standard deviation | | |
|---|---|---|---|---|
| | | Month 3 | Month 6 | Month 9 |
| Hemoglobin concentration (g/dL) | 10.95 | 1.24 ± 0.90 | 1.92 ± 0.82 | 2.24 ± 0.89 |
| Platelet count (×10⁹/L) | 57.5 | 8.9 ± 11.20 | 23.4 ± 24.63 | 40.6 ± 30.68 |
| Liver (% of body weight) | 4.43 | NA | −0.67 ± 0.64 | −0.79 ± 0.48 |
| Spleen (% of body weight) | 3.63 | NA | −1.62 ± 0.67 | −1.89 ± 0.75 |

Demographics and Disposition:

A total of thirteen patients were screened and all consented to participate in this study; one patient (0004) was excluded because of imiglucerase antibodies. All the patients were treatment-naïve at advent according to the protocol by virtue of not having been exposed to any Gaucher-specific therapy in the 12 months prior to enrolment although in the more distant past, 2 patients (0008 and 0009) had each received 3 infusions of imiglucerase, one patient (0003) had been exposed to miglustat, and two patients (0005 and 0007) had been exposed to both miglustat and imiglucerase.

The intent-to-treat population (Table 2) included twelve patients who received at least one dose of velaglucerase alfa; of these, 11 patients (92%) completed the Phase VII study (one patient, 0006, withdrew after a sudden death in the family withdrew consent after receiving three infusions).

At enrollment of the Phase VII trial, seven patients (58%) were female; mean age was 41.7 (SD±17.3; range 19-70) years; mean weight was 59.6 (SD±9.1 range 50-73) kg and mean height was 169 (SD±8.0; range 160-184) cm. Two patients (16.7%) had avascular necrosis (AVN) of the hip joint at enrollment and another had a destructive lesion in each ankle. Table 2 provides the demographic, genotypic, and clinical characteristics at baseline, as well as the clinical findings of each intent-to-treat patient at key data collection points within the Phase VII studies.

TABLE 2

Patient Demographics and Characteristics

| Patient | Age | Sex | Genotype | Hemoglobin g/dL | | | | | Platelets, 10/L | | | | | Normalized spleen volume, multiple of normal | | | | | Normalized liver volume, multiple of normal | | | | |
|---|---|---|---|---|---|---|---|---|---|---|---|---|---|---|---|---|---|---|---|---|---|---|---|
| | | | | BL | 6 Mo | 9 Mo | 24 Mo | 48 Mo | BL | 6 Mo | 9 Mo | 24 Mo | 48 Mo | BL | 6 Mo | 9 Mo | 24 Mo | 45 Mo | BL | 6 Mo | 9 Mo | 24 Mo | 45 Mo |
| 1 | 24 | F | N370S/N370S | 10.8 | 12.2 | 12.5 | 12.4 | 12.7 | 80 | 123 | 149 | 155 | 130 | 17.5 | 11.0 | 10.0 | 8.0 | 6.5 | 2.3 | 1.8 | 1.9 | 1.5 | 1.2 |
| 2 | 62 | M | N370S/L444P | 12.7 | 14.1 | 14.8 | 14.3 | 14.2 | 69 | 74 | 90 | 127 | 142 | 11.0 | 7.5 | 6.0 | 4.0 | 3.0 | 1.0 | 1.0 | 0.9 | 1.0 | 0.8 |
| 3 | 35 | M | N370S/Other | 13.5 | 15.7 | 16.5 | 15.7 | 16.0 | 48 | 95 | 128 | 140 | 151 | 17.5 | 8.0 | 6.5 | * | * | 2.2 | 1.6 | 1.7 | 1.3 | 1.2 |
| 5 | 35 | F | N370S/N370S | 10.6 | 11.7 | 12.0 | | | 52 | 68 | 72 | | | 32.5 | 23.0 | 24.5 | | | 1.7 | 1.8 | 1.6 | | |
| 6 | 44 | F | N370S/IVS2 + 1 | 10.9 | | | | | 56 | | | | | 16.0 | | | | | 2.1 | | | | |
| 7 | 42 | F | N370S/N370S | 10.5 | 12.5 | 12.5 | 13.8 | 13.0 | 37 | 32 | 39 | 42 | 95 | 21.0 | 13.5 | 13.0 | 7.0 | 4.0 | 1.8 | 1.7 | 1.6 | 1.4 | 1.0 |
| 8 | 23 | F | N370S/RecNc1 | 10.0 | 12.1 | 11.8 | 12.7 | 14.2 | 65 | 137 | 150 | 154 | 203 | 19.0 | 9.0 | 7.0 | 3.5 | 3.5 | 2.2 | 1.6 | 1.6 | 1.2 | 1.2 |
| 9 | 25 | M | N370S/RecNc1 | 12.6 | 15.8 | 15.9 | 15.8 | 15.1 | 69 | 97 | 120 | 178 | 183 | 28.0 | 12.5 | 10.0 | 4.0 | 2.5 | 2.0 | 1.4 | 1.4 | 1.1 | 0.9 |
| 10 | 60 | F | N370S/N370S | 10.1 | 11.1 | 12.5 | 12.4 | 12.4 | 48 | 60 | 86 | 121 | 139 | 19.0 | 11.0 | 8.5 | 3.5 | 3.0 | 1.4 | 1.2 | 1.0 | 0.8 | 0.8 |
| 11 | 18 | F | N370S/Other | 11.0 | 13.8 | 13.6 | 13.6 | 12.6 | 59 | 98 | 110 | 122 | 130 | 15.0 | 9.0 | 8.0 | 5.0 | 3.5 | 1.4 | 1.1 | 1.0 | 1.1 | 0.8 |
| 12 | 69 | M | N370S/N370S | 13.5 | 14.4 | 14.1 | | | 59 | 65 | 99 | | | 13.0 | 9.0 | 7.5 | | | 1.0 | 1.0 | 1.0 | | |
| 13 | 56 | M | N370S/V394L | 12.9 | 15.9 | 16.6 | 15.4 | 16.0 | 46 | 40 | 36 | 111 | 135 | 19.5 | 10.0 | 8.0 | 4.5 | 2.5 | 1.0 | 0.8 | 0.8 | 0.8 | 0.7 |

BL, baseline;
Mo, month;
M, Male;
F, Female;
*Spleen volume not interpretable due to technical artifact.

Patient demographics and characteristics at baseline and at select points of evaluation during the Phase I/U and extension trials including the last values collected for each clinical parameter for the cohort. Normalized liver and spleen volumes are defined as 2.5% and 0.2% respectively of total body weight in kilograms (Pastores G M et al., Semin Hematol. 2004; 41:4-14). Multiples of normal is the observed organ volume divided by the normalized organ volume. By 24 months, all patients demonstrated normalization of hemoglobin concentrations and all but one patient demonstrated platelet counts greater than $100*10^9$/L.

Results of liver and spleen magnetic resonance imaging (MRI) scans were blinded and interpreted by a single reviewer to minimize bias. Collection of baseline data from other clinical parameters including PFTs (pulmonary function tests), MRI of the femora and lumbar spine, and bone densitometry were also performed at various time points throughout the study.

The study was comprised of 2 phases, a dose escalation phase and a continuous dose phase. During the dose escalation phase, the first patient was enrolled and administered Intravenous (IV) velaglucerase alfa 15 U/kg, then was followed for 7 days for assessment of safety. After safety was confirmed for the first patient, 2 additional patients were enrolled and administered IV velaglucerase alfa 15 U/kg and followed for 7 days for assessment of safety. After safety was confirmed for all 3 patients who received the 15 U/kg dose, the next two higher doses (30 and 60 U/kg) were administered in the same fashion. Once safety was confirmed for all 3 patients, an additional 9 patients were enrolled and administered the 60 U/kg dose. All patients then received the 60 U/kg dose every other week for a total of 20 doses of velaglucerase alfa.

Pharmacokinetics (PK) in humans were evaluated at Weeks 1, 3, 5, and 37/39 in TKT025. Additional PK studies were conducted at Week 65 of Study TKT025EXT. Velaglucerase alfa was rapidly cleared from blood with first-order elimination kinetics at each evaluation. Elimination half-life values for patients following initial exposure to velaglucerase alfa and following repeat administration of velaglucerase alfa were similar. In contrast, clearance and apparent volume of distribution values were reduced following repeat administration of velaglucerase alfa.

Statistically significant mean increases from baseline in hemoglobin concentration and platelet count were observed 3 months after initiation of biweekly dosing of 60 U/kg velaglucerase alfa in Study TKT025. By Week 25 (Month 6) in TKT025, mean hemoglobin concentrations were 13.57 g/dL (within normal range) and remained within normal ranges for the rest of the study. At the end of the study, 10 of 11 patients experienced normalization of hemoglobin concentration. Statistically significant increases from baseline ($57.3 \times 10^3$/mm$^3$) in mean platelet count were observed by Week 13 (Month 3) and continued throughout the study. At Week 37, mean platelet counts had increased to $98.1 \times 10^3$/mm$^3$.

Additionally, statistically significant reductions from baseline in mean and normalized (corrected by percentage of body weight) liver and spleen volumes were observed 6 (Week 25) and 9 months (Week 37) after initiating velaglucerase alfa treatment. Marked reductions in biomarker values (serum chitotriosidase and Chemokine (C-C motif) ligand 18 [CCL18]) were observed by Month 3. Overall, mean improvement in all of these parameters was continual during the course of velaglucerase alfa administration. Moreover, each patient experienced improvement in at least 2 of the 4 therapeutic parameters specific for Gaucher disease (e.g., hemoglobin concentrations, platelet counts, and spleen and liver volumes).

Figure 2:
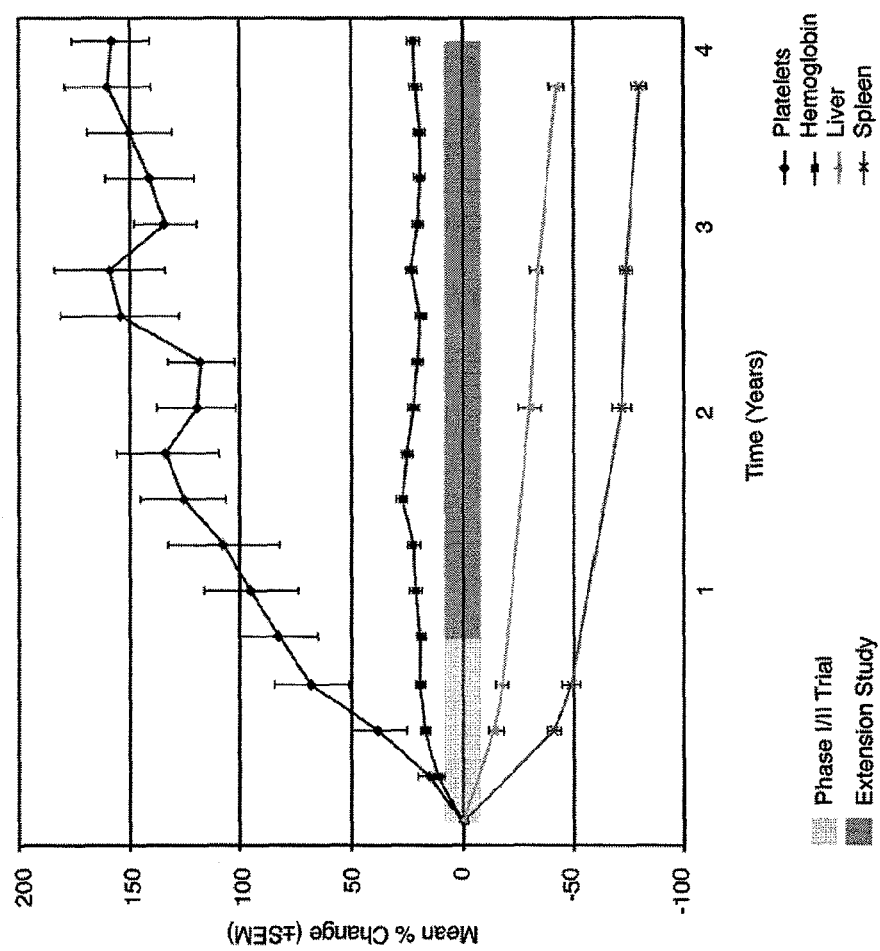
FIG. 2 depicts mean % change of key clinical parameters in phase I/II and extension trials.

In summary, FIGS. 1A-1F presents the mean percent change in hematological parameters, organ volumes, and biomarkers for the Phase I/II study. A marked increase in (a) hemoglobin concentration and (b) platelet count is observed during weeks 25 and 37 along with a marked reduction in (c) liver and (d) spleen volumes. Although biomarker sampling for (e) chitotriosidase and (f) CCL18 was incomplete, a general decrease in both biomarkers relative to baseline is observed per patient over time. Statistically significant improvements ($p<0.003$) were noted in the mean percent change from baseline to nine months for hemoglobin concentration (+21.7%), platelet counts (+67.6%), normalized liver volume (−18.2%), and normalized spleen volume (−49.5%), with statistically significant improvements from baseline in both hemoglobin concentration and platelet counts achieved within the first 3 months (FIG. 2). In FIG. 2, the mean percent change in hemoglobin concentration, platelet counts, liver volume and spleen volume is plotted across time and demarcated for both the Phase I/II and extension studies. A statistically significant change from baseline is observed from baseline to 9 months ($p<0.003$) for each parameter. The most marked changes were observed for platelet count and spleen volume.

In TKT025, all 12 patients experienced 1 or more AEs (Adverse events); in total, 103 AEs were reported. Two AEs (dizziness and hyperhidrosis) were reported by 1 patient during the 15 U/kg dose; the remaining 101 AEs were reported by patients receiving the 60 U/kg dose. The most frequently reported AEs were dizziness, bone pain, and headache (5 patients each; 41.7%). Arthralgia, back pain, pain in the extremities, influenza, upper abdominal pain, and asthenia each occurred in 3 patients (25%). All AEs were mild (Grade 1) except 1 event of bone pain, which was of moderate (Grade 2) severity and unrelated to study drug. None of the 103 AEs was considered severe or life threatening (Grade 3 or 4). No patient was withdrawn from the study due to an adverse event.

The majority of AEs observed during TKT025 were determined by the investigator as not related to administration of study drug (Table 3A). Ten (10) patients experienced 22 AEs that were considered possibly or probably related to study drug; most commonly dizziness (3 patients); back pain, bone pain, headache, increased body temperature, and nausea (each 2 patients). Nine (9) patients experienced a total of 17 infusion-related adverse events, which were defined in the protocol as an AE that occurred on the day of the infusion, began either during or after the infusion, and was judged as possibly or probably related to study drug. These AEs included dizziness, headache, back pain, bone pain, body temperature increased, each occurring in 2 patients. All infusion-related adverse events were reported for patients receiving the 60 U/kg dose. One patient was dose-increased to 60 U/kg/infusion every-other-week 24 months following dose reduction because of worsening bone pain but experienced no relief following dose increase. Therefore, there was no drug-related serious adverse events, regardless of infusion setting. No pre-medications were administered and no patient withdrew due to an adverse event. No patient developed antibodies to velaglucerase alfa.

TABLE 3A

Treatment emergent adverse events determined to be possibly or probably related to velaglucerase alfa (GA-GCB) administration observed during the phase I/II Trial (TKT025)

| System Organ Class Preferred Term | velaglucerase alfa 60 U/kg EOW n = 12 patients | |
| --- | --- | --- |
|  | Patients, n (%) | Events, n (%) |
| Any Adverse Event | 10 (83.3) | 22 (21.8) |
| Nervous System Disorders | | |
| Dizziness | 3 (25.0) | 4 (4.0) |
| Headache | 2 (16.7) | 2 (2.0) |
| Burning sensation | 1 (8.3) | 1 (1.0) |
| Migraine | 1 (8.3) | 3 (3.0) |
| Tremor | 1 (8.3) | 1 (1.0) |
| Gastrointestinal Disorders | | |
| Nausea | 2 (16.7) | 2 (2.0) |
| Upper abdominal pain | 1 (8.3) | 1 (1.0) |
| Musculoskeletal and Connective Tissue Disorders | | |
| Back pain | 2 (16.7) | 2 (2.0) |
| Bone pain | 2 (16.7) | 2 (2.0) |
| Pain in extremity | 1 (8.3) | 1 (1.0) |
| General Disorders and Administration Site Conditions | | |
| Asthenia | 1 (8.3) | 1 (1.0) |
| Investigations | | |
| Body temperature increased | 2 (16.7) | 2 (2.0) |

Percentages of patients are based on the total number of patients in the treatment group. Adverse events are coded using MedDRA Version 7.0 dictionary. EOW: every other week.

Results from TKT025EXT (Long-Term, 30-60 U/Kg Velaglucerase Alfa)

Summary:

TKT025EXT is an open-label extension study of velaglucerase alfa therapy in patients with type 1 Gaucher disease who completed study TKT025. The primary objective of TKT025EXT is to evaluate the long-term safety of velaglucerase alfa when administered IV at a dose of 30 or 60 U/kg every other week for a total of 4 years. The secondary objective is to continue to assess the effects of velaglucerase alfa on clinical activity in these patients as measured in hematological parameters and reductions in liver and spleen volumes. Plasma chitotriosidase and CCL18 as well as PFTs, MRI of the femoral neck and lumbar spine, skeletal survey, and bone densitometry are also being evaluated.

Figure 3:
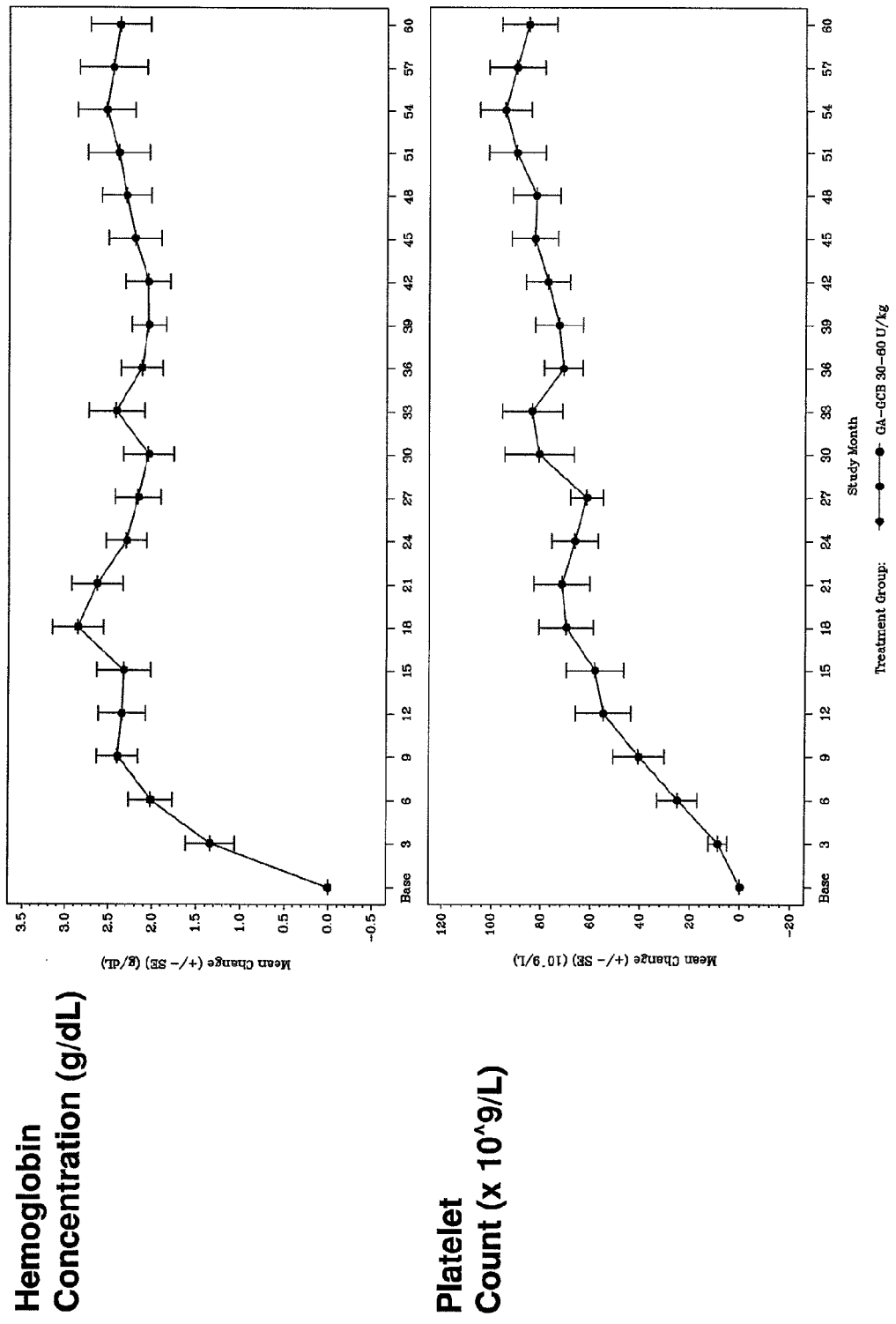
FIG. 3 depicts TKT025EXT (N=10) mean hematological parameters change from baseline in TKT025.
Figure 4:
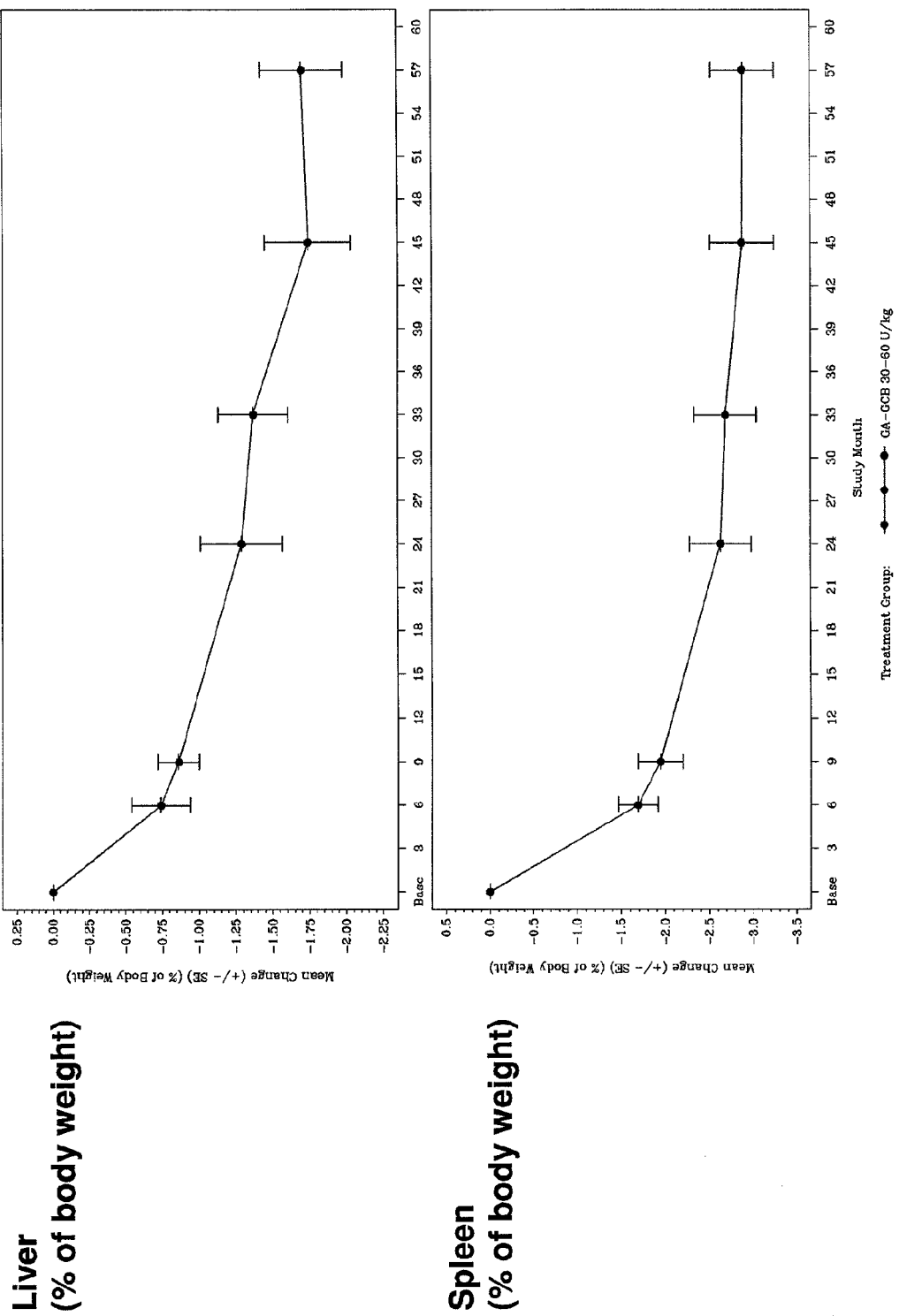
FIG. 4 depicts TKT025EXT (N=10) mean normalized organ volumes change from baseline in TKT025.

Ten patients were elected to participate in this clinical study. After 60 months of cumulative treatment (TKT025+TKT025EXT) velaglucerase alfa was well tolerated and no patient developed antibodies. Continued and sustained clinically and statistically significant improvements in hematological parameters and organ volumes continue to be seen (Table 4). FIG. 3 shows the increase of mean hemoglobin concentration and platelet count from baseline in the patients treated with velaglucerase alfa for 60 months. FIG. 4 shows the decrease of mean liver and spleen volumes from baseline in patients treated with velaglucerase alfa for 60 months.

TABLE 4

TKT025EXT Clinical Results (N = 10)

| Clinical Activity Parameter | Median Baseline Value | Mean Change from Baseline [95% Confidence Interval] | | | |
|---|---|---|---|---|---|
| | | Month 24 | Month 36[a] | Month 48[a] | Month 60[a] |
| Hemoglobin concentration (g/dL) | 10.90 | 2.30 [1.78, 2.82] | 2.13 [1.59, 2.67] | 2.31 [1.66, 2.96] | 2.38 [1.60, 3.16] |
| Platelet count (×10⁹/L) | 55.5 | 66.5 [45.3, 87.7] | 71.1 [53.6, 88.6] | 82.3 [60.1, 104.5] | 85.1 [59.8, 110.4] |
| Liver (% of body weight) | 4.40 | −1.29 [−1.91, −0.67] | −1.37 [−1.90, −0.84] | −1.74 [−2.40, −1.08] | −1.70 [−2.33, −1.07] |
| Spleen (% of body weight) | 3.80 | −2.63 [−3.44, −1.83] | −2.69 [−3.51, −1.87] | −2.88 [−3.72, −2.03] | −2.89 [−3.72, −2.06] |

[a]Organ volumes were assessed at Months 33, 45 and 57 from the start of TKT025

Demographics and Disposition:

Upon completion of Week 41 evaluations in TKT025, patients were eligible to participate in TKT025EXT. Of the 11 patients who completed Study TKT025, 10 patients entered Study TKT025EXT. One patient (0012) did not consent to enter the extension study because of the inconvenience of every-other-week hospital attendance, and one patient (0005) withdrew from the extension study because of pregnancy. Table 2 provides the demographic, genotypic, and clinical characteristics at baseline, as well as the clinical findings of each intent-to-treat patient at key data collection points within the extension studies.

All patients enrolled initially received velaglucerase alfa 60 U/kg every other week. Doses were titrated down to 30 U/kg provided patients had improvements in hematological parameters (hemoglobin concentration or platelet levels) and/or improvements in organ volumes (liver or spleen) after 1 year of cumulative treatment. All 10 patients initially enrolled in TKT025EXT met the required dose reduction criteria and were transitioned to the 30 U/kg dose.

All 9 patients in TKT025EXT had hemoglobin concentration and platelet count data available up to Month 42, while 3 patients had data available up to Month 45. The mean (standard error [SE]) changes in hemoglobin from pretreatment baseline at 42 months were 2.18 (0.25) g/dL (p=0.004), corresponding to a mean percent changes from pretreatment baseline of 19.0%. With respect to platelet count, the mean (SE) change from pretreatment baseline was 82.1 (8.4)×10³/mm³ (p=0.004) at Month 42, corresponding to a mean percent change from pretreatment baseline of 149.8%.

Liver and spleen volumes normalized for percent of body weight were analyzed through Month 33; all 9 patients had liver data available and 8 patients had spleen data available for this assessment. The mean (SE) change from pretreatment baseline in normalized liver and spleen volumes at Month 33 was −1.5 (0.22) and −2.8 (0.37), respectively. The results corresponded to −34.0% and −73.5% mean percent changes from pretreatment baseline for normalized liver and spleen volumes, (p=0.004 and p=0.008, respectively). Further improvements were also observed for both plasma chitotriosidase and CCL18 parameters.

In summary, FIG. 2 presents the mean percent change in hemoglobin concentration, platelet counts, liver volume and spleen volume that is plotted across time and demarcated for the extension studies. A statistically significant change is observed from baseline to 48 months (p<0.004) for each parameter. The most marked changes were observed for platelet count and spleen volume. Hemoglobin values normalized for all patients by 24 months. Liver volumes approached normal. Continuous improvement in these clinical parameters was noted throughout the extension study (FIG. 2) and normalization of hemoglobin was observed in all patients by 24 months (Table 2). The mean percent change from baseline to 48 months was statistically significant (p<0.004) for hemoglobin concentration (+21.7%), platelet counts (+157.8%), liver volume (−42.8%), and spleen volume (−79.3%).

Safety and clinical activity data for Study TKT025EXT available up to a certain date were analyzed. Patients enrolled in this study had a cumulative mean duration of exposure of 43.2 months (range: 13.2-45.0 months). A total of 248 adverse events were reported among all 10 patients enrolled. The majority of AEs were mild to moderate in severity. Three severe (Grade 3) adverse events, considered unrelated to study drug by the Investigator, were reported for 2 patients (arthralgia and aseptic necrosis bone in 1 patient, and headache in 1 patient). Three (3) SAEs have been reported (2 events of aseptic bone necrosis in 1 patient, and 1 event of scar in 1 patient). Each of these SAEs was considered unrelated to study drug by the Investigator, and each resolved without sequelae. The most frequently reported treatment-emergent adverse events were influenza (8 patients, 24 events); arthralgia (8 patients, 21 events); headache (6 patients, 13 events); back pain (6 patients, 10 events); pharyngolaryngeal pain (5 patients, 7 events); abdominal pain upper (5 patients, 7 events); and gingival bleeding, pyrexia and fatigue (each 4 patients, 4 events).

The majority of adverse events reported in TKT025EXT were considered by the Investigator to be unrelated to study drug (Table 3B). A total of 7 treatment-related adverse events were reported in 4 patients, including epistaxis (2 patients, 1 event each) abdominal pain (1 patient, 1 event), abdominal pain upper (1 patient, 1 event), fatigue (1 patient, 1 event), and pain exacerbated (1 patient, 1 event). Two patients experienced 1 infusion-related AE each: moderate (Grade 2) pain in extremity in 1 patient, and mild (Grade 1) tremor in 1 patient. Therefore, there was no drug-related serious adverse events regardless of infusion setting. In addition, no patient had an infusion-related adverse event requiring interruption of administration of velaglucerase alfa.

No patient developed antibodies to velaglucerase alfa. During the first year of the extension study all seven residents of Israel were successfully transitioned to home therapy.

TABLE 3B

Treatment emergent adverse events determined to be possibly or probably related to velaglucerase alfa (GA-GCB) administration observed during the extension study (TKT025 EXT)

| System organ class preferred term | velaglucerase alfa 30 U/kg-60 U/kg EOW | |
|---|---|---|
| | Patients, n (%) N = 10 | Events, n (%) N = 311 |
| Any Related Adverse Event | 4 (40.0) | 7 (2.8) |
| Nervous System Disorders | | |
| Tremors | 1 (10.0) | 1 (0.32) |
| Respiratory, Thoracic or Mediastinal disorders | | |
| Epistaxis | 2 (20.0) | 2 (0.6) |
| Gastrointestinal Disorders | | |
| Abdominal pain | 2 (20.0) | 2 (0.6) |
| Musculoskeletal and Connective Tissue Disorders | | |
| Pain in extremity | 1 (10.0) | 1 (0.3) |
| General Disorders and Administration Site Conditions | | |
| Fatigue | 1 (10.0) | 1 (0.3) |

Percentages of patients are based on the total number of patients in the safety population. Percentages of events are based on the total number of events experienced by patients in the safety population. Adverse events are coded using MedDRA Version 9.0 dictionary. EOW: every other week.

Results of Bone Mineral Density in Type 1 Gaucher Disease Patients in TKT025 and TKT025EXT Long term bone mineral density (BMD) changes were evaluated in Type 1 Gaucher disease patients treated with velaglucerase alfa. Patients demonstrated significant and continuous improvement in BMD.

Assessments:

During TKT025 enrollment, skeletal surveys and dual energy X-ray absorptiometry (DEXA) were used to evaluate skeletal pathology. Z-scores of the lumbar spine and femoral neck were analyzed at predefined times throughout the study. For some patients, DEXA scans were performed, but Z-scores could not be assessed from the scans. Missing Z-scores included: one patient—femoral neck at baseline and Month 9; one patient—lumbar spine at baseline; and one patient—femoral neck at Month 9. Lumbar spine and femoral neck Z-scores were also not evaluated for two patients after they withdrew from the study: one patient before Month 24 and one patient before Month 57.

T-scores were used to compare bone density to a "young, normal" healthy 30-year-old adult with peak bone density. Clinical bone status at baseline and 69 months was characterized according to the WHO criteria for T-scores: $\geq -1$ is normal; $>-2.5$ and $<-1$ is osteopenia; $\leq -2.5$ is osteoporosis.

Methods:

Analysis Population:

The primary analysis was conducted in the intent-to-treat (ITT) population (N=10), defined as all patients who signed the informed consent to participate in the long-term extension study and received $\geq 1$ full or partial dose of velaglucerase alfa. The effect of velaglucerase alfa on BMD was also assessed in subgroups who did or did not receive bisphosphonates concomitant with ERT.

Statistical Methodology:

Missing baseline Z-scores were replaced with the next value. Last observation carried forward (LOCF) analysis was used for subsequent missing Z-scores. Linear mixed models were used as a repeated measures analysis to analyze Z-scores over time. The y-intercept and the slope estimate, showing the annual increase in Z-score units, are displayed. A shift from osteoporosis to osteopenia or normal, and from osteopenia to normal was recorded and reported.

Results:

Baseline Characteristics:

All patients enrolled in TKT025EXT had GD1-related bone pathology. Clinical status of lumber spine (LS) bone pathology was: 1 patient (10%) was in the normal range; 8 patients (80%) had osteopenia; and 1 patient (10%) had osteoporosis. Clinical status of femoral neck (FN) bone pathology was: 1 patient (10%) was in the normal range; 5 patients (50%) had osteopenia; and 4 patients (40%) patients had osteoporosis. DXA Z-scores were (median [range]): LS, −1.8 [−2.9 to −0.4], FN −1.5 [−2.9 to −0.2]. Through 69 months the average velaglucerase alfa dose was 40 U/kg. Four of ten patients were also treated with bisphosphonates.

Figure 5:
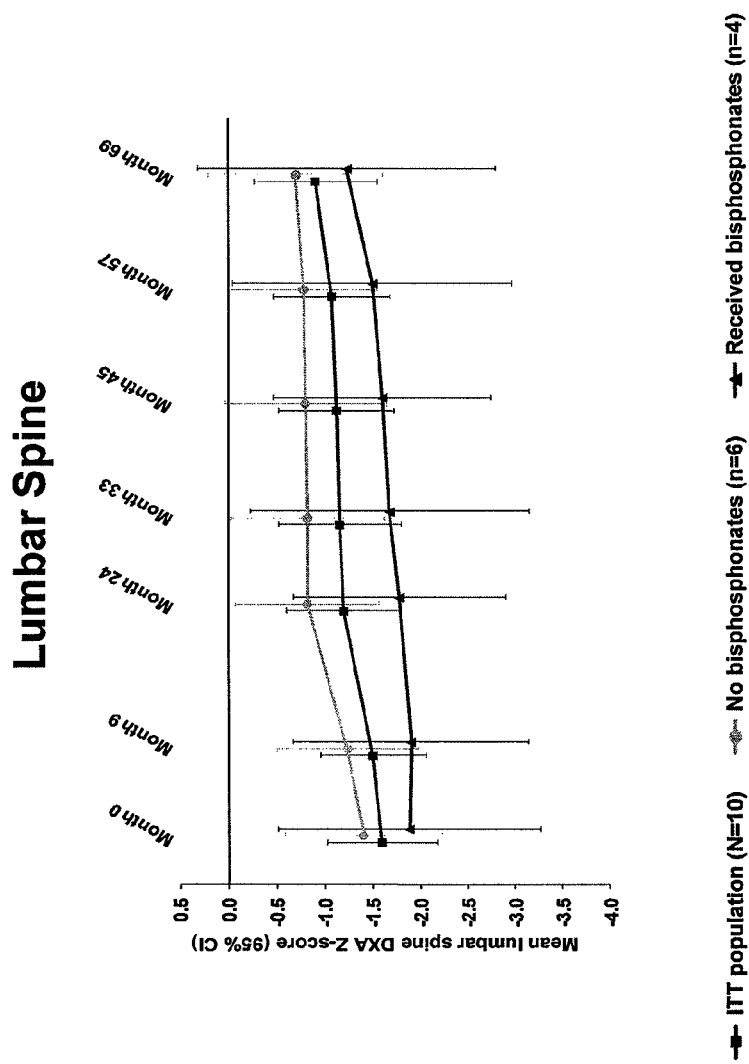
FIG. 5 depicts TKT025 and TKT025EXT temporal change in mean Z-scores of lumbar spine from baseline.
Figure 6:
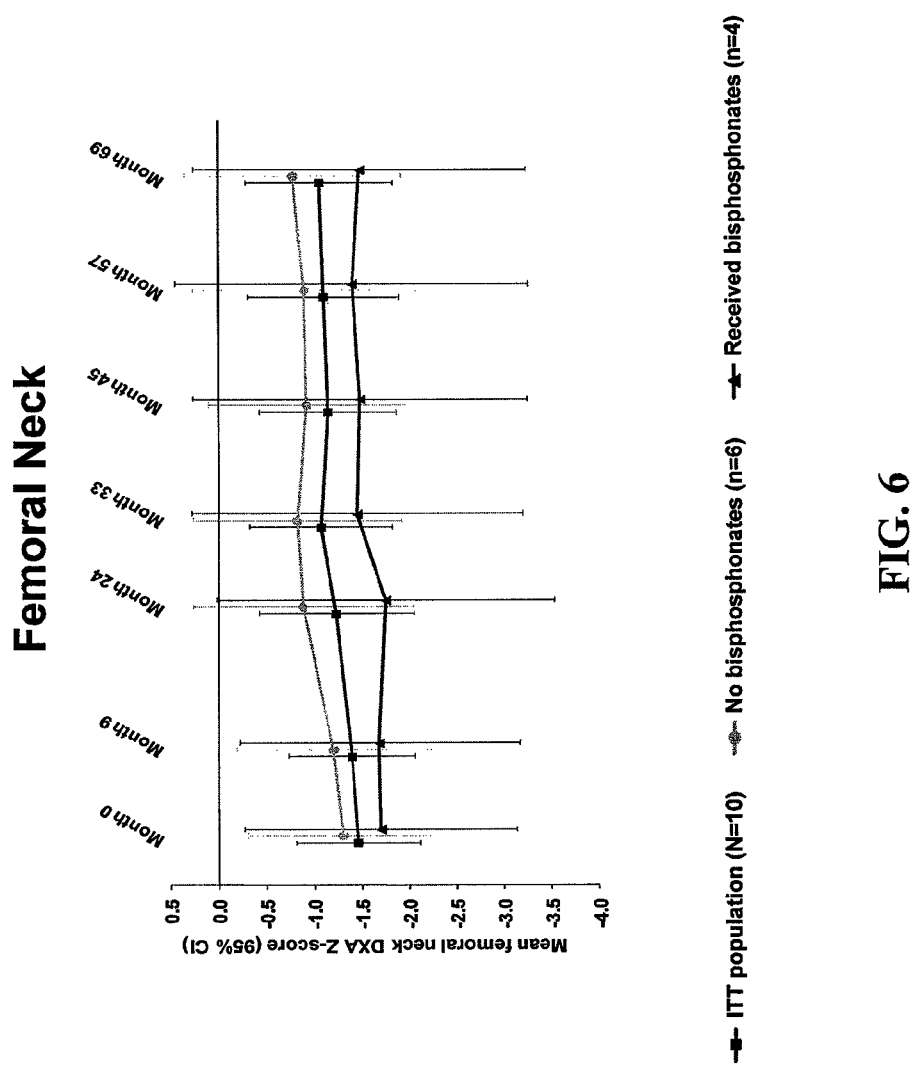
FIG. 6 depicts TKT025 and TKT025EXT temporal change in mean Z-score of femoral neck from baseline.

Z-Scores:

Z-scores at baseline and various timepoints for ITT population (n=10), patients who received concomitant bisphosphonates, and patients who did not received bisphosphonates are shown in Tables 5-7, respectively. Temporal changes in mean Z-scores of lumber spine and femoral neck are also shown in FIGS. 5 and 6, respectively.

TABLE 5

Z-scores; N = 10, ITT

| | Z-Scores | |
|---|---|---|
| Time | Lumbar Spine Mean [95% CI] | Femur Mean [95% CI] |
| Baseline | −1.59 [−2.17, −1.01] | −1.46 [−2.11, −0.81] |
| Month 9 | −1.50 [−2.05, −0.95] | −1.39 [−2.06, −0.72] |
| Month 24 | −1.20 [−1.80, −0.60] | −1.23 [−2.04, −0.42] |
| Month 33 | −1.16 [−1.80, −0.52] | −1.07 [−1.82, −0.32] |
| Month 45 | −1.12 [−1.72, −0.52] | −1.14 [−1.86, −0.42] |
| Month 57 | −1.07 [−1.68, −0.46] | −1.10 [−1.89, −0.31] |
| Month 69 | −0.91 [−1.55, −0.27] | −1.06 [−1.83, −0.29] |

TABLE 6

Z-scores; n = 4 [with bisphosphonates]

| | Z-Scores | |
|---|---|---|
| Time | Lumbar Spine Mean [95% CI] | Femur Mean [95% CI] |
| Baseline | −1.88 [−3.25, −0.50] | −1.70 [−3.13, −0.27] |
| Month 9 | −1.90 [−3.14, −0.66] | −1.68 [−3.15, −0.20] |
| Month 24 | −1.78 [−2.89, −0.66] | −1.75 [−3.52, 0.02] |
| Month 33 | −1.68 [−3.14, −0.21] | −1.45 [−3.19, 0.29] |
| Month 45 | −1.60 [−2.74, −0.46] | −1.48 [−3.23, 0.28] |
| Month 57 | −1.50 [−2.96, −0.04] | −1.40 [−3.25, 0.45] |
| Month 69 | −1.23 [−2.78, 0.33] | −1.48 [−3.22, 0.27] |

TABLE 7

| | Z-scores; n = 6 [no bisphosphonates] | |
|---|---|---|
| | Z-Scores | |
| Time | Lumbar Spine Mean [95% CI] | Femur Mean [95% CI] |
| Baseline | −1.40 [−2.22, −0.58] | −1.30 [−2.30, −0.30] |
| Month 9 | −1.23 [−1.97, −0.50] | −1.20 [−2.22, −0.18] |
| Month 24 | −0.82 [−1.57, −0.06] | −0.88 [−2.03, 0.26] |
| Month 33 | −0.82 [−1.62, −0.02] | −0.82 [−1.91, 0.28] |
| Month 45 | −0.80 [−1.64, 0.04] | −0.92 [−1.95, 0.11] |
| Month 57 | −0.78 [−1.55, −0.01] | −0.90 [−2.07, 0.27] |
| Month 69 | −0.70 [−1.61, 0.21] | −0.78 [−1.91, 0.34] |

Changes in Z-scores of lumbar spine (LS) and femoral neck (FN) from baseline Z-scores during a course of 69 months are shown in Table 8.

TABLE 8

| Scheduled Visit | No bisphosphonates n = 6 | Bisphosphonates* n = 4 | ITT Population N = 10 |
|---|---|---|---|
| | Lumbar Spine Change From Baseline Z-scores (95% CI) | | |
| Month 9 | 0.17 (−0.03, 0.36) | −0.03 (−0.18, 0.13) | 0.09 (−0.04, 0.22) |
| Month 24 | 0.58 (0.08, 1.09) | 0.10 (−0.27, 0.47) | 0.39 (0.06, 0.72) |
| Month 33 | 0.58 (−0.06, 1.22) | 0.20 (−0.14, 0.54) | 0.43 (0.06, 0.80) |
| Month 45 | 0.60 (0.03, 1.17) | 0.28 (−0.12, 0.67) | 0.47 (0.14, 0.80) |
| Month 57 | 0.62 (0.05, 1.18) | 0.38 (−0.04, 0.79) | 0.52 (0.20, 0.84) |
| Month 69 | 0.70 (0.16, 1.24) | 0.65 (−0.04, 1.34) | 0.68 (0.35, 1.01) |
| | Femoral Neck Change From Baseline Z-scores (95% CI) | | |
| Month 9 | 0.10 (−0.03, 0.23) | 0.03 (−0.18, 0.23) | 0.07 (−0.02, 0.16) |
| Month 24 | 0.42 (−0.04, 0.87) | −0.05 (−0.47, 0.37) | 0.23 (−0.08, 0.54) |
| Month 33 | 0.48 (0.10, 0.87) | 0.25 (−0.13, 0.63) | 0.39 (0.16, 0.62) |
| Month 45 | 0.38 (0.18, 0.59) | 0.23 (−0.15, 0.60) | 0.32 (0.17, 0.47) |
| Month 57 | 0.40 (0.06, 0.74) | 0.30 (−0.20, 0.80) | 0.36 (0.14, 0.58) |
| Month 69 | 0.52 (0.22, 0.81) | 0.23 (−0.25, 0.70) | 0.40 (0.18, 0.62) |

P ≤ 0.05 vs baseline value

As shown in Table 8, BMD for the intent-to-treat population improved significantly by Months 24 (LS: 0.39 (0.06, 0.72)) and Months 33 (FN: 0.39 (0.16, 0.62)). BMD for the patients who did not receive concomitant bisphosphonates improved significant by Months 24 (LS: 0.58 (0.08, 1.09)) and Months 33 (FN: 0.48 (0.10, 0.87)).

Linear Mixed Model Estimated Z-Scores:

Z-scores (ITT population, n=10, 95% CI) were significantly lower than the reference population (LS y-intercept=−1.56 [−2.09, −1.03]; P<0.0001) and FN (y-intercept=−1.42 [−2.06, −0.79]; P=0.0007). Both parameters improved significantly over time (LS slope per month=+0.011 [0.005, 0.017], P=0.0021 (slope +0.011 Z-score units/month corresponds to +0.132/year); FN slope per month=+0.007 [0.004, 0.009], P=0.0005 (slope +0.007 Z-score units/month corresponds to +0.084/year)).

Among patients who only received velaglucerase alfa (n=6, 95% CI), the Z-score LS y-intercept was −1.29 [−1.97, −0.62] (P=0.0045), FN y-intercept was −1.24 [−2.21, −0.27] (P=0.0216) and significant improvement was seen over time [LS slope per month=+0.013 [0.002, 0.024] (P=0.028) (corresponds to +0.158 per year), FN slope per month=+0.009 [0.004, 0.013] (P=0.0055) (corresponds to +0.103 per year).

Among patients who received bisphosphonates concomitantly (n=4, 95% CI), the Z-score LS y-intercept was −1.97 [−3.06, −0.88] (P=0.0104), FN y-intercept was −1.71 [−3.02, −0.40] (P=0.0252) and improvement was seen over time [LS slope per month=+0.009 [0.001, 0.017] (P=0.0351) (corresponds to +0.111 per year), FN slope per month=+0.004 [−0.001, 0.010] (P=0.0867) (corresponds to +0.048 per year).

In a linear mixed model based upon an analysis of an observational database (International Collaborative Gaucher Group Gaucher Registry), GD1 patients treated with the ERT imiglucerase had significantly lower Z-scores than the reference population at the start of follow-up (n=340, Y-intercept −1.17, P<0.001) (Wenstrup et al. *J Bone Min Res.* 2007; 22: 119-26). However, a dose-response improvement was observed in Z-score slopes per year (15 U/kg [n=113]: +0.064; 30 U/kg [n=116]: +0.086; 60 U/kg [n=111]: +0.132; all P<0.001) (Wenstrup et al. *J Bone Min Res.* 2007; 22: 119-26).

BMD Status at Baseline and 69 Months:

Clinical bone status at baseline and 69 months was characterized using WHO criteria (normal=T-scores: ≥−1; osteopenia=T-score >−2.5 and <−1; osteoporosis= T-score ≤−2.5). Status change was observed in patients who received velaglucerase alfa without concomitant bisphosphonates (n=6). By 69 months, two LS and one FN osteopenic patients normalized and one FN osteoporotic patient became osteopenic. All four patients on bisphosphonates had no change in WHO category.

Repeated Measures Analysis (Longitudinal) Slope Estimates:

In the repeated measures analysis, Z-score estimates [95% CI] for ITT population (N=10) were: LS intercept=−1.56 [−2.09, −1.03], P<0.0001; LS slope (per month)=0.011 [0.005, 0.017], P=0.0021; FN intercept=−1.42 [−2.06, −0.79], P=0.0007; LS slope (per month)=0.007 [0.004, 0.009], P=0.0005. A lumbar spine slope of 0.011 increases per month corresponds to a 0.132 increase per year, and a femoral neck slope of 0.007 increase per month corresponds to a 0.084 increase per year.

Z-score estimates [95% CI] for patients who did not receive bisphaphanates (N=6) were: LS intercept=−1.29 [−1.97, −0.62], P=0.0045; LS slope (per month)=0.013 [0.002, 0.024], P=0.0280; FN intercept=−1.24 [−2.21, −0.27], P=0.0216; LS slope (per month)=0.009 [0.004, 0.013], P=0.0055. A lumbar spine slope of 0.013 increase per month corresponds to a 0.158 increase per year, and a femoral neck slope of 0.009 increase per month corresponds to a 0.103 increase per year.

Z-score estimates [95% CI] for patients who received bisphaphanates (N=4) were: LS intercept=−1.97 [−3.06, −0.88], P=0.0104; LS slope (per month)=0.009 [0.001, 0.017], P=0.0351; FN intercept=−1.71 [−3.02, −0.40], P=0.0252; LS slope (per month)=0.004 [−0.001, 0.010], P=0.0867. A lumbar spine slope of 0.009 increase per month corresponds to a 0.111 increase per year, and a femoral neck slope of 0.004 increase per month corresponds to a 0.048 increase per year.

The statistical model used all available data and no data imputation was used.

Conclusions:

In patients with Gaucher disease and baseline osteopenia/osteoporosis who were treated with velaglucerase alfa, BMD improved in both lumbar spine (Month 24) and femoral neck (Month 36). Since the velaglucerase alfa dose was reduced from 60 to 30 unit/kg/infusion during Year 2, the improvement in bone pathology was not dependent upon continuous high-dose therapy.

Achievement of Long-Term Therapeutic Goals

Therapeutic goals have been described to monitor achievement, maintenance and continuity of therapeutic response in patients with type 1 Gaucher disease receiving ERT (Pastores G et al., (2004) *Seminars in Hematology*, 41 (suppl 5): 4-14)

To benchmark the impact of velaglucerase alfa treatment against therapeutic goals for 5 key clinical parameters of type 1 Gaucher disease (anemia, thrombocytopenia, hepatomegaly, splenomegaly and skeletal pathology), the proportion of patients at goal for anemia, thrombocytopenia, hepatomegaly and splenomegaly at baseline was compared with the proportion achieving each of these goals at 4 years. Complete data for anemia, thrombocytopenia, hepatomegaly, splenomegaly and skeletal pathology at baseline and 4 years are available for 8 patients (3 male, 5 female). The proportion achieving the skeletal pathology goal at 4 years was determined on the basis of Z-score improvement from baseline to 4 years. In addition, the proportion of patients who achieved all 5 goals at 4 years was compared with the proportion at goal for all 5 parameters at baseline.

At baseline, no patient was at goal for all clinical parameters (Table 9). After 1 year of treatment, all patients maintained goals present at baseline, and all achieved ≥2 goals. All 8 patients began step-wise dose reduction to velaglucerase alfa 30 U/kg EOW between 15 and 18 months. By year 4 of treatment, all patients met goal for all 5 clinical parameters; therefore, 100% achievement was seen for each of the 5 long-term, therapeutic goals (Table 9).

TABLE 9

|  | Baseline | Year 4 |
| --- | --- | --- |
| Anemia | 4/8 (50%) | 8/8 (100%) |
| Thrombocytopenia | 0/8 (0%) | 8/8 (100%) |
| Hepatomegaly | 4/8 (50%) | 8/8 (100%) |
| Splenomegaly | 0/8 (0%) | 8/8 (100%) |
| Skeletal pathology | — | 8/8 (100%) |
| All 5 goals | 0/8 (0%) | 8/8 (100%) |

Skeletal pathology was measured as improvement in bone mineral density (BMD) at year 4 relative to baseline.

In this velaglucerase alfa Phase I/II and extension study, clinically meaningful achievement of each long-term, therapeutic goal was observed for each patient, despite dose reduction after 1 year. This is the first report of a cohort where all patients receiving ERT for type 1 Gaucher disease achieved all 5 of these long-term, therapeutic goals within 4 years of starting treatment.

Summary of Results from TKT025 and TKT025EXT

The findings reported herein demonstrate that adverse events associated with velaglucerase alfa were generally mild in severity and were mostly unrelated to therapy. Treatment-emergent adverse events were mild to moderate and were mostly not drug-related. No patient enrolled in these studies developed antibodies, no drug related serious adverse events were observed regardless of infusion setting or duration of exposure, and no patient withdrew from the study because of adverse events. Following an initial period of observation at the study site, eligible patients were successfully transitioned to home-based, nurse-administered velaglucerase alfa.

Velaglucerase alfa demonstrated efficacy in the four disease parameters studied with statistically significant and clinically meaningful improvements from baseline observed within the first six months of treatment and throughout the course of the trial and extension study. Within 24 months of initiation of therapy, all patients achieved normalization of hemoglobin level, all but one patient achieved platelet counts of greater than 100,000/mm$^3$, all patients achieved near normalization in liver volumes, and all patients but one exhibited a reduction of more than 50% in spleen volume. Moreover, these improvements were observed throughout the duration of the studies, including the dose-reduction phase. The only patient who was returned to the original dose of 60 U/kg/every-other-week did so at 39 months secondary to bone pain following an initial dose reduction at 15 months. This patient had boney destructive lesions in both her ankles at enrollment (imaging pathology could not rule out AVN) and had a prior history of osteomyelitis. The principle investigator (AZ) attributed the worsening pain to the preexisting destructive lesion and prior pathology, and likely not related to the dose reduction or treatment failure.

The observed safety profile including the transition to home treatment and the significant changes observed in the clinical parameters despite dose reduction, have led to further three subsequent Phase III trials for velaglucerase alfa (which allowed children), as well as a global early access program, and an FDA-accepted treatment protocol.

Example 2

TKT032 Study (12M, 45 or 60 U/Kg Velaglucerase Alfa)

Example 2.1

Summary

This example describes a global, multicenter trial to evaluate the efficacy and safety of velaglucerase alfa in type 1 GD. Twenty-five treatment-naïve, anemic, type 1 GD patients (age 4-62 years) were randomized to intravenous velaglucerase alfa 60 U/kg (n=12) or 45 U/kg (n=13) every other week for 12 months.

Figure 7:
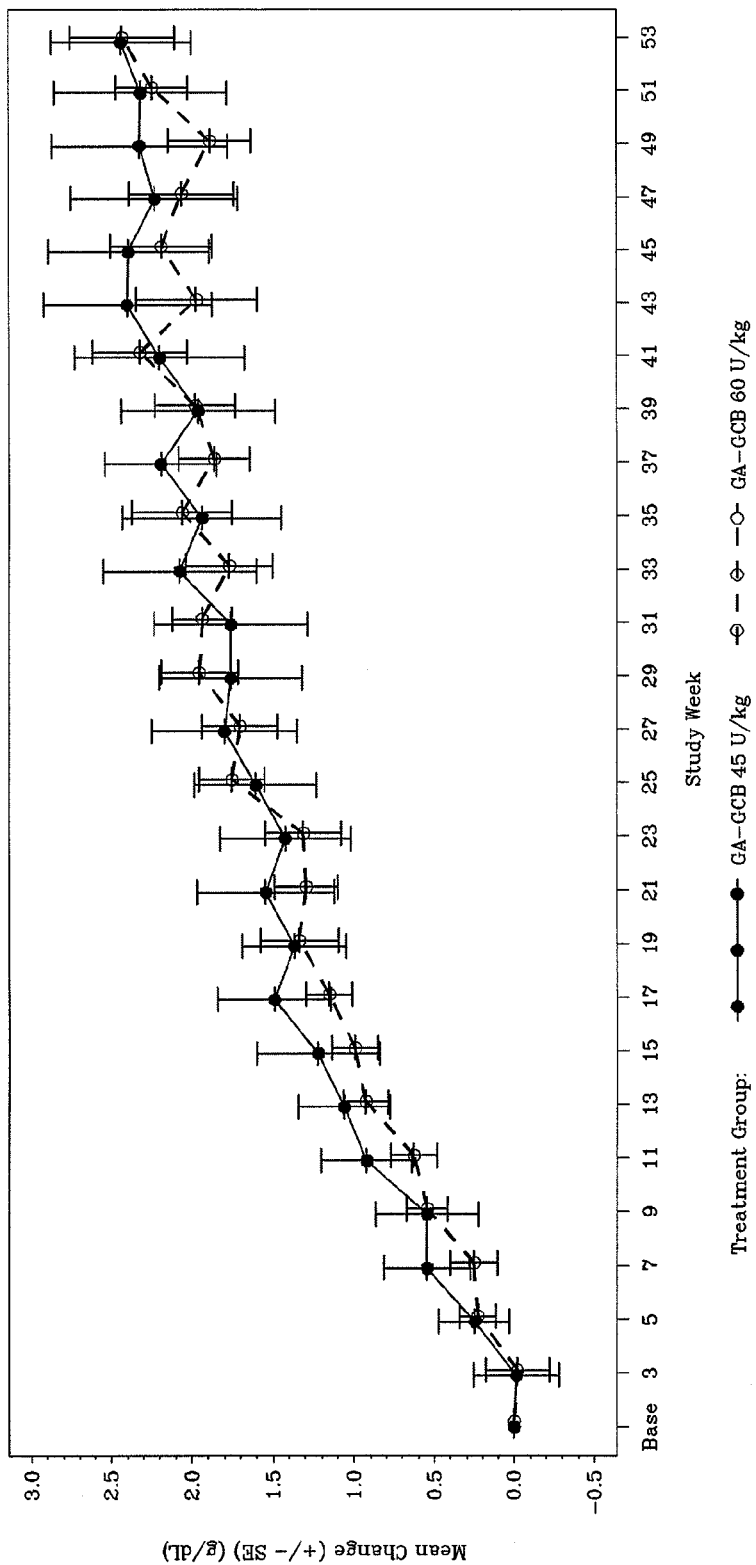
FIG. 7 depicts TKT032 (N=25) mean hemoglobin concentration change from baseline.
Figure 8:
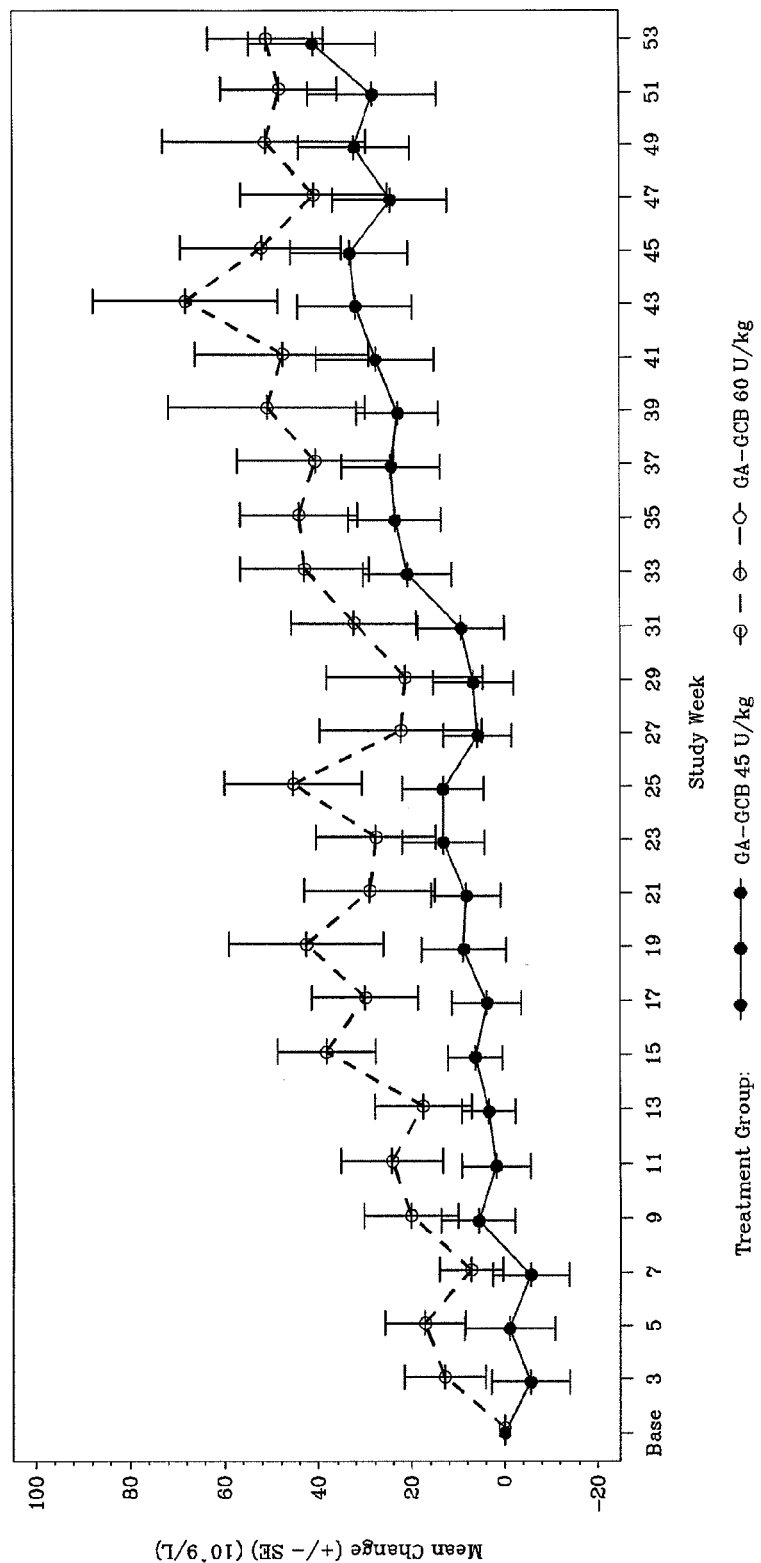
FIG. 8 depicts TKT032 (N=25) mean platelet count change from baseline.
Figure 9:
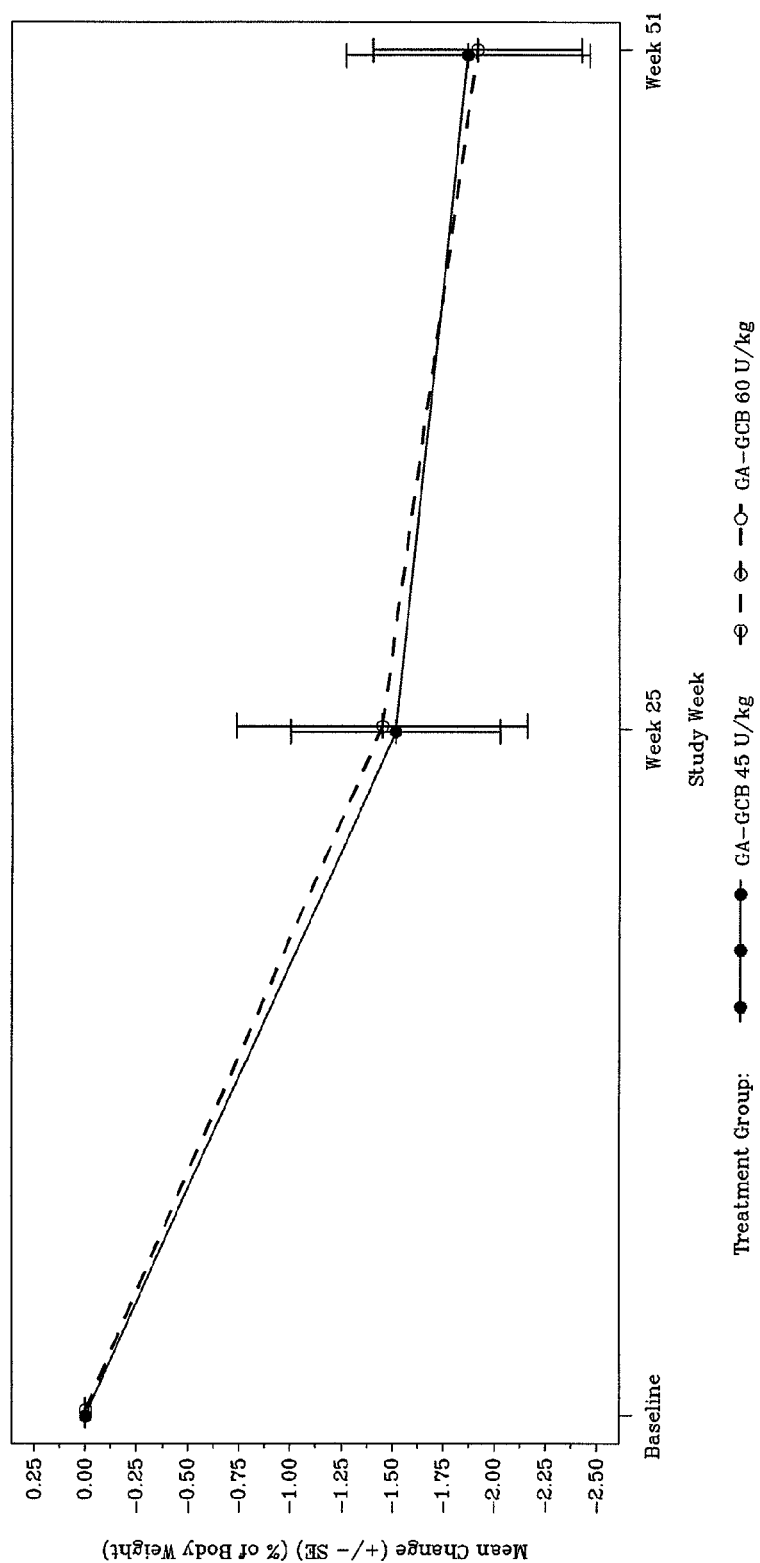
FIG. 9 depicts TKT032 (N=25) mean normalized spleen volume change from baseline.
Figure 10:
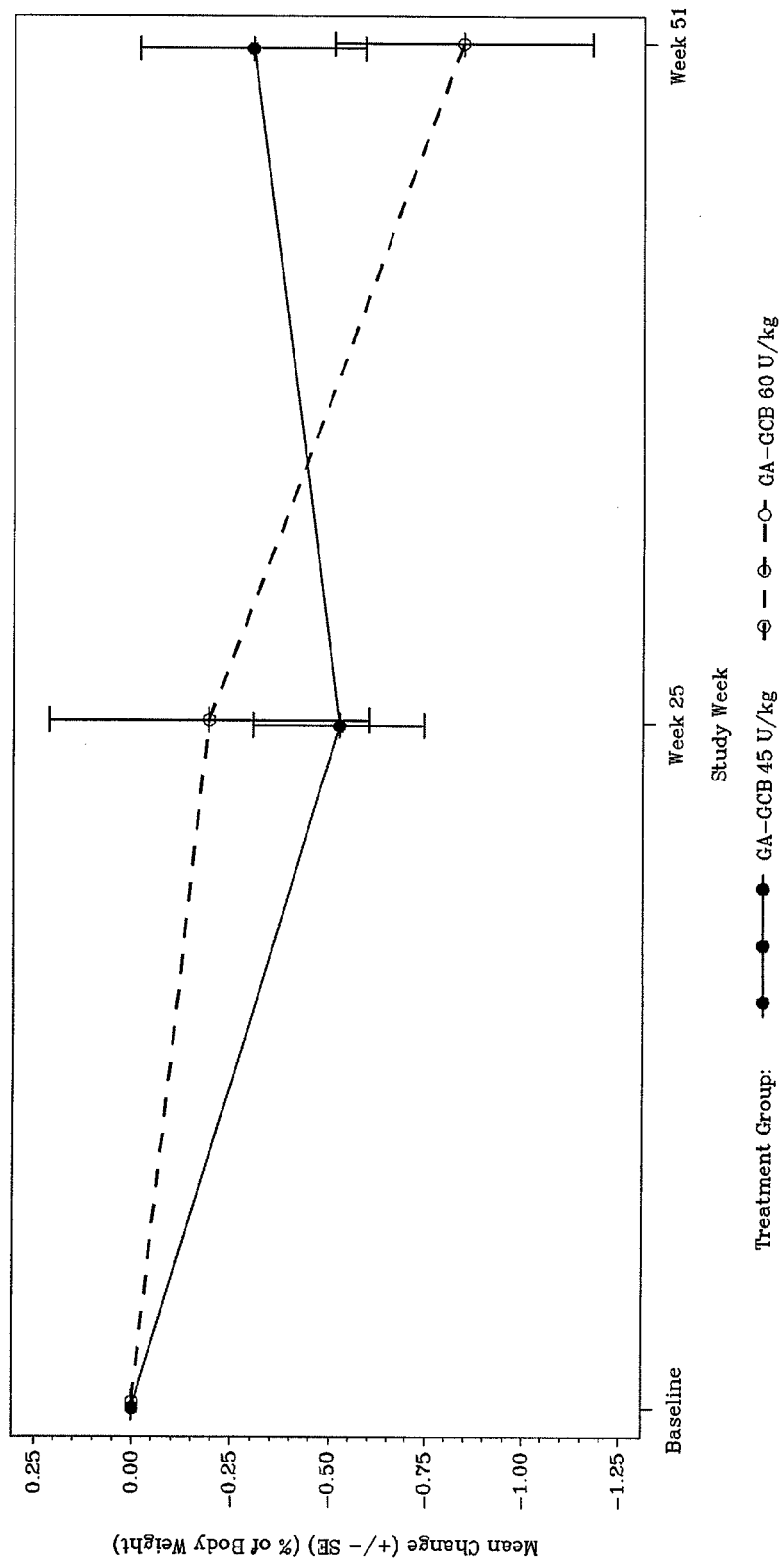
FIG. 10 depicts TKT032 (N=25) mean normalized liver volume change from baseline.

Patients were randomized in 1:1 ratio to receive 45 U/kg (N=13) or 60 U/kg (N=12) velaglucerase alfa. Stratification factors included age (2-17; ≥18) and gender (male; female). The baseline characteristics of the patients are listed in Table 10. Clinically and statistically significant improvements in hematological parameters and spleen volumes were observed at 12 months (Table 11). FIGS. 7 and 8 show the increase of mean hemoglobin concentration and platelet count, respectively, from baseline in the patients treated with 45 U/kg or 60 U/kg velaglucerase alfa for 12 months. FIGS. 9 and 10 show the decrease of mean normalized spleen volume and liver volume, respectively, from baseline in patients treated with 45 U/kg or 60 U/kg velaglucerase alfa for 12 months.

TABLE 10

TKT032 Baseline Characteristics

| Baseline Factor | Velaglucerase alfa 45 U/kg N = 13 | Velaglucerase alfa 60 U/kg N = 12 | Total N = 25 |
|---|---|---|---|
| 2 to 17 years n (%) | 3 (23.1) | 4 (33.3) | 7 (28.0) |
| 2 to 4 years n (%) | 0 | 1 (8.3) | 1 (4.0) |
| 5 to 17 years n (%) | 3 (23.1) | 3 (25.0) | 6 (24.0) |
| ≥18 years n (%) | 10 (76.9) | 8 (66.7) | 18 (72.0) |
| Male n (%) | 8 (61.5) | 7 (58.3) | 15 (60.0) |
| Female n (%) | 5 (38.5) | 5 (41.7) | 10 (40.0) |
| Hemoglobin concentration (g/dL) Median [Min, Max] | 10.90 [8.45, 12.85] | 10.83 [7.05, 12.25] | 10.85 [7.05, 12.85] |
| Platelet count (×10⁹/L) Median [Min, Max] | 58.00 [13.0, 264.0] | 66.75 [47.0, 438.0] | 65.50 [13.0, 438.0] |

TABLE 11

TKT032 Clinical Results (N = 25)

| | n | Baseline Median | Mean Change from Baseline to Month 12 | 95% CI | P-value |
|---|---|---|---|---|---|
| Primary Endpoint | | | | | |
| Hemoglobin 60 U/kg | 12 | 10.83 | 2.43 | [1.72, 3.14] | <0.0001 |
| Secondary Endpoints | | | | | |
| Hemoglobin 45 U/kg | 13 | 10.90 | 2.44 | [1.49, 3.39] | 0.0001 |
| Platelets 60 U/kg | 12 | 66.75 | 50.88 | [23.97, 77.78] | 0.0016 |
| Platelets 45 U/kg | 13 | 58.00 | 40.92 | [11.20, 70.64] | 0.0111 |
| Spleen 60 U/kg | 12 | 2.80 | −1.92 | [−3.04, −0.79] | 0.0032 |
| Spleen 45 U/kg | 13 | 2.90 | −1.87 | [−3.17, −0.57] | 0.0085 |
| Liver 60 U/kg | 12 | 3.65 | −0.84 | [−1.58, −0.11] | 0.0282a |
| Liver 45 U/kg | 13 | 3.50 | −0.30 | [−0.92, 0.32] | 0.3149 | aNot statistically significant after adjusting for multiple testing.

Velaglucerase alfa was well tolerated. One patient developed antibodies at the end of the study (12 months). Table 12 summarizes the results of TKT032 safety test.

TABLE 12

TKT032 Safety

| DESCRIPTION | velaglucerase alfa 45 U/kg N = 13 | velaglucerase alfa 60 U/kg N = 12 | Total N = 25 |
|---|---|---|---|
| Experienced No Adverse Events | 2 (15.4) | 0 | 2 (8.0) |
| Experienced At Least 1 Adverse Event | 11 (84.6) | 12 (100.0) | 23 (92.0) |
| Experienced At Least 1 Drug-Related Adverse Event | 9 (69.2) | 6 (50.0) | 15 (60.0) |
| Experienced At Least 1 Infusion-Related Adverse Event | 8 (61.5) | 6 (50.0) | 14 (56.0) |
| Experienced At Least 1 Severe Or Life-Threatening Adverse Event | 2 (15.4) | 0 | 2 (8.0) |
| Experienced At Least 1 Serious Adverse Event | 0 | 1 (8.3) | 1 (4.0) |
| Discontinued Due To An Adverse Event | 0 | 0 | 0 |
| Deaths | 0 | 0 | 0 |
| Developed anti-velaglucerase alfa antibodies | 1 (7.7) | 0 | 1 (4.0) |

At 12 months, mean hemoglobin concentration increased (60 U/kg: +23%; +2.4 g/dL [95% confidence interval (CI): 1.5, 3.4; P<0.001]; 45 U/kg: +24%; +2.4 g/dL [95% CI: 1.5, 3.4; P<0.001]), as did mean platelet count (60 U/kg: +65.9%; +51×10⁹/L [95% CI: 24, 78; P=0.002]; 45 U/kg: +66%; +41×10⁹/L [95% CI: 11, 71; P=0.01]). Mean spleen volume decreased (60 U/kg: −50% [95% CI: −62, −39%] from 14.0 to 5.8 multiples of normal [MN] [P=0.003]; 45 U/kg: −40% [95% CI: −52, −28%], from 14.5 to 9.5 MN [P=0.009]); as did mean liver volume (60 U/kg: −17% [95% CI: −27, −7%], from 1.5 to 1.2 MN [P=0.03]; 45 U/kg: −6% [95% CI: −18, 6%], from 1.4 to 1.2 MN [P=0.32]. No drug-related serious adverse events or withdrawals were observed. One patient developed antibodies.

Study Objectives

The primary objective of this study is to determine the efficacy of every other week dosing of velaglucerase alfa at a dose of 60 U/kg in patients with type 1 Gaucher disease as measured by increases in hemoglobin concentration.

The secondary objectives of this study are to evaluate the safety of every other week dosing of velaglucerase alfa at doses of 60 and 45 U/kg; to evaluate the efficacy of every other week dosing of velaglucerase alfa at a dose of 45 U/kg as measured by increases in hemoglobin concentration; to evaluate the efficacy of every other week dosing of velaglucerase alfa at doses of 60 and 45 U/kg by assessing increases in platelet counts, decreases in spleen and liver volumes, and decreases in levels of plasma chitotriosidase and Chemokine (C-C motif) ligand 18 (CCL18); to evaluate the effect of every other week dosing of velaglucerase alfa at doses of 60 and 45 U/kg on overall quality of life (QoL); and to evaluate the single- and repeat-dose pharmacokinetics of every other week dosing of velaglucerase alfa when administered at doses of 60 and 45 U/kg.

The tertiary objectives of this study are to determine the time from Baseline to achieve a hemoglobin response, defined as an increase in hemoglobin concentration of 1 g/dL, after every other week dosing with velaglucerase alfa at doses of 60 or 45 U/kg; to evaluate the effect of every other week dosing of velaglucerase alfa at doses of 60 and 45 U/kg on pulmonary function tests (PFTs) in patients ≥18 years-old; to evaluate growth velocity and Tanner staging in patients between 2 and 17 years-old; to evaluate changes in skeletal age in patients between 2 and 17 years-old by radiography of the left hand and wrist; to establish a Baseline from which to evaluate bone disease in patients between 2 and 17 years-old by magnetic resonance imaging (MRI) of the lumbar spine and femoral neck; and to establish a Baseline from which to evaluate the long-term effect of velaglucerase alfa therapy on Gaucher-related local and systemic bone disease in patients ≥18 years-old by: DXA of the lumbar spine and femoral neck (including coronal imaging); and serum alkaline phosphatase, N-Telopeptide cross-links (NTx), and C-Telopeptide cross-links (CTx).

Overall Study Design

This is a multicenter, Phase III randomized, double-blind, parallel group, 2-dose study designed to evaluate the efficacy and safety of velaglucerase alfa therapy for patients with type I Gaucher disease.

This study was comprised of 5 phases as follows: (1) Screening: Day −21 through Day −4; Baseline: Day −3 through Day 0 (prior to first dose); Treatment Phase: Week 1 (Day 1; first dose) through Week 51 (a total of 26 infusions were administered per patient); End of Study Visit: Week 53; Follow-up: 30 days after the final infusion (for patients who discontinue/withdraw prior to the Week 53 evaluation, or for patients who complete this study but do not elect to enroll in the subsequent long-term clinical study).

At Screening, patients who provided written informed consent to participate in this study were reviewed against the study entrance criteria to determine study eligibility and underwent Screening evaluations. In particular, patients provided a blood sample to measure hemoglobin concentration. Only those patients who had a hemoglobin concentration that was at least 1 g/dL below the lower limit of normal for age and gender were eligible to continue into the baseline phase. For statistical analysis purposes, an additional blood sample was collected at screening for evaluation of hemoglobin concentration.

Patients who were eligible for study participation after completing the Screening evaluations underwent Baseline procedures and evaluations (i.e., Days −3 to 0) prior to the first dose. To confirm that their hemoglobin concentration was at least 1 g/dL below the lower limit of normal for age and gender, patients provided a blood sample at Baseline. Hemoglobin concentration were analyzed and reported. Only those patients who had a hemoglobin concentration that was at least 1 g/dL below the lower limit of normal for age and gender at both Screening and Baseline were eligible for randomization. For statistical analysis purposes, an additional blood sample was collected at Baseline for evaluation of hemoglobin concentrations. Additional Baseline procedures and evaluations were conducted prior to administration of the first dose.

Following completion of Baseline evaluations and confirmation of eligibility, patients were randomized in a 1:1 ratio to receive either velaglucerase alfa 60 U/kg or velaglucerase alfa 45 U/kg via a computer generated randomization schedule.

Patients received a total of 26 IV infusions of double-blind study medications at the clinical site once every other week for a total of 51 weeks. Safety and efficacy assessments were made at regular intervals during the treatment period. The final assessments of safety and efficacy were made at the Week 51 and Week 53 visits. Safety was assessed throughout the study by assessments of adverse events (including infusion-related adverse events), concomitant medications, and vital signs. Additional safety assessments, including, 12-lead electrocardiograms, physical examinations, clinical laboratory tests (hematology, serum chemistry, and urinalysis), were made at Weeks 13, 25, 37, and 53. Determination of the presence of anti-velaglucerase alfa antibodies and enzyme neutralizing antibodies were conducted approximately every 6 weeks until Week 53.

Efficacy was assessed via hemoglobin concentration and platelet count, liver and spleen volume, and plasma chitotriosidase and CCL18 level. Additional efficacy assessments included growth velocity and Tanner staging, QoL indicators, skeletal growth and pulmonary function testing.

Single-dose and repeat-dose velaglucerase alfa pharmacokinetic profiles were also evaluated during the study. Blood samples were collected at Week 1 (Day 1) and Week 37, respectively, for these analyses.

Patients who completed this study were provided the opportunity to enroll in a subsequent long-term clinical study. For patients who elected to enroll in this long-term study, certain assessments from the Week 51 and the Week 53 visits in TKT032 were used as the Baseline assessments; patients received their first velaglucerase alfa infusion for the long-term clinical study at the Week 53 visit, after the Week 53 procedures scheduled for TKT032 were completed. Therefore, it was intended that patients would receive continuous velaglucerase alfa treatment across the 2 studies. Patients who completed this study and did not elect to enroll in the subsequent long-term clinical study would have a safety evaluation by site visit or telephone 30 days after their last infusion of velaglucerase alfa.

Selection of Study Population

Of 39 patients assessed, 14 were not eligible for randomization (12 did not meet inclusion criteria; 2 did not meet exclusion criteria). Twenty five participants were randomized to velaglucerase alfa at a dose of 45 U/kg (n=13) or 60 U/kg (n=12). All randomized patients who received at least 1 infusion (or partial infusion) were included in the intent-to-treat (ITT) patient population.

Eligible participants were males or females age ≥2 years with diagnosed type 1 Gaucher disease (deficient glucocerebrosidase activity in leukocytes, or by genotype analysis), and disease-related anemia (hemoglobin levels ≥1 g/dL below the local laboratory's lower limit of normal for age and gender). Participants also had 1 or more of the following: at least moderate splenomegaly (2 to 3 cm below the left costal margin) by palpation; disease-related thrombocytopenia (platelet count <90×10$^3$ platelets/mm$^3$); or readily palpable enlarged liver. Participants could not have received treatment for Gaucher disease within 30 months prior to study entry.

Participants were excluded if they had a splenectomy; had (or were suspected of having) type 2 or 3 Gaucher disease; were antibody-positive or had experienced an anaphylactic shock to imiglucerase. Other exclusion criteria included treatment with any non-Gaucher disease-related investigational drug or device within 30 days prior to study entry; positive test for HIV, or hepatitis B or C; exacerbated anemia (vitamin B12, folic acid, or iron deficiency-related), or any significant co-morbidity that could affect study data. Pregnant or lactating women were excluded and women of child-bearing potential were required to use a medically acceptable method of contraception at all times.

Study Treatments

Treatment Assignment:

Patients were randomized in a 1:1 ratio to receive: velaglucerase alfa 60 U/kg every other week for 51 weeks (12 patients, 26 infusions); or velaglucerase alfa 45 U/kg every other week for 51 weeks (12 patients, 26 infusions).

Randomization:

Following the completion of Baseline evaluations and confirmation of eligibility, patients were randomized in a ratio of 1:1 via a computer generated randomization schedule to receive either velaglucerase alfa 45 U/kg or 60 U/kg every other week infusions for 51 weeks.

The pursuit of balance on prognostic factors was important in small trials on the grounds of statistical efficiency for the primary analyses. To achieve this balance across a number of prognostic factors (e.g., age and gender) dynamic allocation techniques were used. For the dynamic randomization procedure, the allocation of patients was influenced by the current balance on the stratifying factors for the patient in question. This technique used the approach as suggested by Pocock and Simon and was very consistent with the guidance provided in ICH-9 (Pocock et al. *Biometrics.* 1975; 31:105-115).

Treatment Schedule:

Patients received their first infusion at Week 1. All patients were treated every other week for 12 months (51 weeks); therefore, a total of 26 infusions of velaglucerase alfa were administered.

Dose Calculation:

The actual dose of study drug was calculated based on the patient's weight at Baseline. A change in weight of ≥5% noted at Weeks 13, 25, or 37 from the prior assessment would have required recalculation of the dose of study medication.

Velaglucerase Alfa Administration:

Velaglucerase alfa was administered as a continuous IV infusion at both the 60 and 45 U/kg dose levels. All infusions were administered over a 1-hour duration. All infusions were reconstituted in 4.3 mL of preservative-free, Sterile Water for Injection, and then diluted in normal saline (0.9% sodium chloride) to yield a 100 mL total volume. Study drug infusions occurred on approximately the same day of the week but might occur every 14 days (±3 days) of the scheduled day in order to facilitate patient scheduling.

Study Procedures and Data Collection Methods

Genotyping:

All patients provided a blood sample at Screening for Gaucher disease genotyping and plasma chitotriosidase genotyping.

Medical History:

At Screening, the patient's complete medical history was recorded. This included a review of body systems, documentation of current and prior medical procedures, and documentation of current and prior concomitant medication usage, and documentation that the patient had not been treated for Gaucher disease within the 30 months prior to study entry.

Vital Signs:

Vital signs parameters that were recorded included pulse, blood pressure, respiration rate, and temperature. The following schedule was followed for recording vital signs at infusion visits: start of infusion (within 10 minutes prior to starting the infusion), during infusion (30 minutes (±5 minutes)), after infusion (within 5 minutes, 30 minutes (±5 minutes), and 60 minutes (±5 minutes) after completing the infusion). At Screening, Baseline, and Week 53, vital signs were collected at one time point only.

Physical Examinations:

Physical examinations were performed at Screening, Baseline and at Study Weeks 13, 25, 37, and 53. Physical examinations included the following: general appearance, endocrine, head and neck, cardiovascular, eyes, abdomen, ears, genitourinary, nose, skin, throat, musculoskeletal, chest and lungs, and neurological. In addition, liver and spleen palpations were performed during Screening to confirm that the patient had moderate splenomegaly (2 to 3 cm below the left costal margin) and a Gaucher disease-related enlarged liver.

Height and Weight:

Height and weight were recorded at Baseline and at Study Weeks 13, 25, 37, and 53.

12-Lead Electrocardiograms:

A 12-Lead ECG was performed at Baseline and Study Weeks 13, 25, 37, and 53. Each 12-lead ECG included assessment of PR, QRS, QT, and QTc intervals, and heart rate.

Clinical Laboratory Testing:

Blood and urine samples were collected as described below for clinical laboratory testing. All blood samples were collected via venipuncture.

Hematology:

Blood samples were collected at Screening, Baseline, and Weeks 13, 25, 37, and 53 for complete hematology testing. The following hematology parameters were evaluated: complete blood count (CBC) with differential, activated partial thromboplastin time (aPPT), reticulocyte count (analyzed and reported by the clinical site's local laboratory), platelet count, and prothrombin time (PT). At Screening, Baseline, and at every study visit (except at the Week 1 visit), blood samples were collected to measure hemoglobin concentration and platelet count.

Serum Chemistry:

Blood samples were collected for serum chemistry testing at Screening, Baseline, and at Study Weeks 13, 25, 37, and 53. The following serum chemistry parameters were evaluated: sodium, alanine aminotransferase, potassium, aspartate aminotransferase, glucose, lactate dehydrogenase, total calcium, gammaglutamyltransferase, total protein, creatinine phosphokinase, albumin, NTx*, creatinine, CTx*, urea nitrogen, folic acid (screening only), total bilirubin, vitamin $B_{12}$ (screening only), alkaline phosphatase* (* results were used for assessments of bone biomarkers).

Urinalysis:

Urine samples were collected for urinalysis at Screening, Baseline, and at Study Weeks 13, 25, 37, and 53. The following urinalysis parameters were evaluated: pH, macroscopic evaluation, microscopic evaluation.

Serum Anti-Imiglucerase Antibody Determination:

All patients had a blood sample collected during Screening only for determination of serum anti-imiglucerase antibodies. Patients with a positive result were excluded from the study.

Serum Anti-Velaglucerase Alfa Antibody Determination:

Patients provided blood samples to measure anti-velaglucerase alfa antibodies in serum at Baseline and approximately every 6 weeks during the treatment phase (Weeks 7, 13, 19, 25, 31, 37, 43, and 49), and at Week 53. During the treatment phase, these blood samples were collected prior to the infusion.

Adverse Events:

Adverse events were monitored throughout the study from informed consent/assent through 30 days after the last infusion for patients who completed the study and did not elect to enroll in the long-term clinical study from the study prior to the Week 53 visit. For patients who completed this study and elected to enroll in the long-term clinical study, adverse events were monitored from informed consent/assent through the Week 53 visit.

Prior and Concomitant Illnesses:

Additional illnesses present at Baseline were regarded as concomitant illnesses and were documented on the appropriate pages of the medical history CRF. Illnesses first occurring or detected during the study, or worsening of a concomitant illness during the study, were regarded as AEs and documented as such in the CRF.

Liver and Spleen MRI:

Patients had MRI of the liver and spleen at Baseline, Week 25 and Week 51. Liver and spleen size were measured using quantitative abdominal MRI.

Plasma Chitotriosidase Levels:

Blood samples (approximately 2.5 mL) were collected for the evaluation of plasma chitotriosidase levels at Baseline, Weeks 13, 25, 37, and at Week 53.

Plasma CCL18 Levels:

Blood samples (approximately 2.5 mL) were collected for the evaluation of plasma CCL18 levels at Baseline, Week 13, 25, 37 and at Week 53.

Quality of Life Testing:

At Baseline and at Week 53, patients' quality of life was evaluated using validated questionnaires, including the Short Form 36 (SF-36), version 2 (for patients ≥18 years-old) and the Childhood Health Questionnaire (CHQ), PF50 (for patients 5 to 17 years-old).

Growth Velocity and Tanner Staging:

For patients 2 to 17 years-old, growth was assessed at Baseline and Weeks 13, 25, 37, and 53. Growth velocity was calculated using height and weight measurements, recorded at regular time points during this study. Growth rates of patients in this study were measured against growth rates for normal individuals of comparable ages obtained from the Centers for Disease Control and Prevention height and weight data. Tanner stage was recorded at Baseline and Weeks 13, 25, 37, and 53.

Skeletal Growth:

Patients between 2 and 17 years-old underwent radiography of the left hand and wrist at Baseline and Week 51 for evaluation of skeletal age.

Pulmonary Function Testing:

At Baseline and Week 53, patients 18 years-old who were enrolled at study sites with the capability to perform spirometry had PFTs.

Spirometry was performed according to the guidelines published by the American Thoracic Society or European Respiratory Society for standardization of spirometry (American Thoracic Society. Standardization of Spirometry. *Am J Respir Crit. Care Med.* 1995; 152:1107-1136; Quanjer et al. *Eur Respir J.* 1993; 16(Suppl):5-40) Both Forced Vital Capacity (FVC) and Forced Expiratory Volume/second ($FEV_1$) were expressed as absolute values and % predicted of normal, which were calculated based on published reference values for adults (Hankinson et al. *Am J Respir. Crit. Care Med.* 1999; 159:179-187). Current standing height was used for the calculations.

Lung volume and Diffusion Capacity ($DL_{CO}$) determinations were performed at the same time as spirometric testing. Lung volume measurements were include Total Lung Capacity (TLC), and Residual Volume (RV), which were recorded as absolute values and % predicted of normal based on published reference values. $DL_{CO}$ was also expressed as absolute values and % predicted of normal based on published reference values.

Pharmacokinetic Evaluations:

For patients 18 years-old, blood samples were collected at the following times at Week 1 (Day 1) and Week 37: immediately before first dose, during infusion (sample collected at 5, 10, 15, 20, 40 and 60 (end of infusion) minutes), and after infusion (sample collected at 65, 70, 80, 90, 105 and 120 minutes).

For patients 2 to 17 years-old, blood samples were collected at the following times at Week 1 (Day 1) and Week 37: immediately before first dose, during infusion (sample collected at 10, 20, 40 and 60 (end of infusion) minutes), and after infusion (sample collected at 70, 80 and 90 minutes).

Serum samples were evaluated for the presence of administered velaglucerase alfa using a glucocerebrosidase antigen immunoassay. The following PK parameters were evaluated: AUC (Area under the curve), $C_{max}$ (Maximum serum concentration), $T_{max}$ (Time to maximum serum concentration), CL (mL/min/kg) (Serum clearance, normalized for body weight), $V_{ss}$ (mL) (Apparent volume of distribution at steady-state), $V_{ss}$ (% BW) ($V_{ss}$ normalized for body weight), MRT (Mean residence time), and $T_{1/2}$ (Elimination half-life (analyzed with appropriate PK models)

Bone Biomarkers:

At Baseline only, patients ≥18 years-old underwent DXA of the lumbar spine and femoral neck, including coronal imaging, to determine Gaucher-related local and systemic bone disease. Bone loss and demineralization were also evaluated by measuring serum alkaline phosphatase, NTx, and CTx. Results for these parameters were obtained from blood samples collected for clinical laboratory testing at Baseline only.

For patients 2 to 17 years-old, MRI of the femoral neck and lumbar spine was obtained at Baseline (i.e., at the same time patients underwent MRI of the liver and spleen). It was not expected that any treatment effect would be apparent for these parameters during this study; therefore, measurements were collected at Baseline only to establish a reference point from which to monitor these biomarkers during the long-term clinical study.

Adverse Events

Adverse Event Definition:

An adverse event (AE) is any noxious, pathologic, or unintended change in anatomical, physiologic, or metabolic function as indicated by physical signs, symptoms, and/or laboratory changes occurring in any phase of a clinical trial, and whether or not considered study drug-related. This includes an exacerbation of a pre-existing condition. Adverse events were collected from informed consent/assent until 30 days after the last dose of study medication and/or until the event had been resolved/stabilized or an outcome was reached, whichever came first. For patients who completed this study and elected to enroll in the subsequent long-term clinical study, adverse events were monitored from the time the patient provided informed consent through the Week 53 visit of TKT032.

AEs include: worsening (change in nature, severity, or frequency) of conditions present at the onset of the study; intercurrent illnesses; drug interactions; events related to or possibly related to concomitant medications; abnormal laboratory values (this includes significant shifts from Baseline within the range of normal that the Investigator considers to be clinically important); clinically significant abnormalities in physical examination, vital signs, weight, and ECG.

In addition, AEs might also include unexpected laboratory values that became significantly out of range and determined to be clinically significant by the Investigator.

Infusion-Related Adverse Event Definition:

An infusion-related adverse event is defined as an adverse event that 1) begins either during or within 12 hours after the start of the infusion, and 2) is judged as possibly or probably related to study medication. Other AEs which occurred prior to the infusion, along with AEs associated with protocol-defined testing and assessments (e.g., laboratory testing, ECGs, and physical examinations) which were performed prior to the infusion, are not defined as infusion-related adverse events.

Serious Adverse Event Definition:

A serious AE (SAE) is any AE occurring at any dose that results in any of the following outcomes: death, is life-threatening, requires inpatient hospitalization, requires prolongation of existing hospitalization, a persistent or significant disability/incapacity, and a congenital anomaly/birth defect.

Important medical events that may not result in death, be life-threatening, or require hospitalization may be considered as SAEs when, based upon appropriate medical judgment, they may jeopardize the patient and may require medical or surgical intervention to prevent one of the outcomes listed above.

A life-threatening AE is defined as an AE that placed the patient, in the view of the initial reporter, at immediate risk of death from the AE as it occurred (i.e., it does not include an AE that, had it occurred in a more severe form, might have caused death).

Classification of Adverse Events and Serious Adverse Events:

The National Cancer Institute Common Toxicity Criteria (NCI CTC) Version 3.0 grading scale was referenced when assessing the severity of an AE. If an AE was not described in the NCI CTC, the severity was recorded based on the scale below. The severity of all AEs/SAEs were recorded on the appropriate CRF page as Grade 1, 2, 3 or 4 corresponding, respectively, to a severity of mild, moderate, severe, or life-threatening. Grade 1 (mild) is defined as no limitation of usual activities. Grade 2 (moderate) is defined as some limitation of usual activities; Grade 3 (severe) is defined as inability to carry out usual activities; and Grade 4 (life-threatening) is defined as immediate risk of death.

Relationship of an adverse event or serious adverse event to blinded study medication was determined by the Investigator based on the following definitions. "Not related" is defined as unrelated to study drug. "Possibly related" is defined as a clinical event/laboratory abnormality with a reasonable time sequence to administration of study drug, but which could also be explained by concurrent disease or other drugs/chemicals. "Probably related" is defined as a clinical event/laboratory abnormality with a reasonable time sequence to administration of study drug, unlikely to be attributable to concurrent disease or other drugs and chemicals and which follows a clinically reasonable response on dechallenge. The association of the clinical event/laboratory abnormality must also have some biologic plausibility, at least on theoretical grounds.

Clarification between Serious and Severe:

The term "severe" is often used to describe the intensity (severity) of a specific event (as in mild, moderate, or severe myocardial infarction); the event itself, however, may be of relatively minor medical significance (such as severe headache). This is not the same as "serious," which is based on the outcome or action criteria usually associated with events that pose a threat to life or functioning. Seriousness (not severity) and causality serve as a guide for defining regulatory reporting obligations.

Adverse Event Monitoring and Period of Observation:

For the purposes of this study, the period of observation extended from informed consent/assent until the patient's final evaluation of the study. For safety purposes, the final evaluation was defined as the post-study safety evaluation performed approximately 30 days after the last infusion for patients who completed the study and did not elect to enroll in the long-term study. For patients who completed this study and elected to enroll in the long-term clinical study, adverse events were monitored from the time the patient provides informed consent through the Week 53 visit of TKT032.

Statistical Methods

General Statistical Methodology:

Statistical analyses were based on the ITT principle for all efficacy variables. The ITT analysis was based on all randomized patients who received at least one infusion (full or partial infusion). Summary statistics were provided for the changes and percent changes from Baseline for each parameter by treatment group. Two-sided 95% confidence intervals in the mean changes and mean percent changes from Baseline were presented by treatment group for each endpoint.

Continuous data collected at Baseline and subsequent study visits were summarized, and the mean, standard deviation, minimum, maximum, and median values for each variable were tabulated to facilitate the search for trends over time which might be attributable to study drug. Categorical variables were presented in terms of frequencies and percent. Within group changes were examined using paired t-tests. Statistical significance was defined at the 0.05 level.

Demographic and Baseline characteristics were summarized as frequencies and percentages, and data were presented using descriptive statistics. Additional analyses were conducted specifically for patients between 2 and 17 years old.

In general, descriptive statistics and graphs were used for presentation of study results, including, if relevant, graphs showing the development over time for patients individually and for each treatment group.

Safety was evaluated on the basis of AEs reported, clinical laboratory data, ECG recordings, medical histories, vital signs, and physical examinations. In addition, blood samples were analyzed for determination of the presence of anti-velaglucerase alfa antibodies.

Hypothesis Testing:

All hypothesis testing was 2-sided and was performed at the 0.05 level of significance. Each variable was quantified as a mean change from Baseline or mean percent change from Baseline. The null hypothesis for each variable being tested is that, at Week 51 or Week 53, there is no change from Baseline. The alternative hypothesis is that there is a change in either direction from Baseline.

Screen Failures:

The disposition of all patients screened for entry into the study was tabulated along with reasons for screen failure. The disposition of all randomized patients was tabulated by treatment and visit, and reasons for discontinuation were tabulated by treatment.

Sample Size Justification:

The sample size for this study was chosen to have a high power to detect a clinically significant difference in mean hemoglobin concentrations from Baseline to 12 months. A total of 12 patients per treatment arm were required for the primary analysis. This number was based on results from the Phase I/II Study TKT025, examining the within patient change from Baseline results. It was observed that at Week 25, the average hemoglobin increase from Baseline was 1.92 g/dL with a standard deviation of 0.824. The assumption was that the standard deviation of the mean change was approximately the same. Using a two-sided alpha level of 0.05 and assuming a 1-unit change in hemoglobin is considered clinically significant, the standard deviation of the change from Baseline is 0.824, then 10 patients would be needed for the trial to have a power of 90%. Assuming a 20% drop out rate, then 12 patients per treatment group would be needed. To gather additional safety data and to protect against possible patient dropout(s), and to achieve the target patient population, up to 30 patients could be enrolled in this study Analysis Populations:

The primary population for analyses of efficacy data was the ITT patient population, defined as all enrolled and treated patients who receive at least one velaglucerase alfa infusion (or partial infusion). It was anticipated that attrition from the original random sample due to lack of post-Baseline data would be sufficiently small (5% or less) so as to minimize concerns regarding bias due to the exclusion of such patients.

The safety population consisted of all randomized patients who received at least one study infusion (or partial infusion). Any patient in the safety population who did not receive the study infusion to which he or she was randomized was analyzed according to the infusion they predominantly received rather than the randomized treatment. Such patients were excluded from the Per-Protocol (PP) patient population. The PP patient population is defined as all randomized patients who have receive 80% of the scheduled infusions, and who have valid Baseline and Week 51 and/or Week 53 evaluations.

Efficacy Analyses:

The disposition of all patients Screened for entry into the study was tabulated, along with reason(s) for Screening failure. The disposition of all randomized patients was tabulated by treatment group and visit, and reason(s) for discontinuation (s) was tabulated.

The primary clinical activity variable is hemoglobin concentrations in the patients randomized to 60 U/kg of velaglucerase alfa. The primary objective is to demonstrate efficacy by showing a mean change in hemoglobin from Baseline to 12 months in patients randomized to 60 U/kg of velaglucerase alfa. For analysis purposes, hemoglobin values collected at Screening and Baseline were averaged to establish the Baseline used to calculate change. The null hypothesis is that there will be no change from Baseline in hemoglobin concentrations to 12 months. The mean difference from Baseline to 12 months was tested using a paired t-test or Wilcoxon signed rank test. A 95% confidence interval for the mean difference was also presented.

Secondary and tertiary clinical activity variables are: hemoglobin concentrations (change from Baseline to 12 months (Week 53) was assessed for the 45 U/kg group); platelet counts (change from Baseline to 12 months (Week 53) was assessed for both treatment groups); spleen volume (percent change from Baseline to 12 months (Week 51) was assessed for both treatment groups; in addition to observed values, spleen volumes were normalized by body weight and also presented by multiples of normal); liver volume (percent change from Baseline to 12 months (Week 51) was assessed for both treatment groups; in addition to observed values, liver volumes were normalized by body weight and also presented by multiples of normal); plasma chitotriosidase (change from Baseline to 12 months (Week 53) was assessed for both treatment groups; a statistically significant decrease expected after 12 months of treatment); plasma CCL18 (change from Baseline to 12 months (Week 53) was assessed for both treatment groups; a statistically significant decrease expected after 12 months of treatment); quality of life (SF-36 and CHQ) (change from Baseline to 12 months (Week 53) was assessed for both treatment groups); hemoglobin response (time to achieve a hemoglobin response, defined as an increase in hemoglobin concentration of $\geq 1$ g/dL was assessed for both treatment groups); growth velocity and Tanner staging (change from Baseline to 12 months (Week 53) was evaluated for both treatment groups in patients between 2 and 17 years-old); skeletal age (change from Baseline to 12 months (Week 51) was evaluated for both treatment groups, as measured by radiography of the left hand and wrist, in patients 2 to 17 years-old); and PFTs (change from Baseline to 12 months (Week 53) was assessed for both treatment groups in patients $\geq 18$ years-old).

For the secondary objective used to demonstrate a mean change in hemoglobin from Baseline to 12 months (Week 53) in patients randomized to 45 U/kg of velaglucerase alfa, the null hypothesis is that there will be no change from Baseline to 12 months (Week 51 or Week 53). For analysis purposes, hemoglobin values collected at Screening and Baseline were averaged to establish the Baseline used to calculate change. The mean difference from Baseline to 12 months (Week 51 or Week 53) was tested using a paired t-test or Wilcoxon signed rank test. A 95% confidence interval for the mean difference was also presented.

For the remaining secondary parameters, the null hypothesis is that there will be no change from Baseline to 12 months (Week 51 or Week 53) for each treatment group. For analysis purposes, platelet values collected at Screening and Baseline were averaged to establish the Baseline used to calculate change for both the treatment groups. The mean difference from Baseline to 12 months (Week 51 or Week 53) was tested using a paired t-test or Wilcoxon signed rank test. A 95% confidence interval for the mean difference was also presented.

For time to hemoglobin response, Kaplan-Meier (product limit) survival curves were presented for each treatment group. The median time and 95% confidence interval were obtained. Patients who did not experience the event at the end of the study (i.e., at Week 53) were censored at Week 53. In addition, the proportion of patients who achieved a hemoglobin level within the normal range during this study was presented.

For the remaining tertiary parameters that examine change from Baseline, the null hypothesis is that there will be no change from Baseline to 12 months (Week 51 or Week 53) for each treatment group. The mean difference between Baseline to 12 months (Week 51 or Week 53) was tested using a paired t-test or Wilcoxon signed rank test. A 95% confidence interval for the mean difference was also presented.

Safety Analyses:

All patients who received at least one dose of study drug (or partial dose) were assessed for clinical safety and tolerability. No formal statistical tests were performed on the safety parameters. Vital signs, 12-lead ECG, clinical chemistry, hematology, and urinalysis safety monitoring were listed for each patient and abnormal values were flagged. For categorical variables, such as AEs, the number and percentage of patients experiencing each AE were tabulated. AEs were summarized by severity of event. The number and percentage of patients experiencing drug related AEs as well as AEs that were not considered related to study drug were also displayed.

Clinical laboratory evaluations (hematology, serum chemistry, urinalysis, and determination of anti-velaglucerase alfa antibodies) were used to assess the safety of velaglucerase alfa.

Analysis of Subgroups:

Additional analyses were conducted specifically for patients between 2 to 17 years old. Also, consideration was given in the analysis to disease severity with regard to hemoglobin Baseline values.

Pharmacokinetic Analyses:

The single- and repeat-dose pharmacokinetic profiles for velaglucerase alfa were established by analyzing standard PK parameters at Week 1 and Week 37, respectively.

Results

At 12 months, mean hemoglobin concentration increased in both groups (60 U/kg: 23.3% increase, +2.4±0.3 g/dL, P=0.0001; 45 U/kg: 23.8% increase, +2.4±0.5 g/dL, P=0.0001), as did mean platelet count (60 U/kg: 66% increase, +51±12×10$^9$/L, P=0.0016; 45 U/kg: 66% increase, +41±12×10$^9$/L; P=0.0111). Mean spleen volume decreased in both groups (60 U/kg: 50% decrease, −1.9±0.5% body weight, P=0.0032, from 14.0 multiples of normal [MN] at baseline to 5.6 MN; 45 U/kg: 40% decrease, −1.9±0.6% body weight, P=0.0085; from 14.5 to 9.5 MN) as did liver volume (60 U/kg: 17% decrease, 0.8±3. % body weight, P=0.0282, from 1.5 to 1.2 MN; 45 U/kg: 6% decrease, −0.3±0.3% body weight, P=0.3149, from 1.4 to 1.2 MN).

In both groups, three-quarters of patients achieved ≤1 g/dL increase in hemoglobin concentration by Week 15; in the 60 U/kg group, all patients achieved ≥1 g/dL increase by Week 27 vs Week 37 for the 45 U/kg group.

Patients were excluded from the analysis of chitotriosidase if they had 2 copies of the chitotriosidase mutation (patient 6, 45 U/kg) or if they had baseline chitotriosidase activity less than 5700 (patient 4, 60 U/kg; patient 15, 45 U/kg). Following 12 months of treatment, mean plasma chitotriosidase activity decreased from baseline for both treatment groups: by 83% (95% CI: −91.15, −74.08%; N=11; p<0.001) in the 60 U/kg group and by 60% (95% CI: −73.26, −46.63%; N=11; p<0.001) in the 45 U/kg group. Mean CCL18 levels also decreased over 1 year of treatment with velaglucerase alfa 60 U/kg and 45 U/kg by 66% (95% CI: −77.81, −54.22; p<0.001) and 47% (95% CI: −63.37, −30.15%; p<0.001), respectively.

Velaglucerase alfa was generally well tolerated with no drug-related serious AEs, and no patient withdrew due to an AE. The most common AEs were headache, nasopharyngitis, injury, arthralgia, cough, and pyrexia. A single patient developed antibodies.

In conclusion, in this global, multicenter study, velaglucerase alfa 60 U/kg and 45 U/kg was generally well tolerated and effective as a first-line treatment for adults and children with type 1 Gaucher disease. Both doses were associated with rapid improvement in hemoglobin values, with the majority of patients responding as early as 15 weeks. All clinical parameters measured demonstrated clinically meaningful improvements after 12 months, with a greater response seen with velaglucerase alfa 60 U/kg.

Example 3

HGT-GCB-039 (9M, 60 U/Kg Velaglucerase Alfa or Imiglucerase)

Summary

This example describes a multicenter, Phase III, randomized, double-blind, parallel-group study designed to compare the safety and efficacy of the enzyme replacement therapy velaglucerase alfa with imiglucerase in the treatment of patients with type 1 Gaucher disease.

The primary objective of this example is to demonstrate that velaglucerase alfa is not inferior to imiglucerase as measured by a change from baseline in hemoglobin concentration to Week 41 (9M). The key secondary objective is to demonstrate that there are no differences in increases in platelet counts or reductions in liver/spleen volumes to Week 41 between the two groups.

Figure 11:
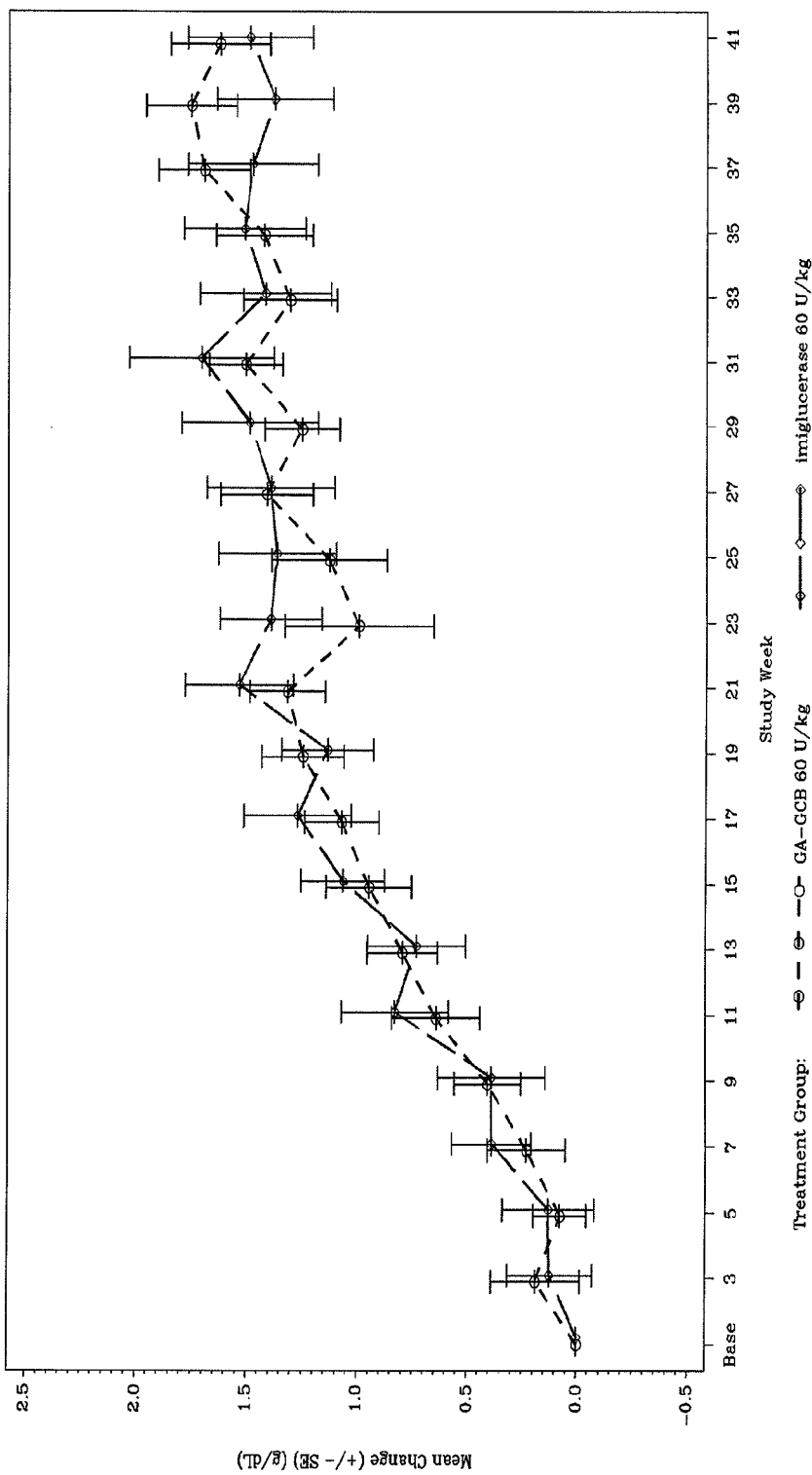
FIG. 11 depicts HGT-GCB-039 (N=34) mean hemoglobin concentration change from baseline.
Figure 12:
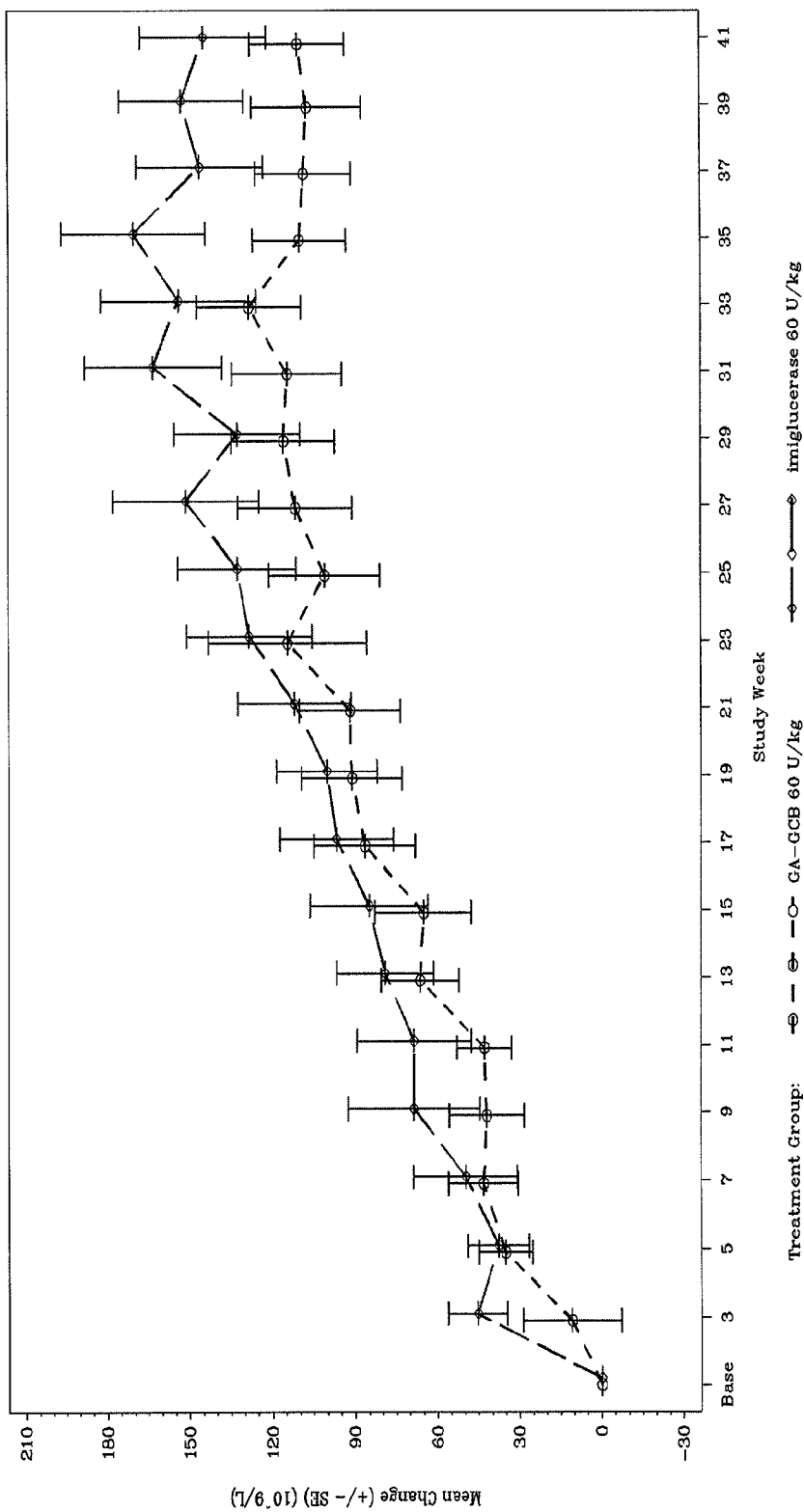
FIG. 12 depicts HGT-GCB-039 (N=34) mean platelet count change from baseline.
Figure 13:
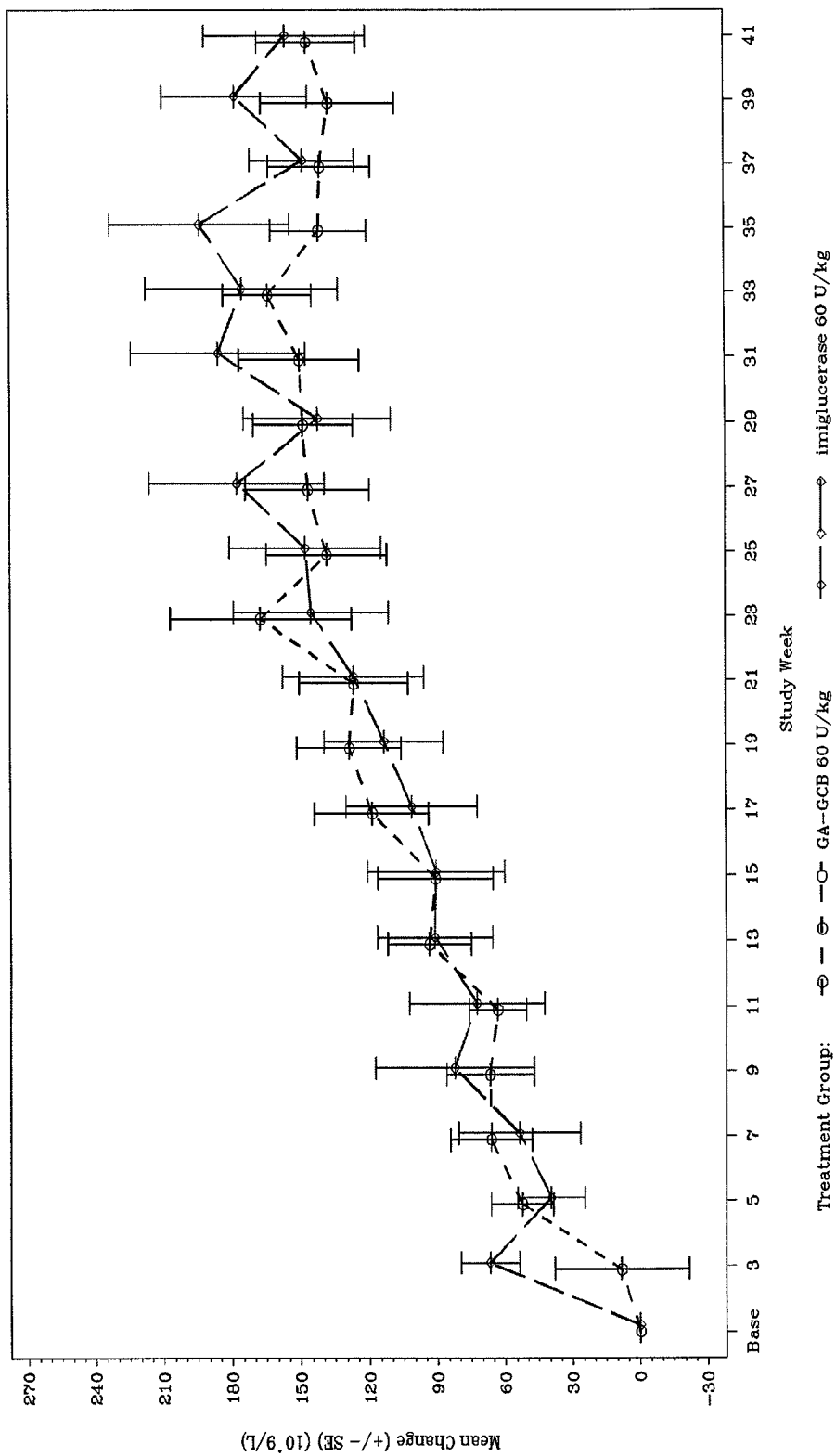
FIG. 13 depicts HGT-GCB-039 (N=34) mean change from baseline of platelet count in patients without spleen.
Figure 14:
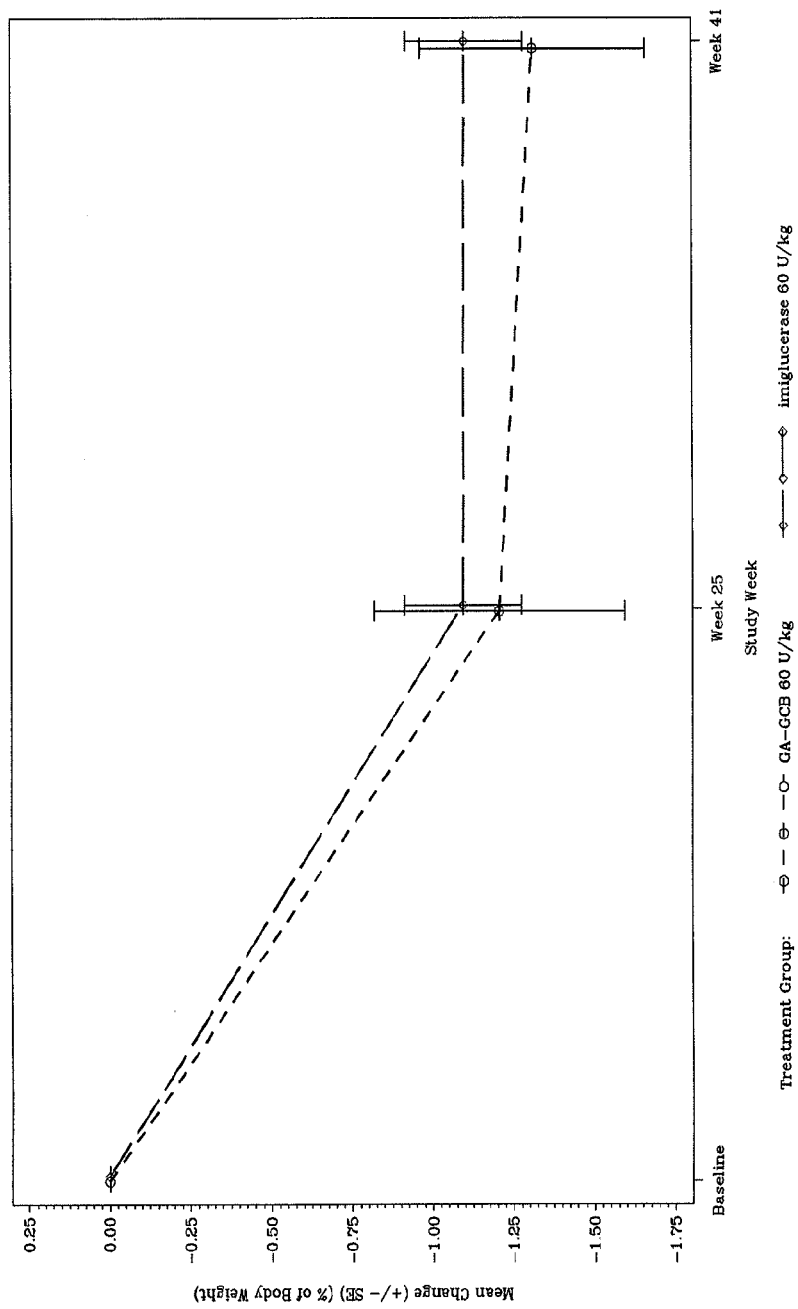
FIG. 14 depicts HGT-GCB-039 (N=34) mean normalized liver volume change from baseline.
Figure 15:
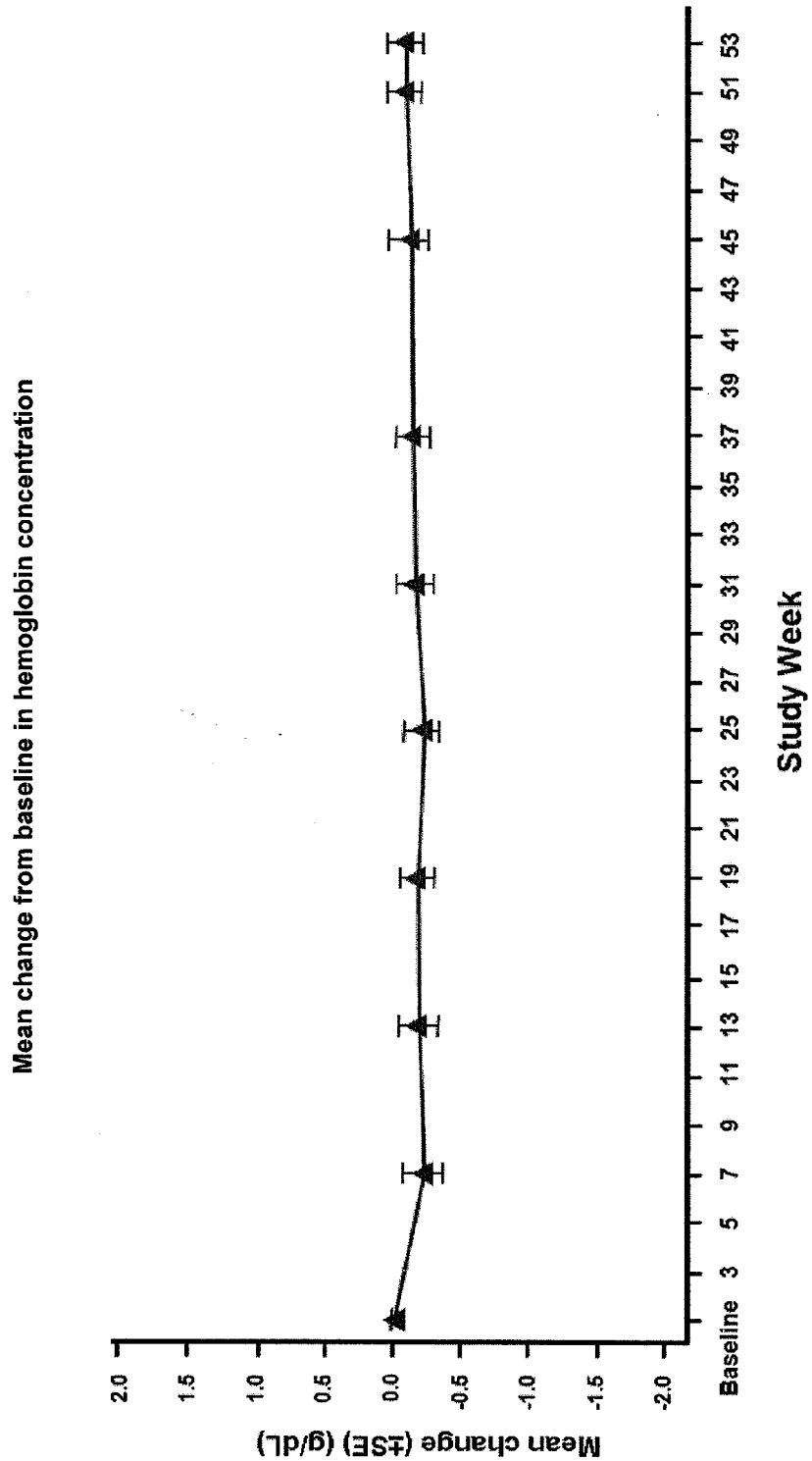
FIG. 15 depicts TKT034 mean change from baseline in hemoglobin concentration.
Figure 16:
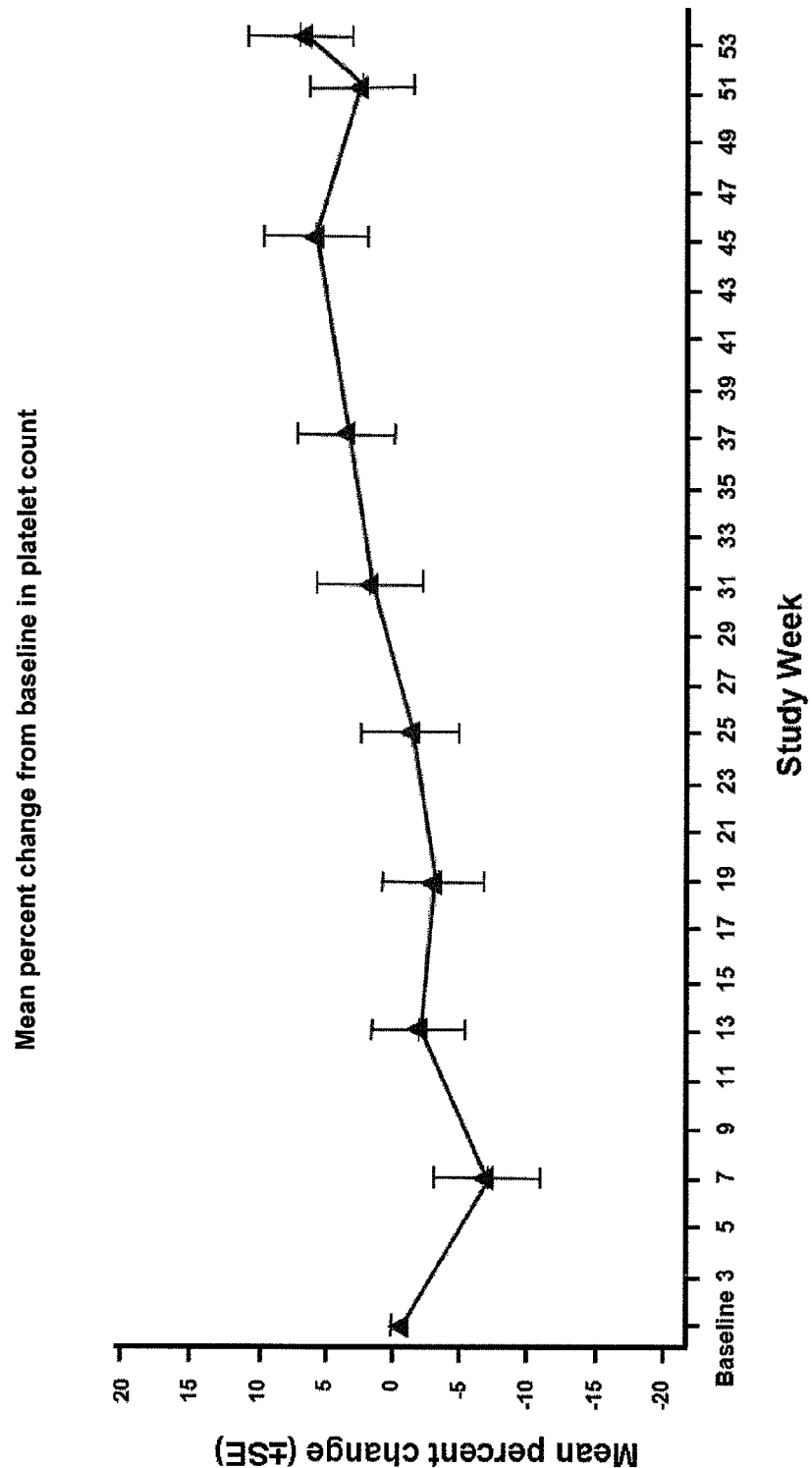
FIG. 16 depicts TKT034 mean n percent change from baseline in platelet count.
Figure 17:
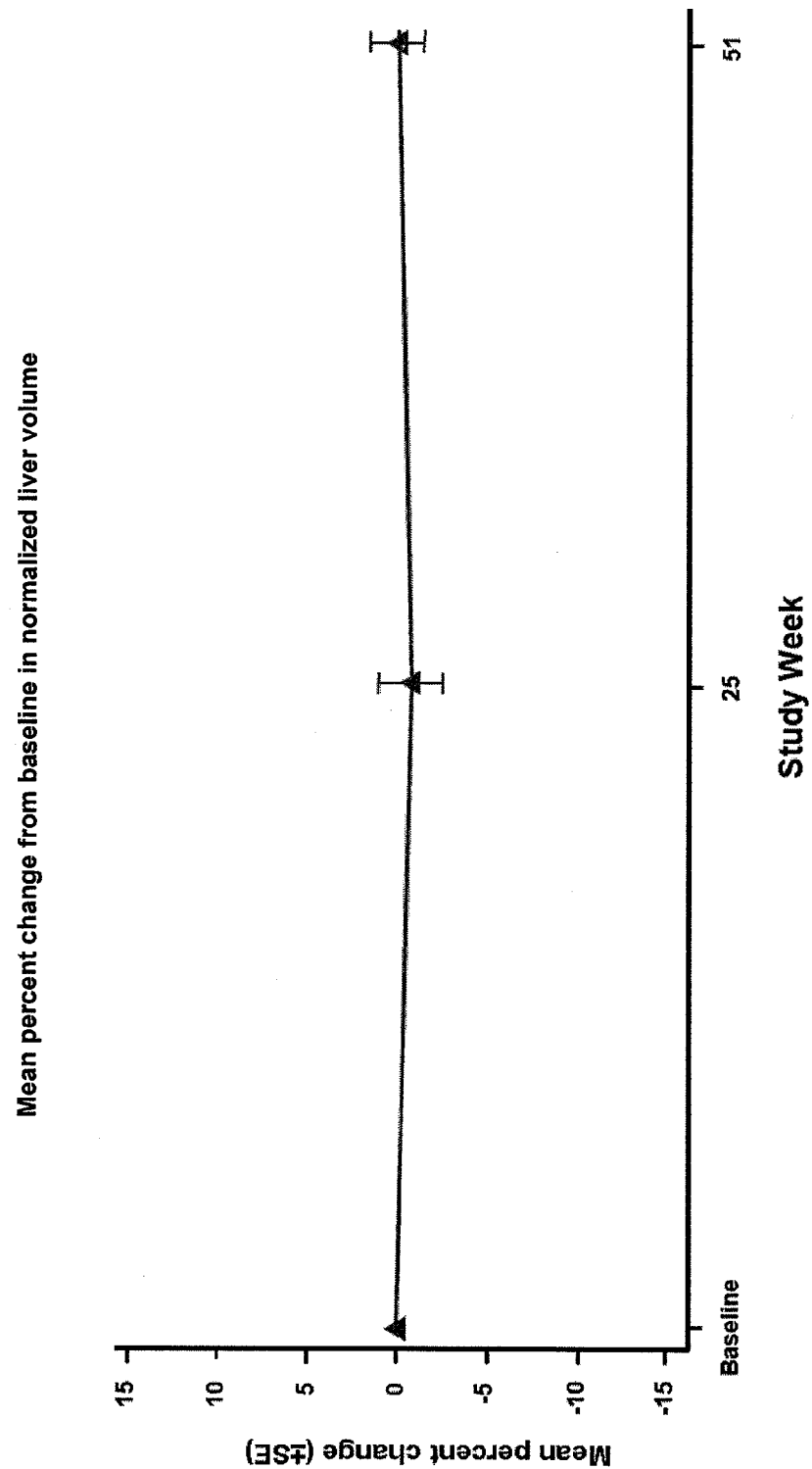
FIG. 17 depicts TKT034 mean percent change from baseline in normalized liver volume.
Figure 18:
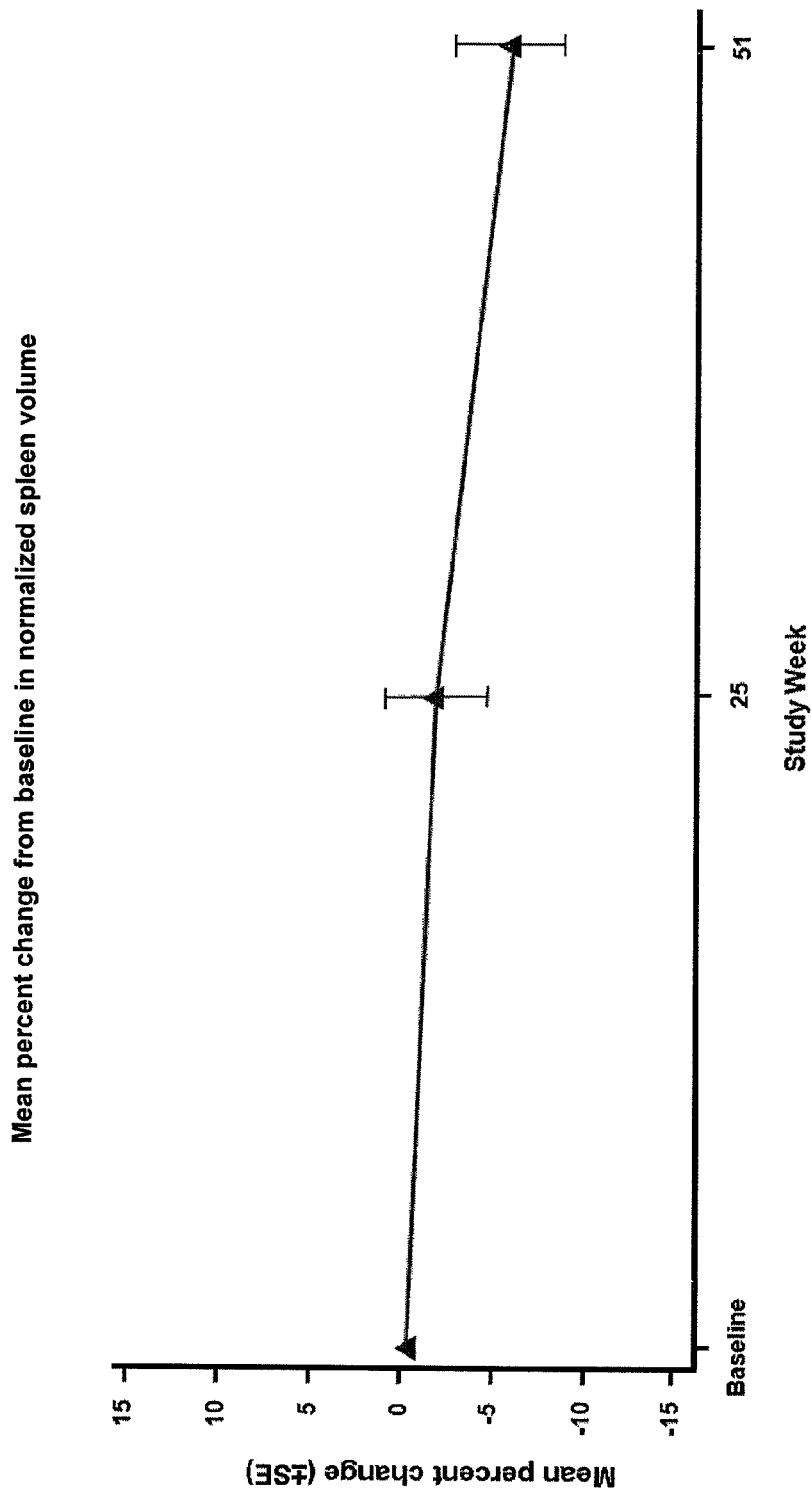
FIG. 18 depicts TKT034 mean percent change from baseline in normalized spleen volume.

Patients were randomized in 1:1 ratio to receive 60 U/kg of velaglucerase alfa (N=17) or imiglucerase (N=17). The baseline characteristics of the patients are listed in Tables 13 and 14. Stratification factors included age (2-17; ≥18) and splenectomy status (Y; N). Both primary and secondary objectives were met. The results for the primary and secondary efficiency assessments are shown in Tables 15 and 16, respectively. FIGS. 11 and 12 show the comparable increase of mean hemoglobin concentration and platelet count, respectively, from baseline in the patients treated with 60 U/kg velaglucerase alfa or imiglucerase for 41 weeks. FIG. 13 shows the comparable increase of mean platelet count from baseline in the patients without spleen treated with 60 U/kg velaglucerase alfa or imiglucerase for 41 weeks. FIG. 14 shows the comparable decrease of mean normalized liver volume from baseline in the patients treated with 60 U/kg velaglucerase alfa or imiglucerase for 41 weeks. There were no significant differences in safety between velaglucerase alfa and imiglucerase. Treatment emergent adverse events are summarized in Table 17. No patient receiving velaglucerase alfa developed antibodies (Table 18). Four patients receiving imiglucerase developed anti-imiglucerase antibodies (Table 18).

TABLE 13

HGT-GCB-039 Baseline Characteristics of ITT

| Baseline Factor | velaglucerase alfa 60 U/kg N = 17 | imiglucerase 60 U/kg N = 17 |
|---|---|---|
| 2 to 17 years n (%) | 4 (23.5) | 5 (29.4) |
| 2 to 4 years n (%) | 0 | 4 (23.5) |
| 5 to 17 years n (%) | 4 (23.5) | 1 (5.9) |
| ≥18 years n (%) | 13 (76.5) | 12 (70.6) |
| Male n (%) | 8 (47.1) | 8 (47.1) |
| Female n (%) | 9 (52.9) | 9 (52.9) |
| Splenectomized | 10 (58.8) | 10 (58.8) |
| With intact spleen | 7 (41.2) | 7 (41.2) |
| BL Hemoglobin concentration (g/dL) Median [Min, Max] | 11.40 [9.65, 14.35] | 10.60 [8.10, 13.05] |
| BL Platelet count (×10$^9$/L) Median [Min, Max] | 172.00 [44.0, 310.5] | 188.00 [63.0, 430.5] |

TABLE 14

HGT-GCB-039 Baseline Characteristics by Age Group

| Baseline Factor | 2-4 Years Old<br>N = 4 | >5 Years Old<br>N = 30 |
|---|---|---|
| Male n (%) | 4 (100.0) | 12 (40.0) |
| Female n (%) | 0 | 18 (60.0) |
| Splenectomized | 1 (25.0) | 19 (63.3) |
| With intact spleen | 3 (75.0) | 11 (36.7) |
| BL Hemoglobin concentration (g/dL) Median [Min, Max] | 9.275 [8.10, 9.70] | 11.300 [8.95, 14.35] |
| BL Platelet count (×10$^9$/L) Median [Min, Max] | 70.75 [63.0, 188.0] | 176.25 [44.0, 430.5] |
| BL Spleen Volume (% body Weight) Median [Min, Max] | 8.90 [7.3, 8.9] | 1.70 [0.6, 6.3] |
| BL Liver Volume (% body Weight) Median [Min, Max] | 5.8 [5.4, 7.0] | 3.85 [1.7, 12.2] |

TABLE 15

HGT-GCB-039 Primary Efficacy Assessments-Mean Change at Week 41 from Baseline in Hgb One-sided CI for Non-inferiority (velaglucerase alfa-imiglucerase)

| | Treatment Difference in the Change from Baseline to Week 41 | | | |
|---|---|---|---|---|
| | ITT Population | | Per Protocol Population | |
| Parameter/Endpoint | n | Mean Treatment Difference | Lower Bound of a 97.5% One-sided CI | n | Mean Treatment Difference | Lower Bound of a 97.5% One-sided CI |

Hemoglobin Concentration (g/dL)

| | 34 | 0.135 | −0.596 | 30 | 0.157 | −0.599 |

TABLE 16

HGT-GCB-039 Secondary Efficacy Assessments - Difference in Mean Change at Week 41 from Baseline (velaglucerase alfa - imiglucerase)

| | Change from Baseline to Week 41 | | |
|---|---|---|---|
| Parameter | n | Mean Treatment Difference | 95% CI |
| Platelets$^a$ (×10$^9$/L) | 34 | −38.71 | (−88.42, 10.99) |
| Normalized Liver Volume$^a$ (% of Body Weight) | 34 | −0.07 | (−0.43, 0.29) |
| Normalized Spleen$^b$ Volume$^c$ (% of Body Weight) | 14 | 0.08 | (−0.52, 0.68) |
| Chitotriosidasea $^d$ (nmol/mL/h) | 21 | −703.6 | (−11762.3, 10355.1) |
| Chemokine (C-C motif) Ligand 18 (ng/mL) | 34 | 145.7 | (−188.6, 480.0) |

$^a$Based on a mixed model adjusting for age at informed consent, splenectomy status and baseline values.
$^b$There are 20 splenectomized patient(s) excluded (10 velaglucerase alfa 60 U/kg; 10 imiglucerase 60 U/kg).
$^c$Based on a mixed model adjusting for age at informed consent and baseline values.
$^d$There are 13 patient(s) deficient in chitotriosidase activity excluded (7 velaglucerase alfa 60 U/kg; 6 imiglucerase 60 U/kg).

TABLE 17

HGT-GCB-039 Overall Summary of Treatment Emergent Adverse Events

| | Patients n(%) | |
|---|---|---|
| DESCRIPTION | velaglucerase alfa 60 U/kg N = 17 | imiglucerase 60 U/kg N = 17 |
| Experienced No Adverse Events | 1 (5.9) | 1 (5.9) |
| Experienced At Least 1 Adverse Event | 16 (94.1) | 16 (94.1) |
| Experienced At Least 1 Drug-Related Adverse Event | 8 (47.1) | 6 (35.3) |
| Experienced At Least 1 Infusion-Related Adverse Event | 5 (29.4) | 4 (23.5) |
| Experienced At Least 1 Severe Or Life-Threatening Adverse Event | 3 (17.6) | 2 (11.8) |
| Experienced At Least 1 Serious Adverse Event | 3 (17.6) | 0 |

TABLE 17-continued

HGT-GCB-039 Overall Summary of Treatment Emergent Adverse Events

| | Patients n(%) | |
|---|---|---|
| DESCRIPTION | velaglucerase alfa 60 U/kg N = 17 | imiglucerase 60 U/kg N = 17 |
| Experienced at least 1 drug-related SAE | 1 (5.9) | 0 |

TABLE 18

HGT-GCB-039 Antibodies

| | velaglucerase alfa 60 U/kg N = 17 n (%) | imiglucerase 60 U/kg N = 17 n (%) |
|---|---|---|
| Anti-imiglucerase Antibody Result | | |
| Negative | 17 (100.0) | 13 (76.5) |
| Positive$^a$ | 0 | 4 (23.5) |
| IgG | 0 | 4 (23.5) |
| IgA | 0 | 0 |
| IgM | 0 | 0 |
| IgE | 0 | 0 |
| Neutralizing antibodies | 0 | 1 (5.9) |

TABLE 18-continued

HGT-GCB-039 Antibodies

| | velaglucerase alfa 60 U/kg N = 17 n (%) | imiglucerase 60 U/kg N = 17 n (%) |
|---|---|---|
| Anti-velaglucerase alfa Antibody Result | | |
| Negative | 17 (100.0) | 16 (94.1) |
| Positive<sup>a</sup> | 0 | 1 (5.9) |
| IgG | 0 | 1 (5.9) |
| IgA | 0 | 0 |
| IgM | 0 | 0 |
| IgE | 0 | 0 |
| Neutralizing antibodies | 0 | 1 (5.9) |

Study Objectives

The primary objective of this study was to compare the effects of velaglucerase alfa and imiglucerase on hemoglobin concentration in patients with type 1 Gaucher disease.

The secondary objectives of this study were: to compare the effects of velaglucerase alfa and imiglucerase on platelet count; to compare the effects of velaglucerase alfa and imiglucerase on liver and spleen volumes (by MRI); to compare the effects of velaglucerase alfa and imiglucerase on Gaucher disease-specific biomarkers (plasma chitotriosidase and CCL18 levels); to evaluate the safety of velaglucerase alfa and imiglucerase in patients with type 1 Gaucher disease, as measured by standard clinical laboratory assessments (including rates of antibody formation and enzyme neutralizing antibody activity) and safety evaluations (including rates of infusion-related adverse events and the proportion of patients requiring premedication use to manage infusion-related adverse events) for each treatment group; and to compare the effects of velaglucerase alfa and imiglucerase on the earliest time to response for hemoglobin (defined as a 1 g/dL improvement in hemoglobin levels relative to Baseline).

The tertiary objectives of this study are: to evaluate the effects of velaglucerase alfa and imiglucerase on growth velocity and Tanner staging in patients between 2 and 17 years-old; to evaluate the effects of velaglucerase alfa and imiglucerase on changes in skeletal age in patients between 2 and 17 years-old by radiography of the left hand and wrist; to evaluate the effects of velaglucerase alfa and imiglucerase on changes in overall QoL, as measured by the SF-36 for patients ≥18 years of age and the CHQ PF-50 for patients 5 to 17 years-old; to evaluate the effects of velaglucerase alfa and imiglucerase on immune and inflammatory responses in patients ≥18 years of age as measured by selected cytokine assessments (TNF-α, IL6, IL1b, IL8, IL13, CD14, and GM-CSF); to establish a baseline from which to evaluate bone disease in patients between 2 and 17 years-old by MRI of the lumbar spine and femoral neck; and to establish a baseline from which to evaluate the long-term effect of velaglucerase alfa therapy on Gaucher-related local and systemic bone disease in patients ≥18 years-old by: dual energy X-ray absorptiometry (DXA) of the lumbar spine and femoral neck, including coronal imaging; and serum alkaline phosphatase, N-telopeptide cross-links (NTx), and C-telopeptide cross-links (CTx).

Study Endpoints

The primary endpoint of this study is to measure the mean change from Baseline to week 41/End of Study (EOS) in hemoglobin concentration between the two treatment groups.

The secondary endpoints of this study are: to evaluate the safety of velaglucerase alfa and imiglucerase, as assessed by adverse events and infusion-related adverse events (and the proportion of patients requiring premedication use to manage infusion-related adverse events), clinical laboratory values, vital signs, 12-lead electrocardiograms (ECG), antibody formation and enzyme neutralizing antibody activity; to compare the mean and percent changes from Baseline in platelet count between treatment groups; to compare the mean and percent changes from Baseline in liver and spleen volumes by MRI between treatment groups; to compare the mean and percent changes from Baseline in plasma chitotriosidase and plasma CCL18 levels between treatment groups; and to compare time to response for hemoglobin concentration (defined as a ≥1 g/dL improvement in hemoglobin levels relative to Baseline) between treatment groups.

The tertiary endpoints of this study are: to evaluate change from Baseline in growth velocity and Tanner staging for patients between 2 and 17 years-old within each treatment group; to evaluate change from Baseline in the SF-36 parameters for patients ≥18 years-old within each treatment group; to evaluate the effects of velaglucerase alfa and imiglucerase on immune and inflammatory responses in patients ≥18 years-old as measured by selected cytokine assessments (TNF-α, IL6, IL1b, IL8, IL13, CD14, and GM-CSF); to evaluate change from Baseline in the CHQ (PF-50) parameters for patients 5 to 17 years-old within each treatment group; and to evaluate change from Baseline in skeletal age as measured by radiography of the left hand and wrist for patients between 2 and 17 years old within each treatment group.

Overall Study Design

This study was comprised of 5 phases as follows: Screening: Day −21 through Day −4; Baseline: Day −3 through Day 0 (through patient randomization); Treatment: Week 1 (Day 1, i.e., day of first dose) through Week 39; End of Study Visit: Week 41; Follow-up Contact: 30 days after the final infusion (for patients who discontinue/withdraw prior to the Week 41 evaluation, or for patients who do not elect to enroll in the long-term clinical study).

At Screening, patients who provided written informed consent to participate in this study were reviewed against the study entrance criteria to determine eligibility. Patients provided blood samples to measure hemoglobin concentration. Only those patients who had a hemoglobin concentration that was below the lower limit of normal for age and gender were eligible for enrollment. For statistical analysis purposes, an additional blood sample was collected at screening for evaluation of hemoglobin concentration.

Patients who were eligible for study participation after completing the Screening evaluations underwent Baseline procedures and evaluations (i.e., Days −3 to 0). To confirm that their hemoglobin concentration was below the lower limit of normal for age and gender, patients provided a blood sample at Baseline. Hemoglobin concentration was analyzed and reported. Only those patients who had a hemoglobin concentration that was below the lower limit of normal for age and gender at both Screening and Baseline were eligible for enrollment. For statistical analysis purposes, an additional blood sample was collected at Baseline for evaluation of hemoglobin concentrations. Additional Baseline procedures and evaluations were conducted prior to administration of the first dose of blinded study medication.

Upon completion of Screening and Baseline procedures and confirmation of patient eligibility, patients were randomized in a 1:1 ratio to receive double-blind study medication (either velaglucerase alfa 60 U/kg or imiglucerase 60

U/kg). Randomization was accomplished via a centralized procedure. A computer generated randomization schedule was utilized to allocate patients to treatment groups. An attempt was made to obtain treatment groups that were comparable in certain prognostic variables, such as age, hemoglobin concentration, and whether the patient had undergone splenectomy. The randomization schedule was prepared prior to the study.

Patients received a total of 20 IV infusions of double-blind study medications at the clinical site once every other week for a total of 39 Weeks. Safety and efficacy assessments were made at regular intervals during the treatment phase. The final assessments of safety and efficacy were made at the Week 41 visit (2 weeks after the last infusion).

Safety was assessed throughout the study by assessments of adverse events (including infusion-related adverse events), concomitant medications, and vital signs. Additional safety assessments, including, 12-lead electrocardiograms, physical examinations, clinical laboratory tests (hematology, serum chemistry, and urinalysis), were made at Weeks 13, 25, and 41. Determination of the presence of anti-velaglucerase alfa or anti-imiglucerase antibodies and enzyme neutralizing antibodies was conducted approximately every 6 weeks until Week 41.

Efficacy was assessed via hemoglobin concentration and platelet count, liver and spleen volume, and plasma chitotriosidase and CCL18 level. Additional efficacy assessments included growth velocity and Tanner staging, QoL indicators, skeletal growth. Immune and inflammatory response (as measured by selected cytokine parameters) was measured in patients who are ≥18 years of age at study entry. The duration of treatment in this study was 39 weeks and the duration of patient participation in this study was up to 11 months (from Screening through follow-up). Patients who completed this study were provided the opportunity to enroll in a subsequent open-label long-term clinical study, in which all patients would receive velaglucerase alfa. For patients who elected to enroll in the subsequent open-label long-term clinical study, certain assessments from the Week 41 visit were used as the baseline assessments for that clinical study; patients would receive their first velaglucerase alfa infusion for the long-term clinical study following completion of the Week 41 procedures and evaluations scheduled for this study. Therefore, it was intended that patients would receive continuous treatment across the 2 studies. Patients who completed this study and did not elect to enroll in the long-term clinical study would have a safety evaluation by site visit or telephone 30 days after their last infusion in this study.

Selection of Study Population 34 patients were enrolled (17 patients assigned to each treatment group).

Eligible participants were males or females age ≥2 years with diagnosed type 1 Gaucher disease (deficient glucocerebrosidase activity in leukocytes, or by genotype analysis), and disease-related anemia (hemoglobin levels below the local laboratory's lower limit of normal for age and gender). Participants also had 1 or more of the following: at least moderate splenomegaly (2 to 3 cm below the left costal margin) by palpation; disease-related thrombocytopenia (platelet count <$120 \times 10^3$ platelets/mm$^3$); or readily palpable enlarged liver. Participants could not have received treatment for Gaucher disease within 12 months prior to study entry.

Participants were excluded if they had a splenectomy; had (or were suspected of having) type 2 or 3 Gaucher disease; were antibody-positive or had experienced an anaphylactic shock to imiglucerase. Other exclusion criteria included treatment with any non-Gaucher disease-related investigational drug or device within 30 days prior to study entry; positive test for HIV, or hepatitis B or C; exacerbated anemia (vitamin B12, folic acid, or iron deficiency-related), or any significant co-morbidity that could affect study data. Pregnant or lactating women were excluded and women of child-bearing potential were required to use a medically acceptable method of contraception at all times.

Study Treatments

Treatment Assignment:

Patients were randomized in a 1:1 ratio prior to administration of the first dose of: velaglucerase alfa 60 U/kg every other week for 39 Weeks (up to 16 patients, 20 infusions), or imiglucerase 60 U/kg every other week for 39 Weeks (up to 16 patients, 20 infusions). All study medication was administered by IV infusion over 1 hour to maintain the treatment blind.

Treatment Administration

Study Medication Infusions:

Double-blind study medication infusions were administered at the clinical site as a continuous 1-hour IV infusion to maintain the treatment blind. Study medication infusions occurred on approximately the same day of the week but occurred every 14 days (±3 days) in order to facilitate patient scheduling.

Dose Calculation:

The first dose of double-blind study medication was based on the patient's weight at Baseline. A change in weight of ≥5% from Baseline or from the most recent recorded measurement (Week 13 or Week 25) would require recalculation of the dose of study medication.

Description of Study Medications

Velaglucerase Alfa:

Velaglucerase alfa is a lyophilized product that was supplied and shipped to the clinical study site to be stored at 2 to 8° C.

Imiglucerase (Cerezyme®):

Imiglucerase (Cerezyme) was supplied as a sterile, non-pyrogenic, white to off-white lyophilized product.

Study Procedures and Data Collection Methods

Study Entrance Criteria:

At Screening patients were reviewed for eligibility against the study entrance criteria. Patients who did not meet the study entrance criteria were considered Screen failures.

Confirmation of Eligibility:

At Screening, patients provided blood samples to measure hemoglobin concentration to determine study eligibility. Only those patients who had a hemoglobin concentration that was below the local laboratory's lower limit of normal for age and gender were eligible for enrollment.

At Baseline, patients provided a blood sample to confirm that their hemoglobin concentration was below the local laboratory's lower limit of normal for age and gender. Only those patients who had a hemoglobin concentration that was below the lower limit of normal for age and gender at both Screening and Baseline were confirmed eligible for this study.

Genotyping:

All patients provided a blood sample at Screening for Gaucher disease genotyping and plasma chitotriosidase genotyping.

Medical History:

At Screening, the patient's complete medical history was recorded. This included a review of body systems, documentation of current and prior medical procedures, and documentation of current and prior concomitant medication usage, and documentation that the patient had not been treated for Gaucher disease within the 12 months prior to study entry.

Vital Signs:

Vital signs parameters that were recorded included pulse, blood pressure, respiration rate, and temperature. The following schedule was followed for recording vital signs at infusion visits: start of infusion (within 10 minutes prior to starting the infusion), during infusion (30 minutes (±5 minutes)), after infusion (within 5 minutes, 30 minutes (±5 minutes), and 60 minutes (±5 minutes) after completing the infusion). At Screening, Baseline, and Week 41, vital signs were collected at one time point only.

Physical Examinations:

Physical examinations were performed at Screening, Baseline and at Study Weeks 13, 25, and 41. Physical examinations included the following: general appearance, endocrine, head and neck, cardiovascular, eyes, abdomen, ears, genitourinary, nose, skin, throat, musculoskeletal, chest and lungs, and neurological. Any abnormal change in physical findings was recorded as an adverse event on the appropriate CRF page(s).

Height and Weight:

Height and weight were recorded at Baseline and at Study Weeks 13, 25, and Week 41. For pediatric patients (i.e., 2 to 17 years-old), height and weight assessments were used to determine growth velocity.

12-Lead Electrocardiograms:

A 12-lead ECG was performed at Baseline and at Study Weeks 13, 25, and 41, and included assessment of PR, QRS, QT, and QTc intervals, and heart rate.

Clinical Laboratory Testing:

Blood and urine samples were collected as described below for clinical laboratory testing.

Hematology:

Blood samples were collected during Screening and at Baseline to measure hemoglobin levels for statistical analysis. Blood samples were also collected at Screening, Baseline, and Weeks 13, 25, and 41 for complete hematology testing. The following hematology parameters were evaluated: complete blood count (CBC) with differential, platelet count, activated partial thromboplastin time (aPPT), reticulocyte count (analyzed and reported by the clinical site's local laboratory), and prothrombin time (PT). Blood samples were collected at Screening, Baseline, and at every study visit (except at the Week 1 visit) to measure hemoglobin concentration and platelet count.

Serum Chemistry:

Blood samples were collected for serum chemistry testing at Screening, Baseline, and at Study Weeks 13, 25, and 41. The following serum chemistry parameters were evaluated: sodium, alanine aminotransferase, potassium, aspartate aminotransferase, glucose, lactate dehydrogenase, total calcium, gammaglutamyltransferase, total protein, creatinine phosphokinase, albumin, NTx*, creatinine, CTx*, urea nitrogen, folic acid (to determine study eligibility), total bilirubin, vitamin $B_{12}$ (screening only), alkaline phosphatase* (* results were used for assessments of bone biomarkers). Patients who at Screening had folic acid and/or vitamin $B_{12}$ deficiency-related anemia, and so did not meet study entry criteria were considered a screen failure.

Urinalysis:

Urine samples were collected for urinalysis at Screening, Baseline, and at Study Weeks 13, 25, and 41. The following urinalysis parameters were evaluated: pH, microscopic evaluation, and macroscopic evaluation.

Serum Anti-velaglucerase alfa Antibodies:

Patients provided blood samples to measure anti-velaglucerase alfa antibodies in serum at Screening and approximately every 6 weeks during the treatment phase (Weeks 7, 13, 19, 25, 31, and 37), and at Week 41. During the treatment phase, these blood samples were collected prior to the infusion of double-blind study medication.

Blood samples collected for anti-velaglucerase alfa antibody determination were evaluated. These samples were screened using an enzyme-linked immunosorbence assay (ELISA), and all positive samples were confirmed positive using a radioimmunoprecipitaion assay (RIP). Positive samples were isotyped (IgG, IgA, IgM, or IgE). In addition, positive samples were tested for enzyme neutralizing activity using an in vitro assay.

Serum Anti-imiglucerase Antibody Determination:

Patients provided blood samples at Screening to measure anti-imiglucerase antibodies. The anti-imiglucerase antibody analyses were performed using the same samples obtained for anti-velaglucerase alfa antibody analyses.

These blood samples were evaluated to determine the presence of anti-imiglucerase antibodies. These samples were screened using an enzyme-linked immunosorbence assay (ELISA), and all positive samples were confirmed positive using a radioimmunoprecipitaion assay (RIP). Positive samples were isotyped (IgG, IgA, IgM, or IgE). In addition, positive samples were tested for enzyme neutralizing activity using an in vitro assay.

Patients who test positive for anti-imiglucerase antibodies at Screening were not eligible for this study.

Antibody cross-reactivity testing (to velaglucerase alfa) was conducted for patients who develop anti-imiglucerase antibodies during this study.

Immune and Inflammatory Response Testing:

Patients who were ≥18 years of age provided blood samples for immune and inflammatory response testing at Baseline and at Weeks 13, 25, and 41. One sample was obtained at Baseline. At Weeks 13, 25, and 41, samples were obtained before, immediately following, and 1 hour after each infusion with study drug.

Adverse Events:

Adverse events were monitored throughout the study from the time the patient provided informed consent through 30 days after the last infusion for patients who completed the study and did not elect to enroll in the subsequent open-label long-term clinical study, or for patients who discontinue or withdraw from the study prior to the Week 41 visit. For patients who completed this study and elected to enroll in the subsequent open-label long-term clinical study, adverse events were monitored from informed consent through completion of the Week 41 visit.

Management of Infusion-Related Adverse Events:

Infusions of proteins can be associated with reactions to the infusion. An infusion-related adverse event is defined as an adverse event that 1) begins either during or within 12 hours after the start of the infusion, and 2) is judged as possibly or probably related to blinded study medications.

Liver and Spleen MRI:

Patients underwent MRI of the liver and spleen at Baseline and at Weeks 25 and 41/EOS. Liver and spleen size were measured using quantitative abdominal MRI.

Plasma Chitotriosidase Levels:

Blood samples were collected for the evaluation of plasma chitotriosidase levels at Baseline and at Weeks 1, 5, 9, 13, 17, 21, 25, 29, 33, 37, and Week 41. Chitotriosidase was analyzed using an enzyme activity assay.

Plasma CCL18 Levels:

Blood samples were collected for the evaluation of plasma CCL18 levels at Baseline and at Weeks 1, 5, 9, 13, 17, 21, 25, 29, 33, 37, and Week 41. CCL18 levels were measured by an enzyme-linked immunosorbent assay (ELISA) in a commercially available kit.

Quality of Life Testing:

At Baseline and Week 41, patients' quality of life was evaluated using validated questionnaires, including the Short Form 36 (SF-36), version 2, for patients ≥18 years-old and the Childhood Health Questionnaire (CHQ), PF50 for patients 5 to 17 years-old (*Ware Arch Phys Med Rehabil* Vol 84, Suppl 2, April 2003:43-51; SF-36v2™ Health Survey© 1996, 2000 by QualityMetric Incorporated and Medical Outcomes Trust. All Rights Reserved; Landgraf et al. Child Health Questionnaire: A User's Manual. $2^{nd}$ printing, Health Act, Inc., Boston Mass., 1999; Landgraf et al. *Quality of Life Research.* 1998; 7(5):433-445).

Growth Velocity and Tanner Staging:

For patients 2 to 17 years-old, growth was assessed at Baseline and Weeks 13, 25, and 41. Growth velocity was calculated using height and weight measurements that were recorded at regular time points during this study, and correlated with Tanner staging. Tanner stage was recorded at Baseline and Weeks 13, 25, and 41. The change from Baseline for each patient between 2 and 17-years old in each treatment group was evaluated as a tertiary efficacy parameter.

Skeletal Growth:

Patients between 2 and 17 years-old underwent radiography of the left hand and wrist at Baseline and Week 41 for evaluation of skeletal age.

Bone Biomarkers:

At Baseline and Week 41, patients who were ≥18 years-old underwent DXA of the lumbar spine and femoral neck, including coronal imaging, to determine Gaucher-related local and systemic bone disease. Bone loss and demineralization were evaluated for these patients by measuring serum alkaline phosphatase, NTx, and CTx at Baseline and Week 41.

For patients 2 to 17 years-old, MRI of the femoral neck and lumbar spine was obtained at Baseline and Week 41, at the same time these patients underwent MRI of the liver and spleen.

It was not expected that any treatment effect would be apparent for these parameters during this study, however, the measurements collected at Baseline and Week 41 would be utilized to establish a reference point from which to monitor these biomarkers during the subsequent open-label long-term clinical study.

Prior and Concomitant Illnesses:

Additional illnesses present at Baseline were regarded as concomitant illnesses and were documented on the appropriate pages of the medical history CRF. Illnesses first occurring or detected during the study, or worsening of a concomitant illness during the study, were regarded as AEs and were documented as such in the CRF.

Patients did not receive treatment with red blood cell growth factor or investigational drug(s) or device(s) at any point during this study or within 30 days after the last infusion.

During the treatment phase of this study, patients might receive corticosteroids as premedications to mitigate potential infusion-related adverse events.

Adverse Events

Adverse Event Definition:

An adverse event (AE) is any noxious, pathologic, or unintended change in anatomical, physiologic, or metabolic function as indicated by physical signs, symptoms, and/or laboratory changes occurring in any phase of a clinical trial, and whether or not considered study drug-related. This includes an exacerbation of a pre-existing condition. Adverse events were collected from the time the patient provides signed informed consent until 30 days after the last dose of blinded study medication and/or until the event had been resolved/stabilized or an outcome was reached, whichever comes first. For patients who discontinued or were withdrawn prior to the Week 41 visit, AEs were followed up to 30 days after their last infusion. For patients who completed this study and elected to enroll in the long-term clinical study, adverse events were monitored from the time the patient provides informed consent through the Week 41 visit.

AEs include: worsening (change in nature, severity, or frequency) of conditions present at the onset of the study; intercurrent illnesses; drug interactions; events related to or possibly related to concomitant medications; abnormal laboratory values (this includes significant shifts from Baseline within the range of normal that the Investigator considers to be clinically important); clinically significant abnormalities in physical examination, vital signs, weight, and ECG.

In addition, AEs might also include unexpected laboratory values that became significantly out of range and determined to be clinically significant by the Investigator. In the event of an unexpected out-of-range value, the laboratory test was repeated until it returned to normal or could be explained and the patient's safety was not at risk.

Infusion-Related Adverse Event Definition:

An infusion-related adverse event was defined as an adverse event that 1) begins either during or within 12 hours after the start of the infusion, and 2) is judged as possibly or probably related to blinded study medication. Other AEs which occurred prior to the infusion, along with AEs associated with protocol-defined testing and assessments (e.g., laboratory testing, ECGs, and physical examinations) which were performed prior to the infusion, were not defined as infusion-related adverse events.

Serious Adverse Event Definition:

A serious AE (SAE) is any AE occurring at any dose that results in any of the following outcomes: death, is life-threatening, requires inpatient hospitalization, requires prolongation of existing hospitalization, a persistent or significant disability/incapacity, and a congenital anomaly/birth defect.

Important medical events that may not result in death, be life-threatening, or require hospitalization may be considered as SAEs when, based upon appropriate medical judgment, they may jeopardize the patient and may require medical or surgical intervention to prevent one of the outcomes listed above.

A life-threatening AE is defined as an AE that placed the patient, in the view of the initial reporter, at immediate risk of death from the AE as it occurred (i.e., it does not include an AE that, had it occurred in a more severe form, might have caused death).

Classification of Adverse Events and Serious Adverse Events:

The National Cancer Institute Common Toxicity Criteria (NCI CTC) Version 3.0 grading scale was referenced when assessing the severity of an AE. If an AE was not described in the NCI CTC, the severity was recorded based on the scale below. The severity of all AEs/SAEs were recorded on the appropriate CRF page as Grade 1, 2, 3 or 4 corresponding, respectively, to a severity of mild, moderate, severe, or life-threatening. Grade 1 (mild) is defined as no limitation of usual activities. Grade 2 (moderate) is defined as some limitation of usual activities; Grade 3 (severe) is defined as inability to carry out usual activities; and Grade 4 (life-threatening) is defined as immediate risk of death.

Relationship of an adverse event or serious adverse event to blinded study medication was determined by the Investigator based on the following definitions. "Not related" is defined as unrelated to study drug. "Possibly related" is defined as a clinical event/laboratory abnormality with a reasonable time sequence to administration of study drug, but which could also be explained by concurrent disease or other drugs/chemicals. "Probably related" is defined as a clinical event/laboratory abnormality with a reasonable time sequence to administration of study drug, unlikely to be attributable to concurrent disease or other drugs and chemicals and which follows a clinically reasonable response on dechallenge. The association of the clinical event/laboratory abnormality must also have some biologic plausibility, at least on theoretical grounds.

Clarification Between Serious and Severe:

The term "severe" is often used to describe the intensity (severity) of a specific event (as in mild, moderate, or severe myocardial infarction); the event itself, however, may be of relatively minor medical significance (such as severe headache). This is not the same as "serious," which is based on the outcome or action criteria usually associated with events that pose a threat to life or functioning. Seriousness (not severity) and causality serve as a guide for defining regulatory reporting obligations.

Adverse Event Monitoring and Period of Observation:

For the purposes of this study, the period of observation extended from the time the patient provided informed consent until the patient's final evaluation of the study. For safety purposes, the final evaluation was defined as the post-study safety evaluation performed approximately 30 days after the last infusion for patients who completed the study and did not elect to enroll in the long-term study, or for patients who discontinued or withdrew from the study prior to the Week 41 visit. For patients who completed this study and elected to enroll in the long-term clinical study, adverse events were monitored from the time the patient provides informed consent through the Week 41 visit. If the Investigator considered it necessary to report an AE in a study patient after the end of the observation period, he or she would contact the Sponsor to determine how the AE should be documented and reported.

Statistical Method

General Statistical Methodology:

Two data sets were considered for the statistical analyses of efficacy: 1) the intention-to-treat (ITT) data set and 2) the per-protocol (PP) data set. The ITT data set is comprised of all randomized patients who received at least one full or partial dose of study drug. The PP data set is a subset of the ITT data set, which includes patients who completed 41 weeks of the study, had both the Baseline and the Week 41 measurements of the primary efficacy variable collected, and received at least 80% of their scheduled dose of infusion.

For variables following a continuous distribution, tabular summaries consisted of n, mean, standard deviation, minimum, maximum, and median. Graphs of the key efficacy variables were presented by treatment groups. For categorical variables, tabular summaries consisted of presenting the frequency and the percentage in each category by treatment group. The primary efficacy variable was presented by treatment group, and included: raw values: the untransformed value of the variable in the originally reported scale; the absolute change in the value from Baseline, i.e., X−B (where B is the Baseline value and X is a post-Baseline value); and the percent change in the value from Baseline, i.e., 100*(X−B)/B (where B is the Baseline value and X is a post-Baseline value).

Hypothesis Testing:

This study compared the effect of velaglucerase alfa with imiglucerase. The intent was to show that velaglucerase alfa was clinically at least as good as imiglucerase at the 0.025 level of significance.

The null hypothesis for the primary efficacy endpoint is that the mean change in hemoglobin concentration from Baseline to Week 41 for velaglucerase alfa is at least 1 g/dL inferior to the mean change in hemoglobin concentration from Baseline to Week 41 for imiglucerase. The hypothesis to be tested can be stated as:

$H_0$: $\mu_{Vela} - \mu_{IMIG} \leq -1$ vs. $H_A$: $\mu_{Vela} - \mu_{IMIG} > -1$ Or $H_0$: velaglucerase alfa is inferior with respect to the mean hemoglobin response $H_A$: velaglucerase alfa is non-inferior with respect to the mean hemoglobin response Screen Failures and Patient Disposition:

The disposition of all patients screened for entry into the study was tabulated along with reasons for screen failure. The disposition of all randomized patients was tabulated by treatment arm and visit, and reasons for discontinuation were tabulated by treatment arm.

Sample Size Justification:

When the sample size in each treatment group is 14, a two-group 0.025 one-sided t-test will have an 80% power to reject the null hypothesis that the difference in means for hemoglobin is ≤−1 g/dL in favor of the alternative hypothesis that the difference in means is greater than −1, assuming that the expected difference in means is 0, and the common standard deviation is 0.90.

Assuming a 15% dropout, a total of 32 patients (16 patients per treatment arm) were enrolled into the study.

Efficacy Analysis

Analysis Populations:

Two data sets were considered for the statistical analyses of efficacy (the intention-to-treat (ITT) data set and the per-protocol (PP) data set).

Primary Efficacy Analyses:

The primary efficacy endpoint is the mean change from Baseline to Week 41 in hemoglobin concentration between the two treatment groups. The primary analysis was carried out using the ITT population. This is a non-inferiority randomized controlled trial designed to demonstrate that velaglucerase alfa is non-inferior to imiglucerase in terms of efficacy in treating patients with type 1 Gaucher disease.

A one-sided 97.5% confidence interval was used. Non-inferiority was demonstrated by either a one-sided confidence interval or a hypothesis test for testing the null hypothesis that the treatment difference is less than or equal to the lower equivalence margin in hemoglobin (−1 g/dL) versus the alternative that imiglucerase treatment difference is greater than the lower equivalence margin. In other words, focusing on just one end of the confidence interval and ignoring the other results in a one-sided 97.5% confidence interval [(a, ∞)], where a is the lower bound of the 1-sided confidence interval, an efficacy conclusion could be drawn.

Secondary Efficacy Analyses:

For the secondary efficacy parameters (platelet counts, liver, and spleen volumes, chitotriosidase, and CCL18) that compare changes from Baseline between treatment groups, statistical tests evaluated if the mean changes from Baseline to Week 41 between the two treatment groups is statistically significant (statistically significant will be defined as a p-value less than 0.05). A 95% confidence interval was presented for the difference in mean changes from Baseline between the two treatment arms using an analysis of covariance (ANCOVA) model, which included, e.g., Baseline age as a covariate.

For time to event outcome measures (i.e., time to first hemoglobin response ≥1 g/dL from baseline), Kaplan-Meier (product limit) survival curves were presented for each treatment group and a log-rank test were used to compare curves between treatment groups. The median time and 95% confidence interval were presented for each treatment group. Patients who did not experience the event by the end of the study (i.e., by Week 41) were censored at Week 41. Patients who withdrew or were discontinued prior to the Week 41 evaluation and who did not achieve a response at the time of withdrawal or discontinuation were censored at the time of the last known evaluation for that patient. In addition, the proportion of patients who responded versus non-responders were presented and compared between treatment groups using Fisher's Exact Test.

Safety Analyses:

All patients who received at least one dose of study drug (or partial dose) were assessed for clinical safety and tolerability. No formal statistical tests were performed on the safety parameters. Vital signs, 12-lead ECG, clinical chemistry, hematology, and urinalysis safety monitoring were summarized. For categorical variables, such as AEs, the number and percentage of patients experiencing each AE were tabulated. AEs were summarized by severity of event. The number and percentage of patients experiencing drug related AEs and infusion-related AEs, as well as AEs that were not considered related to study drug will also be displayed. Clinical laboratory evaluations (hematology, serum chemistry, urinalysis, and determination of anti-velaglucerase alfa antibodies) were used to assess the safety of velaglucerase alfa.

Example 4

TKT034 Study (Multi-Center Open-Label Study in Patients Who Transitioned from Treatment with Imiglucerase)

Summary

This example describes a global, open-label, 12-month study to examine the safety and efficacy of velaglucerase alfa in patients with type 1 Gaucher disease previously receiving imiglucerase. Patients aged ≥2 years received velaglucerase alfa at a dose equal to their prior imiglucerase dose, with infusions administered over 1 hour every other week.

Forty patients received velaglucerase alfa (18 male; 4 previously splenectomized; age range, 9-71 years). Median prior imiglucerase use was 67 months (range 22-192 months). Velaglucerase alfa doses were: 15-22.5 U/kg (n=14) ("the 15 U/kg group"), 22.5-37.5 U/kg (n=12) ("the 30 U/kg group"), 37.5-52.5 U/kg (n=7) ("the 45 U/kg group"), and >52.5 U/kg (n=7) ("the 60 U/kg group"). Velaglucerase alfa was generally well tolerated with most adverse events (AEs) of mild or moderate severity. Eleven patients (28%) experienced an AE considered possibly or probably related to study drug; the majority were considered infusion related. No patient experienced a life-threatening AE. One serious AE was considered probably related to treatment: one patient had a grade 2 hypersensitivity reaction during the first infusion, and chose to discontinue the study. This patient tested negative for IgE, IgM, IgG, IgA and neutralizing antibodies at the time of the infusion and 2 weeks later. No patients developed IgG antibodies to velaglucerase alfa. Hemoglobin concentration, platelet count, liver and spleen volume were sustained at therapeutic levels through 1 year.

In conclusion, adult and pediatric patients with type 1 Gaucher disease, previously treated with imiglucerase for ≥22 months, were successfully transitioned to velaglucerase alfa, with stability in clinical disease measures over 12 months.

Study Objectives

The primary objective of this study was to evaluate the safety of every other week dosing of velaglucerase alfa in patients with type 1 Gaucher disease who were previously treated with imiglucerase.

The secondary objectives were: to evaluate changes from Baseline in hemoglobin concentration after every other week dosing of velaglucerase alfa, to evaluate changes from Baseline in platelet count after every other week dosing of velaglucerase alfa, and to evaluate changes from Baseline in liver and spleen volume by abdominal MRI after every other week dosing of velaglucerase alfa.

The tertiary/exploratory objectives were: to evaluate changes from Baseline in levels of plasma chitotriosidase and Chemokine (C-C motif) ligand 18 (CCL18) after every other week dosing of velaglucerase alfa, to evaluate changes in skeletal age in patients between 2 and 17 years-old by radiography of the left hand and wrist after every other week dosing of velaglucerase alfa, to evaluate changes in growth velocity and Tanner staging in patients between 2 and 17 years-old after every other week dosing of velaglucerase alfa, to establish a Baseline from which to monitor the long term effect of velaglucerase alfa therapy on Gaucher-related local and systemic bone disease in patients ≥18 years-old, as measured by bone density (DXA) of the lumbar spine and femoral neck (including coronal imaging), serum alkaline phosphatase, N-telopeptide cross-links (NTx), and C-telopeptide cross links (CTx), and to establish a Baseline from which to evaluate bone disease in patients between 2 and 17 years-old by MRI of the lumbar spine and femoral neck.

Overall Study Design

This is a multicenter, Phase II/III, open-label study designed to evaluate the safety of velaglucerase alfa therapy for patients currently receiving imiglucerase therapy for type I Gaucher disease. 41 patients were enrolled to receive the same number of units of velaglucerase alfa as their imiglucerase dose. Doses ranged between 15 U/kg and 60 U/kg. Patients had received the same dose of imiglucerase during the 6 months prior to study enrollment. The overall duration of the study for each patient was approximately 14 months (from Screening through the End of Study and/or follow-up, as appropriate).

The study was comprised of 5 phases as follows: Screening (Day −14 through Day −4), Baseline (Day −3 through Day 0 (prior to first dose)), Treatment Phase: Week 1 (Day 1; first dose) through Week 51 (a total of 26 infusions were administered per patient), End of Study Visit: Week 53, Follow-up: 30 days after the final infusion (for patients who discontinued/withdrew prior to the Week 53 evaluation, or for patients who completed this study but did not elect to enroll in the subsequent long-term clinical study).

Patients (or parent/legal guardian) who provided written informed consent underwent Screening evaluations within two weeks prior to their first dose to determine eligibility for enrollment. To determine study eligibility, a blood sample was collected from each patient during Screening to evaluate hemoglobin concentration and platelet count.

An additional blood sample was collected during Screening for evaluation of hemoglobin concentration and platelet count for statistical analysis purposes.

Administration of the first dose of study drug was defined as Week 1 (Day 1). Velaglucerase alfa infusions were administered every other week for 12 months (51 weeks) for a total of 26 infusions. Patients received the same number of units of velaglucerase alfa as their imiglucerase dose. Doses ranged between 15 U/kg and 60 U/kg. Infusion time was 60 minutes (1 hour). Increased infusion durations (e.g., 2 hours) were documented in the source documentation and appropriate CRF. Infusions were not less than 1 hour in duration.

The first 3 velaglucerase alfa infusions for each patient were administered at the clinical site. Patients who did not experience a treatment-related serious adverse event or a velaglucerase alfa infusion-related adverse event might receive their subsequent infusions at home by qualified and trained medical personnel, per the discretion and direction of the Investigator. Patients who experienced an infusion-related adverse event might be re-evaluated at a later time point during the study for consideration to transition to home infusions. Patients receiving velaglucerase alfa as home therapy were required to return to the clinical site at Weeks 7, 13, 19, 25, 31, 37, 45, and 51 and 53.

The study completion visit is defined as Week 53. Patients were considered to have completed this study once they have 1) completed the 51-week treatment period, and 2) complete the study visits at Week 51 and Week 53.

Patients who completed this study were provided the opportunity to enroll in a subsequent long-term open-label clinical study. For patients who elect to enroll in the subsequent long-term open-label clinical study, certain assessments from the Week 51 and the Week 53 visits for this study (TKT034) were used as the Baseline assessments for that study; patients would receive their first infusion for the subsequent long-term open-label clinical study at the Week 53 visit, after they completed all of the assessments for that visit and provided written informed consent to participate in the subsequent long-term open-label clinical study. Therefore, it was intended that patients would receive continuous velaglucerase alfa treatment across the 2 studies. Patients who completed this study and did not elect to enroll in the subsequent long-term open-label clinical study would have a safety assessment (for collection of adverse events and concomitant medications) by site visit or telephone 30 days after their last infusion.

Selection of Study Population

All enrolled patients who received at least 1 infusion (or partial infusion) were included in the ITT patient population.

Eligible participants were males or females age ≥2 years with diagnosed type 1 Gaucher disease (deficient glucocerebrosidase activity in leukocytes, or by genotype analysis), who had received consistent treatment with imiglucerase for a minimum of 30 consecutive months; one patient was allowed to participate having had 22 consecutive months of previous treatment with imiglucerase.

Participants were excluded if they had both hemoglobin concentration ≤10 g/dL and platelet count ≤80×10$^3$ platelets/mm$^3$; had unstable hemoglobin concentration (exceeded a range of ±1 g/dL of the screening value) or platelet count (exceeded ±20% of the screening value) during the 6 months prior to screening; had (or were suspected of having) type 2 or 3 Gaucher disease; had experienced an anaphylactic shock to imiglucerase; had inconsistent treatment with imiglucerase or had received miglustat in the 6 months prior to study entry; or had radiologically-confirmed active, clinically significant spleen infarction or worsening bone necrosis within 12 months of screening.

Other exclusion criteria included treatment with any investigational drug or device within 30 days prior to study entry; positive test for HIV, hepatitis B or C; non-Gaucher disease-related anemia at screening; or any significant co-morbidity that could affect study data. Pregnant or lactating women were excluded and women of child-bearing potential were required to use a medically acceptable method of contraception at all times.

Study Treatments

Treatment Assignment:

Patients received velaglucerase alfa infusions every other week at the same number of units of as their imiglucerase dose. The patient's current imiglucerase dose was recorded at Baseline. Velaglucerase alfa doses ranged between 15 U/kg and 60 U/kg.

Treatment Schedule:

Patients received their first infusion on Week 1 (Day 1). All patients received velaglucerase alfa once every other week for 12 months (51 weeks); therefore, a total of 26 infusions are to be administered.

All doses of velaglucerase alfa were administered as continuous IV infusions at a maximum rate of 1 U/kg/minute. Infusion time was 60 minutes (1 hour). Increased infusion durations (e.g., 2 hours) were documented in the source documentation and appropriate CRF. Infusions might not be less than 1 hour in duration. Patients received their final imiglucerase dose a maximum of 30 days prior to study entry and a minimum of 14 days prior to study entry.

Dose Calculation:

A change in weight of ≥5% from Baseline or the previously recorded weight used to calculate dose at Weeks 13, 25, or 37 required recalculation of the dose of study medication.

Dose Adjustments:

Patients were monitored throughout the treatment period for changes in clinical parameters (i.e., hemoglobin concentration, platelet count, and liver and spleen volume). If a patient demonstrated a clinically significant change in these parameters the investigator evaluated the option of increasing the patient's dose by 15 U/kg. A dose adjustment was considered if two or more of the following four criteria were met and consistent over two consecutive evaluations: decrease from Baseline in hemoglobin concentration of >1 g/dL; a decrease from Baseline in platelet count of >20%; an increase in liver volume as indicated by organ palpation and confirmed to be >15% relative to Baseline as measured by MRI; and an increase in spleen volume as indicated by organ palpation and confirmed to be >15% relative to Baseline as measured by MRI.

If the clinical parameter values did not return to Baseline levels within three months, the Investigator had the option of increasing the dose by increments of 15 U/kg. No dose increase was offered to patients receiving a dose of 60 U/kg, and no dose above 60 U/kg was allowed. If the patient failed to respond to the maximum dose of 60 U/kg, the patient might be withdrawn if deemed appropriate based on the Investigator's clinical judgment.

Velaglucerase Alfa Administration

General Instructions for Velaglucerase Alfa Administration:

Velaglucerase alfa was administered intravenously. Study drug infusions occurred on approximately the same day of the week but might occur every 14 days (±3 days) of the target day in order to facilitate patient scheduling. If at all possible, missed infusions should be avoided. If a patient was not dosed within 17-days from their scheduled dose, the patient would receive the next infusion as soon as possible after approval for the patient to continue in the study. It might be acceptable to give the next infusion as early as 7 days after the previous infusion. Subsequent infusions would return to the original schedule.

Home Infusion Instructions for Velaglucerase alfa Administration:

The first three velaglucerase alfa infusions were administered at the clinical site. After the first three doses, patients who had not experienced a treatment-related serious adverse event or an infusion-related adverse event might receive their subsequent infusions at home. Patients who had experienced an infusion-related adverse event might be re-evaluated at a later time point during the study for consideration to transition to home infusions. Patients receiving velaglucerase alfa as home therapy were required to return to the clinical site at Weeks 7, 13, 19, 25, 31, 37, 45, 51, and 53.

In the home setting, vital signs and documentation of adverse events were collected at each visit Management of Infusion-Related Adverse Events:

An infusion-related adverse event was defined as an adverse event that 1) begins either during or within 12 hours after the start of the infusion, and 2) is judged as possibly or probably related to study drug.

Description of Study Drug:

Velaglucerase alfa is a lyophilized product that was supplied and shipped by a qualified distributor to the clinical study site to be stored at 2 to 8° C.

Gaucher Disease Specific Treatment History:

At Screening, all Gaucher disease-specific treatments, including the patient's current imiglucerase dose, were recorded. The patient's initial velaglucerase alfa dose was based on the current imiglucerase dose recorded.

Historical Hemoglobin and Platelet Values:

All evaluations of hemoglobin concentration and platelet count within the 30 months prior to study entry were collected and reviewed to determine patient eligibility.

Gaucher Disease and Chitotriosidase Genotyping:

At Screening only, all patients had a blood sample collected for Gaucher disease and plasma chitotriosidase genotyping.

Vital Signs:

Vital signs parameters recorded included pulse, blood pressure, respiration rate, and temperature.

The following schedule was followed for recording vital signs at all infusion visits: start of infusion (within 10 minutes prior to starting the infusion; during infusion (30 minutes (±5 minutes)); after infusion (within 5 minutes after the infusion is completed, 30 minutes (±5 minutes) after completing the infusion, and 60 minutes (±5 minutes) after completing the infusion)

Physical Examinations:

Physical examinations were performed at the Baseline visits, and at Weeks 13, 25, 37, 51 and 53. Physical examinations included the following: general appearance, endocrine, head and neck, cardiovascular, eyes, abdomen, ears, genitourinary, nose, skin, throat, musculoskeletal, chest and lungs, and neurological. Any abnormal change in physical findings was recorded as an adverse event on the appropriate CRF page(s).

Height and Weight:

Height and weight were recorded at the Baseline visit, and at Weeks 13, 25, 37 and 51. Growth velocity was calculated using height and weight measurements, and correlated with Tanner staging.

12-Lead Electrocardiograms:

A 12-Lead ECG was performed at the Baseline visit, and at Weeks 13, 25, 37 and 51. Each 12-lead ECG included assessment of PR, QRS, QT, and QTc intervals, and heart rate.

Clinical Laboratory Testing:

Blood and urine samples were collected as described below for the following evaluations.

Hematology:

Blood samples were collected for hematology testing at the Screening and Baseline visits, and at Weeks 7, 13, 19, 25, 31, 37, 45, 51 and 53. The following hematology parameters were evaluated: complete blood count (CBC) with differential, activated partial thromboplastin time (aPPT), reticulocyte count (performed by the site's local laboratory), platelet count, and prothrombin time (PT). At Screening, Baseline, and at every study visit (except at the Week 1 visit), blood samples were collected to measure hemoglobin concentration and platelet count.

An additional blood sample was collected during Screening to measure hemoglobin and platelet count for statistical analysis purposes.

Serum Chemistry:

Blood samples were collected for serum chemistry testing at the Baseline visit, and at Weeks 13, 25, 37, 51 and 53.

The following serum chemistry parameters were evaluated: sodium, total bilirubin, potassium, alkaline phosphatase*, glucose, alanine aminotransferase, total calcium, aspartate aminotransferase, total protein, lactate dehydrogenase, albumin, Gamma-glutamyl transferase, creatinine, creatinine phosphokinase, urea nitrogen, CTx, NTx* (* results were used for assessments of bone biomarkers). Patients who at Screening had folic acid and/or vitamin $B_{12}$ deficiency-related anemia, and so did not meet study entry criteria were considered a screen failure. These patients might be treated for their folic acid and/or vitamin $B_{12}$ deficiency-related anemia for up to 12 weeks at the Investigator's discretion, according to the clinical site's standard practice. Such patients might be re-screened for this study after they completed the folic acid and/or vitamin $B_{12}$ treatment regimen.

Urinalysis:

Urine samples were collected for urinalysis at the Baseline visit, and at Weeks 13, 25, 37, 51 and 53. The following urinalysis parameters were evaluated: pH, microscopic evaluation, and macroscopic evaluation.

Serum Anti-imiglucerase Antibody Determination:

All patients had a blood sample at Baseline only for determination of serum anti-imiglucerase antibodies. Patients were eligible for enrollment in this study regardless of their anti-imiglucerase antibody status. Patients who were anti-imiglucerase antibody positive would be allowed to enter this study. These blood samples were evaluated to determine the presence of anti-imiglucerase antibodies.

Serum Anti-Velaglucerase Alfa Antibody Determination:

Blood samples were collected for determination of anti-velaglucerase alfa antibodies at the Baseline visit, and at Weeks 7, 13, 19, 25, 31, 37, 45 and 51. Blood samples collected for anti-velaglucerase alfa antibody determination were evaluated. These samples were screened using an enzyme-linked immunosorbence assay (ELISA).

Adverse Events:

Adverse events were monitored throughout the study from the time the patient provides signed informed consent through 30 days after their last infusion for patients who completed the study and did not elect to enroll in the subsequent long-term open-label clinical study, or for patients who discontinued or withdrew from the study prior to the Week 53 visit. For patients who completed this study and elected to enroll in the subsequent long-term open-label clinical study, adverse events were monitored from informed consent through the Week 53 visit of this study (TKT034).

Prior and Concomitant Illnesses:

Additional illnesses present at Baseline were regarded as concomitant illnesses and were documented on the appropriate medical history pages of the CRF. Illnesses first occurring or detected during the study, or worsening of a concomitant illness during the study, were regarded as AEs and were documented as such in the CRF.

Study Procedures for Efficacy Evaluations

Hemoglobin Concentration:

Hemoglobin concentration was measured at the time points described herein. The change from Baseline to 12 months in hemoglobin concentration was a secondary endpoint of this study.

Platelet Count:

Platelet count was measured at the time points described herein. The change from Baseline to 12 months in platelet count was a secondary endpoint of this study.

Liver and Spleen Volumes Measured by Abdominal MRI:

Patients underwent quantitative abdominal MRI of the liver and spleen at Baseline, Week 25, and Week 51. The change from Baseline to 12 months in liver and spleen volume was a secondary endpoint of this study.

Plasma Chitotriosidase and CCL19 Levels:

Blood samples were collected for the evaluation of plasma chitotriosidase and CCL18 levels at the Baseline visit, and at Weeks 13, 25, 37, 51 and 53. The change from Baseline to 12 months in chitotriosidase and CCL18 levels was a tertiary endpoint of this study.

Growth Velocity and Tanner Staging:

For patients 2 to 17 years-old, growth was assessed at the time points defined herein. Growth velocity was calculated using height and weight measurements recorded at regular time points during this study, and correlated with Tanner staging. The change from Baseline to 12 months in growth velocity and Tanner staging was a tertiary endpoint of this study.

Skeletal Growth:

Patients between 2 and 17 years-old underwent radiography of the left hand and wrist at Baseline and Week 51 for evaluation of skeletal age. The change from Baseline to 12 months in skeletal growth in patients 2 to 17 years of age was a tertiary endpoint of this study.

Additional Study Procedures

Bone Biomarkers:

At Baseline only, patients ≥18 years-old underwent DXA of the lumbar spine and femoral neck, including coronal imaging, to determine Gaucher-related local and systemic bone disease. Bone loss and demineralization were also evaluated by measuring serum alkaline phosphatase, NTx, and CTx. Results for these parameters were obtained from blood samples collected for clinical laboratory testing at Baseline only.

For patients 2 to 17 years-old, MRI of the femoral neck and lumbar spine were obtained at Baseline (at the same time patients undergo MRI of the liver and spleen). It was not expected that any treatment effect would be apparent for these parameters during this study, therefore, measurements were collected at Baseline only to establish a reference point from which to monitor these biomarkers during the subsequent long-term open-label clinical study.

Adverse Events

Adverse Event Definition:

An adverse event (AE) is any noxious, pathologic, or unintended change in anatomical, physiologic, or metabolic function as indicated by physical signs, symptoms, and/or laboratory changes occurring in any phase of a clinical study, and whether or not considered study drug-related. This includes an exacerbation of a pre-existing condition. Adverse events were collected from informed consent until 30 days after the last dose of study drug and/or until the event had been resolved/stabilized or an outcome was reached, whichever came first. For patients who discontinued or were withdrawn prior to the Week 53 visit, AEs were followed up to 30 days after their last infusion of velaglucerase alfa.

AEs include: worsening (change in nature, severity, or frequency) of conditions present at the onset of the study; intercurrent illnesses; drug interactions; events related to or possibly related to concomitant medications; abnormal laboratory values (this includes significant shifts from Baseline within the range of normal that the Investigator considers to be clinically important); clinically significant abnormalities in physical examination, vital signs, weight, and ECG.

In addition, AEs might also include unexpected laboratory values that become significantly out of range and determined to be clinically significant by the Investigator. In the event of an unexpected out-of-range value, the laboratory test would be repeated until it returns to normal or can be explained and the patient's safety is not at risk.

Infusion-Related Adverse Event Definition:

An infusion-related adverse event was defined as an adverse event that 1) begins either during or within 12 hours after the start of the infusion, and 2) is judged as possibly or probably related to study drug. Other AEs which occurred prior to the infusion, along with AEs associated with protocol-defined testing and assessments (e.g., laboratory testing, ECGs, and physical examinations) which were performed prior to the infusion, was not be defined as infusion-related adverse events. Infusion-related adverse events were managed as defined above.

Serious Adverse Event Definition:

A serious AE (SAE) is any AE occurring at any dose that results in any of the following outcomes: death, is life-threatening, requires inpatient hospitalization, requires prolongation of existing hospitalization, a persistent or significant disability/incapacity, and a congenital anomaly/birth defect.

Important medical events that may not result in death, be life-threatening, or require hospitalization may be considered as SAEs when, based upon appropriate medical judgment, they may jeopardize the patient and may require medical or surgical intervention to prevent one of the outcomes listed above.

A life-threatening AE is defined as an AE that placed the patient, in the view of the initial reporter, at immediate risk of death from the AE as it occurred (i.e., it does not include an AE that, had it occurred in a more severe form, might have caused death).

Classification of Adverse Events and Serious Adverse Events:

The National Cancer Institute Common Toxicity Criteria (NCI CTC) Version 3.0 grading scale was referenced when assessing the severity of an AE. If an AE was not described in the NCI CTC, the severity was recorded based on the scale below. The severity of all AEs/SAEs were recorded on the appropriate CRF page as Grade 1, 2, 3 or 4 corresponding, respectively, to a severity of mild, moderate, severe, or life-threatening. Grade 1 (mild) is defined as no limitation of usual activities. Grade 2 (moderate) is defined as some limitation of usual activities; Grade 3 (severe) is defined as inability to carry out usual activities; and Grade 4 (life-threatening) is defined as immediate risk of death.

Relationship of an adverse event or serious adverse event to blinded study medication was determined by the Investigator based on the following definitions. "Not related" is defined as unrelated to study drug. "Possibly related" is defined as a clinical event/laboratory abnormality with a reasonable time sequence to administration of study drug, but which could also be explained by concurrent disease or other drugs/chemicals. "Probably related" is defined as a clinical event/laboratory abnormality with a reasonable time sequence to administration of study drug, unlikely to be attributable to concurrent disease or other drugs and chemicals and which follows a clinically reasonable response on dechallenge. The association of the clinical event/laboratory abnormality must also have some biologic plausibility, at least on theoretical grounds.

Clarification Between Serious and Severe:

The term "severe" is often used to describe the intensity (severity) of a specific event (as in mild, moderate, or severe myocardial infarction); the event itself, however, may be of relatively minor medical significance (such as severe headache). This is not the same as "serious," which is based on the outcome or action criteria usually associated with events that pose a threat to life or functioning. Seriousness (not severity) and causality serve as a guide for defining regulatory reporting obligations.

Adverse Event Monitoring and Period of Observation:

For the purposes of this study, the period of observation extended from the time the patient provides signed informed consent until the patient's final evaluation of the study. For safety purposes, the final evaluation was defined as the post-study safety evaluation performed approximately 30 days after the last infusion for patients who completed the study and did not elect to enroll in the subsequent long-term open-label clinical study, or for patients who discontinued or withdrew from the study prior to Week 53. For patients who elected to enroll in the subsequent long-term open-label clinical study, adverse events were monitored until Week 53; adverse events that had not resolved as of the Week 53 visit for this study were recorded in the patient's medical history for the subsequent long-term open-label clinical study.

Statistical Methods

General Statistical Methodology:

The intent-to-treat (ITT) patient population was defined as all enrolled patients who received at least one infusion (full or partial infusion). Statistical data analyses were performed on the ITT population. Continuous data collected at Baseline and at subsequent study visits were summarized using descriptive statistics (m, mean, median, minimum, maximum, and standard deviation). Categorical data were summarized as frequencies and percentages. Descriptive statistics were presented for all patients in the ITT population according to demographic and Baseline characteristics.

Analysis of the secondary endpoints (i.e., clinical parameters) was based on a non-inferiority hypothesis as described below.

Sample Size Justification:

This was a safety trial, and it was difficult to identify a single primary safety outcome variable for the study. However, the sample size selected which was based on the efficacy parameters was suitable for the evaluation of less common adverse effects.

The inclusion of at least 26 patients provided basic information on safety and tolerability. From the TKT025 study, the average change at 6 months across patients does not indicate any worsening of adverse events (AEs) from Baseline. Some patients will have their AEs resolved, some patients a worsening of their AEs. Assuming the natural variability of the patients, then the chance of seeing a worsening for a single patient is 11%. This 11% failure rate is for one patient. The likelihood that all 26 patients in the trial will not have an SAE is equal to the likelihood of patient 1 not having an SAE multiplied by the likelihood of patient 2 not having an SAE multiplied by ( . . . etc. . . . ) the likelihood of patient 26 not having an SAE. That is 95% likelihood that at least one patient out of 26 will show a worsening of an AE from Baseline $[1-(0.89)^{26}=0.95]$. In other words, for a sample size of 26, the probability of observing at least one event will be 0.95, when the probability of the event is 0.11. Or, when no events are observed, to obtain an upper bound of 0.11 on the 95% confidence interval to the probability of a rare event, would require a sample size of 26.

The null hypothesis is that the mean changes from Baseline (i.e., the end of imiglucerase treatment) to Month 12 for each of the selected clinical parameters (hemoglobin concentration, platelet count, liver and spleen volumes) are within the pre-specified clinically significantly values. Clinically significant changes from Baseline to Week 53 for hemoglobin was defined as a change of no less than 1 gm/dL, and a 20% change in platelet count. For normalized liver and spleen volume, the changes from Baseline to Week 53 were defined as being no more than 15% increase. The sample size estimate of 26 patients was based on a paired t-test of means, with a standard deviation of 0.671 with a two-sided alpha level of 0.05, and 80% power.

Primary Analysis:

All patients who received at least one full or partial dose of study drug were assessed for clinical safety and tolerability. Vital signs, clinical chemistry and hematology that were collected for safety monitoring were listed for each patient and abnormal values were flagged. For categorical variables such as AEs, the number and percentage of patients experiencing each AE were tabulated. AEs were summarized by severity of event. The number and percentage of patients experiencing drug related AEs and AEs that were not considered related to study drug were also displayed. Infusion-related adverse events reactions and rates of anti-velaglucerase alfa antibody formation were also summarized.

The primary clinical variable was to evaluate the safety of velaglucerase alfa administered every other week to patients with type I Gaucher disease who were clinically stable on imiglucerase. Safety was evaluated by assessing vital signs and documenting adverse events (by type, frequency, and severity) at each study visit, as well as by performance of physical examinations and changes in laboratory assessments at required visits.

All AEs were coded using MedDRA Coding Dictionary. AE summaries in general were based on all AEs occurring after the patient's first infusion of study drug (treatment-emergent).

Secondary Analyses:

Secondary endpoints of this study are: change from Baseline to 12 months in hemoglobin concentration; change from Baseline to 12 months in platelet count; change from Baseline to 12 months in spleen volume by abdominal MRI (evaluated as % change) (Spleen volumes were normalized by body weight); and change from Baseline to 12 months in liver volume by abdominal MRI (evaluated as % change) (Liver volumes were normalized by body weight).

For each clinical activity parameter, the alternative hypothesis is that the mean change from Baseline (i.e., the end of imiglucerase treatment) to Month 12 was within the specified clinically significant levels for the parameters to be evaluated (where the population mean change from Baseline for hemoglobin is within 1 g/dL, the platelet count is within 20%, and the liver and spleen volumes are within 15%. This was evaluated using a 2-sided 90% confidence interval for the true difference from Baseline for these clinical parameters. For example, efficacy of velaglucerase alfa was concluded if the confidence interval for the change from Baseline of hemoglobin was within the interval −1 to 1 g/dL.

The Sponsor's expectation is that the mean hemoglobin concentration was essentially constant over the 12-month period. For example, instead of using a 90% confidence interval for secondary efficacy analysis for hemoglobin, the following pair of statistical hypothesis tests, each at an alpha level of 0.05, could be used.

$H_{01}$: $\mu_d \geq 1$ Vs $H_{11}$: $\mu_d < 1$
$H_{02}$: $\mu_d \leq -1$ Vs $H_{21}$: $\mu_d > -1$ By rejecting the first null hypothesis ($H_{01}$) in favor of the first alternative hypothesis ($H_{11}$), one concludes at the 0.05 significance level that the treatment mean change from Baseline for hemoglobin is less than 1 g/dL higher than the Baseline value. By rejecting the second null hypothesis ($H_{02}$) in favor of the second alternative hypothesis ($H_{21}$), one concludes at the 0.05 significance level that the treatment mean change from Baseline for hemoglobin is greater than 1 g/dL lower than the Baseline value. Because $H_{01}$ and $H_{02}$ cannot be simultaneously true, the overall Type I error rate is 0.05 for the above pair of hypothesis tests. Therefore, by rejecting both null hypotheses in favor of the alternative hypotheses, one concludes at the 0.05 significance level that the treatment (velaglucerase alfa) hemoglobin concentration is within is within the interval −1 to 1 g/dL.

The sponsor considers the confidence interval method to be easier to interpret than the corresponding method using hypothesis tests. Therefore the confidence interval method will be used for the secondary inference.

Tertiary Analyses:

The tertiary endpoints for this study are: change from Baseline to 12 months in plasma chitotriosidase and CCL18 levels; change from Baseline to 12 months in skeletal age in patients 2 to 17 years old; and change from Baseline to 12 months in growth velocity and Tanner staging.

The tertiary endpoints were summarized using descriptive statistics (mean, median, standard deviation, minimum and maximum) at each time point. For endpoints where data were collected at Baseline and other time points during the study, the within group changes were examined.

Analysis of Subgroups:

Additional analyses were conducted specifically for patients between 2 to 17 years old. Also, consideration was given in the analysis to disease severity with regard to hemoglobin Baseline values.

Results 40 patients were included in the intent-to-treat (ITT) analysis (Table 19), and 38 patients (93%) completed the study. One patient discontinued before receiving study drug; and two patients in the 15 U/kg group discontinued, one due to an anaphylactoid reaction during her first infusion with velaglucerase alfa, and one at Week 31 because of a perceived lack of improvement in Gaucher-related symptoms.

Patients received velaglucerase alfa at the same number of units to their prior imiglucerase regimen. Median prior imiglucerase use was 67 months (range 22-192 months). Velaglucerase alfa doses were grouped into four ranges: ≤22.5 U/kg (n=14), 22.5-37.5 U/kg (n=12), 37.5-52.5 U/kg (n=7), and >52.5 U/kg (n=7). Investigators had the option to increase the velaglucerase alfa dose (to a maximum of 60 U/kg every other week) if a patient demonstrated a clinically significant change in hemoglobin or platelet counts. No dose adjustments were made during the study.

TABLE 19

TKT034 Patient characteristics at baseline

| | ITT population (n = 40) |
|---|---|
| Age, mean (range) | 36 years (9-71 years); 25% <18 years |
| Gender, n (%) | 18 (45%) male/22 (55%) female |
| Clinical parameters, median (range) | |
| Hemoglobin | 13.8 g/dL (10.4-16.5 g/dL) |
| Platelet count | 162 × 10$^9$/L (29-399 × 10$^9$/L) |
| Liver volume* | 0.8 MN (0.6-1.6 MN) |
| Spleen volume** | 2.5 MN (1.0-16.0 MN) |
| Biomarkers, median | |
| Chitotriosidase | 3071.3 nmol/mL/h |
| C-C motif ligand 18 chemokine (CCL18) | 325.0 ng/mL |
| Prior imiglucerase use, median (range) | 67 months (22-192 months) |
| Anti-imiglucerase antibody positive prior to receiving velaglucerase alfa, n (%) | 3 (8%) |

*A normal liver volume is 2.5% of body weight.
**In 36 patients with spleen intact; four patients had undergone a splenectomy prior to enrollment. A normal spleen volume is 0.2% of body weight. MN = multiples of normal.

Clinical parameters were sustained at therapeutic levels through 1 year (Table 20).

TABLE 20

| | n | Baseline median | Mean change or % change from baseline to month 12 | 90% CI | Clinically significant cutoffs |
|---|---|---|---|---|---|
| Hemoglobin concentration (g/dL) | 40 | 10.8 | −0.1 | −0.3, 0.1 | −1, 1 |
| Platelet count (×10$^9$/L) | 40 | 162 | 7.0% | 0.5%, 13.5% | −20%, 20% |
| Normalized liver volume (% of body weight) | 40 | 1.9 | 0.0% | −2.6%, 2.6% | −15%, 15% |
| Normalized spleen volume (% of body weight) | 36 | 0.5 | −5.6% | −10.8%, −0.4% | −15%, 15% |

Velaglucerase alfa was generally well tolerated, with most adverse events (AEs) of mild or moderate severity (Table 21). The most frequently reported AEs were nasopharyngitis (8/40 patients), arthralgia (9/40 patients), and headache (12/40 patients). Overall, 11 of 40 patients (28%) experienced an AE considered possibly or probably related to study drug; the majority of these events were considered infusion related. No patient experienced a life-threatening AE. One severe adverse event was considered probably related to treatment and occurred in a patient who had a severe hypersensitivity reaction. This patient tested negative for all 4 isotypes (IgE, IgM, IgG, IgA), including neutralizing antibodies, both at the time of the infusion and 2 weeks later. One patient (in the 15 U/kg group) experienced an anaphylactoid reaction that led to discontinuation; no other patients discontinued due to AEs. No patients developed IgG antibodies to velaglucerase alfa, including three patients who tested positive for anti-imiglucerase alfa antibodies at screening.

TABLE 21

TKT034 Safety summary

| | Patients, n (%) | | | | |
|---|---|---|---|---|---|
| | Total (n = 40) | 15 U/kg (n = 15) | 30 U/kg (n = 12) | 45 U/kg (n = 6) | 60 U/kg (n = 7) |
| Experienced ≥1 treatment-emergent AE* | 34 (85) | 12 (80) | 11 (92) | 5 (83) | 6 (86) |
| Experienced ≥1 drug-related AE | 11 (28) | 6 (40) | 3 (25) | 1 (17) | 1 (14) |
| Experienced ≥1 infusion-related AE† | 9 (23) | 6 (40) | 2 (17) | 0 | 1 (14) |
| Experienced ≥1 severe AE | 5 (13) | 0 | 2 (17) | 1 (17) | 2 (29) |
| Experienced ≥1 life-threatening AE | 0 | 0 | 0 | 0 | 0 |
| Experienced ≥1 serious AE | 4 (10) | 1 (7) | 1 (8) | 2 (33) | 0 |
| Discontinued due to an AE | 1 (3) | 1 (7) | 0 | 0 | 0 |
| Deaths | 0 | 0 | 0 | 0 | 0 |
| Developed anti-velaglucerase alfa antibodies | 0 | 0 | 0 | 0 | 0 |

*A treatment-emergent AEs was defined AEs that occurred on or after the day of the first infusion until 30 days after the patient's last infusion.
†An infusion-related AE was defined as an AE that 1) began either during or within 12 hours after the start of the infusion, and 2) was judged as possibly or probably related to study drug.

The first three infusions for each patient were administered at the clinical site, after which patients who had not experienced a drug-related serious AE or an infusion-related AE were eligible to receive subsequent infusions at home. During the study, 25 (63%) of 40 eligible patients received home therapy at least once, ten patients (67%) in the 15 U/kg group, six (50%) in the 30 U/kg group, five (83%) in the 45 U/kg group, and four (57%) in the 60 U/kg group.

For hemoglobin concentration, the mean change from Baseline was −0.1 g/dL, with a 90% confidence interval of −0.3 to 0.1 g/dL, within the predefined efficacy criterion of ±1 g/dL. For platelet counts, the percent change from Baseline was +7.0%, with a 90% confidence interval of 0.5 to 13.5%, within the predefined efficacy criterion of ±20%. For liver volume, the percent change from Baseline was −0.0%, with a 90% confidence interval of −2.6 to 2.6% within the predefined efficacy criterion of ±15%. For spleen volume, the percent change from Baseline was −5.6%, with a 90% confidence interval of −10.8 to −0.4% within the predefined efficacy criterion of ±15%. Hemoglobin concentration, platelet counts, and liver and spleen volume were sustained at therapeutic levels through 1 year of velaglucerase alfa treatment, as demonstrated by pre-specified efficacy criteria for clinically significant change. Mean change in hemoglobin and mean percent change in platelet count and organ volumes are shown in FIGS. 15-18. For each parameter, similar results were seen across the four dose groups.

Figure 19:
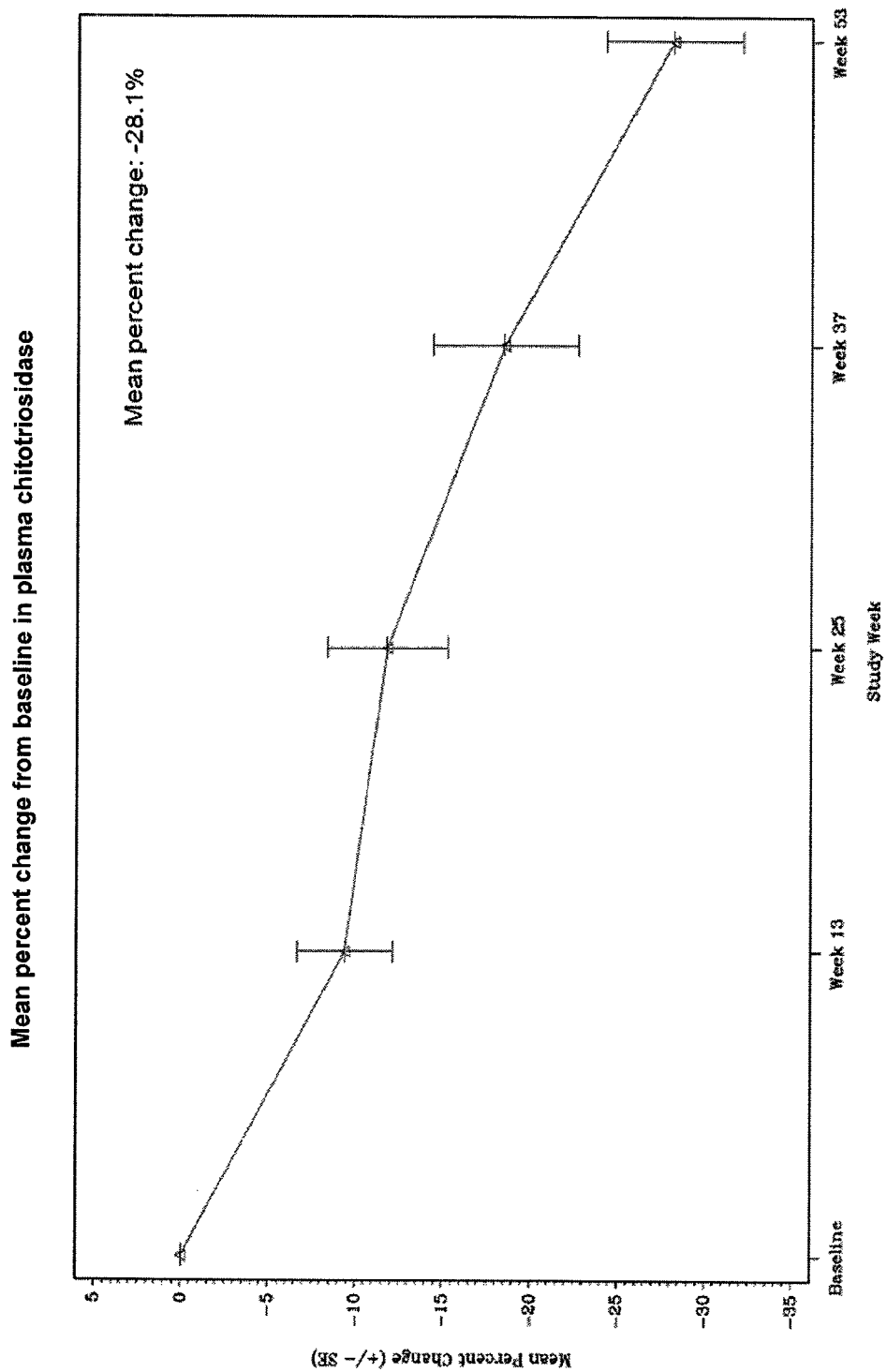
FIG. 19 depicts TKT034 mean percent change from baseline in plasma chitotriosidase.
Figure 20:
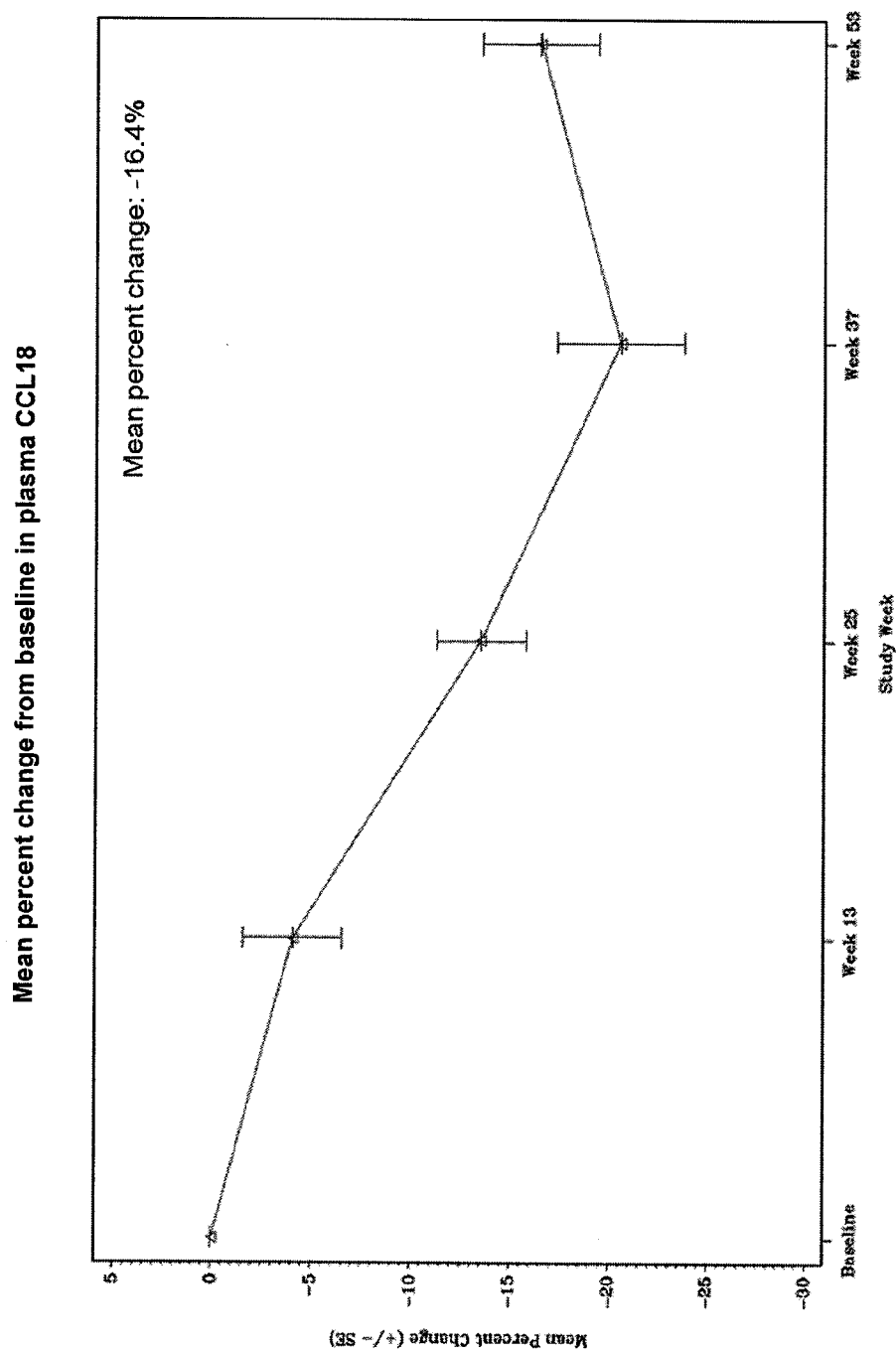
FIG. 20 depicts TKT034 mean percent change from baseline in plasma CCL18.

The percent change in plasma chitotriosidase and plasma CCL18 are shown in FIGS. 19 and 20. Levels of both biomarkers were sustained and possibly reduced over the 12-month treatment period.

Example 5

HGT-GCB-058 Study

Summary

HGT-GCB-058 is a multicenter, open-label treatment study to observe the safety of velaglucerase alfa in patients with Gaucher disease type 1 who were newly diagnosed (treatment naïve) or transitioned from imiglucerase to velaglucerase alfa. The study design was for male or female patients two years old or older. Velaglucerase was administered at a dose of 15-60 U/kg every other week (EOW) by 1-hour intravenous (IV) infusion—Patients received the same number of units of velaglucerase alfa as their prior imiglucerase dose (patients receiving <15 U/kg imiglucerase EOW received 15 U/kg velaglucerase alfa). The rate of infusion was a maximum of 1 U/kg/minute.

Patients and Methods

HGT-GCB-058 was initiated to provide an alternative treatment option for patients who would otherwise have limited or no access to imiglucerase due to supply constraints. The primary endpoint was to observe the safety of velaglucerase alfa.

For HGT-GCB-058, within 3 months of the first site initiated, 20 clinical sites across the US were enrolling patients. Between Sep. 1, 2009 and Jan. 31, 2010 more than 150 patients enrolled onto HGT-GCB-058 and received at least one infusion of velaglucerase alfa. Only 3 patients were treatment naïve; all others were previously treated with imiglucerase.

Preliminary Safety Results

Discontinued: <10%; Withdrawal of consent & other (<10%); AE experience including SAE (<2%).

Treatment Emergent Adverse Events (TE-AE):

Treatment Naïve Patients (n=3):

No serious AEs; no severe AEs; two patients experienced moderate AEs: headache (moderate) and back pain (moderate) (infusion related—possibly related)

Previously Treated with Imiglucerase (n>150):

35.8% at least one TE-AE; 18.2% at least one possibly/probably related TE-AE; 13.8% at least one infusion related reaction; <1%—serious AE (a 69-year-old female experienced a severe cerebrovascular accident requiring hospitalization) not related; 3.1%—at least one severe AE: arthralgia (not related), fatigue (probably related), bone pain (not related), pain in extremity (not related), leucopenia (possibly related), cerebrovascular accident (not related).

Example 6

Comparative Study

The objective of this example is to compare the efficacy of Ceredase®, Cerezyme®, veluglucerase alfa, Genz-112638, and Zavesca® in treating type 1 Gaucher disease. Hemoglobin concentration, platelet count, liver volume, and spleen volumes were measured after 6, 9, or 12 months of treatment.

Doses:

Enzyme replacement therapy (ERT): 60 U/kg EOW; Genz112638: 50 & 100 mg BID; Zavesca: 100 mg TID Ratio of Males to Females:

Cerezyme (8 to 7); Ceredase (3 to 2); Velaglucerase Ph I/II TKT025 study (5 to 7); Velaglucerase-TKT032 study-45 U/kg dose (8 to 5); Velaglucerase-TKT032 study-60 U/kg dose (7 to 5); Zavesca (1 to 1); Genz-112638 (3 to 4)

Inclusion Criteria:

Cerezyme & Ceredase: anemia & splenomegaly
Velaglucerase TKT025: anemia and thrombocytopenia
Genz-112638: anemia, thromb, & splenomegaly
Zavesca dose: organomegaly & <100/nL Pl or <11.5 Hb
Velaglucerase HGT-GCB-039 and TKT032: anemia and 1 other parameter manifestation Baseline comparison in naïve patients is shown in Table 22.

TABLE 22

|  | Hemoglobin (g/dL) | Platelets (cells/nL) | Liver Vol. MN (L) | Spleen Vol. MN (L) |
|---|---|---|---|---|
| Ceredase ® | 10.8 | 71 | 1.83 | 24 |
| Cerezyme ® | 10.7 | 72 | 1.65 | 19 |
| Velaglucerase (Ph I/II TKT025) | 11.6 | 57 | 1.95 (2.4 L) | 19 (2.1 L) |
| Velaglucerase (TKT032-45 U/kg dose) | 10.9 | 58 | 3.50 (% of body weight) | 2.90 (% of body weight) |
| Velaglucerase (TKT032) 60 U/kg dose | 10.83 | 66 | 3.60 (% of body weight) | 2.90 (% of body weight) |
| Genz-112638 | 11 | 70 | 1.7 | 19 |
| Zavesca ® | 11.9 | 77 | (2.4 L) | (1.6 L) |

MN = Multiple of Normal

Comparative results from patients treated with Ceredase®, Cerezyme®, veluglucerase alfa, or Genz-112638 for six months are shown in Table 23.

TABLE 23

|  | Mean Spleen Volume Reduction (%) | Mean Liver Volume Reduction (%) | Mean Platelet Increase (%) [actual] | Mean Hemoglobin Increase (g/dL) |
|---|---|---|---|---|
| Ceredase ®[1] 6 mo | 32.1 ± 8.8 | 11.4 ± 9.4 | 34 [16/nL] | 1.60 |
| Cerezyme ®[1] 6 mo | 37.3 ± 13.6 | 13.4 ± 13.1 | 22 [23/nL] | 1.82 |
| velaglucerase[2] 6 mo (n = 11) | 41.3 ± 9.8 | 14.7 ± 12.0 | 38 [23.4 ± 24.6/nL] | 1.92 ± 0.82 |
| Genz-112638[3] 6 mo (n = 17-21) | 27 | 7 | 18 [12.5/nL[4]] | 0.9 |

[1]Cerezyme and Ceredase data as reported by Grabowski et al. (1995) *Ann. Intern. Med.* 122, 33-39. Mean increase in platelet count in cells/nL for Cerezyme and Ceredase are from the Cerezyme SBA.
[2]velaglucerase alfa Phase I/II results
[3]Oppenheimer Analyst Report: May 8, 2008 from Genzyme Analyst Day 2008
[4]Calculated by multiplying baseline by percent change ERT administered at 60 U/kg EOW, Genz112638 administered at 50 & 100 mg BID Comparative results from patients treated with Ceredase®, Cerezyme®, veluglucerase alfa, or Genz-112638 for nine and twelve months are shown in Table 24.

TABLE 24

|  | Mean Spleen Volume Reduction (%) | Mean Liver Volume Reduction (%) | Mean Platelet Increase (%) [actual] | Mean Hemoglobin Increase (g/dL) |
|---|---|---|---|---|
| Ceredase[1] 9 mo (n = 15) | 42.2 ± 6.9 | 16.4 ± 8.4 | 53.2 [25.1/nL] | 2.28 |
| Cerezyme[1] 9 mo (n = 15) | 47.1 ± 13.7 | 21.4 ± 10.8 | 43.5 [30.9/nL] | 2.54 |
| velaglucerase[2] 9 mo (n = 11) | 49.5 ± 12.6 | 18.2 ± 8.2 | 67.6 [40.6 ± 30.7/nL] | 2.24 ± 0.89 |
| Velaglucerase[3] 1 yr (n = 10) | not available | not available | 95.3 ± 21.2 [54.9 ± 11.1] | 2.35 ± 0.3 |
| Velaglucerase[4] 1 yr (n = 12) | 50.4 ± 5.3 | 17.0 ± 4.5 | 65.9 ± 16.9 [50.88 ± 12.2] | 2.43 ± 0.3 |
| Velaglucerase[5] 1 yr (n = 10) |  |  | 40.92 | 2.44 |
| Genz-112638[5] 1 yr (n = 11-13) | 40 | 17 | 40 [26/nL4] | 1.6 |

[1]Cerezyme and Ceredase 9-Mo data as reported by Grabowski et al. (1995) *Ann. Intern. Med.* 122, 33-39. Dose was 60 U/kg every other week (EOW). Mean increase in platelet count in cells/nL calculated from raw data
[2]velaglucerase alfa 9-Mo data from TKT025 (Ph I/II) - 60 U/kg dose EOW
[3]velaglucerase alfa 12-Mo data from TKT025Extension - 60 U/kg dose EOW
[4]velaglucerase alfa 12 Mo data from TKT032 - 60 U/kg dose dose EOW
[5]velaglucerase afa 12 Mo data from TKT032 - 45 U/kg dose EOW
[3]WORLD meeting presentation, Feb. 20, 2009 - administered at 50 & 100 mg BID Conclusions:

this study shows that velaglucerase alfa was at least as effective as Ceredase®, Cerezyme®, Genz-112638, and Zavesca® in treating type 1 Gaucher disease based on the measurement of hemoglobin concentration, platelet count, liver volume, and spleen volume, 6, 9, or 12 months after the treatment was initiated.

Example 7

Anti-Drug Antibody (ADA) Assays

Summary

Development of antibodies to therapeutic proteins can impact patient safety, efficacy and drug pharmacokinetics. A panel of anti-drug antibody (ADA) and neutralizing antibody (NAb) assays were developed and validated in order to evaluate and compare antibody response in patients receiving velaglucerase alfa or imiglucerase in one of three velaglucerase alfa Phase III studies.

Assessment of potential immunogenicity of a biological therapy such as enzyme replacement therapy (ERT) was performed by the following steps:
 1. Screen for antibody to the ERT
  i. Allow for false positives
  ii. Broad specificity for all isotypes
  iii. Tolerant to presence of drug
 2. Confirmatory step
  i. Rule out false positives
  ii. Isotype specific
 3. Titer step
  i. Relative concentration
 4. Test for neutralizing antibody
  i. In vitro activity
  ii. In vitro cellular uptake This assessment can be performed for any ERT.

Figure 21:
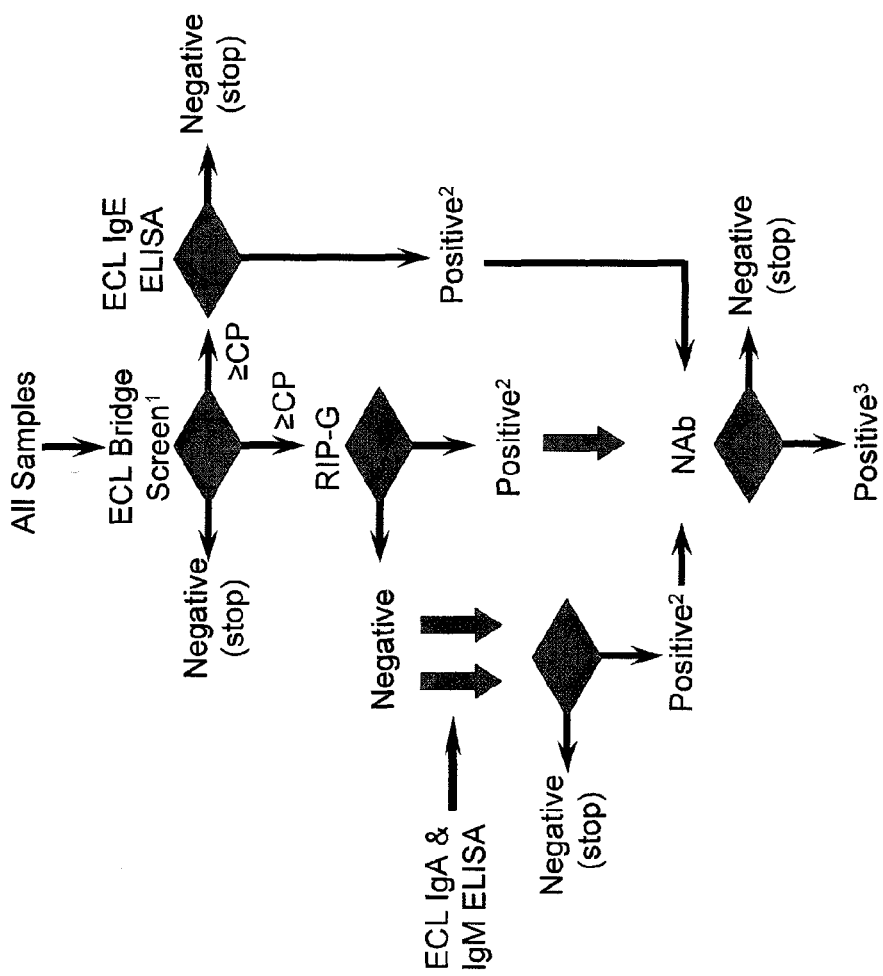
FIG. 21 depicts an immunogenicity evaluation of patients in velaglucerase alfa clinical studies.

An example of such an assessment is shown in FIG. 21.

Immunoassay Methods

Anti-velaglucerase alfa and anti-imiglucerase antibodies were evaluated identically using bridge immunoassays and immunoglobulin (Ig) subclass-specific indirect immunoassays, all based on an electrochemiluminescent platform, as well as RIP assays. The bridge electrochemiluminescent immunoassay detected all immunoglobulin subclasses and was considered the antibody screening assay. The Ig subclass electrochemiluminescent immunoassays were confirmatory assays for the presence of IgA, IgM and IgE antibodies, while the RIP assay was confirmatory for the presence of IgG antibodies. The antibody screening assays and IgG assays were calibrated, quantitative and utilized human antibody positive controls. The IgA, IgM and IgE assays were semi-quantitative and utilized hybrid (human-sheep) positive controls.

All anti-velaglucerase alfa and anti-imiglucerase immunoassays were identical, including positive cut off criteria, except that either velaglucerase alfa or imiglucerase were used to interrogate the sample. These assays are high throughput, provide increased surface area for detection, allow use of high serum sample concentration with minimum non-specific binding and detect all antibody subclasses.

Antibody Screening Assays

Figure 22:
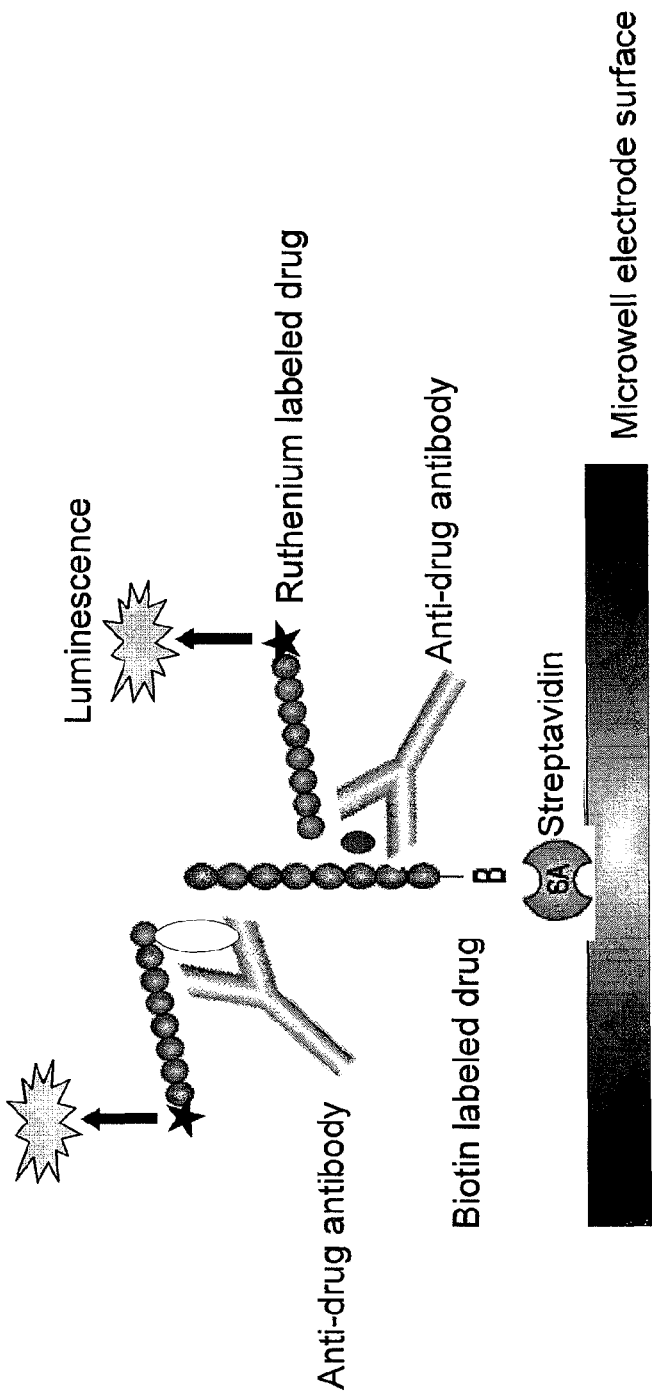
FIG. 22 depicts an anti-drug antibody screening by electro-chemiluminescence (ECL) immunoassay.

As shown in FIG. 22, anti-drug antibody screening can be performed using an electrochemilluminescence (ECL) immunoassay.

Anti-velaglucerase alfa (anti-imiglucerase) antibodies were detected using immobilized biotin-conjugated velaglucerase alfa (or imiglucerase) on streptavidin-coated microwell plates. Immobilized biotinylated velaglucerase alfa (or imiglucerase) captured anti-velaglucerase alfa (anti-imiglucerase) antibodies present in patients' sera and unbound proteins were removed by washing. Ruthenium complex-labeled velaglucerase alfa (or imiglucerase) was added to each microwell resulting in the formation of a complex with the bound anti-velaglucerase alfa (anti-imiglucerase) antibodies. This was followed by a second wash step, in which unbound labeled proteins were removed.

Labeled molecules bound near the micro well surface emit light in a process triggered by the electrochemiluminescent reaction, measured by an MSD SECTOR Imager 2400 instrument (www.mesoscale.com/CatalogSystemWeb/WebRoot/products/imagec2400.aspx). A mouse monoclonal antibody with cross-reactivity to velaglucerase alfa and imiglucerase was used as a calibrator within each assay plate and a human anti-imiglucerase antibody cross-reactive with velaglucerase alfa was use as positive assay control. The concentration of anti-velaglucerase alfa (anti-imiglucerase) antibodies in test samples was estimated by interpolating the unknown's measured electrochemiluminescent signal on the calibration curve.

A minimum of 67 Gaucher patient baselines were tested in order to set the antibody positive cut points for these assays. The test design included at least three analysts testing replicate samples using different plate lot numbers over a period of at least 14 days. At least three different microwell plate lots were used. Two available MSD instruments were used randomly for a total of 1269 determinations for each assay. The assay cut point for anti-velaglucerase alfa (anti-imiglucerase) antibodies was established as the mean plus 1.645 standard deviation of electrochemiluminescent values obtained as recommended in Mire-Sluis, A R et al. *Journal of Immunological Methods* 289 (2004), pp 1-16. The assay sensitivity was estimated to be 33.4 and 65.6 ng/mL for anti-velaglucerase alfa and anti-imiglucerase antibodies, respectively.

The screening characteristics for this assay (using velaglucerase as the drug) are shown in Table 25.

The specification for each parameter shows highly sensitive and reproducible ADA screening assays were validated for evaluating antibody response in patients receiving velaglucerase alfa or imiglucerase.

TABLE 25

| Parameter | Specification |
|---|---|
| Imprecision, % RSD | |
| Intra assay | ≤6.2 |
| Inter assay | ≤8.5 |
| Accuracy, % | 93.5-107.7 |
| Sensitivity, 1 ng/mL | 100 |
| LOD, 2 ng/mL | 5 |
| LOQ, ng/mL | 15 |
| Positive controls | Human & sheep ADA |
| Calibrator | Mouse monoclonal ADA |

Figure 23:
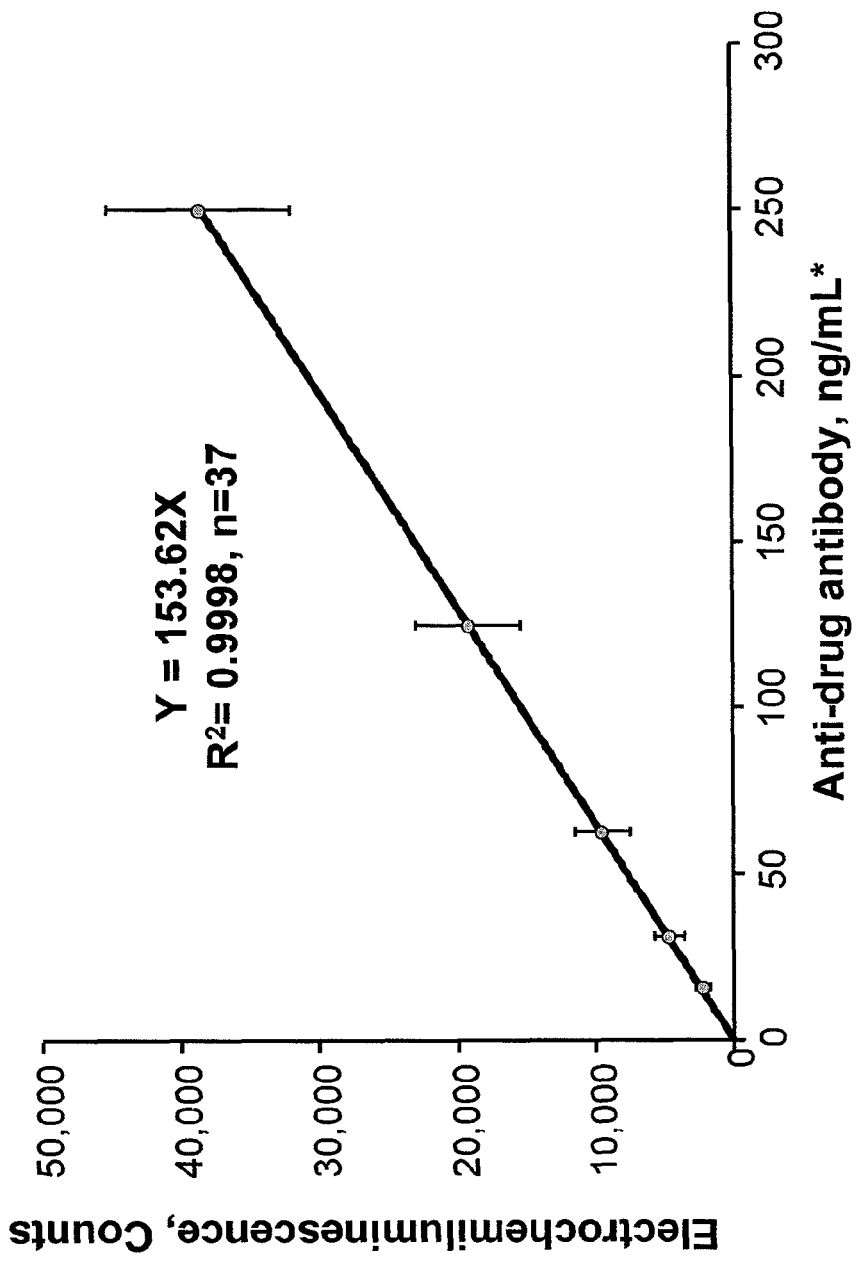
FIG. 23 depicts a screening assay dose response curve.

ADA = anti-drug antibody;
LOD = limits of detection;
LOQ = limit of quantification;
RSD = relative standard deviation The screening assay dose response curve for velaglucerase is shown in FIG. 23.

An example of the affinity and binding kinetics of a monoclonal ADA on the BIACORE® platform are shown in Table 26. Similar ligand affinity and binding kinetics were observed for the ADA assay calibrator.

TABLE 26

| Ligand | ka (1/Ms) | kd (1/s) | KD (M) |
|---|---|---|---|
| velaguacerase alfa | 9.2E+05 | 2.7E−04 | 3.0E−10 |
| imiglucerase | 2.8E+06 | 1.0E−04 | 3.7E−10 |
| Biotinylated velaglucerase alfa | 4.0E+05 | 2.2E−04 | 5.4E−10 |
| Biotinylated imiglucerase | 2.0E+06 | 9.5E−04 | 4.8E−10 |

Radioimmunoprecipitation Assay

Figure 24:
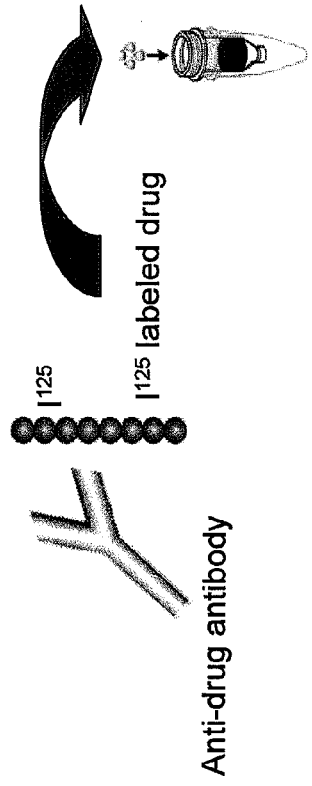
FIG. 24 depicts an IgG ADA confirmatory assay.

If anti-drug antibody is detected in a sample, confirmatory assays to determine the Ig isotype of the antibody can be performed. Immunoglobulin G (IgG) antibodies were detected using radioimmunoprecipitation. A radioimmunoprecipitation (RIP) assay is shown in FIG. 24.

In the radioimmunoprecipitation assay, anti-velaglucerase alfa (anti-imiglucerase) IgG antibodies present in patient serum bound $^{125}$I-velaglucerase alfa (or imiglucerase) in solution phase and formed antigen/antibody complexes that were captured using Protein G mini-columns. The mini-columns were washed to remove free label and quantified directly in a gamma counter. The radioactive counts retained in the mini-column were proportional to the concentration of anti-velaglucerase alfa (anti-imiglucerase) IgG antibodies in the test sample. The concentration of anti-velaglucerase alfa (anti-imiglucerase) IgG antibodies in test samples was estimated from a calibration curve using the same monoclonal antibody calibrator discussed above. The same human antibody positive control described above was used in this assay.

The least squares line fit to the high purity, monoclonal antibody based calibration curve, using well characterized known concentrations of antibody, provided a reliable and consistent method for calculating uncertainty in assay determinations. This tool allows for normalization of the cut point for inter-assay changes in counts that may occur from reagent radiolabel decay, radioautolysis and/or assay handling variability as well as allowing for changes in non specific binding and for changing assay readouts that may occur over time.

A total of 59 Gaucher patient baselines were tested in order to set the antibody positive cut point for this assay. The assay cut points for anti-velaglucerase alfa (imiglucerase) IgG were established as described above and recommended in Mire-Sluis et al[2]. Assay sensitivity was estimated to be 28.3 and 64.5 ng/mL for the anti-velaglucerase alfa IgG and anti-imiglucerase IgG assays, respectively.

An example of the results obtained with such an assay using velaglucerase as the drug is shown in Table 27.

Highly sensitive and reproducible IgG ADA confirmatory assays were validated for evaluating antibody response in patients receiving velaglucerase alfa or imiglucerase.

TABLE 27

| Parameter | Specification |
|---|---|
| Imprecision, % RSD | |
| Intra assay | ≤8.7 |
| Inter assay | ≤12.0 |
| Accuracy, % | 90.5-132.8 |
| Sensitivity, 1 ng/mL | 80 |
| LOD, 2 ng/mL | 4 |

TABLE 27-continued

| Parameter | Specification |
|---|---|
| LOQ, ng/mL | 13 |
| Positive controls | Human & sheep ADA |
| Calibrator | Mouse monoclonal ADA |

Figure 25:
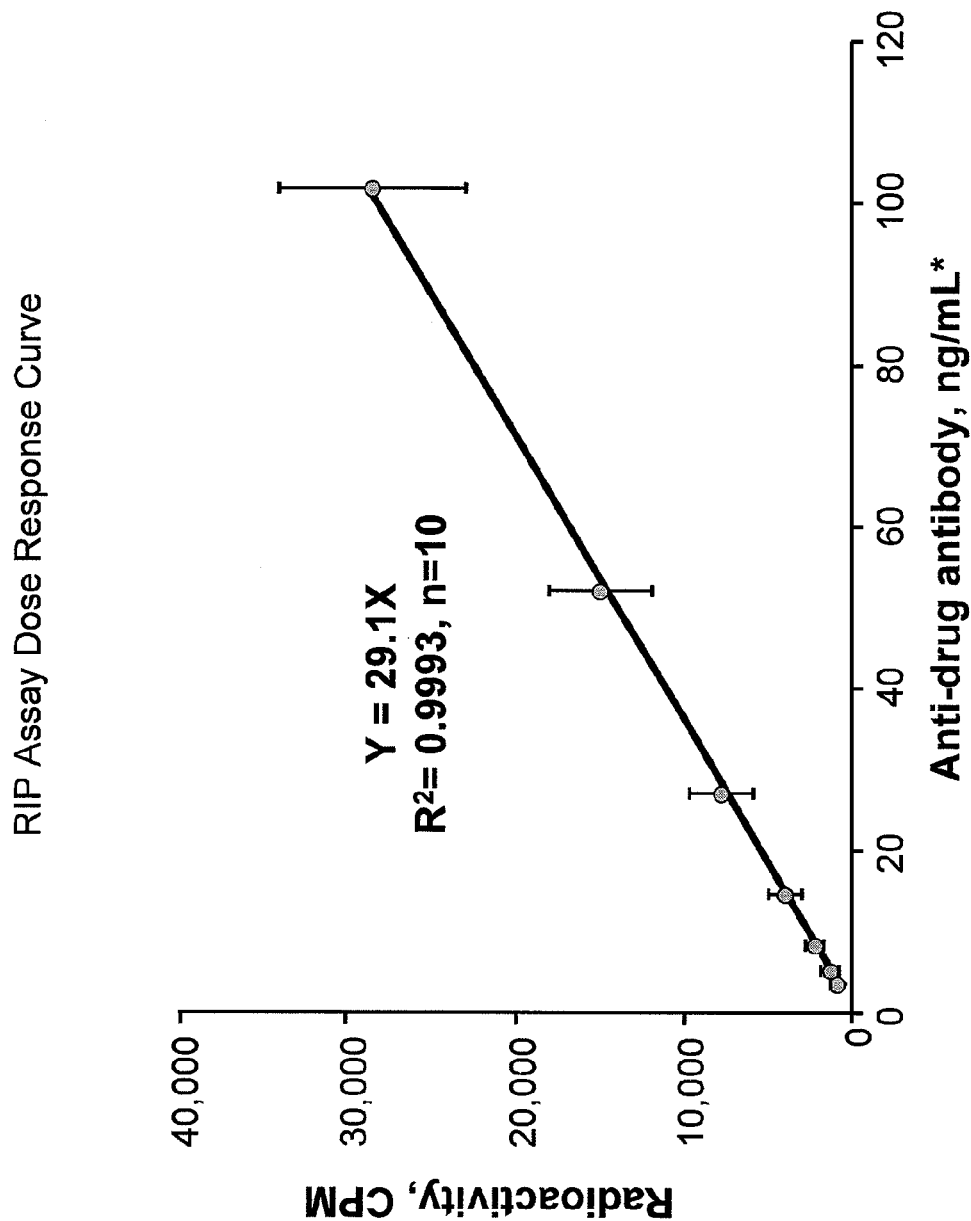
FIG. 25 depicts an RIP assay dose response curve.

ADA = anti-drug antibody;
LOD = limits of detection;
LOQ = limit of quantification;
RSD = relative standard deviation An example of a dose response curve obtained for a RIP assay using velaglucerase is shown in FIG. 25.

Indirect Electrochemiluminescent Immunoassays

Parallel to screening for IgG antibodies, assays are performed to screen for the presence of IgE antibodies. Assays can also be performed to detect the presence of IgA and IgM antibodies.

Figure 26:
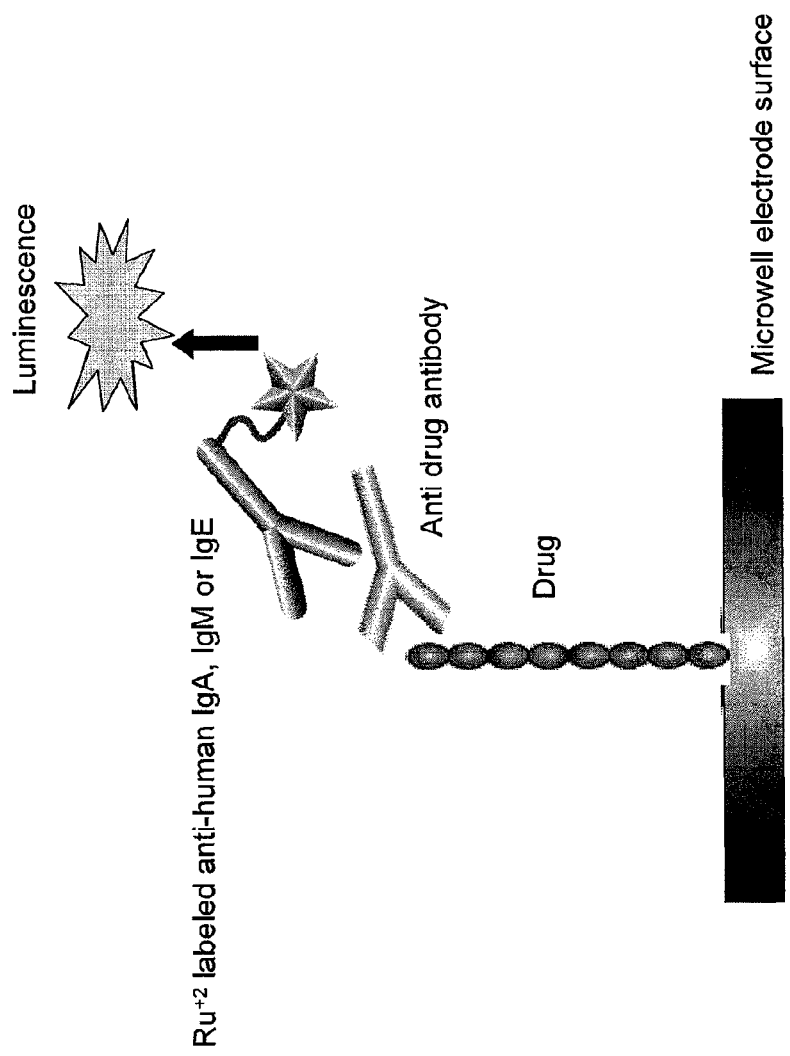
FIG. 26 depicts IgA, IgM and IgE ADA confirmatory assays.

IgA, IgM, and IgE ADA were detected using ECL assays. An example of such an assay is shown in FIG. 26.

Anti-velaglucerase alfa (imiglucerase) antibodies were analyzed for their Ig subclass using indirect electrochemiluminescent immunoassays. Antibodies were detected in serum by immobilizing biotinylated velaglucerase alfa (imiglucerase) on streptavidin-coated microwell plates. Diluted serum samples were added to the immobilized velaglucerase alfa (imiglucerase), which captured any anti-velaglucerase alfa (anti-imiglucerase) antibodies present in the sample. After sample incubation, the microwells were washed to remove unbound proteins. Next, ruthenium complex-labeled anti-human secondary antibodies against IgA, IgM or IgE were added separately and further incubated resulting in the formation of an Ig class-specific complex with any bound anti-velaglucerase alfa or imiglucerase antibodies. This was followed by another wash step, in which unbound labeled secondary antibody was removed. The labeled molecules bound near the microwell surface then emit light as described above.

Artificial antibody positive controls were prepared for these assays since anti-velaglucerase alfa (anti-imiglucerase) IgA, IgM or IgE antibodies were not available. Human IgA-, IgM- and IgE-antibody hybrids were synthesized by chemically cross-linking purified, non-specific human IgA, IgM or IgE fragments to an antibody raised in sheep hyperimmunized with velaglucerase alfa and cross-reactive with imiglucerase. The IgA-, IgM- and IgE-antibody hybrids therefore bound to velaglucerase alfa (or imiglucerase) through the sheep antibody domain, and were detected using ruthenium complex-tagged anti-human secondary antibodies against the human IgA, IgM or IgE domains, respectively.

The assay cut points for anti-velaglucerase alfa (imiglucerase) IgA, IgM and IgE were established as described above and recommended in Mire-Sluis et al[2]. Assay sensitivity was estimated to be 10.6 and 11.0 ng/mL for the anti-velaglucerase alfa IgE and anti-imiglucerase IgE assays, respectively. For anti-velaglucerase alfa (imiglucerase) IgA and IgM antibodies, the assay positive cut points had to be met in addition to a ratio greater than or equal to 2.0 of the time point signal to the pre-infusion baseline signal[3].

For these assays, hybrid positive controls can be used. For example:
Sheep ADA IgG, and human IgA, IgM and IgE are treated to yield pyridylthiol-activated proteins (see Gu M. L., Feng S. L., and Glenn J. K. Development of an animal-human antibody complex for use as a control in ELISA. *J. Pharmaceutical and Biomedical Analysis*, 32 (2003), 523-529)

Activated IgA, IgM and IgE are reduced and desalted
Activated IgG is mixed with reduced IgA, IgM or IgE
The formed hybrid antibodies were characterized by size exclusion chromatography and ECL ELISA
Human/sheep molar ratios of 5 for IgA and IgM, and 2 for IgE were obtained An example of IgA, IgM and IgE confirmatory assay characteristics (when velaglucerase was used as the drug) are shown in Table 28.

Highly sensitive and reproducible IgA, IgM, and IgE ADA isotyping assays were validated for evaluating antibody response in patients receiving velaglucerase alfa or imiglucerase.

TABLE 28

| Parameter[4] | IgA Assay Specification | IgM Assay Specification | IgE Assay Specification |
|---|---|---|---|
| Imprecision, % RSD | | | |
| Intra assay | ≤3.1 | ≤6.2 | ≤6.6 |
| Inter assay | ≤4.8 | ≤3.7 | ≤13.3 |
| Specificity | α-chain Fc | μ-chain Fc | ε-chain Fc |
| Linearity,[1] ng/mL | 156-2000 | 156-2500 | 156-10000 |
| LOD,[2] ECL counts | 260 | 460 | 240 |
| Positive controls[3] | Hybrid ADA | Hybrid ADA | Hybrid ADA |

[1]based on hybrid control response;
[2]positive cut point; ratio of time point to baseline must be ≥2.0;
[3]human/sheep ADA hybrid controls;
[4]highly sensitive and reproducible IgA, IgM and IgE ADA isotyping assays were validated for evaluating antibody response in patients receiving velaglucerase alfa or imiglucerase
ADA = anti-drug antibody;
LOD = limits of detection;
LOQ = limit of quantification;
RSD = relative standard deviation Antibody Inhibition of In Vitro Enzymatic Activity Inhibition of in vitro enzymatic activity by anti-velaglucerase alfa (imiglucerase) antibodies was tested using an assay that detects and quantifies antibodies that inhibit velaglucerase alfa (imiglucerase) activity. The method is based on a colorimetric activity assay that measures the ability of velaglucerase alfa (imiglucerase) to hydrolyze the synthetic substrate 4-nitrophenyl-β-D-glucopyranoside to p-nitrophenol and D-glucopyranoside.

Anti-velaglucerase alfa (imiglucerase) antibody positive serum samples were pre-incubated with a fixed amount of velaglucerase alfa or imiglucerase, respectively for 30 minutes at 37° C. Sheep polyclonal antibodies known to inhibit velaglucerase alfa and imiglucerase in vitro activity were used as positive controls. The 4-nitrophenyl-β-D-glucopyranoside substrate solution was then added and incubated with the serum sample/enzyme mixture for one hour at 37° C. The enzymatic reaction was stopped by addition of glycine/sodium carbonate buffer (pH 10.7) and the product (p-nitrophenol) was measured at the absorbance wavelength of 405 nm. One unit of velaglucerase alfa (imiglucerase) activity was defined as the amount of enzyme required to hydrolyze one μmole of the substrate 4-nitrophenyl-β-D-glucopyranoside in one minute at 37° C. Enzymatic activity was quantified by comparison of the released p-nitrophenol in test samples and assay controls to a p-nitrophenol calibration curve measured in the same assay plate. Results of the test samples were expressed relative to the activity of velaglucerase alfa (imiglucerase) measured in the absence of serum sample and reported as % inhibition.

The assay cut point was determined from individual healthy human donor sera (N=52) and enzyme replacement therapy-naïve Gaucher patients (N=35). The cut point for the velaglucerase alfa and imiglucerase neutralizing antibody assays was defined as inhibition >20.0% based on these 87 samples. Therefore, a patient sample was considered to be negative for inhibitory antibodies if the level of inhibition observed was ≤20.0% and to be positive if inhibition >20.0%.

In Vitro Cell-Based Assay

An in vitro cell-based assay was used to assess anti-drug antibodies to determine if the antibodies were neutralizing.

Table 29 shows the specification of assay characteristics for neutralizing levels of anti-drug antibody (velaglucerase was used as the drug).

TABLE 29

| Parameter | Specification |
|---|---|
| Imprecision, % RSD | |
| Intra assay | ≤12.9 |
| Inter assay | ≤6.1 |
| Accuracy, % | 86.7-92.7 |
| Linearity, mU/mL | 0.3-33.3 |
| Positive cut point,[1] % inhibition | >20 |
| LOD, mU/mL | 0.3 |
| LOQ, mU/mL | 1.0 |
| Positive controls | Human & sheep ADA |

[1]n = 104 NHS and 70 ERT-naïve Gaucher sera
LOD = limits of detection;
LOQ = limit of quantification;
RSD = relative standard deviation With respect to neutralizing antibodies in ERT such as ERT for Gaucher disease, points to consider include:

Receptor-mediated cell uptake is critical for in vivo function of therapeutic agent
Receptor binding interference by ADA can hinder enzyme trafficking
Inhibition of cell uptake is an important tool to evaluate successful ERT since
  It closely mimics the mechanism by which NAb may exert an effect in vivo, and
  NAb could reduce or abolish the biological activity of the therapeutic agent
Cell-based assays provide the most appropriate biological model for assessment of NAb Samples from patients undergoing ERT in clinical trials for Gaucher disease were evaluated for neutralizing antibodies to velaglucerase or imiglucerase. Results are shown in Table 30.

TABLE 30

| | | Inhibition of imiglucerase uptake, % mean Visit Week | | | | Inhibition of velaglucerase alfa uptake, % mean Visit Week | | | |
|---|---|---|---|---|---|---|---|---|---|
| Patient ID | Treatment | 0 | 13 | 19 | 41 | 0 | 13 | 19 | 41 |
| 032-191-0002 | velaglucerase | NS[2] | | | | NS | | | |
| 039-009-0001 | imiglucerase | | | | | | | | |
| 039-194-0001 | imiglucerase | | | | | | | | |
| 039-194-0002 | imiglucerase | | | | | | | | |
| 039-167-0001 | imiglucerase | NT3 | 38 | 38 | 33 | NT | 4 | 5 | 5 |
| 034-027-0002 | imiglucerase[1] | NS | NT[3] | | | NS | NT | | |

TABLE 30-continued

|  |  | Inhibition of imiglucerase uptake, % mean Visit Week | | | | Inhibition of velaglucerase alfa uptake, % mean Visit Week | | | |
|---|---|---|---|---|---|---|---|---|---|
| Patient ID | Treatment | 0 | 13 | 19 | 41 | 0 | 13 | 19 | 41 |
| 034-154-0001 | imiglucerase[1] | 5 | | | | 10 | | | |
| 034-164-0001 | imiglucerase[1] | 38 | | | | 10 | | | |

A marked cell-based inhibition of imiglucerase uptake was observed in two ADA-positive patients
Cell-based inhibition of velaglucerase alfa uptake was either negligible or not observed in any ADA-positive patient tested

[1] previously receiving imiglucerase treatment and switched to velaglucerase alfa at trial inception;
[2] not significant (less than the limit of quantification);
[3] not tested as yet; time point negative for anti-velaglucerase alfa antibodies In Vitro Cell-Based Assay I Major Objectives:

Experiments were conducted to determine the ability of human antibodies reactive with velaglucerase alfa and/or imiglucerase to inhibit (block or neutralize) CD206-mediated uptake of the recombinant enzymes by a human cell line (HT1080) engineered to express CD206, and to compare in this respect anti-drug antibodies (ADA) produced in response to imiglucerase to those produced in response to velaglucerase alfa. The hypothesis is that antigenic differences exist between velaglucerase alfa and imiglucerase; these epitopes will differentiate velaglucerase alfa from imiglucerase with respect to the functional effect of ADA on cell binding, cell internalization, and/or intracellular trafficking of the therapeutic agent.

Materials and Equipment:

Critical Materials

1. Cell line MRC1-18 is derived from the line HT1080 and is stably-transfected with human CD206 (the macrophage mannose receptor; MMR, also referred to as MRC1, mannose receptor C type 1). HT1080(saf) cells were transfected with an expression vector carrying the gene encoding the MMR (that was isolated from a human liver cDNA library) by electroporation and immediately plated into 96-well plates. Stable clones were selected using media containing 0.4 mg/mL G418. MRC1 expression was analyzed using FITC anti-MRC1 staining and analysis by fluorescence shift. Expression of MMR on MRC1-18 was confirmed by surface staining with anti-MMR Ab. Additionally, MRC1-18 has been verified by immunostaining and flow cytometry to be negative for expression of Fc (gamma) receptors.

2. Alexa FLUOR® 488 conjugated velaglucerase alfa and imiglucerase: velaglucerase alfa or imiglucerase was conjugated with Alexa FLUOR® 488 using the Alexa FLUOR®r 488 protein labeling kit following the manufacturer's protocol (Molecular Probes, catalog #A 10235).

3. Imiglucerase or velaglucerase alfa ADA-positive patient sera from clinical trials TKT-032, TKT-034, and HGT-GCB-039 (see Table 31 for sample IDs)

4. Assay Positive Control (PC): 250 µg/mL purified polyclonal sheep anti-velaglucerase alfa antibody (G140) in Normal Human Serum (NHS; BRH127439)

5. Negative control samples: human serum samples from normal healthy donors (Bioreclamation, Catalog #HMSM, BRH127438, BRH127439), or baseline serum samples from patients enrolled in clinical trial TKT-032 (N=25).

6. Mannan: Sigma Catalog #M7054

7. D-Mannose-6-phosphate: Sigma Catalog# M3655

8. Growth medium: 50% CD-CHO (Invitrogen catalog #10743) and 50% CD-293 (Invitrogen catalog#11913) supplemented with 4 mM L-glutamine (Invitrogen Catalog#25230) and 0.4 mg/mL Geneticin (G418, Invitrogen Catalog #11811-031).

9. 0.05% trypsin-EDTA: Invitrogen catalog#25300

10. Wash buffer: PBS/0.5% BSA

11. BD Cytometer setup and tracking beads: BD Bioscience catalog#641319

Partial List of Equipment 1. 37° C. Incubator with 5% $CO_2$: Form a Scientific Model 3033

2. Centrifuge: Thermo Scientific Model Sorvall Legend T+

3. Cell counter: Mexcelom Bioscience LLC, Model Cellometer Auto T 4

4. Flow cytometer: BD Bioscience, FACSCanto II

Methods:

Patient sera that tested positive for anti-drug antibodies by antibody screening and confirmatory assay were further examined by an in vitro cell uptake assay, utilizing an HT1080 cell line engineered to express the human macrophage mannose receptor (MMR). Briefly, MRC1-18 cells were maintained in CD media supplemented with 0.5 mg/mL G418. For each assay, $1.5 \times 10^5$ cells/well in CD media with G418 were added in a flat bottom 96-well plate, and pre-incubated with 1:20 diluted test patient serum samples, 1:20 diluted normal human serum (NHS), or assay positive controls (G140 antibody, 5 mg/mL mannan) in 1:20 diluted NHS at 37° C. for 15 minutes. Then 5 nM Alexa FLUOR® 488 labeled velaglucerase alfa or imiglucerase was added, and incubated at 37° C. for an additional 2 hours. A calibration curve of Alexa FLUOR® 488 labeled velaglucerase alfa or imiglucerase was included in each experiment by incubation of MRC1-18 cells with Alexa FLUOR® 488 labeled velaglucerase alfa or imiglucerase (0-10 nM) in 1:20 diluted NHS at 37° C. for 2 h.

After a 2-hour incubation, media was removed by centrifugation, cells were treated with trypsin-EDTA for 3 minutes to remove surface-bound velaglucerase alfa or imiglucerase, then neutralized by addition of an equal volume of media with 10% FBS. Cells were washed with PBS/0.5% BSA once, resuspended in PBS/0.5% BSA and analyzed by BD FACS Canto II with the fixed instrument setting. The Canto II instrument was set up with the BD Cytometer setup and tracking beads before each analysis. The results were analyzed with FlowJo software, and the mean fluorescence intensity (MFI) for each sample recorded. The adjusted MFI was calculated by subtraction of the MFI of the background sample (cells with 0 nM drug) from the MFI of each sample. Inhibition of velaglucerase alfa and imiglucerase uptake by patient samples was determined relative to a normal human serum sample (NHS) or the patient's own naive baseline sample, when available. Percent inhibition can be calculated using the following equation:

$$\% \text{ inhibition} = 1 - (\text{Adj. MFI of test sample}/\text{Adj. MFI of patient baseline or NHS}) \times 100$$

Results:

Assay Development:

The following initial results were obtained upon development of this assay (data not shown):

The internalization of velaglucerase alfa and imiglucerase by the MRC1-18 cell line is dose dependent.

The internalization of velaglucerase alfa and imiglucerase by the MRC1-18 cell line is mediated by the mannose receptor, since the internalization was inhibited by mannan (5 mg/mL, >89%), but not by M6P (5 mM).

G140 antibody spiked in 1:20 diluted NHS (normal human serum) inhibits velaglucerase alfa and imiglucerase uptake by the MRC1-18 cell line. The inhibition is dose dependent.

Twelve lots of NHS tested at 1:20 dilution did not inhibit velaglucerase alfa uptake by the MRC1-18 cell line.

Assay Variability:

Twenty-five individual naive Gaucher serum samples from a clinical study were tested over three days (N=75) to establish the baseline effect on the uptake of velaglucerase alfa or imiglucerase into the MRC1-18 cell line.

The average baseline serum effect on the uptake of velaglucerase alfa is similar to the baseline serum effect on the uptake of imiglucerase. However, the variability, calculated as the CV %, is much greater for imiglucerase than for velaglucerase alfa (28% vs 15%) (data not shown).

ADA-Positive Patient Serum Samples Results and Reproducibility of the Assay:

The inhibition of velaglucerase alfa and imiglucerase uptake by patient serum samples previously determined to have antibodies against imiglucerase or velaglucerase alfa was tested. Each serum sample was tested in parallel for its ability to block imiglucerase uptake as well as velaglucerase alfa uptake, regardless of which enzyme preparation initially elicited the production of the antibodies. Table 31 lists the patient serum samples and the protein treatment received (only one antibody positive patient, ENU, received treatment with velaglucerase alfa).

TABLE 31

ADA-Positive Patient Serum Samples

| Patient | Patient Initials | Treatment Received |
|---|---|---|
| 032-191-0002 | ENU | Velaglucerase alfa |
| 039-009-0001 | RW | imiglucerase |
| 039-194-0001 | GAJ | imiglucerase |
| 039-194-0002 | AVL | imiglucerase |
| 039-167-0001 | KM | imiglucerase |
| 034-027-0002 | SB | imiglucerase |
| 034-154-0001 | JMS | imiglucerase |
| 034-164-0001 | MPQ | imiglucerase |

Samples from patients ENU, RW, GAJ, AVL, and SB showed no inhibition of either imiglucerase or velaglucerase alfa uptake (data not shown). The reproducibility of inhibition of velaglucerase alfa and imiglucerase uptake by patient samples JMS, KM, MPQ, and SB (as a negative control) was determined over three days relative to a normal human serum sample or the patient's own naive baseline sample, when available (Table 32).

Patient KM (039-167-0001) was naive at baseline and was then treated with imiglucerase in a subsequent study. Samples from all three visits showed a significant inhibition of imiglucerase uptake (24-52% inhibition relative to its baseline), relative to the equivalent inhibition of velaglucerase alfa uptake (0-15%, which is within the range of variability of the assay).

Patients SB (034-027-0002), JMS (034-154-0001), and MPQ (034-164-0001) were previously treated with imiglucerase. Serum from patient SB showed no inhibition of either imiglucerase uptake (0%) or of velaglucerase alfa uptake (0%) relative to a normal human serum sample. The inhibition of imiglucerase uptake (0-14%) by serum from patient JMS was consistent with the inhibition observed of velaglucerase alfa uptake (0-20%). The inhibition of imiglucerase uptake (32-45%) by serum from patient MPQ was significantly greater than the equivalent inhibition of velaglucerase alfa uptake (0-15%, which is within the range of variability of the assay).

These preliminary results suggest that neutralizing antibodies present in the serum from patients KM and MPQ inhibit imiglucerase uptake but not velaglucerase alfa uptake into cells.

TABLE 32

Inhibition of Imiglucerase or Velaglucerase alfa Uptake by ADA-Positive Patient Samples

| Patient # | Initials | Visit | Treatment | Inhibition of imiglucerase Uptake | | | | Inhibition of Velaglucerase alfa Uptake |
|---|---|---|---|---|---|---|---|---|
| | | | | Day 1 | Day 2 | Day 3 | Mean | |
| 039-167-0001 | KM | Week 13 | naive at baseline, then treated with imiglucerase | 38% | 24% | 52% | 38% | 0-8% |
| | | Week 19 | | 29% | 45% | 40% | 38% | |
| | | Early termination | | 28% | 38% | 33% | 33% | |
| 034-027-0002 | SB | Baseline visit | Previously treated with imiglucerase | 0% | 0% | 0% | 0% | 0-14% |
| 034-154-0001 | JMS | Baseline visit | Previously treated with imiglucerase | 14% | 0% | 2% | 5% | 0-20% |
| 034-164-0001 | MPQ | Baseline visit | Previously treated with imiglucerase | 45% | 32% | 40% | 38% | 0-15% |

Inhibition of uptake of imiglucerase or velaglucerase alfa by the mannose inhibitor mannan and by polyclonal sheep anti-velaglucerase alfa antibody G140 (positive control) was also determined over three days (Table 33). Mannan inhibits the uptake of both imiglucerase and velaglucerase alfa into MRC1-18 cells through the mannose receptor. The G140 antibody inhibits the uptake of both imiglucerase and velaglucerase alfa into MRC1-18 cells by an equivalent amount.

TABLE 33

Inhibition of Imiglucerase or Velaglucerase alfa Uptake by Positive Controls

|  |  | Inhibition of Imiglucerase Uptake | | Inhibition of Velaglucerase alfa Uptake | |
| --- | --- | --- | --- | --- | --- |
|  |  | Mean | CV % | Mean | CV % |
| G140 | 5 µg/mL | 52% | 37% | 42% | 14% |
| G140 | 10 µg/mL | 78% | 11% | 71% | 7% |
| Mannan | 5 mg/mL | 92% | 3% | 91% | 3% |

Conclusions:

Velaglucerase alfa and imiglucerase differ structurally, with regard to both protein sequence (e.g., R495H mutation in imiglucerase) and carbohydrate structure. Experiments were performed to address the hypotheses that antigenic differences exist between velaglucerase alfa and imiglucerase, and that these epitopes differentiate velaglucerase alfa from imiglucerase with respect to the ability of anti-drug antibodies (ADA) to block cell binding and/or cell internalization of each therapeutic. Experiments were conducted using the recently developed HT1080 cell line in which uptake of therapeutic is facilitated principally by the MMR, and is minimally confounded by other known cell uptake mechanisms. The inhibition of imiglucerase or velaglucerase alfa uptake by patient serum samples was measured relative to each other. The data show that out of a total of 7 serum samples taken from patients that produced ADA in response to imiglucerase treatment, and 1 serum sample taken from a patient that produced ADA in response to velaglucerase alfa treatment, 2 sera (2/7=29%) from patients that produced ADA in response to imiglucerase caused 24% to 52% inhibition of cell uptake of imiglucerase, but only 0-15% inhibition of cell uptake of velaglucerase alfa which is within assay variability. In comparison, only one patient has been identified to date that produced antibody in response velaglucerase alfa treatment; this serum did not inhibit uptake.

Each serum sample was tested in parallel for its ability to block imiglucerase uptake and/or velaglucerase alfa uptake, regardless of which enzyme preparation initially elicited the production of the antibodies. Such comparisons of the inhibition of velaglucerase alfa uptake, versus inhibition of imiglucerase uptake, allow for crude "mapping" of epitopes to biologically-relevant portions of each therapeutic (with the caveat that the antisera tested herein are polyclonal, and thus each antiserum likely contains a mixture of antigen specificities, perhaps recognizing multiple epitopes). With these precautions in mind, the inhibition of uptake observed with anti-imiglucerase antisera seems to be restricted to imiglucerase since the same antisera do not inhibit internalization of velaglucerase alfa tested in parallel. These data suggest that some ADA produced in response to imiglucerase inhibit cellular internalization via epitopes that are uniquely exposed in imiglucerase. Furthermore, the difference in variability observed of the serum effect on imiglucerase vs. velaglucerase alfa uptake can perhaps be due to a greater homogeneity in the velaglucerase alfa preparation than in the imiglucerase preparation in terms of post translational modifications.

Inhibition of enzyme uptake by anti-velaglucerase alfa (imiglucerase) antibodies was tested using a cell-based assay that detects and quantifies antibodies that interfere with macrophage mannose receptor (MMR)-mediated velaglucerase alfa (imiglucerase) uptake. The method is based on quantification of fluorescently-labeled velaglucerase alfa (imiglucerase) which is internalized by MRC1-18 cells under defined conditions. MRC1-18 is a cell line engineered at Shire HGT from HT1080 cells that were stably-transfected with the human macrophage mannose receptor C, type 1.

Briefly, anti-velaglucerase alfa (imiglucerase) antibody positive serum samples were pre-incubated with MRC1-18 cells in culture media in flat-bottom, 96-well plates at 37° C. for 15 minutes. Pooled normal human serum (NHS) was used as negative control. Sheep polyclonal antibodies known to inhibit velaglucerase alfa and imiglucerase uptake as well as mannan, the MMR-specific ligand (Sung S J et al. *J. Cell Biol.* 1983; 96:160-166) were used as positive controls to block enzyme uptake.

Following preincubation, Alexa Fluor-488-labeled velaglucerase alfa or imiglucerase was added, and incubated at 37° C. for an additional 2 hours. A calibration curve consisting of incubation of Alexa Fluor-488-labeled enzyme with MRC1-18 cells was included in each experiment. After incubation, media was removed by centrifugation, cells were treated with trypsin-EDTA for 3 minutes to remove surface-bound enzyme, and finally the reaction pH was returned to neutral with by addition of an equal volume of culture media. Cells were washed once and resuspended using phosphate buffered saline containing 0.5% BSA. Cells were analyzed using a Becton Dickinson FACS Canto II instrument calibrated before each analysis using the instrument's cytometer setup and tracking beads.

The results were analyzed with the instrument's FlowJo software, and the mean fluorescence intensity (MFI) for each sample was recorded. The adjusted MFI was calculated by subtracting the background MFI from sample wells containing no enzyme from each unknown and control sample MFI. Inhibition of enzyme uptake by patient serum samples was estimated relative to the NHS control according to the following equation:

$$\% \text{ Inhibition} = [1 - [\text{Adjusted MFI of test sample} / \text{Adjusted MFI of NHS}]] \times 100$$

The assay cut point was determined by analysis of 25 individual sera collected from treatment-naïve Gaucher patients. Each serum was tested on four separate days for a total of 100 values and the positive cut point was defined as inhibition greater than the mean of these values plus 1.645 standard deviations.

In Vitro Cell-Based Assay II

This assay was developed to compare uptake of velaglucerase alfa to imiglucerase.

Methods:

For Design of Experiments (DOE) assays, general factorial design was assisted by Statease DESIGN EXPERT™ software. DOE utilized macrophages derived from phorbol myristate acetate (PMA) induced U937 cells, and were conducted in the presence of 5 mM mannose-6-phosphate (M6P). For internalization comparisons, U937-derived macrophages were incubated for 3 hours with GCB at pH 7.5 with 10 mM calcium. Internalized drug was measured by an activity assay with a synthetic substrate (4-MU-glc) that fluoresces upon cleavage.

Results:

Comparison in U937 cells of the internalization rates of velaglucerase alfa and imiglucerase showed that velaglucerase alfa is internalized up to 2.5-fold more efficiently than imiglucerase. This differentiation in cellular internalization was also observed using the MMR-expressing murine cell line J774. Under specific assay conditions, the addition of calcium mildly inhibited the cellular uptake of imiglucerase while it enhanced the uptake of velaglucerase alfa. The internalization of both enzymes could be inhibited by addition of mannan to the culture medium, although the inhibition of velaglucerase alfa uptake by J774 cells was more complete than that of imiglucerase. DOE assays revealed that: i) the interaction of calcium with pH greatly impacts uptake; and ii) bioassay sample comparisons required the presence of calcium, consistent with the known calcium-dependence of the MMR. The presence of mannose-6-phosphate (M6P) in DOE experiments ensured that the M6P receptor on U937 cells did not contribute to the measured internalization.

These data suggest that velaglucerase alfa is internalized more efficiently than imiglucerase. While both enzymes are primarily internalized via the MMR, a small portion, greater for imiglucerase than for velaglucerase alfa, is internalized by an alternative mechanism. These data may prove valuable in differentiating velaglucerase alfa, imiglucerase, and other future therapies.

SUMMARY

From these studies, a summary of antibody detection methods is as follows:
Equivalent assays validated for velaglucerase alfa and imiglucerase ADA as per ICH and FDA guidelines. See, e.g., www Jda.gov/downloads/Regulatory Information/Guidances/UCM 128049.pdf and www.ich.org/LOB/media/MEDIA417.pdf
  Screening
  Confirmatory
  Titer
  Isotype
  Neutralizing
Masked patient specimens evaluated for velaglucerase alfa and imiglucerase ADA in parallel
Controls and calibrators covered a broad range of antibody affinities
Developed isotype-specific hybrid controls when human positive sera not found
Immunogenicity Status of Patients in Phase III Studies:
TKT032: patients randomized to velaglucerase alfa 60 U/kg or 45 U/kg EOW
  One patient ADA-negative at baseline developed NAb in response to velaglucerase alfa
TKT034: patients previously stable on imiglucerase switched to velaglucerase alfa 15-60 U/kg
  Three patients anti-imiglucerase positive at baseline, were anti-velaglucerase negative through the 12-month treatment.
HGT-GCB-039: patients randomized to velaglucerase alfa 60 U/kg or imiglucerase 60 U/kg EOW
  Four patients ADA-negative at baseline, seroconverted in response to imiglucerase
  Of these, one developed NAb reactive against both imiglucerase and velaglucerase alfa, while three developed non-inhibitory IgG ADA reactive against only imiglucerase The patient seroconversion summary is shown in Table 34. Of the 99 patients who were treated, 82 received velaglucerase alfa and 17 received imiglucerase. One of 82 patients receiving velaglucerase alfa and four of 17 patients receiving imiglucerase developed antibodies during the trials.

TABLE 34

| Study Months | Treatments | U/kg EOW | n | Seroconversion |
|---|---|---|---|---|
| TKT032 | | | | |
| 12 months | velaglucerase alfa | 60 | 12 | 0/12 patients |
|  | velaglucerase alfa | 45 | 13 | 1/13 patients |
| TKT034 | | | | |
| 12 months | velaglucerase alfa | 15-60 | 40 | To date: 0 patients (3 patients imiglucerase antibody-positive at baseline) |
| HGT-GCB-039 | | | | |
| 9 months | velaglucerase alfa | 60 | 17 | 0/17 patients |
|  | imiglucerase | 60 | 17 | 4/17 patients |

The clinical implications of the studies discussed in this example are as follows:
Highly sensitive and equivalent methods were developed, optimized and validated to directly assess and compare patient antibody response to velaglucerase alfa and imiglucerase treatments
Results show seroconversion in 1% of patients treated with velaglucerase alfa and 23% of patients who were treated with imiglucerase, suggesting significant antigenic differences between velaglucerase alfa and imiglucerase
In addition, there was marked cell uptake inhibition by ADA of imiglucerase but not velaglucerase alfa Example 8

Effect of Moisture Content on the Stability of a Lyophilized Velaglucerase Product Purpose:
To assess the effect of moisture content on the stability of a lyophilized velaglucerase product.

Methods:
The protein was formulated into a sucrose-containing solution and lyophilized using a FTS lab-scale lyophilizer (Lyostar II). The lyophilized vials were removed at intervals after primary drying with a sample thief to yield samples with varying moisture content. The secondary structure of the lyophilized protein was examined by FT-IR. The thermal stability of these samples was characterized by physical appearance, moisture content, size exclusion and reversed phase HPLC, and oxidation by peptide mapping methods.

Upon reconstitution with Sterile Water for Injection, the velaglucerase product contains approximately 2.5 mg/mL (40 U/mL) of velaglucerase alfa, 50 mg/mL sucrose, 12.9 mg/mL sodium citrate dihydrate, 1.3 mg/mL citric acid monohydrate and 0.11 mg/mL polysorbate 20.

Results:

A moisture content range of 1.3% to 6.2% was achieved in the lyophilized product. Cake collapse was observed at accelerated temperature (40° C.) in drug product with high moisture content (≥5%). However, chemical stability testing results for the reconstituted solution demonstrate that the samples with higher moisture content (≥3%) showed significantly less degradation than the drier samples by both SE-HPLC and RP-HPLC methods, as well as showing lower amounts of oxidation. This stability trend correlates with changes observed in the secondary structure by FT-IR of the dried product.

Conclusion:

Higher moisture content resulted in better chemical stability of a lyophilized protein. This stability trend is explained by fewer changes to the secondary structure in the solid phase with higher moisture content. A choice of proper moisture content in the lyophilized product needs to balance both structural stability of the cake and chemical stability of the protein.

Example 9

Analysis of Therapeutic Goals for Velaglucerase Alfa

Therapeutic goals have been described to monitor achievement, maintenance and continuity of therapeutic response in patients with type 1 Gaucher disease receiving ERT (Pastores G et al., (2004) *Seminars in Hematology,* 41 (suppl 5): 4-14)

To benchmark the impact of velaglucerase alfa treatment against therapeutic goals for clinical parameters of type 1 Gaucher disease (anemia, thrombocytopenia, hepatomegaly, and splenomegaly), the proportion of patients at goal for anemia, thrombocytopenia, hepatomegaly and splenomegaly at baseline was compared with the proportion achieving each of these goals at 9 months or 1 year.

No data imputation was utilized. Only patients who have data for each goal at both time points are included. For hematologic parameters, Baseline was the average of the screening and baseline values; 1 year therapeutic goal values were the average of Week 51 and Week 53 values for TKT032 and TKT034, and the average of Week 39 and Week 41 values for HGT-GCB-039. For organ volumes, Week 41 value was applied to 1 year therapeutic goal criteria in HGT-GCB-039.

Therapeutic goals for TKT032, HGT-GCB-039, HGT-GCB-039 patients with intact spleen, HGT-GCB-039 splenectomized patients, TKT034, and TKT025 are described in Tables 35-40.

TABLE 35

| Therapeutic goals | velaglucerase alfa 60 U/kg N = 12 | | velaglucerase alfa 45 U/kg N = 13 | | velaglucerase alfa Overall N = 25 | |
| --- | --- | --- | --- | --- | --- | --- |
| | Baseline | 1 Year | Baseline | 1 Year | Baseline | 1 Year |
| Hemoglobin concentration | 2/12 (17%) | 11/12 (92%) | 3/13 (23%) | 12/13 (92%) | 5/25 (20%) | 23/25 (92%) |
| Platelet count | 2/11 (18%) | 6/11 (55%) | 4/13 (31%) | 9/13 (69%) | 6/24 (25%) | 15/24 (63%) |
| Liver | 5/11 (45%) | 11/11 (100%) | 7/12 (58%) | 8/12 (67%) | 12/23 (52%) | 19/23 (83%) |
| Spleen | 3/11 (27%) | 11/11 (100%) | 4/12 (33%) | 11/12 (92%) | 7/23 (30%) | 22/23 (96%) |
| ≥3 goals | 1/11 (9%) | 10/11 (91%) | 5/12 (42%) | 9/12 (75%) | 6/23 (26%) | 19/23 (83%) |
| All 4 goals | 1/10 (10%) | 6/10 (60%) | 0/12 (0%) | 7/12 (58%) | 1/22 (5%) | 13/22 (59%) |

TABLE 36

| Therapeutic goals | velaglucerase alfa 60 U/kg N = 17 | | imiglucerase 60 U/kg N = 17 | |
| --- | --- | --- | --- | --- |
| | Baseline | 9 Months | Baseline | 9 Months |
| Hemoglobin concentration | 10/16 (63%) | 15/16 (94%) | 4/15 (27%) | 12/15 (80%) |
| Platelet count | 8/16 (50%) | 16/16 (100%) | 9/15 (60%) | 15/15 (100%) |
| Liver | 8/16 (50%) | 15/16 (94%) | 4/16 (25%) | 16/16 (100%) |
| Spleen | 1/6 (17%) | 6/6 (100%) | 3/6 (50%) | 6/6 (100%) |
| ≥3 goals | 1/16 (6%) | 14/16 (88%) | 1/15 (7%) | 12/15 (80%) |
| All 4 goals | 0/6 (0%) | 6/6 (100%) | 0/6 (0%) | 6/6 (100%) |

TABLE 37

| Therapeutic goals | velaglucerase alfa 60 U/kg N = 7 | | imiglucerase 60 U/kg N = 7 | |
|---|---|---|---|---|
| | Baseline | 9 Months | Baseline | 9 Months |
| Hemoglobin concentration | 5/7 (71%) | 7/7 (100%) | 2/6 (33%) | 6/6 (100%) |
| Platelet count | 0/7 (0%) | 7/7 (100%) | 0/6 (0%) | 6/6 (100%) |
| Liver | 6/7 (86%) | 7/7 (100%) | 1/6 (17%) | 6/6 (100%) |
| Spleen | 1/6 (17%) | 6/6 (100%) | 3/6 (50%) | 6/6 (100%) |
| ≥3 goals | 1/7 (14%) | 7/7 (100%) | 1/6 (17%) | 6/6 (100%) |
| All 4 goals | 0/6 (0%) | 6/6 (100%) | 0/6 (0%) | 6/6 (100%) |

TABLE 38

| Therapeutic goals | velaglucerase alfa 60 U/kg N = 10 | | imiglucerase 60 U/kg N = 10 | |
|---|---|---|---|---|
| | Baseline | 9 Months | Baseline | 9 Months |
| Hemoglobin concentration | 5/9 (56%) | 8/9 (89%) | 2/9 (22%) | 6/9 (67%) |
| Platelet count | 8/9 (89%) | 9/9 (100%) | 9/9 (100%) | 9/9 (100%) |
| Liver | 2/9 (22%) | 8/9 (89%) | 3/10 (30%) | 10/10 (100%) |
| ≥2 goals | 6/9 (67%) | 9/9 (100%) | 5/9 (56%) | 9/9 (100%) |
| All 3 goals | 0/9 (0%) | 7/9 (78%) | 0/9 (0%) | 6/9 (67%) |

TABLE 39

| Therapeutic goals | velaglucerase alfa overall N = 40 | |
|---|---|---|
| | Baseline | 1 Year |
| Hemoglobin concentration | 37/38 (97%) | 37/38 (97%) |
| Platelet count | 29/36 (81%) | 29/36 (81%) |
| Liver | 37/37 (100%) | 37/37 (100%) |
| Spleen | 30/34 (88%) | 31/34 (91%) |
| ≥3 goals | 32/37 (86%) | 33/37 (89%) |
| All 4 goals | 26/32 (81%) | 26/32 (81%) |

TABLE 40

| Therapeutic goals | TKT025 velaglucerase alfa 60 U/kg N = 12 | | TKT032 velaglucerase alfa 60 U/kg N = 12 | |
|---|---|---|---|---|
| | Baseline | Month 9 | Baseline | Year 1 |
| Hemoglobin concentration | 5/10 (50%) | 10/10 (100%) | 2/12 (17%) | 11/12 (92%) |
| Platelet count | 0/10 (0%) | 7/10 (70%) | 2/11 (18%) | 6/11 (55%) |
| Liver | 5/10 (50%) | 7/10 (70%) | 5/11 (45%) | 11/11 (100%) |
| Spleen | 0/10 (0%) | 9/10 (90%) | 3/11 (27%) | 11/11 (100%) |
| ≥3 goals | 0/10 (10%) | 8/10 (80%) | 1/11 (9%) | 10/11 (91%) |
| All 4 goals | 0/10 (10%) | 5/10 (50%) | 1/10 (10%) | 6/10 (60%) |

Example 10

Efficacy and Safety Study of Velaglucerase Alfa in Children and Adolescents with Type 3 Gaucher Disease Gaucher disease is a rare lysosomal storage disorder caused by the deficiency of the enzyme glucocerebrosidase (GCB). Gaucher disease has been classified into 3 clinical subtypes based on the presence or absence of neurological symptoms and the severity of neurological symptoms. Patients with type 2 Gaucher disease present with acute neurological deterioration, and those with type 3 disease typically display a more sub acute neurological course; type 1 Gaucher disease, the most common form accounting for more than 90% of all cases, does not involve the central nervous system.

Velaglucerase alfa is an approved enzyme replacement therapy (ERT) for pediatric and adult patients with type 1 Gaucher disease. ERT has been proven to reduce organomegaly, improve hematological parameters and positively impact health-related quality of life. ERT has not been shown cross the blood brain barrier and as a result has shown limited ability to improve the neurological (Central Nervous System; CNS) manifestations associated with Gaucher disease.

This study will provide a basis for exploring the efficacy and safety of velaglucerase alfa in patients with type 3 Gaucher disease. The study will be an interventional multicenter, open label, efficacy and safety study of velaglucerase alfa enzyme replacement therapy in children and adolescents with type 3 Gaucher disease. Primary outcome measures will include; change from baseline in hemoglobin concentration; change from baseline in platelet count; change from baseline in normalized liver volumes measured using magnetic resonance imaging (MRI); change from baseline in normalized spleen volumes measured using magnetic resonance imaging (MRI); and change from baseline in neurological symptoms. Safety assessments will include the assessment of adverse events and infusion related adverse events; serious adverse events; clinical laboratory values; urinalysis; vital signs; 12-lead electrocardiogram (ECG) recordings; physical examination; and anti-velaglucerase alfa antibody formation. The experimental arm of the study will receive velaglucerase alfa by intravenous infusion, every other week.

For inclusion in the study each patient must meet all of the following criteria; a confirmed diagnosis of type 3 Gaucher disease; ≥2 and <18 years of age at the time of enrollment; either naive to treatment or has not received treatment (investigational or approved) for Gaucher disease within 12 months prior to study entry; the patient must have Gaucher disease-related anemia, defined as a hemoglobin concentration below the lower limit of normal for age and sex. The patient must also meet one or more of the following criteria; at least moderate splenomegaly (2 to 3 cm below the left costal margin) by palpation; Gaucher disease-related thrombocytopenia, defined as a platelet count <120×10,000 platelets/cubic mm; a Gaucher disease-related readily palpable enlarged liver. Patients who have undergone splenectomy may still be eligible to participate in the study. Female patients of child-bearing potential must agree to use a medically acceptable method of contraception at all times during the study. Pregnancy testing will be performed at the time of enrollment and as required throughout participation in the study. Male patients must agree to use a medically acceptable method of contraception at all times during the study and report a partner's pregnancy to the Investigator. The patient's parent(s) or the patient's legally authorized representative(s) must provide written informed consent that has been approved by the Institutional Review Board/Independent Ethics Committee (IRB/IEC).

Patients who meet any of the following criteria will be excluded from this study; the patient is suspected of having type 2 or type I Gaucher disease; the patient is <2 years of age; the patient has experienced a severe (Grade 3 or higher) infusion-related hypersensitivity reaction (anaphylactic or anaphylactoid reaction) to any enzyme replacement therapy for Gaucher disease (approved or investigational); the patient has received any non-Gaucher disease-related treatment with an investigational drug within 30 days prior to study entry; the patient is a pregnant and/or lactating female.

A number of embodiments of the invention have been described. Nevertheless, it will be understood that various modifications may be made without departing from the spirit and scope of the invention. Accordingly, other embodiments are within the scope of the following claims.

What is claimed:

1. A method of treating a neurological parameter or a neurological symptom associated with Gaucher Type III disease in a subject with Gaucher Type III disease, the method comprising (i) administering a glucocerebrosidase enzyme replacement therapy by intravenous infusion to the subject over a period of less than 2 hours and (ii) evaluating whether the neurological parameter or the neurological symptom has changed, wherein the neurological parameter or the neurological symptom is selected from the group consisting of eye movement parameters, hearing parameters, abnormal brainstem auditory evoked potentials, seizures, progressive myoclonic seizures, electroencephalogram (EEG) abnormalities, dementia, cognitive impairment, ataxia, loss of muscle coordination, and poor mobility.

2. The method of claim 1, wherein the glucocerebrosidase enzyme replacement therapy is administered over a period of 90 minutes or less.

3. The method of claim 1, wherein the glucocerebrosidase enzyme replacement therapy is administered over a period of 60 minutes or less.

4. The method of claim 1, further comprising administering a second glucocerebrosidase enzyme replacement therapy by intravenous infusion to the subject over a period of less than 2 hours.

5. The method of claim 1, wherein the glucocerebrosidase enzyme replacement therapy is selected from the group consisting of: velaglucerase, imiglucerase and uplyso.

6. The method of claim 1, wherein the glucocerebrosidase enzyme replacement therapy is administered at a dose of 15 to 60 U/kg.

7. The method of claim 1, wherein the subject is a child or an adolescent.

8. The method of claim 1, wherein the glucocerebrosidase enzyme replacement therapy is velaglucerase.

9. A method for preventing progression of a neurological parameter or a neurological symptom associated with Gaucher Type III disease in a subject with Gaucher Type III disease, the method comprising (i) administering a glucocerebrosidase enzyme replacement therapy by intravenous infusion to the subject over a period of less than 2 hours and (ii) evaluating whether the neurological parameter or the neurological symptom has changed, wherein the neurological parameter or the neurological symptom is selected from the group consisting of eye movement parameters, hearing parameters, abnormal brainstem auditory evoked potentials, seizures, progressive myoclonic seizures, electroencephalogram (EEG) abnormalities, dementia, cognitive impairment, ataxia, loss of muscle coordination, and poor mobility.

10. The method of claim 9, wherein the glucocerebrosidase enzyme replacement therapy is administered over a period of 90 minutes or less.

11. The method of claim 9, wherein the glucocerebrosidase enzyme replacement therapy is administered over a period of 60 minutes or less.

12. The method of claim 9, further comprising administering a second glucocerebrosidase enzyme replacement therapy by intravenous infusion to the subject over a period of less than 2 hours.

13. The method of claim 9, wherein the glucocerebrosidase enzyme replacement therapy is selected from the group consisting of velaglucerase, imiglucerase and uplyso.

14. The method of claim 9, wherein the glucocerebrosidase enzyme replacement therapy is velaglucerase.

15. The method of claim 9, wherein the glucocerebrosidase enzyme replacement therapy is administered at a dose of 15 to 60 U/kg.

16. The method of claim 9, wherein the subject is a child or an adolescent.

* * * * *